(12) United States Patent
Kanasty et al.

(10) Patent No.: US 11,576,859 B2
(45) Date of Patent: Feb. 14, 2023

(54) GASTRIC RESIDENCE SYSTEMS FOR SUSTAINED RELEASE OF THERAPEUTIC AGENTS AND METHODS OF USE THEREOF

(71) Applicant: Lyndra Therapeutics, Inc., Watertown, MA (US)

(72) Inventors: Rosemary Kanasty, Somerville, MA (US); Andrew Bellinger, Wellesley, MA (US); Colin Gardner, Concord, MA (US); Tyler Grant, Cambridge, MA (US); Saumya Moorthy, Medford, MA (US)

(73) Assignee: Lyndra Therapeutics, Inc., Watertown, MA (US)

( * ) Notice: Subject to any disclaimer, the term of this patent is extended or adjusted under 35 U.S.C. 154(b) by 200 days.

(21) Appl. No.: 15/769,949

(22) PCT Filed: Oct. 21, 2016

(86) PCT No.: PCT/US2016/058309
§ 371 (c)(1),
(2) Date: Apr. 20, 2018

(87) PCT Pub. No.: WO2017/070612
PCT Pub. Date: Apr. 27, 2017

(65) Prior Publication Data
US 2018/0311154 A1      Nov. 1, 2018

Related U.S. Application Data

(60) Provisional application No. 62/402,947, filed on Sep. 30, 2016, provisional application No. 62/264,806, filed on Dec. 8, 2015, provisional application No. 62/264,799, filed on Dec. 8, 2015, provisional application No. 62/264,795, filed on Dec. 8, 2015, provisional application No. 62/245,789, filed on Oct. 23, 2015, provisional application No. 62/245,797, filed on Oct. 23, 2015.

(51) Int. Cl.
| | | |
|---|---|---|
| A61K 9/14 | (2006.01) | |
| A61K 31/519 | (2006.01) | |
| A61K 9/00 | (2006.01) | |
| A61K 31/365 | (2006.01) | |
| A61K 31/495 | (2006.01) | |
| A61K 31/505 | (2006.01) | |

(52) U.S. Cl.
CPC ............ *A61K 9/0065* (2013.01); *A61K 9/146* (2013.01); *A61K 31/365* (2013.01); *A61K 31/495* (2013.01); *A61K 31/505* (2013.01); *A61K 31/519* (2013.01)

(58) Field of Classification Search
None
See application file for complete search history.

(56) References Cited

U.S. PATENT DOCUMENTS

| | | |
|---|---|---|
| 1,957,564 A | 5/1934 | West |
| 3,154,461 A | 10/1964 | Johnson |
| 3,531,368 A | 9/1970 | Okamoto |
| 3,716,614 A | 2/1973 | Watanabe |
| 3,844,285 A | 10/1974 | Laby |
| 3,976,764 A | 8/1976 | Watanabe |
| 4,304,767 A | 12/1981 | Heller et al. |
| 4,451,260 A | 5/1984 | Mitra |
| 4,525,358 A | 6/1985 | Baltes |
| 4,676,507 A | 6/1987 | Patterson |
| 4,735,804 A | 4/1988 | Caldwell et al. |
| 4,758,436 A | 7/1988 | Caldwell et al. |
| 4,767,627 A | 8/1988 | Caldwell |
| 4,812,012 A | 3/1989 | Terada |
| 4,996,058 A | 2/1991 | Sinnreich |
| 5,002,772 A | 3/1991 | Curatolo |
| 5,007,790 A | 4/1991 | Shell |
| 5,047,464 A | 9/1991 | Pogany |
| 5,121,329 A | 6/1992 | Crump |
| 5,340,433 A | 8/1994 | Crump |
| 5,369,142 A | 11/1994 | Culbertson |
| 5,443,843 A | 8/1995 | Curatolo |
| 5,491,586 A | 2/1996 | Phillips |
| 5,840,332 A | 11/1998 | Lerner |
| 5,939,467 A | 8/1999 | Wnuk et al. |

(Continued)

FOREIGN PATENT DOCUMENTS

| | | |
|---|---|---|
| AU | 6199090 A | 3/1991 |
| CA | 2951884 A1 | 12/2015 |

(Continued)

OTHER PUBLICATIONS

Yerraounta et al. (J Pharm Bioall Sci. 7(1) 37-44. Jan.-Mar. 2015) Development of a novel 3-month drug releasing . . . .*
Dumortier et al. ( Pharmaceutical Research, vol. 23 (12), 2709-2728, 2006) A Review of Poloxamer 407 Pharmaceutical . . . .*
Muthu et al. (Nanomedicine 3(3), 305-319, 2008) Studies on biodegradable polymeric nanoparticles of risperidone: . . . .*
Bellinger, A.M. et al. (Nov. 16, 2016). "Oral, Ultra-Long-Lasting Drug Delivery: Application Toward Malaria Elimination Goals," *Sci. Transl. Med.* 8(365ra157):1-12., (with Supplementary Material), 20 pages.
Zhang, S. et al. (Oct. 2015; e-pub. Jul. 27, 2015). "A pH-Responsive Supramolecular Polymer Gel as an Enteric Elastomer for Use in Gastric Devices," *Nature Materials* 14(10):1065-1071, 19 pages.
International Preliminary Report on Patentability dated May 3, 2018 for International Application No. PCT/US2016/058309, filed on Oct. 21, 2016, six pages.

(Continued)

*Primary Examiner* — Tigabu Kassa
(74) *Attorney, Agent, or Firm* — Morrison & Foerster LLP

(57) ABSTRACT

Gastric residence systems comprising therapeutic agent formulations for sustained gastric release of therapeutic agents are disclosed, as well as methods for using such systems. The systems are characterized by use of a dispersant in the formulations, which improves the burst release characteristics and long-term release rate characteristics of the systems. Milling of therapeutic agent can also be performed to prepare agent particles of desired size.

22 Claims, 53 Drawing Sheets

(56) References Cited

U.S. PATENT DOCUMENTS

| | | | |
|---|---|---|---|
| 6,120,803 A * | 9/2000 | Wong | A61P 31/12 424/473 |
| RE37,314 E | 8/2001 | Hirai et al. | |
| 6,306,420 B1 | 10/2001 | Cheikh | |
| 6,306,439 B1 | 10/2001 | Penners et al. | |
| 6,316,460 B1 | 11/2001 | Creekmore et al. | |
| 6,375,649 B1 | 4/2002 | Jellie | |
| 6,436,069 B1 | 8/2002 | Jellie | |
| 6,488,962 B1 | 12/2002 | Berner | |
| 6,500,168 B1 | 12/2002 | Jellie | |
| 6,548,083 B1 | 4/2003 | Wong | |
| 6,685,962 B2 | 2/2004 | Friedman | |
| 6,776,999 B1 | 8/2004 | Krumme | |
| 6,780,168 B2 | 8/2004 | Jellie | |
| 6,825,308 B1 | 11/2004 | Kulkarni | |
| 6,962,579 B2 | 11/2005 | Jellie | |
| 7,276,252 B2 | 10/2007 | Payumo | |
| 7,691,151 B2 | 4/2010 | Kutsko | |
| 7,964,196 B2 | 6/2011 | De | |
| 8,021,384 B2 | 9/2011 | Weiss | |
| 8,038,659 B2 | 10/2011 | Boyden | |
| 8,158,143 B2 | 4/2012 | Lendlein | |
| 8,267,888 B2 | 9/2012 | Marco et al. | |
| 8,277,843 B2 | 10/2012 | Singh | |
| 8,298,574 B2 | 10/2012 | Tsabari | |
| 8,377,453 B2 | 2/2013 | Han | |
| 8,414,559 B2 | 4/2013 | Gross | |
| 8,586,083 B2 | 11/2013 | Mohammad | |
| 8,609,136 B2 | 12/2013 | Tsabari | |
| 8,753,678 B2 | 6/2014 | Tsabari | |
| 8,771,730 B2 | 7/2014 | Navon | |
| 9,072,663 B2 | 7/2015 | Navon | |
| 9,107,816 B2 | 8/2015 | Lee | |
| 9,220,688 B2 | 12/2015 | Alon | |
| 9,259,387 B2 | 2/2016 | Navon | |
| 10,182,985 B2 | 1/2019 | Bellinger | |
| 10,195,143 B2 | 2/2019 | Zalit et al. | |
| 10,485,758 B2 | 11/2019 | Menachem et al. | |
| 10,517,820 B2 | 12/2019 | Bellinger | |
| 10,532,027 B2 | 1/2020 | Bellinger | |
| 10,610,482 B2 | 4/2020 | Bellinger | |
| 2002/0022048 A1 | 2/2002 | Bromberg | |
| 2002/0132008 A1 | 9/2002 | Mumper | |
| 2003/0021822 A1 | 1/2003 | Lloyd | |
| 2003/0232895 A1 | 12/2003 | Omidian | |
| 2004/0180086 A1 | 9/2004 | Ramtoola | |
| 2004/0219186 A1 | 11/2004 | Ayres | |
| 2005/0033331 A1 | 2/2005 | Burnett | |
| 2005/0165136 A1 | 7/2005 | Mays | |
| 2005/0175702 A1 | 8/2005 | Muller-Schulte | |
| 2005/0249807 A1 * | 11/2005 | Brown | A61K 9/1617 424/464 |
| 2006/0069214 A1 | 3/2006 | Deiss | |
| 2006/0142794 A1 | 6/2006 | Lendlein | |
| 2006/0182788 A1 | 8/2006 | Singh | |
| 2007/0048383 A1 | 3/2007 | Helmus | |
| 2007/0104754 A1 | 5/2007 | Sterling | |
| 2007/0123809 A1 | 5/2007 | Weiss | |
| 2007/0129784 A1 | 6/2007 | Lendlein | |
| 2007/0131144 A1 | 6/2007 | Winter et al. | |
| 2007/0264307 A1 | 11/2007 | Chen | |
| 2008/0075766 A1 | 3/2008 | Li | |
| 2008/0153779 A1 | 6/2008 | Liao | |
| 2008/0241238 A1 | 10/2008 | Dharmadhikari | |
| 2008/0249156 A1 | 10/2008 | Palepu | |
| 2008/0260824 A1 | 10/2008 | Nangia | |
| 2008/0292691 A1 | 11/2008 | Lloyd | |
| 2009/0092415 A1 | 4/2009 | Murakami | |
| 2009/0105531 A1 | 4/2009 | Boyden | |
| 2009/0182424 A1 | 7/2009 | Marco | |
| 2009/0246142 A1 | 10/2009 | Bhatia | |
| 2009/0324694 A1 | 12/2009 | Mohammad | |
| 2010/0152410 A1 | 6/2010 | East | |
| 2010/0168439 A1 | 7/2010 | Olson | |
| 2010/0256342 A1 | 10/2010 | Salemme | |
| 2010/0266655 A1 | 10/2010 | Dadey | |
| 2010/0297009 A1 | 11/2010 | Olson | |
| 2010/0316712 A1 | 12/2010 | Nangia | |
| 2011/0038912 A1 | 2/2011 | Darby et al. | |
| 2011/0040318 A1 | 2/2011 | Marco | |
| 2011/0052700 A1 | 3/2011 | Han | |
| 2011/0097395 A1 | 4/2011 | Babul et al. | |
| 2011/0245909 A1 | 10/2011 | Schmid | |
| 2011/0268666 A1 | 11/2011 | Friedman | |
| 2011/0305685 A1 | 12/2011 | Tseng | |
| 2012/0116285 A1 | 5/2012 | Duggirala | |
| 2012/0165793 A1 | 6/2012 | Ortiz | |
| 2012/0165794 A1 | 6/2012 | Ortiz | |
| 2012/0301547 A1 | 11/2012 | Gan | |
| 2012/0321706 A1 | 12/2012 | Masri | |
| 2013/0045530 A1 | 2/2013 | Gracias | |
| 2013/0131637 A1 | 5/2013 | Dicesare et al. | |
| 2013/0226104 A1 | 8/2013 | Hyde | |
| 2013/0273135 A1 | 10/2013 | Brooks | |
| 2014/0050784 A1 | 2/2014 | Kagan | |
| 2014/0052171 A1 | 2/2014 | Tegels | |
| 2014/0249499 A1 | 9/2014 | Selaru | |
| 2015/0265536 A1 | 9/2015 | Muley | |
| 2015/0335592 A1 | 11/2015 | Barnscheid | |
| 2015/0342877 A1 | 12/2015 | Menachem | |
| 2016/0317796 A1 | 11/2016 | Zhang et al. | |
| 2017/0051099 A1 | 2/2017 | Diciccio | |
| 2017/0106099 A1 | 4/2017 | Bellinger et al. | |
| 2017/0128576 A1 | 5/2017 | Zhang et al. | |
| 2017/0135954 A1 | 5/2017 | Bellinger et al. | |
| 2017/0266112 A1 | 9/2017 | Bellinger et al. | |
| 2018/0250226 A1 | 9/2018 | Betser et al. | |
| 2018/0311154 A1 | 11/2018 | Kanasty et al. | |
| 2018/0369138 A1 | 12/2018 | Zalit et al. | |
| 2019/0070107 A1 | 3/2019 | Bellinger | |
| 2019/0070108 A1 | 3/2019 | Bellinger | |
| 2019/0125667 A1 | 5/2019 | Bellinger | |
| 2019/0133936 A1 | 5/2019 | Bellinger | |
| 2019/0175500 A1 | 6/2019 | Bellinger | |
| 2019/0231697 A1 | 8/2019 | Bellinger | |
| 2019/0254966 A1 | 8/2019 | Bellinger | |
| 2019/0262265 A1 | 8/2019 | Bellinger | |
| 2019/0365645 A1 | 12/2019 | Traverso et al. | |
| 2019/0365646 A1 | 12/2019 | Menachem et al. | |
| 2019/0366064 A1 | 12/2019 | Traverso et al. | |
| 2020/0030589 A1 | 1/2020 | Ben Menachem et al. | |
| 2020/0085736 A1 | 3/2020 | Bellinger et al. | |
| 2020/0085737 A1 | 3/2020 | Bellinger et al. | |
| 2020/0146979 A1 | 5/2020 | Kanasty | |
| 2020/0230244 A1 | 7/2020 | Traverso et al. | |
| 2020/0376242 A1 | 12/2020 | Ben Menachem et al. | |
| 2020/0405635 A1 | 12/2020 | Menachem et al. | |

FOREIGN PATENT DOCUMENTS

| | | |
|---|---|---|
| CN | 1049787 A | 3/1991 |
| CN | 1754898 A | 4/2006 |
| CN | 102245127 A | 11/2011 |
| CN | 103654903 A | 3/2014 |
| EP | 0202159 A2 | 11/1986 |
| EP | 0253554 A2 | 1/1988 |
| EP | 0253554 A3 | 7/1988 |
| EP | 0344939 A2 | 12/1989 |
| EP | 0388234 A1 | 9/1990 |
| EP | 0415671 A2 | 3/1991 |
| EP | 0202159 B1 | 7/1991 |
| EP | 0344939 B1 | 1/1993 |
| EP | 0820258 B1 | 10/2002 |
| EP | 1124534 61 | 1/2004 |
| EP | 1687379 A1 | 8/2006 |
| EP | 1911518 A1 | 4/2008 |
| EP | 2324822 A2 | 5/2011 |
| EP | 2329810 A1 | 6/2011 |
| EP | 1528916 61 | 12/2012 |
| JP | S58174312 A | 10/1983 |
| JP | 6226215 A | 2/1987 |
| JP | 6323815 A | 8/1987 |
| JP | 0229268 A | 11/1989 |
| JP | 03128934 A | 5/1991 |

(56) References Cited

FOREIGN PATENT DOCUMENTS

| | | |
|---|---|---|
| JP | 03163011 A | 7/1991 |
| JP | 2006518392 A | 8/2006 |
| JP | 2013500293 A | 1/2013 |
| JP | 2013530193 A | 7/2013 |
| JP | 2004325508 A | 11/2018 |
| RU | 2070029 C1 | 12/1996 |
| RU | 2242219 C2 | 12/2004 |
| WO | 199738969 A1 | 10/1997 |
| WO | WO200025742 A1 | 5/2000 |
| WO | WO200137812 A2 | 5/2001 |
| WO | WO200137812 A3 | 2/2002 |
| WO | WO2003015745 A1 | 2/2003 |
| WO | WO2004010978 A1 | 2/2004 |
| WO | WO2004073690 A1 | 9/2004 |
| WO | WO2004112755 A1 | 12/2004 |
| WO | WO 2005065660 * | 7/2005 |
| WO | WO2006072948 A2 | 7/2006 |
| WO | WO2006084164 A2 | 8/2006 |
| WO | WO2006072948 A3 | 11/2006 |
| WO | WO2006084164 A3 | 11/2006 |
| WO | WO2007027812 A2 | 3/2007 |
| WO | WO2007048223 A2 | 5/2007 |
| WO | WO2007048223 A3 | 6/2007 |
| WO | WO2007083309 A2 | 7/2007 |
| WO | WO2007093999 A1 | 8/2007 |
| WO | WO2007083309 A3 | 9/2007 |
| WO | WO2008015162 A1 | 2/2008 |
| WO | 2008039698 A1 | 4/2008 |
| WO | WO2008140651 A2 | 11/2008 |
| WO | WO2008140651 A3 | 1/2009 |
| WO | WO2007027812 A3 | 4/2009 |
| WO | 2009132461 A1 | 11/2009 |
| WO | WO2009144558 A1 | 12/2009 |
| WO | 2010042879 A2 | 4/2010 |
| WO | WO2010035273 A2 | 4/2010 |
| WO | 2010042879 A3 | 6/2010 |
| WO | WO2010064100 A1 | 6/2010 |
| WO | WO2010064139 A2 | 6/2010 |
| WO | WO2010035273 A3 | 7/2010 |
| WO | 2010099466 A2 | 9/2010 |
| WO | WO2010064139 A3 | 9/2010 |
| WO | 2010099466 A3 | 1/2011 |
| WO | 2011012369 A2 | 2/2011 |
| WO | WO2011032087 A2 | 3/2011 |
| WO | WO2011032087 A3 | 6/2011 |
| WO | 2011012369 A3 | 9/2011 |
| WO | 2011139796 A2 | 11/2011 |
| WO | 2012003968 A1 | 1/2012 |
| WO | 2011139796 A3 | 3/2012 |
| WO | WO2012087658 A1 | 6/2012 |
| WO | 2013049188 A1 | 4/2013 |
| WO | WO2014014348 A1 | 1/2014 |
| WO | WO2015083171 A1 | 6/2015 |
| WO | 2015187746 A1 | 12/2015 |
| WO | 2015191922 A1 | 12/2015 |
| WO | WO-2015/191920 A1 | 12/2015 |
| WO | WO2015191925 A1 | 12/2015 |
| WO | WO2017100367 A1 | 6/2017 |
| WO | WO-2017/205844 A2 | 11/2017 |
| WO | WO-2018/064630 A1 | 4/2018 |
| WO | WO2018227147 A1 | 12/2018 |
| WO | WO2019060458 A1 | 3/2019 |
| WO | 2019111132 A1 | 6/2019 |
| WO | 2020102650 A2 | 5/2020 |
| WO | 2020102650 A3 | 8/2020 |

OTHER PUBLICATIONS

International Search Report and Written Opinion of the International Searching Authority dated Dec. 29, 2016 for International Application No. PCT/US2016/058309, filed on Oct. 21, 2016, twelve pages.

U.S. Appl. No. 15/782,021, filed Jun. 6, 2018 by Bellinger et al. (Copy not submitted herewith pursuant to the waiver of 37 C.F.R. § 1.98(a)(2)(iii) issued by the Office on Sep. 21, 2004.).

"Guidance for Industry: Size, Shape, and Other Physical Attributes of Generic Tables and Capsules," (2013). Retrieved from www:v.regulations.gov/#ldocumentDetail;D=FDA-2013-N-1434-0002, last visited Dec. 2013, 11 pages.

"Q3C—Tables and List Guidance for Industy," (2017). Retrieved from www.fda.gov/downloads/drugs/guidances/ucm073395.pdf, last visited Jun. 2017, 10 pages.

Agrawal, A. et al. (Jul. 2006). "Clinical Relevance of the Nutcracker Esophagus: Suggested Revision of Criteria for Diagnosis," J Clin Gastroenterol. 40(6):504-509.

Ajili, S.H. et al. (Jun. 2009, e-pub. Jan. 3, 2009). "Polyurethane/Polycaprolactane Blend With Shape Memory Effect as a Proposed Material for Cardiovascular Implants," Acta Biomaterialia 5(5): 1519-1530.

Alhnan, M.A. et al. (Aug. 2016; e-published on May 18, 2016). "Emergence of 3D Printed Dosage Forms: Opportunities and Challenges," Pharm. Res. 33(8):1817-1832.

Belknap, R. et al. (Jan. 7, 2013). "Feasibility of an Ingestible Sensor-Based System for Monitoring Adherence to Tuberculosis Therapy," Plos One 8(1):e53373, pp. 1-5.

Byrne, C. et al. (Mar. 2007; e-pub. Dec. 18, 2006). "The Ingestible Telemetric Body Core Temperature Sensor: A Review of Validity and Exercise Applications," Brit J Sport Med. 41(3):126-133.

Cargill, R. et al. (Aug. 1988). "Controlled Gastric Emptying. 1. Effects of Physical Properties on Gastric Residence Times of Nondisintegrating Geometric Shapes in Beagle Dogs," Pharm Res. 5(8):533-536.

Cargill, R. et al. (Jun. 1989). "Controlled Gastric Emptying. II. In Vitro Erosion and Gastric Residence Times of an Erodible Device in Beagle Dogs," Pharm Res. 6(6):506-509.

Choudhry, N.K. et al. (Dec. 1, 2011; e-pub. Nov. 14, 2011). "Full Coverage for Preventive Medications After Myocardial Infarction," N Engl J Med. 365:2088-2097.

Cirillo, G. et al. (Jan. 21, 2014). "Carbon Nanotubes Hybrid Hydrogels in Drug Delivery: A Perspective Review," BioMed Res Intl. 2014(Article ID 825017), 17 pages.

Dash, S. et al. (May-Jun. 2010). "Kinetic Modeling on Drug Release From Controlled Drug Delivery Systems," Acta Poloniae Pharmaceutica 67(3):217-223.

Davies, G.C. et al. (Mar. 1993). "Release Characteristics, Ovarian Activity and Menstrual Bleeding Pattern with a Single Contraceptive Implant Releasing 3-Ketodesogestrel," Contraception 47(3):251-261.

Edwards, D.A.W. (Nov. 1961). "Physiological Concepts of the Pylorus," Proceedings of the Royal Society of Medicine 54:930-933.

Ereqat, S. et al. (Sep. 2011). "MDR Tuberculosis and Non-Compliance With Therapy," Lancet Infect Dis. 11(9):662.

European Extended Search Report dated Jul. 5, 2019, for Application No. EP 16873798.9.0, filed on Apr. 26, 2018, 9 pages.

European Search Report dated May 27, 2019 for Application No. EP 16858392.0, filed on Apr. 26, 2018, 10 pages.

Extended European Search Report dated Dec. 20, 2017 for Application No. EP 15806017.8, filed on Apr. 26, 2018, 10 pages.

Extended European Search Report dated Nov. 20, 2019 for Application No. EP 17803732.1, 9 pages.

Fallon, S.C. et al. (Apr. 2013). "The Surgical Management of Rapunzel Syndrome: A Case Series and Literature Review," J Pediatr Surg. 48(4):830-834.

Farra, R. et al. (Feb. 22, 2012; e-pub Feb. 16, 2012.). "First-in-Human Testing of a Wirelessly Controlled Drug Delivery Microchip," Sci Transl Med. 4(122):122ra21, 12 pages.

Fix, J.A. et al. (1993). "Controlled Gastric Emptying. III. Gastric Residence Time of a Nondisintegrating Geometric Shape in Human Volunteers," Pharm. Res. 10(7):1087-1089.

Fuhrmann, G. et al. (Jul. 2013). "Sustained Gastrointestinal Activity of Dendronized Polymer-Enzyme Conjugates," Nat Chem. 5:582-589.

Genco, A. et al. (2005). "Bioenterics Intragastric Balloon: The Italian Experience With 2,515 Patients," Obes Surg. 15:1161-1164.

(56) References Cited

OTHER PUBLICATIONS

Gordi, T. et al. (May 2008). "Pharmacokinetics of Gabapentin After a Single Day and at Steady State Following the Administration of Gastric-Retentive-Extended-Release and Immediate-Release Tablets: A Randomized, Open-Label, Multiple-Dose, Three-Way Crossover, Exploratory Study in Healthy Subjects," Clin Ther. 30(5):909-916.
Haslauer, C.M. et al. (Jul. 2015; e-published on Sep. 17, 2014). "Translating Textiles to Tissue Engineering Creation and Evaluation of Microporous, Biocompatible, Degradable Scaffolds Using Industry Relevant Manufacturing Approaches and Human Adipose Derived Stem Cells," J. Biomed. Mater. Res. B Appl. Biomater. 103(5):1050-1058, 22 pages.
Hiemke, C. et al. (Sep. 2011; e-published on Sep. 27, 2011). "AGNP Consensus Guidelines for Therapeutic Drug Monitoring in Psychiatry: Update 2011," Pharmacopsychiatry 44(6):195-235.
Huang, W.M. et al. (July-Aug. 2010). "Shape Memory Materials," Materials Today 13(7-8):54-61.
Hwang, S.-J. et al. (1998). "Gastric Retentive Drug-Delivery Systems," Crit Rev Ther Drug Carrier Syst. 15(3):243-284.
International Preliminary Report on Patentability dated Dec. 10, 2019 for PCT Application No. PCT/US2018/036743 filed on Jun. 8, 2018, 16 pages.
International Preliminary Report on Patentability dated Apr. 11, 2019 for PCT Application No. PCT/US2017/054608 filed on Sep. 29, 2017, 16 pages.
International Preliminary Report on Patentability dated Dec. 6, 2018 for PCT Application No. PCT/US2017/034856, filed on May 26, 2017, 11 pages.
International Preliminary Report on Patentability dated Dec. 22, 2016 for PCT Application No. PCT/US2015/035423 filed on Jun. 11, 2015, 11 pages.
International Preliminary Report on Patentability dated Jun. 21, 2018 for PCT Application No. PCT/US2016/065453 filed on Dec. 7, 2016, 11 pages.
International Preliminary Report on Patentability dated May 3, 2018 for PCT Application No. PCT/US2016/058309 filed on Oct. 21, 2016, 6 pages.
International Search Report and Written Opinion dated Dec. 14, 2017 for PCT Application No. PCT/US2017/054608 filed on Sep. 29, 2017, 18 pages.
International Search Report and Written Opinion dated Feb. 28, 2017 for PCT Application No. PCT/US2016/065453 filed on Dec. 7, 2016, 14 pages.
International Search Report and Written Opinion dated Jul. 21, 2016 for PCT Application No. PCT/US2016/030020 filed on Apr. 29, 2016, 10 pages.
International Search Report and Written Opinion dated Nov. 13, 2017 for PCT Application No. PCT/US2017/034856, filed May 26, 2017, 15 pages.
International Search Report and Written Opinion dated Sep. 10, 2018 for PCT Application No. PCT/US2018/036743 filed on Jun. 8, 2018, 26 pages.
International Search Report and Written Opinion dated Sep. 15, 2015 for PCT Application No. PCT/US2015/035423 filed on Jun. 11, 2015, 13 pages.
Invitation to Pay Additional Fees and, Where Applicable, Protest Fee, mailed on Sep. 5, 2017, for PCT Application No. PCT/US2017/034856, filed on May 26, 2017, 3 pages.
Jantratid, E. et al. (Jul. 2008; e-pub. Apr. 11, 2008). "Dissolution Media Simulating Conditions in the Proximal Human Gastrointestinal Tract: An Update," Pharm. Res. 25(7):1663-1676.
Karim, Q.A. et al. (Sep. 3, 2010, e-pub. Jul. 19, 2010). "Effectiveness and Safety of Tenofovir Gel, an Antiretroviral Microbicide, for the Prevention of HIV Infection in Women," Science 329(5996):1168-1174, 19 pages.
Kethu, S.R. et al. (2012). "Endoluminal Bariatric Techniques," Gastrointestinal Endoscopy 76(1):1-7.
Khaled, S.A. et al. (Jan. 30, 2014). "Desktop 3D Printing of Controlled Release Pharmaceutical Bilayer Tablets," International Journal of Pharmaceutics 461 (1-2): 105-111.
Kim, B.K. et al. (1996). "Polyurethanes Having Shape Memory Effects," Polymer 37(26):5781-5793.
Kim, Y.J. et al. (Dec. 24, 2013). "Biologically Derived Melanin Electrodes in Aqueous Sodium-Ion Energy Storage Devices," P Natl Acad Sci USA. 110(52):20912-20917.
Lam, P.L. et al. (2014). "Advanced Progress of Microencapsulation Technologies: In Vivo and In Vitro Models for Studying Oral and Transdermal Drug Deliveries," J. Control Release 178:25-45.
Laulicht, B. et al. (Feb. 8, 2011). "Localization of Magnetic Pills," Proc Natl Acad Sci. 108(6):2252-2257.
Li, L.C. et al. (Oct. 16, 2002). "Polyanhydride Implant for Antibiotic Delivery—From the Bench to the Clinic," Adv Drug Deliv Rev. 54(7):963-986.
Lipton, S.A. (Jan. 2004). "Failures and Successes of NMDA Receptor Antagonists: Molecular Basis For the Use of Open-Channel Blockers Like Memantine in the Treatment of Acute and Chronic Neurologic Insults," NeuroRx: The Journal of the American Society for experimental Neuro Therapeutics 1(1):101-110.
Liu, Y. et al. (2009; e-pub. Aug. 29, 2008). "Review of Electro-Active Shape-Memory Polymer Composite," Compos Sci and Technol. 69(13):2064-2068.
López-Pousa, S. et al. (Sep. 2012). "Consumption of Pharmaceuticals in Primary Non-Alzheimer's Degenerative Dementias: A Cross-Sectional Study by the Registry of Dementias of Girona (ReDeGi)," Drugs Aging 29(9): 733-740.
Marrazzo, J.M. et al. (Feb. 5, 2015). "Tenofovir-Based Preexposure Prophylaxis for HIV Infection Among African Women," N Engl J Med. 372(6):509-518.
Meng, Q. et al. (2009). "A Review of Shape Memory Polymer Composites and Blends," Composites Part A: Applied Science and Manufacturing 40(11):1661-1672.
Mintchev, M.P. et al. (Feb. 2010; e-pub Dec. 11, 2009). "Pilot Study of Temporary Controllable Gastric Pseudobezoars for Dynamic Non-lnvasive Gastric Volume Reduction," Physiol Meas. 31(2):131-144.
Moes, A.J. (Jan. 1993). "Gastroretentive Dosage Forms," Crit Rev Ther Drug Carrier Syst. 10(2):143-195.
Mohr, R. et al. (Mar. 7, 2006; e-pub Feb. 28, 2006.). "Initiation of Shape-Memory Effect by Inductive Heating of Magnetic Nanoparticles in Thermoplastic Polymers," Proc Natl Acad Sci USA. 103(10):3540-3545.
Olson, A.J. et al. (Dec. 26, 2007; e-pub Dec. 18, 2007). "Chemical Mimicry of Viral Capsid Self-Assembly," Proc Natl Acad Sci USA 104(52):20731-20736.
Osterberg, L. et al. (Aug. 4, 2005). "Adherence to Medication," N Engl J Med. 353(5):487-497.
Phadke, A. et al. (Mar. 20, 2012; e-pub Mar. 5, 2012). "Rapid Self-Healing Hydrogels," Proc Natl Acad Sci USA 109(12):4383-4388.
Phillips, M.R. et al. (Jul. 1998). "Gastric Trichobezoar: Case Report and Literature Review," Mayo Clin Proc. 73(7):653-656.
Pittenger, C. (Jun. 2015; e-published on Jun. 11, 2015). "Glutamate Modulators in the Treatment of Obsessive-Compulsive Disorder," Psychiatr. Ann. 45(6):308-315.
Puso, M. A. et al. (Jan. 1, 2006). "A Stabilized Nodally Integrated Tetrahedral," International Journal for Numerical Methods in Engineering 67(6):841-867.
Rammes, G. et al. (Mar. 2008). "Pharmacodynamics of Memantine: An Update," Curr. Neuropharmacol. 6(1):55-78.
Richter, J.E. et al. (Jun. 1987). "Esophageal Manometry in 95 Healthy Adult Volunteers. Variability of Pressures With Age and Frequency of "Abnormal" Contractions," Dig Dis Sci. 32(6):583-592.
Salessiotis, N. (Sep. 1972). "Measurement of the Diameter of the Pylorus in Man: Part I. Experimental Project for Clinical Application," The Amer J of Surgery. 124:331-333.
Salunke, D.M. et al. (Sep. 12, 1986). "Self-Assembly of Purified Polyomavirus Capsid Protein VP1," Cell 46(6): 895-904.
Singer, S.J. et al. (Feb. 18, 1972). "The Fluid Mosaic Model of the Structure of Cell Membranes," Science 175(4023):720-731.

(56) References Cited

OTHER PUBLICATIONS

Singh, B.N. et al. (Feb. 3, 2000). "Floating Drug Delivery Systems: An Approach to Oral Controlled Drug Delivery Via Gastric Retention," J Control Release 63(3):235-259.
Szakács, R. et al. (2012). "The "Blue" Side of Glutamatergic Neurotransmission: NMDA Receptor Antagonists as Possible Novel Therapeutics for Major Depression," Neuropsychopharmacol. Hung. 14(1):29-40.
Tao, H. et al. (Feb. 21, 2012). "Silk-Based Conformal, Adhesive, Edible Food Sensors," Adv Mater. 24(8): 1067-1072.
Timmer, C.J. et al. (Sep. 2000). "Pharmacokinetics of Etonogestrel and Ethinylestradiol Released From a Combined Contraceptive Vaginal Ring," Clin Pharmacokinet. 39(3):233-242.
Traverso, G. et al. (Mar. 26, 2015). "Special Delivery for the Gut," Nature. 519:S19.
U.S. Appl. No. 16/379,727, filed Apr. 9, 2019. (Copy not submitted herewith pursuant to the waiver of 37 C.F.R. § 1.98(a)(2)(iii) issued by the Office on Sep. 21, 2004).
Uhrich, K.E. et al. (1999, e-pub. Oct. 26, 1999). "Polyermic Systems for Controlled Drug Relase," Chem. Rev. 99:3181-3198.
Ursan, I.D. et al. (Mar.-Apr. 2013). "Three-Dimensional Drug Printing: A Structured Review," J. Am. Pharm. Assoc. 53(2):136-144.
Whitesides, G.M. et al. (Mar. 29, 2002). "Self-Assembly at all Scales," Science 295(5564):2418-2421.
Wilber, A.W. et al. (Nov. 7, 2009). "Self-Assembly of Monodisperse Clusters: Dependence on Target Geometry," J Chem Phys. 131(17):175101, 14 pages.
Wilber, A.W. et al. (Nov. 7, 2009; e-pub. Nov. 2, 2009). "Monodisperse Self-Assembly in a Model With Protein-Like Interactions," J Chem Phys. 131(17):175102, 11 pages.
Won, Y.W. et al. (Dec. 2014). "Oligopeptide Complex for Targeted Non-Viral Gene Delivery to Adipocytes," Nat Mater. 13:1157-1164.
Yu, D.G. et al. (Sep. 2008). "Three-Dimensional Printing in Pharmaceutics: Promises and Problems," J. Pharm. Sci. 97(9):3666-3690.
Zhang, X. et al. (2013; e-pub Oct. 15, 2012). "Biodegradable Shape Memory Nanocomposites With Thermal and Magnetic Field Responsiveness," J Biomater Sci Polym Ed. 24(9):1057-1070.
Barbucci, R. et al. (1989). "Vinyl Polymers Containing Amido and Carboxyl Groups as Side Substituents, 2 a). Thermodynamic and Fourier-Transform Infrared Spectroscopic Studies for the Protonation of poly(N-Acryloylglycine) and the poly(N-N-acryoyl-6-aminocaproicacid)," Makromol. Chem. 190:2627-2638.
Cong, H.-P. et al. (2013, e-pub Jul. 23, 2013). "Stretchable and Self-Healing Graphene Oxide-Polymer Composite Hydrogels: A Dual-Network Design," Chem Mater. 25:3357-3362.
Dunn, D.L. et al. (2005). Wound Closure Manual Ethicon, Inc. A Johnson and Johnson company, 127 pages.
Evonik Industries AG, (Dec. 2012). Eudragit Technical Information Sheet, EUDRAGIT L 100 and EUDRAGIT S 100, Specification and Test Methods, 7 pages.
Extended European Search Report dated Feb. 23, 2018 for Application No. EP 15806483.2, filed Jun. 11, 2015, 8 pages.
Harrison, S.K. et al. (2006). "Comparison of Shear Modulus Test Methods," Virginia Tech. 8 pages.
International Preliminary Report on Patentability for PCT/US2015/035425 dated Dec. 15, 2016, filed Jun. 11, 2015, 6 pages.
International Preliminary Report on Patentability for PCT/US2015/035429 dated Dec. 15, 2016, filed Jun. 11, 2015, 8 pages.
International Search Report and Written Opinion for PCT/US2015/035425 dated Sep. 15, 2015, filed Jun. 11, 2015, 8 pages.
International Search Report and Written Opinion for PCT/US2015/035429 dated Sep. 15, 2015, filed Jun. 11, 2015, 9 pages.

Javed, I. et al. (2014). "Drug Release Optimization From Microparticles of Poly(ε-caprolactone) and Hydroxypropyl Methylcellulose Polymeric Blends: Formulation and Characterization," J. Drug Del. Sci. Tech. 24(6);607-612.
Kanis, L.A. et al. (2014). "Cellulose Acetate Butyrate/Poly(caprolactonetriol) Blends: Miscibility, Mechanical Properties, and in vivo Inflammatory Response," J. of Biomaterials Applications 29(5):654-661.
Kao, E.C. et al. (Jan. 1996). "Preparation of Glass Ionomer Cement Using N-acryloyl Substituted Amino Acid Monomers-Evaluationof Physical Properties," Dent Mater. 12:44-51.
Khanna, S.C. et al. (Sep. 1969). "Epoxy Resin Beads as a Pharmaceutical Dosage Form. I.: Method of Preparation," Journal of Pharmaceutical Sciences 58(9):1114-1117.
Miao, L. et al. (2015). "Exploring the Tumor Microenvironment With Nanoparticles," Cancer Treat Res. 166:193-226, 36 pages.
Neto-Ferreira, R. et al. (2013). "Pleiotropic Effects of Rosuvastatin on the Glucose Metabolism and the Subcutaneous and Visceral Adipose Tissue Behavior in C57Bl/6 Mice," Diabetology Metabol Synd. 5:32, 10 pages.
Ren, S. et al. (2009). "Noncovalently Connected Micelles Based on a β-cyclodextrin-Contaiing Polymer and Adamantane End-Capped Poly(ε-ecaprolactone) via Host-Guest Interactions," J Polym Sci. 47:4267-4278.
Singh, P. et al. (2015, e-pub, Dec. 18, 2014). "Synthesis and Characterization of Nano Micelles of poly(N-acrylamidohexanoic acid)-b-poly(N-vinylcaprolactam) Via RAFT Process: Solubilizing and Releasing of Hydrophobic Molecules," Polymer. 57:51-61.
Six-Pentagons (Dec. 23, 2017). "Six-Pentagons Polylink," retreived from http://makingmathvisible.com/polylinks/polylinks-3.html, lasted visited Dec. 23, 2017, 4 pages.
Zu, Y. et al. (2008, e-pub. Sep. 26, 2008). "Effect of Neutralization of poly(methacrylic acid-co-ethyl acrylate) on Drug Release from Enteric-Coated Pellets Upon Accelerated Storage," Drug Dev. Ind. Pharm. 33(4):457-473.
Murphy, CS, et al. (Oct. 2009). "Gastro-Retentive Drug Delivery Systems: Current Developments in Novel System Design and Evaluation," Curr. Drug Deliv. 6(5):451-460.
Welding Techniques for Thermoplastics (2021). retrieved from the Internet: URL:https://www.twi-global.com/technical-knowledge/job-knowledge/welding-techniques-forthermoplastics-055 (http://web.archive.org/web/20150416235739/http://www.twiglobal.com/technical-knowledge/job-knowledge/welding-techniques-for-thermoplastics-055/, last visited Mar. 17, 2021, 8 pages.
Yang X, et al. (May 14, 2014), e-pub. May 5, 2014). "Triple Shape Memory Effect of Star-Shaped Polyurethane," ACS Appl Mater Interfaces 6(9):6545-6554.
Abraham, N. (May 15, 2015). "Dow Corning QP1-2 Liquid Silicone Rubber Supports Cost-Effective Medical Device Designs," Medical Design & Outsourcing, retrieved from the Internet https://www.medicaldesignandoutscourcing.com/dow-coming-qp1-2-liquid-silicone-rubber-supports-cost-effective-medical-device-designs/, last visited Nov. 16, 2021, 8 pages.
Extended European Search Report dated Jun. 4, 2021 for Application No. EP 18813515.6, 8 pages.
Nakamichi, K. (2004). "The Preparation of Enteric Solid Dispersions With Hydroxypropylmethylcellulose Acetate Succinate Using a Twin-Screw Extruder," J. Drug Del. Sci. Tech. 3(14):193-198.
Woodruff, M.A. et al. (Apr. 2010, e-pub. Apr. 7, 2010). "The Return of a Forgotten Polymer—Polycaprolactone in the 21st Century," Progress in Polymer Science 35:1217-1256.
Chourasia, M.K. et al. (2003). "Pharmaceutical Approaches to Colon Targeted Drug Delivery Systems," J. Pharm. Pharmaceut Sci. 6(1):33-66.

\* cited by examiner

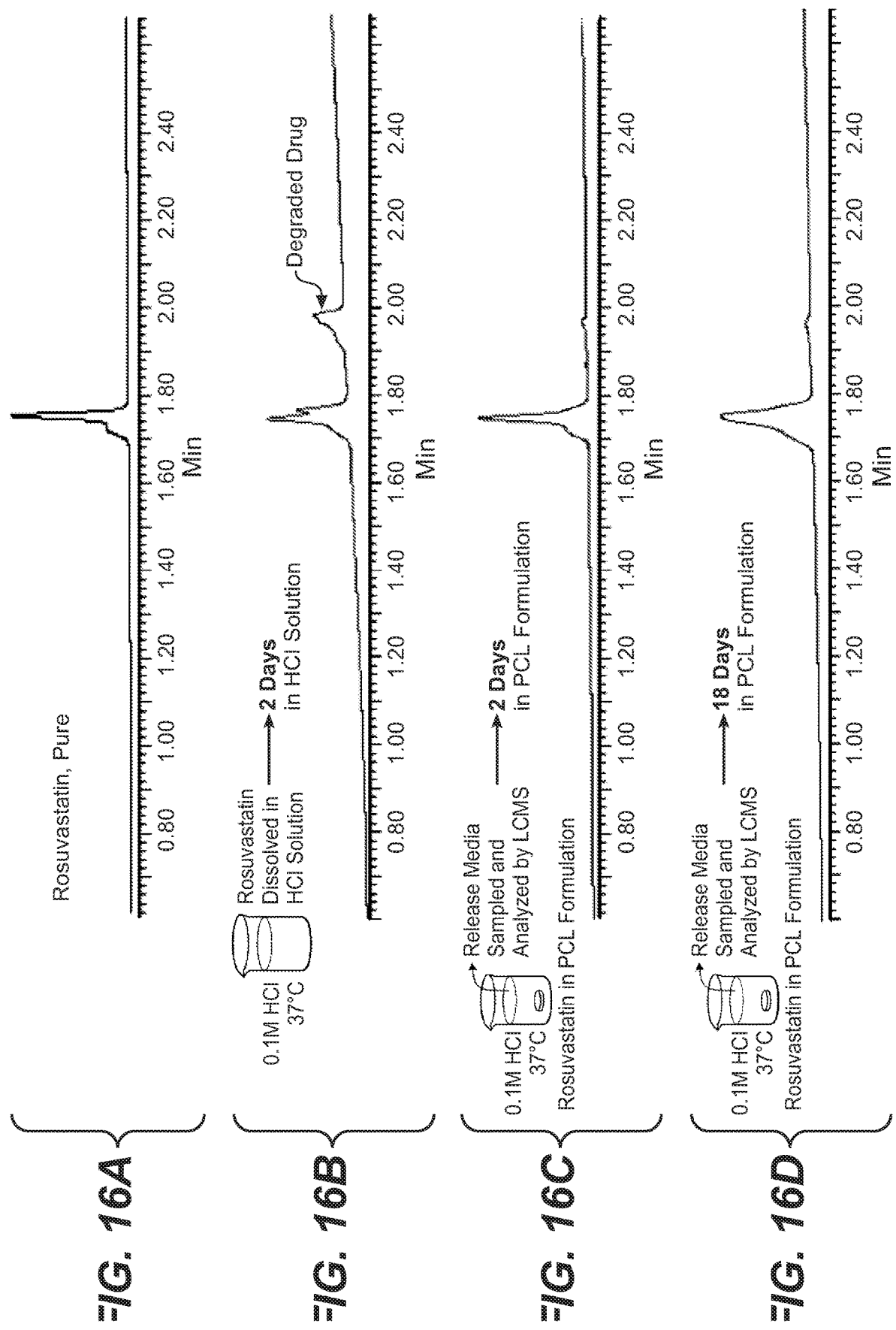

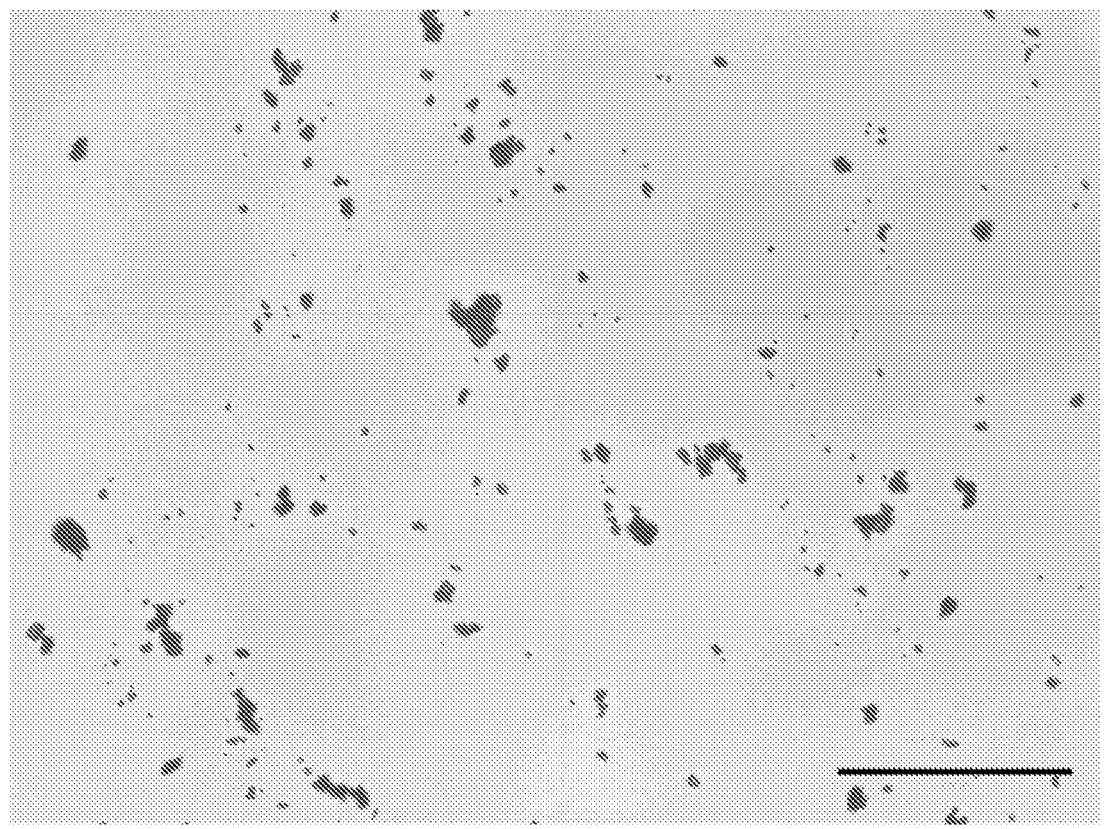
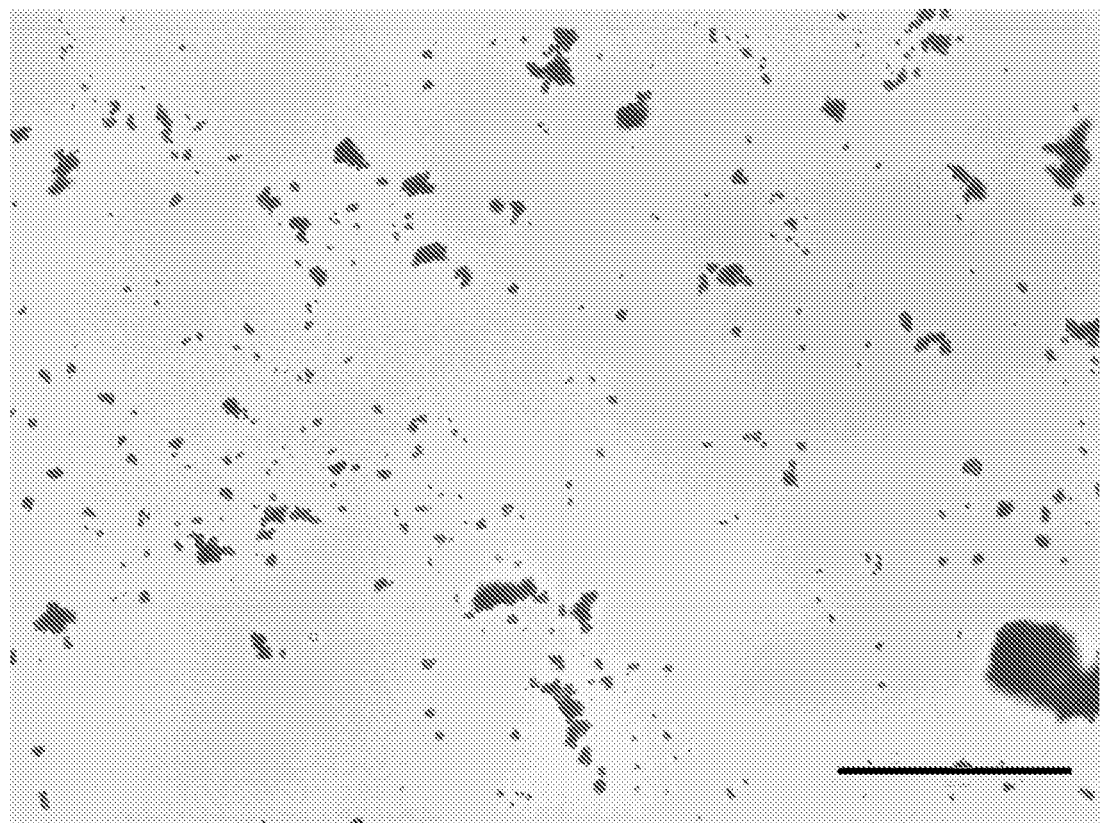
FIG. 17A
FIG. 17B

GASTRIC RESIDENCE SYSTEMS FOR SUSTAINED RELEASE OF THERAPEUTIC AGENTS AND METHODS OF USE THEREOF

CROSS-REFERENCE TO RELATED APPLICATIONS

This application is a National Phase application under 35 U.S.C. 371 of International Application No. PCT/US2016/058309 filed Oct. 21, 2016 and claims priority benefit of U.S. Provisional Patent Application No. 62/245,789, filed Oct. 23, 2015; of U.S. Provisional Patent Application No. 62/245,797, filed Oct. 23, 2015; of U.S. Provisional Patent Application No. 62/264,795, filed Dec. 8, 2015; of U.S. Provisional Patent Application No. 62/264,799, filed Dec. 8, 2015; of U.S. Provisional Patent Application No. 62/264,806, filed Dec. 8, 2015; and of U.S. Provisional Patent Application No. 62/402,947, filed Sep. 30, 2016. The entire contents of each of those patent applications are hereby incorporated by reference herein.

FIELD OF THE INVENTION

The invention relates to gastric residence systems for sustained gastric release of therapeutic agents and methods of use thereof.

BACKGROUND OF THE INVENTION

Gastric residence systems are delivery systems for therapeutic agents which remain in the stomach for days to weeks, or even over longer periods, during which time drugs or other agents can elute from the systems for absorption in the gastrointestinal tract. Examples of such systems are described in International Patent Application No. PCT/US2015/035423 (WO 2015/191920). Gastric residence systems are most conveniently administered to a patient via a capsule in a compacted form. Upon dissolution of the capsule in the stomach, the systems expand to a size which resists passage through the pyloric sphincter over the desired residence period. The need for the system to release a therapeutic agent at a steady rate over an extended time period in the gastric environment places a particularly stringent demand on the formulation of the system.

The current invention describes advancements in formulation of gastric residence systems, including the use of dispersants in the components which elute therapeutic agent during gastric residence, and milling of the agent to desired sizes. The systems described herein provide improved performance of the systems when administered to a patient.

SUMMARY OF THE INVENTION

In some embodiments, the invention provides gastric residence systems for administration to a patient, comprising a plurality of carrier polymer-agent components comprising i) a carrier polymer, and ii) a therapeutic agent or a pharmaceutically-acceptable salt thereof, wherein the carrier polymer-agent components are linked together by one or more coupling polymer components, wherein at least one of the one or more coupling polymer components is an elastomer; wherein the gastric residence systems are configured to have a compacted form in a container, suitable for administration orally or through a feeding tube; and an uncompacted form when released from the container; wherein the gastric residence systems are retained in the stomach for a residence period of between at least about 24 hours and about one month; and wherein the systems release a therapeutically effective amount of the therapeutic agent over an effective release period; and the systems release less than about 20% of the therapeutic agent or pharmaceutically-acceptable salt thereof within about a six-hour period. In some embodiments, the effective release period is less than or equal to the residence period. In some embodiments, the effective release period is less than or equal to the (residence period plus about 24 hours). In some embodiments, the effective release period is less than or equal to the (residence period plus about 48 hours). In some embodiments, the effective release period is less than or equal to the (residence period plus about 72 hours). In some embodiments, the effective release period is about 3 days. In some embodiments, the effective release period is about 7 days. In some embodiments, the effective release period is about 10 days. In some embodiments, the effective release period is about 14 days. In some embodiments, the effective release period is about 20 days. In some embodiments, the effective release period is about 21 days. In some embodiments, the effective release period is about 28 days. In some embodiments, the effective release period is about 30 days. In some embodiments, the effective release period is about one month. In some embodiments, the effective release period can be about 3 days to about one month, about 3 days to about four weeks, about 3 days to about two weeks, about 3 days to about 14 days, about 3 days to about 7 days, or about 3 days to about 5 days. In some embodiments, the effective release period can be about 7 days to about one month, about 7 days to about four weeks, about 7 days to about two weeks, about 7 days to about 14 days, or about 7 days to about 10 days. In any of these embodiments, the residence period can be about 24 hours to about two weeks, about 24 hours to about one week, about 24 hours to 3 days, about 1 day, about 2 days, about 3 days, about 4 days, about 5 days, about 6 days, about 7 days, about 8 days, about 9 days, about 10 days, about two weeks, about three weeks, about four weeks, or about a month. In any of these embodiments, the residence period can be about 24 hours to about two weeks, about 24 hours to about one week, about 24 hours to 3 days, about 1 day, about 2 days, about 3 days, about 4 days, about 5 days, about 6 days, about 7 days, about 8 days, about 9 days, or about 10 days longer than the effective release period.

In some embodiments, the systems release about 30% to about 70% of the therapeutic agent or pharmaceutically-acceptable salt thereof within a time of about 40% to 60% of the effective release period.

In some embodiments, the systems release greater than about 70% of the therapeutic agent or pharmaceutically-acceptable salt thereof within a time of about 90% of the effective release period.

The release of the therapeutic agent or pharmaceutically-acceptable salt thereof can measured in an aqueous environment selected from the group consisting of: 0.1N HCl in water, simulated gastric fluid, fasted-state simulated gastric fluid, fed-state simulated gastric fluid, the stomach of an animal, the stomach of a pig, the stomach of a dog, and the stomach of a human. The release of the therapeutic agent or pharmaceutically-acceptable salt thereof can measured in 0.1 N HCl in water. The release of the therapeutic agent or pharmaceutically-acceptable salt thereof can measured in fasted-state simulated gastric fluid. The release of the therapeutic agent or pharmaceutically-acceptable salt thereof can be measured in fed-state simulated gastric fluid.

In some embodiments of the gastric residence systems, the release of the therapeutic agent or pharmaceutically-acceptable salt thereof increases by no more than about 40% in 40% ethanol/60% 0.1N HCl in water versus the release over the same period of time in 0.1N HCl, or by no more than about 40% in 40% ethanol/60% simulated gastric fluid versus the release over the same period of time in simulated gastric fluid, or by no more than about 40% in 40% ethanol/60% fasted-state simulated gastric fluid versus the release over the same period of time in fasted-state simulated gastric fluid, or by no more than about 40% in 40% ethanol/60% fed-state simulated gastric fluid versus the release over the same period of time in fed-state simulated gastric fluid. The period of time can be about 15 minutes, about 30 minutes, about 45 minutes, about 60 minutes, about 90 minutes, or about 120 minutes.

In some embodiments of the gastric residence systems, the gastric residence systems release no more than about 20% of the therapeutic agent in 40% ethanol/60% 0.1N HCl in water after a period of time which can be about 15 minutes, about 30 minutes, about 45 minutes, about 60 minutes, about 90 minutes, or about 120 minutes. In some embodiments of the gastric residence systems, the gastric residence systems release no more than about 20% of the therapeutic agent in 40% ethanol/60% 0.1N HCl in water after about 120 minutes.

In some embodiments of the gastric residence systems, ii) the therapeutic agent or a pharmaceutically-acceptable salt thereof comprises about 10% to about 35% of the carrier polymer-agent components. The therapeutic agent or a pharmaceutically-acceptable salt thereof can be selected from the group consisting of doxycycline, donepezil, ivermectin, risperidone, cetirizine, and rosuvastatin, and pharmaceutically-acceptable salts thereof. In some embodiments, the therapeutic agent or a pharmaceutically-acceptable salt thereof is doxycycline or a pharmaceutically-acceptable salt thereof. In some embodiments, the therapeutic agent or a pharmaceutically-acceptable salt thereof is donepezil or a pharmaceutically-acceptable salt thereof. In some embodiments, the therapeutic agent or a pharmaceutically-acceptable salt thereof is ivermectin or a pharmaceutically-acceptable salt thereof. In some embodiments, the therapeutic agent or a pharmaceutically-acceptable salt thereof is risperidone or a pharmaceutically-acceptable salt thereof. In some embodiments, the therapeutic agent or a pharmaceutically-acceptable salt thereof is cetirizine or a pharmaceutically-acceptable salt thereof. In some embodiments, the therapeutic agent or a pharmaceutically-acceptable salt thereof is rosuvastatin or a pharmaceutically-acceptable salt thereof. In some embodiments of the gastric residence systems, the therapeutic agent can include adamantane-class drugs, such as memantine; amantadine; adapromine; nitromemantine; rimantadine; bromantane; neramexane; or tromantadine; or a pharmaceutically acceptable salt of memantine, amantadine, adapromine, nitromemantine, rimantadine, bromantane, or tromantadine. In some embodiments of the gastric residence systems, the therapeutic agent can include memantine. In some embodiments of the gastric residence systems, the therapeutic agent can include a pharmaceutically acceptable salt of memantine. In some embodiments of the gastric residence systems, the therapeutic agent can exclude adamantane-class drugs. In some embodiments of the gastric residence systems, the therapeutic agent can exclude any one or more of memantine; amantadine; adapromine; nitromemantine; rimantadine; bromantane; neramexane; or tromantadine; or a pharmaceutically acceptable salt of memantine, amantadine, adapromine, nitromemantine, rimantadine, bromantane, or tromantadine. In some embodiments of the gastric residence systems, the therapeutic agent can exclude memantine. In some embodiments of the gastric residence systems, the therapeutic agent can exclude a salt of memantine or a pharmaceutically acceptable salt of memantine.

In some embodiments of the gastric residence systems, the carrier polymer-agent components further comprise iii) a release enhancer. The release enhancer comprises about 2% to about 30% of the carrier polymer-agent components. For hydrophobic drugs, such as drugs with solubility less than 1 mg/ml, or less than or equal to 1 mg/ml, the release enhancer comprises about 2% to about 50% of the carrier polymer-agent components. The release enhancer can be selected from the group consisting of an acrylate polymer, an acrylate co-polymer, a polydioxanone-polyethylene glycol polymer, and polyvinylpyrrolidone. The acrylate polymer or acrylate co-polymer can comprise a co-polymer of ethyl acrylate, methyl methacrylate and trimethylammonioethyl methacrylate, optionally in a molar ratio of about 1:2:0.1, about 1:2:0.2, or between about 1:2:0.1 to about 1:2:0.2; or the acrylate polymer or acrylate co-polymer can comprise a co-polymer of dimethylaminoethyl methacrylate, butyl methacrylate, and methyl methacrylate, optionally in a molar ratio of from about 2:1:1 to about 1:1:1.

In some embodiments of the gastric residence systems, the carrier polymer-agent components further comprise iv) a dispersant. The dispersant can comprise about 0.1% to about 4% of the carrier polymer-agent components. The dispersant can be selected from the group consisting of a porous inorganic material, a polar inorganic material, a non-toxic metal oxide, an amphiphilic organic molecule, a polysaccharide, cellulose, a cellulose derivative, a fatty acid, a detergent, silica, hydrophilic-fumed silica, hydrophobic colloidal silica, magnesium aluminum silicate, a stearate salt, calcium stearate, magnesium stearate, microcrystalline cellulose, carboxymethylcellulose, hypromellose, a phospholipid, a polyoxyethylene stearate, zinc acetate, alginic acid, lecithin, sodium lauryl sulfate, and aluminum oxide. The dispersant can comprise silica, such as hydrophilic-fumed silica.

In some embodiments of the gastric residence systems, the carrier polymer-agent components further comprise v) a solubilizer. The solubilizer can comprise about 1% to about 10% of the carrier polymer-agent components. The solubilizer can be selected from the group consisting of a polyalkylene oxide, a polyethoxylated castor oil, and a detergent. When the solubilizer is a polyalkylene oxide, it can be selected from the group consisting of polyethylene glycol (PEG), polypropylene glycol (PPG), and a block copolymer of PEG and PPG. When the solubilizer is a block copolymer of PEG and PPG, it can be of the formula H—$(OCH_2CH_2)_x$—(O—$CH(CH_3)CH_2)_y$—$(OCH_2CH_2)_z$—OH, where x and z are independently about 95 to about 105 and y is about 50 to about 60, such as where x and z are about 101 and y is about 56.

In some embodiments of the gastric residence systems, the carrier polymer-agent components further comprise vi) a stabilizer. The stabilizer can comprise about 0.1% to about 2% of the carrier polymer-agent components. The stabilizer can comprise one or more compounds selected from the group consisting of an anti-oxidant, a tocopherol, alpha-tocopherol, ascorbic acid, an ascorbate salt, a carotene, butylated hydroxyanisole, butylated hydroxytoluene, fumaric acid, an anti-microbial, a buffering substance, calcium carbonate, calcium lactate, calcium phosphate, sodium phosphate, and sodium bicarbonate.

In some embodiments of the gastric residence systems, the carrier polymer comprises a polylactone.

In some embodiments, the polylactone comprises polycaprolactone, such as polycaprolactone having an average $M_n$ of about 60,000 to 100,000; polycaprolactone having an average $M_n$ of about 75,000 to 85,000; or polycaprolactone having an average $M_n$ of about 80,000.

In some embodiments of the gastric residence systems, if a solubilizer is present, the solubilizer comprises no more than about 5% of the carrier polymer-agent components; and if one or more of a solubilizer, release enhancer, dispersant, or stabilizer is present, the total combined amount of any solubilizer, release enhancer, dispersant, and stabilizer present comprises no more than about 30% of the carrier polymer-agent components.

In one embodiment, the invention encompasses a gastric residence system for administration to a patient, which comprises plurality of carrier polymer-agent components, wherein the carrier polymer-agent components comprise i) a carrier polymer, ii) a dispersant, and iii) a therapeutic agent or a salt thereof, wherein the plurality of carrier polymer-agent components are linked together by one or more coupling polymer components, wherein at least one of the one or more coupling polymer components is an elastomer; wherein the gastric residence system is configured to have a compacted form in a container, suitable for administration orally or through a feeding tube; and to have an uncompacted form when released from the container in the stomach of the patient; wherein the gastric residence system is retained in the stomach for at least about 24 hours; and wherein the system releases a therapeutically effective amount of the therapeutic agent over at least a portion of the period in which the system is retained in the stomach.

The dispersant can comprise a compound selected from the group consisting of a porous inorganic material, a polar inorganic material, silica, hydrophilic-fumed silica, stearate salts, calcium stearate, magnesium stearate, microcrystalline cellulose, carboxymethylcellulose, hydrophobic colloidal silica, hypromellose, magnesium aluminum silicate, phospholipids, polyoxyethylene stearates, zinc acetate, alginic acid, lecithin, fatty acids, sodium lauryl sulfate, non-toxic metal oxides, and aluminum oxide. The dispersant can comprise silica, or hydrophilic fumed silica, such as CAB-O-SIL® M-5P (CAS #112945-52-5).

In the gastric residence system, the therapeutic agent or salt thereof can be comprised of particles dispersed throughout the carrier polymer. In one embodiment, at least about 80% of the mass of the therapeutic agent particles are between about 2 microns and about 50 microns in diameter.

In one embodiment, the therapeutic agent or a salt thereof in the gastric residence system can be a hydrophilic therapeutic agent or a salt thereof. In one embodiment, the hydrophilic therapeutic agent or salt thereof can have a log $P_{oct}$ less than or equal to about 0.5. In one embodiment, the hydrophilic therapeutic agent or salt thereof can have a solubility in water of at least about 1 mg/ml. In another embodiment, less than about 10% of the hydrophilic therapeutic agent or salt thereof contained in the system elutes within about the first six hours of exposure to gastric fluid. In another embodiment, the amount of hydrophilic therapeutic agent or salt thereof eluted from the system within about the first six hours of exposure to gastric fluid is about 50% or less than the amount of therapeutic agent or salt thereof eluted from the system without the dispersant.

In a further embodiment, when the gastric residence system comprises a hydrophilic therapeutic agent or a salt thereof, the carrier polymer-agent component comprises between about 1% to about 30% hydrophilic therapeutic agent or salt thereof, about 0.5% to about 2.5% of dispersant, and about 67.5% to about 98.5% carrier polymer.

In one embodiment, the therapeutic agent or a salt thereof in the gastric residence system can be a hydrophobic therapeutic agent or a salt thereof. In one embodiment, the hydrophobic therapeutic agent or salt thereof has a log $P_{oct}$ greater than or equal to about 1. In one embodiment, the hydrophobic therapeutic agent or salt thereof can have a solubility in water of less than about 1 mg/ml. In one embodiment, the hydrophobic therapeutic agent or salt thereof has a higher solubility in ethanol than in water. In one embodiment, the hydrophobic therapeutic agent or salt thereof has a higher solubility in 40% ethanol/60% simulated gastric fluid than in 100% simulated gastric fluid.

In a further embodiment, when the gastric residence system comprises a hydrophobic therapeutic agent or a salt thereof, the carrier polymer-agent component comprises between about 1% to about 30% hydrophobic therapeutic agent or salt thereof, about 0.5% to about 2.5% of dispersant, and about 67.5% to about 98.5% carrier polymer.

In any of the embodiments of the gastric residence system, the carrier polymer used in the gastric residence system can comprise polycaprolactone, such as linear polycaprolactone with a number-average molecular weight ($M_n$) range between about 60 kiloDalton (kDa) to about 100 kDa; 75 kDa to 85 kDa; or about 80 kDa; or between about 45 kDa to about 55 kDa.

In any of the embodiments of the gastric residence system, the plurality of carrier polymer-agent components can be linked together by two or more coupling polymer components, wherein at least one of the two or more coupling polymer components is an elastomer and at least another one of the two or more coupling polymer components is an enteric polymer. In further embodiments, the enteric polymer can be selected from the group consisting of poly(methacrylic acid-co-ethyl acrylate), cellulose acetate phthalate, cellulose acetate succinate, and hydroxypropyl methylcellulose phthalate.

In another embodiment, the gastric residence system is retained in the stomach for about 5 days to about 7 days.

The features of any of the embodiments recited above and herein are combinable with any of the other embodiments recited above and herein where appropriate and practical.

BRIEF DESCRIPTION OF THE DRAWINGS

FIG. 16 shows UPLC analyses of rosuvastatin under various conditions. Trace A shows a UPLC analysis of pure rosuvastatin. Trace B shows a UPLC analysis of rosuvastatin after 2 days in 0.1M HCl solution at 37° C. Trace C shows a UPLC analysis of rosuvastatin released from a polycaprolactone formulation after 2 days in 0.1M HCl solution at 37° C. Trace D shows a UPLC analysis of rosuvastatin released from a polycaprolactone formulation after 18 days in 0.1M HCl solution at 37° C.

FIG. 17A shows a bright-field microscopy image of the surface of a polycaprolactone bead that has rolled in rosuvastatin calcium powder. The scale bar in the image is 100 microns.

FIG. 17B shows a bright-field microscopy image of rosuvastatin calcium powder at the edge of a polycaprolactone bead. The scale bar in the image is 100 microns.

DETAILED DESCRIPTION OF THE INVENTION

Figure 1:
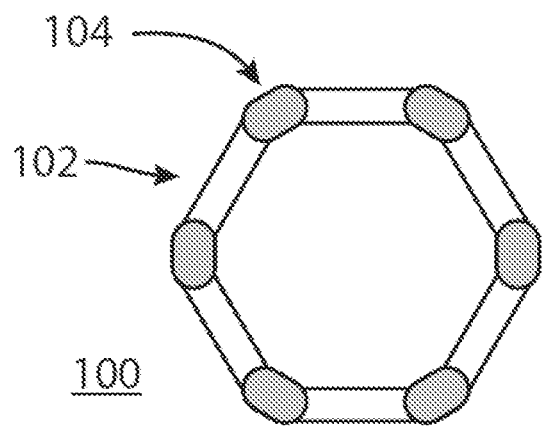
FIG. 1 shows one embodiment of a gastric residence system of the invention.

Advantages of Dispersant in Gastric Residence Systems

Obtaining stable, continuous release of therapeutic agent from a gastric residence device can be challenging. For hydrophilic therapeutic agents in particular, limiting an initial burst phase is important. Hydrophilic agents have the potential to elute rapidly from a gastric residence system in the aqueous gastric environment. The burst of agent is absorbed by the patient, resulting in a sudden rise in blood plasma levels. Burst release can result in an undesired initial peak level of therapeutic agent, and may also result in insufficient agent delivery during the remaining residence time of the system. After the initial period after administration (that is, after the period during which burst release occurs), a stable release rate of therapeutic agent is desirable for predictable dosing and maintenance of an appropriate plasma level of agent. Conversely, for hydrophobic therapeutic agents, obtaining significant release of the agent from the gastric residence system in the aqueous environment of the stomach can pose challenges.

In some embodiments of the invention as described herein, the inclusion of a dispersant in the gastric residence system limits the sudden initial burst release of hydrophilic therapeutic agents after the system is administered. The combination of the dispersant, a hydrophilic therapeutic agent, and a carrier polymer provides more stable initial agent release compared to the combination of the hydrophilic agent and the carrier polymer without the dispersant. The dispersant can ensure better mixing of hydrophilic therapeutic agent into the carrier polymer, preventing exposure of excessive amounts of agent on the surface of the carrier polymer-agent mixture. The dispersants can also prevent large agglomerations of hydrophilic agent "pockets" from forming in the carrier polymer, thus preventing sudden "dumps" of agent.

Inclusion of a dispersant can also aid in administration of hydrophobic therapeutic agents in the gastric residence systems. Small, evenly dispersed particles of hydrophobic agent offer more surface area for contact with water diffusing through the carrier polymer, as compared to larger particles of hydrophobic agent substance.

In some embodiments of the invention as described herein, the inclusion of a release enhancer in the gastric residence system assists in the release of hydrophobic therapeutic agents after the system is administered. Release enhancers include, but are not limited to, porogens and wicking agents. Porogens are materials that dissolve on contact with solution, opening up pores and channels in the carrier polymer matrix in which they are dispersed, and allowing more thorough penetration of water into the matrix. Wicking agents are materials that draw water into the polymer matrix. In both cases, the release enhancer serves to increase the effective surface area of the therapeutic agent in the matrix that is exposed to water, which increases the rate at which the agent is eluted (released) from the carrier polymer. Release enhancers are useful in gastric residence systems comprising hydrophilic therapeutic agents as well. Among other useful properties, release enhancers can promote a higher percentage of delivery of therapeutic agent over the residence period, so that excess agent need not be included in the gastric residence system to provide a therapeutically effective amount to the patient.

Milling of the therapeutic agent to obtain a desired particle size or particle size range, prior to incorporation of the agent into the gastric residence systems, can also contribute to enhanced performance of the systems.

The invention provides various embodiments of gastric residence systems for sustained release of therapeutic agents, including both hydrophilic and hydrophobic therapeutic agents. Several parameters of the systems, such as inclusion of and concentration of release enhancers, inclusion of and concentration of dispersants, inclusion of and concentration of solubilizers, milling of the therapeutic agent to be used in the system, the geometrical configuration of the system, and the chemical and physical properties of the system, can be varied in order to adjust the length of time for which the gastric residence systems remain in the stomach, the effective release period during which a therapeutically effective amount of therapeutic agent is released, and to adjust the release rate of the therapeutic agent.

Advantages of Sustained Therapeutic Agent Release

The invention provides gastric residence systems for release of therapeutic agents over extended periods. Gradual release over a period of time at a zero-order or pseudo-zero-order release rate can provide for substantially constant plasma levels of the therapeutic agent at steady state. In turn, substantially constant plasma levels of the therapeutic agent can provide advantages over the peak-trough plasma levels seen with periodic dosing, such as minimizing side effects while maximizing therapeutic efficacy.

In a study of continuous versus on-demand treatment with an exemplary agent, the hydrophilic compound cetirizine, Ciprandi et al., Ann. Allergy Asthma Immunol. 79(6):507-511 (1997) suggest that consistent levels of cetirizine are advantageous over intermittent administration of cetirizine in reducing the inflammatory response, as measure by skin wheals. Mechanistically, this may be due to the effect of cetirizine on immune cell margination into mucosal tissues. Shimizu et al. Clin. Exp. Allergy 34, 103-109 (2004) found that cetirizine suppresses the expression of macrophage migration inhibitory factor in mice. These immunomodulatory actions of cetirizine may be particularly dependent on sustained drug levels which can be provided by the current invention, thus demonstrating the advantages of embodiments of the invention which deliver cetirizine.

General Principles of Operation

The gastric residence systems of the invention are designed to be administered to the stomach of a patient, either by swallowing or other method of administration (for example, feeding tube or gastric tube). Once a gastric residence system is in place in the stomach, the system remains in the stomach for the desired residence time (such as three days, seven days, two weeks, etc.), which thus entails resistance to passage through the pyloric valve separating the stomach and the small intestine. It releases therapeutic agent over the period of residence, or over at least a portion of the period of residence (the "effective release period"), with minimal burst release. While resident in the stomach, the system does not interfere with the normal passage of food or other gastric contents. The system passes out of the stomach at the end of the desired residence time (that is, at the end of the residence period), and is readily eliminated from the patient. If the system prematurely passes from the stomach into the small intestine, it does not cause intestinal obstruction, and again is readily eliminated from the patient.

Administration

The gastric residence system is contained in a capsule or other container which can be swallowed by the patient, or which is otherwise able to be administered to the stomach for patients unable to swallow (e.g., via gastrostomy tube, feeding tube, gastric tube, or other route of administration to the stomach). Accordingly, the gastric residence system is capable of being compacted or compressed into a form small enough to be swallowed or otherwise administered, and is preferably placed inside a container such as a capsule. Thus, the system is configured to have a compacted form in a container (by folding, compression, or other method of reducing the size of the system).

Figure 2:
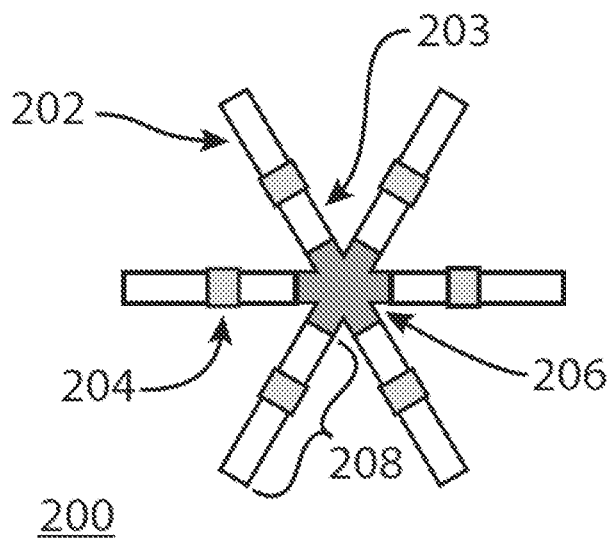
FIG. 2 shows another embodiment of a gastric residence system of the invention.
Figure 2A:
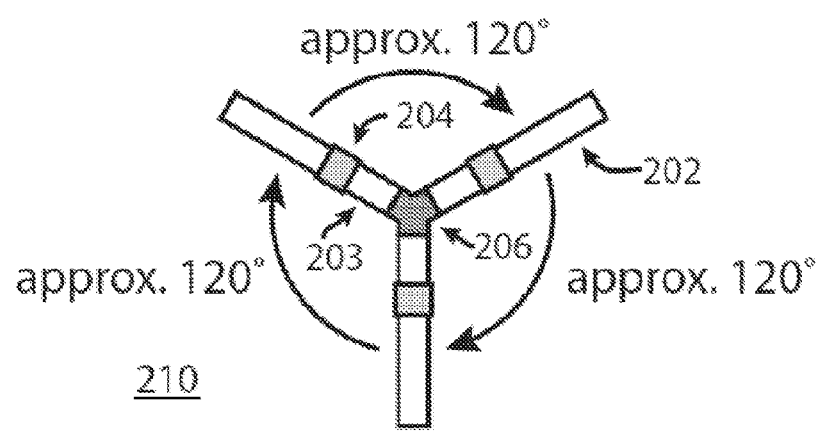
FIG. 2A shows another embodiment of a gastric residence system of the invention.
Figure 3:
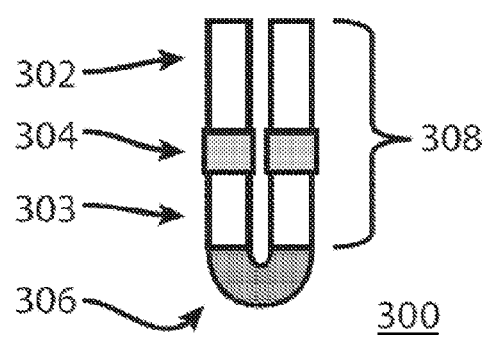
FIG. 3 shows the embodiment of a gastric residence system of FIG. 2 in a folded configuration. The capsule holding the system in the folded configuration is not shown.
Figure 4A:
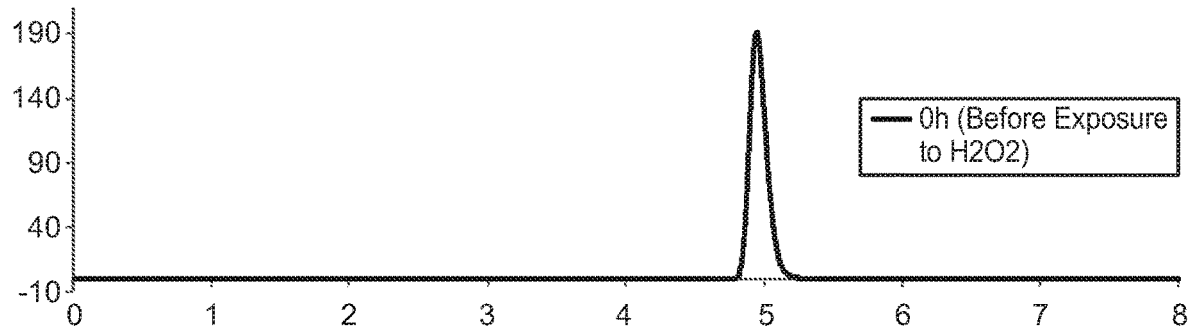
FIG. 4 shows protection of cetirizine against oxidative degradation in carrier polymer formulations. Trace A shows an HPLC analysis of cetirizine extracted from polycaprolactone/Pluronic 407 carrier polymer formulation before exposure to oxidizing conditions. Trace B shows an HPLC analysis of cetirizine in solution exposed to oxidizing conditions. Traces C, D, and E show HPLC analysis of cetirizine in a polycaprolactone/Pluronic 407 carrier polymer formulation after exposure to oxidizing conditions for varying lengths of time.
Figure 4B:
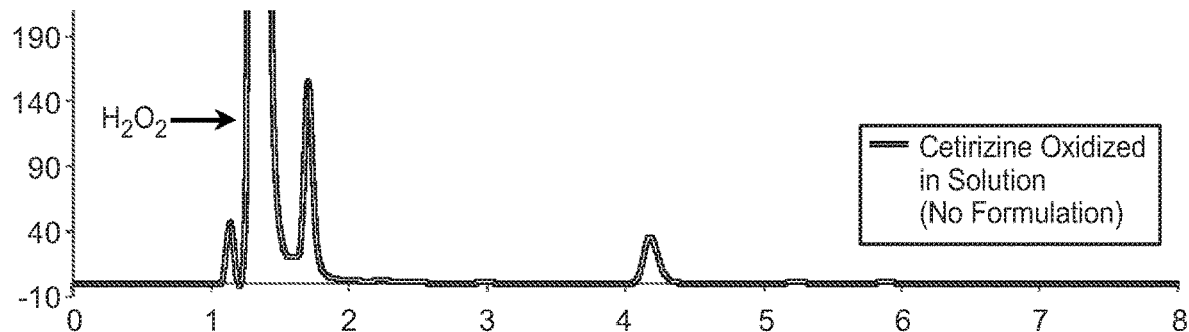
Figure 4C:
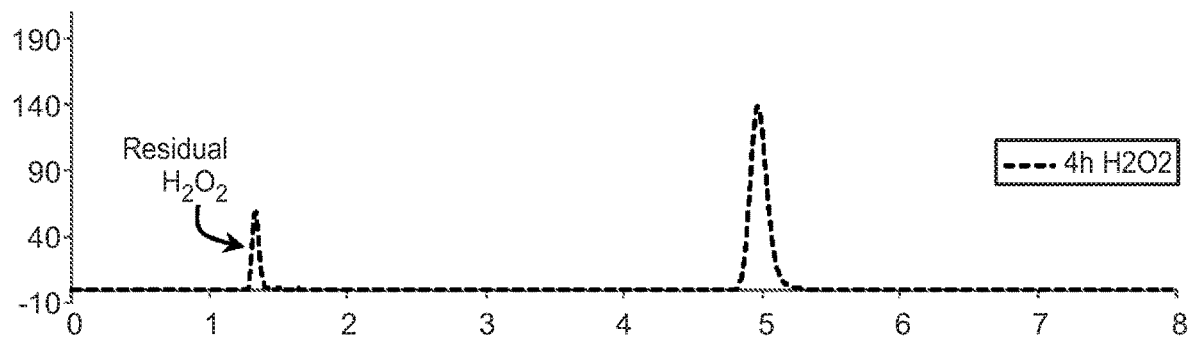
Figure 4D:
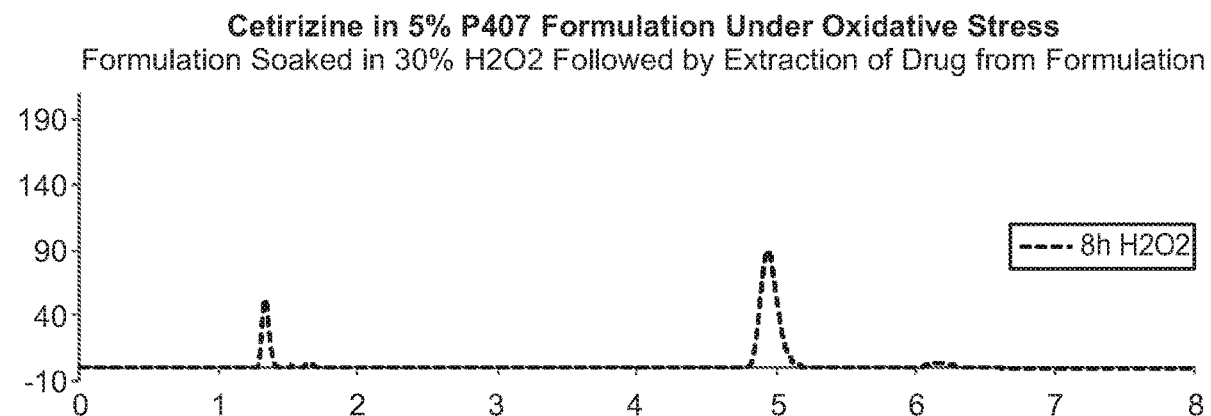
Figure 4E:
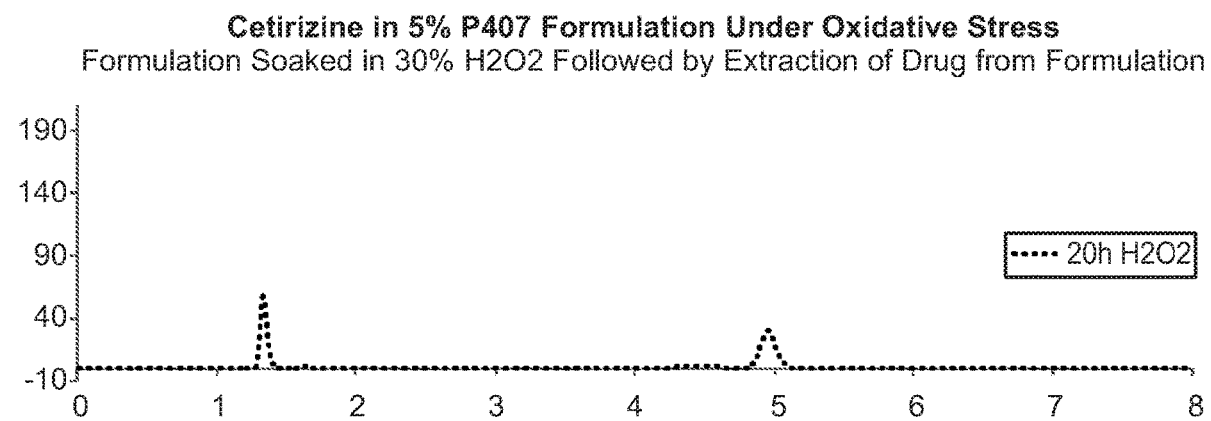

Such compressable or compactable systems are shown in FIG. 1, FIG. 2, and FIG. 2A. The ring-shaped design for a gastric residence system shown in FIG. 1 can be twisted into a double helix, which compresses the structure to a roughly cylindrical shape which can be placed in a capsule. The star-shaped (stellate) design for a gastric residence system shown in FIG. 2 and FIG. 2A can be folded at its central portion as illustrated in FIG. 3, which can then be placed into a capsule. The system is administered to a patient by swallowing the capsule or by gastric tube.

Deployment of the System in the Stomach

Once the capsule or other container arrives in the stomach of the patient, the capsule dissolves and releases the compacted gastric residence system. Upon release, the system returns to its original shape, such as a ring shape or a star shape. The dimensions of the uncompressed/uncompacted system are suitable to prevent passage of the system through the pyloric sphincter for the period of time during which the system is to reside in the stomach.

While in the stomach, the gastric residence system is compatible with digestion and other normal functioning of the stomach or gastrointestinal tract. The gastric residence system does not interfere with or impede the passage of chyme (partially digested food) or other gastric contents which exit the stomach through the pyloric sphincter into the duodenum.

Elution of Therapeutic Agent from the System while Resident in the Stomach; Linearity of Release The gastric residence system comprises a plurality of carrier polymer-agent components. The carrier polymer-agent components comprise a carrier polymer and a therapeutic agent (or a salt thereof). Release enhancers, solubilizers, dispersants, and stabilizers can also be added to the carrier polymer-agent components. The plurality of carrier polymer-agent components are linked together by one or more coupling polymer components. Agent is eluted from the carrier polymer-agent components into the gastric fluid of the patient over the effective release period or the desired residence time (residence period) of the system. Release of the therapeutic agent is controlled by appropriate formulation of the carrier polymer-agent components, including by the use of the dispersant in formulation of the carrier polymer-agent components, and by milling of the therapeutic agent to particles of desired size prior to blending the agent with the carrier polymer and dispersant.

Elution or release of therapeutic agent is preferably as close to linear as possible. As noted above, dispersants can aid in reducing burst release, which improves linearity. In some embodiments, burst release is below about 20% of total drug load after about 6 hours in 0.1N HCl, about 6 hours in simulated gastric fluid (fasted), about 6 hours in simulated gastric fluid (fed), about 6 hours in a pig stomach, about 6 hours in a dog stomach, or about 6 hours in a human stomach. In some embodiments, burst release is below about 10% of total drug load after about 6 hours in 0.1N HCl, about 6 hours in simulated gastric fluid (fasted), about 6 hours in simulated gastric fluid (fed), about 6 hours in a pig stomach, about 6 hours in a dog stomach, or about 6 hours in a human stomach. In some embodiments, burst release is below about 5% of total drug load after after about 6 hours in 0.1N HCl, about 6 hours in simulated gastric fluid (fasted), about 6 hours in simulated gastric fluid (fed), about 6 hours in a pig stomach, about 6 hours in a dog stomach, or about 6 hours in a human stomach.

When release of therapeutic agent is approximately linear, about half of the total amount of drug to be released would be released at a point about halfway through the residence period or effective release period. Thus, if the residence period of the gastric residence system is D days, about 30% to about 70% of the total drug load will be released after an elapsed time between about 0.4D and 0.6D, such as at time 0.5D, when the gastric residence system is in 0.1N HCl, simulated gastric fluid (fasted), simulated gastric fluid (fed), a pig stomach, a dog stomach, or a human stomach. Similarly, if the effective release period of the gastric residence system is E days, about 30% to about 70% of the total drug load will be released after an elapsed time between about 0.4E and 0.6E, such as at time 0.5E, when the gastric residence system is in 0.1N HCl, simulated gastric fluid (fasted), simulated gastric fluid (fed), a pig stomach, a dog stomach, or a human stomach.

When release of therapeutic agent is approximately linear, most of the agent in the gastric will have eluted. Thus, if the residence period of the gastric residence system is D days, in some embodiments, about 70% or more of the total drug load will be released after an elapsed time between about 0.8D and 1 D, when the gastric residence system is in 0.1N HCl, simulated gastric fluid (fasted), simulated gastric fluid (fed), a pig stomach, a dog stomach, or a human stomach. In some embodiments, about 80% or more of the total drug load will be released after an elapsed time between about 0.8D and 1 D, when the gastric residence system is in 0.1N HCl, simulated gastric fluid (fasted), simulated gastric fluid (fed), a pig stomach, a dog stomach, or a human stomach. In some embodiments, about 90% or more of the total drug load will be released after an elapsed time between about 0.8D and 1 D, when the gastric residence system is in 0.1N HCl, simulated gastric fluid (fasted), simulated gastric fluid (fed), a pig stomach, a dog stomach, or a human stomach. In some embodiments, if the effective release period of the gastric residence system is E days, about 70% or more of the total drug load will be released after an elapsed time between about 0.8 E and 1 E, when the gastric residence system is in 0.1N HCl, simulated gastric fluid (fasted), simulated gastric fluid (fed), a pig stomach, a dog stomach, or a human stomach. In some embodiments, about 80% or more of the total drug load will be released after an elapsed time between about 0.8 E and 1 E, when the gastric residence system is in 0.1N HCl, simulated gastric fluid (fasted), simulated gastric fluid (fed), a pig stomach, a dog stomach, or a human stomach. In some embodiments, about 90% or more of the total drug load will be released after an elapsed time between about 0.8 E and 1 E, when the gastric residence system is in 0.1N HCl, simulated gastric fluid (fasted), simulated gastric fluid (fed), a pig stomach, a dog stomach, or a human stomach.

Additional initial burst release parameters: In some embodiments, the gastric residence systems of the invention release no greater than about 30% of therapeutic agent or salt thereof before about 5% of the residence period has elapsed. In some embodiments, the gastric residence systems of the invention release no greater than about 25% of therapeutic agent or salt thereof before about 5% of the residence period has elapsed. In some embodiments, the gastric residence systems of the invention release no greater than about 20% of therapeutic agent or salt thereof before about 5% of the residence period has elapsed. In some embodiments, the gastric residence systems of the invention release no greater than about 15% of therapeutic agent or salt thereof before about 5% of the residence period has elapsed. In some embodiments, the gastric residence systems of the invention release no greater than about 10% of therapeutic agent or salt thereof before about 5% of the residence period has elapsed. In some embodiments, the gastric residence systems of the invention release no greater than about 30% of therapeutic agent or salt thereof before about 5% of the effective release period has elapsed. In some embodiments, the gastric residence systems of the invention release no greater than about 25% of therapeutic agent or salt thereof before about 5% of the effective release period has elapsed. In some embodiments, the gastric residence systems of the invention release no greater than about 20% of therapeutic agent or salt thereof before about 5% of the effective release period has elapsed. In some embodiments, the gastric residence systems of the invention release no greater than about 15% of therapeutic agent or salt thereof before about 5% of the effective release period has elapsed. In some embodiments, the gastric residence systems of the invention release no greater than about 10% of therapeutic agent or salt thereof before about 5% of the effective release period has elapsed.

Additional initial burst release parameters, continued: In some embodiments, the gastric residence systems of the invention release no greater than about 30% of therapeutic agent or salt thereof before about 6 hours have elapsed. In some embodiments, the gastric residence systems of the invention release no greater than about 25% of therapeutic agent or salt thereof before about 6 hours have elapsed. In some embodiments, the gastric residence systems of the invention release no greater than about 20% of therapeutic agent or salt thereof before about 6 hours have elapsed. In some embodiments, the gastric residence systems of the invention release no greater than about 15% of therapeutic agent or salt thereof before about 6 hours have elapsed.

Intermediate release parameters: In some embodiments, the gastric residence systems of the invention release about 30-70% of therapeutic agent or salt thereof within about 30-70% of the residence period. In some embodiments, the gastric residence systems of the invention release about 30-70% of therapeutic agent or salt thereof within about 40-60% of the residence period. In some embodiments, the gastric residence systems of the invention release about 30-70% of therapeutic agent or salt thereof within about 45-55% of the residence period. In some embodiments, the gastric residence systems of the invention release about 40-60% of therapeutic agent or salt thereof within about 30-70% of the residence period. In some embodiments, the gastric residence systems of the invention release about 40-60% of therapeutic agent or salt thereof within about 40-60% of the residence period. In some embodiments, the gastric residence systems of the invention release about 40-60% of therapeutic agent or salt thereof within about 45-55% of the residence period. In some embodiments, the gastric residence systems of the invention release about 45-55% of therapeutic agent or salt thereof within about 30-70% of the residence period. In some embodiments, the gastric residence systems of the invention release about 45-55% of therapeutic agent or salt thereof within about 40-60% of the residence period. In some embodiments, the gastric residence systems of the invention release about 45-55% of therapeutic agent or salt thereof within about 45-55% of the residence period. In some embodiments, the gastric residence systems of the invention release about 30-70% of therapeutic agent or salt thereof within about 30-70% of the effective release period. In some embodiments, the gastric residence systems of the invention release about 30-70% of therapeutic agent or salt thereof within about 40-60% of the effective release period. In some embodiments, the gastric residence systems of the invention release about 30-70% of therapeutic agent or salt thereof within about 45-55% of the effective release period. In some embodiments, the gastric residence systems of the invention release about 40-60% of therapeutic agent or salt thereof within about 30-70% of the effective release period. In some embodiments, the gastric residence systems of the invention release about 40-60% of therapeutic agent or salt thereof within about 40-60% of the effective release period. In some embodiments, the gastric residence systems of the invention release about 40-60% of therapeutic agent or salt thereof within about 45-55% of the effective release period. In some embodiments, the gastric residence systems of the invention release about 45-55% of therapeutic agent or salt thereof within about 30-70% of the effective release period. In some embodiments, the gastric residence systems of the invention release about 45-55% of therapeutic agent or salt thereof within about 40-60% of the effective release period. In some embodiments, the gastric residence systems of the invention release about 45-55% of therapeutic agent or salt thereof within about 45-55% of the effective release period.

Terminating release parameters: In some embodiments, the gastric residence systems of the invention release at least about 60% of therapeutic agent or salt thereof after about 70% or more of the residence period has elapsed. In some embodiments, the gastric residence systems of the invention release at least about 70% of therapeutic agent or salt thereof after about 70% or more of the residence period has elapsed. In some embodiments, the gastric residence systems of the invention release at least about 70% of therapeutic agent or salt thereof after about 80% or more of the residence period has elapsed. In some embodiments, the gastric residence systems of the invention release at least about 80% of therapeutic agent or salt thereof after about 80% or more of the residence period has elapsed. In some embodiments, the gastric residence systems of the invention release at least about 80% of therapeutic agent or salt thereof after about 90% or more of the residence period has elapsed. In some embodiments, the gastric residence systems of the invention release at least about 90% of therapeutic agent or salt thereof after about 90% or more of the residence period has elapsed. In some embodiments, the gastric residence systems of the invention release at least about 60% of therapeutic agent or salt thereof after about 70% or more of the effective release period has elapsed. In some embodiments, the gastric residence systems of the invention release at least about 70% of therapeutic agent or salt thereof after about 70% or more of the effective release period has elapsed. In some embodiments, the gastric residence systems of the invention release at least about 70% of therapeutic agent or salt thereof after about 80% or more of the effective release period has elapsed. In some embodiments, the gastric residence systems of the invention release at least about 80% of therapeutic agent or salt thereof after about 80% or more of the effective release period has elapsed. In some embodiments, the gastric residence systems of the invention release at least about 80% of therapeutic agent or salt thereof after about 90% or more of the effective release period has elapsed. In some embodiments, the gastric residence systems of the invention release at least about 90% of therapeutic agent or salt thereof after about 90% or more of the effective release period has elapsed.

Gastric residence systems having any combination of the initial burst release parameters, intermediate release parameters, and terminating release parameters recited above are contemplated as part of the invention. For example, in some embodiments, the gastric residence systems of the invention release no greater than about 25% of therapeutic agent or salt thereof before about 5% of the residence period; release about 40-60% of therapeutic agent or salt thereof within about 30-70% of the residence period; and release about 60% or greater of therapeutic agent or salt thereof after about 70% or longer of the residence period. In some embodiments, the gastric residence systems of the invention release no greater than about 20% of therapeutic agent or salt thereof before about 5% of the residence period; release about 40-60% of therapeutic agent or salt thereof within about 40-60% of the residence period; and release about 60% or greater of therapeutic agent or salt thereof after about 70% or longer of the residence period. In some embodiments, the gastric residence systems of the invention release no greater than about 15% of therapeutic agent or salt thereof before about 5% of the residence period; release about 40-60% of therapeutic agent or salt thereof by about 45-55% of the residence period; and release about 70% or greater of therapeutic agent or salt thereof after about 70% or longer of the residence period. In some embodiments, the gastric residence systems of the invention release no greater than about 25% of therapeutic agent or salt thereof before about 5% of the effective release period; release about 40-60% of therapeutic agent or salt thereof within about 30-70% of the effective release period; and release about 60% or greater of therapeutic agent or salt thereof after about 70% or longer of the effective release period. In some embodiments, the gastric residence systems of the invention release no greater than about 20% of therapeutic agent or salt thereof before about 5% of the effective release period; release about 40-60% of therapeutic agent or salt thereof within about 40-60% of the effective release period; and release about 60% or greater of therapeutic agent or salt thereof after about 70% or longer of the effective release period. In some embodiments, the gastric residence systems of the invention release no greater than about 15% of therapeutic agent or salt thereof before about 5% of the effective release period; release about 40-60% of therapeutic agent or salt thereof by about 45-55% of the effective release period; and release about 70% or greater of therapeutic agent or salt thereof after about 70% or longer of the effective release period.

As described above, these release parameters can be measured for the gastric residence system for the specified time in any of the following: 0.1N HCl, simulated gastric fluid (fasted), simulated gastric fluid (fed), a pig stomach, a dog stomach, or a human stomach. 0.1N HCl is preferred for standardization and comparison of release rates.

Gastric residence systems which deliver therapeutic agents that have relatively long half-lives (greater than about 1 day, greater than about 2 days, greater than about 3 days, greater than about 4 days, greater than about 5 days, greater than about 6 days, or greater than about 7 days), and/or relatively large therapeutic windows, have less stringent requirements for linearity of release. That is, any of the ranges for release provided above, both wider and narrower, can be used in such systems. In contrast, gastric residence systems which deliver therapeutic agents that have relatively short half-lives (less than about 1 day, less than about 18 hours, less than about 12 hours, less than about 9 hours, less than about 6 hours, or less than about 3 hours) and/or relatively narrow therapeutic windows should have greater linearity, that is, the narrower ranges of release provided above are preferred in such systems (such as the two narrowest, or most linear, of the ranges for burst release, intermediate release, and terminating release parameters).

Resistance to Alcohol-Induced Release

Release rates of a therapeutic agent from a gastric residence system can be affected by changes in the environment in which the system is deployed. The human stomach environment can change due to consumption of alcoholic beverages (that is, beverages containing ethanol), in addition to changes between a fed state (after a meal) and a fasted state (long after the most recent meal). For any therapeutic agent, and especially hydrophobic therapeutic agents (such as rosuvastatin, discussed in more detail herein), it is desirable that consumption of ethanol should not dramatically affect the release rate of the therapeutic agent from the gastric residence system.

Measurement of ethanol-induced release of therapeutic agent from the gastric residence systems of the invention can be measured by placing the system in 40% ethanol/60% 0.1N HCl for a period of time, such as about two hours, and measuring the release of therapeutic agent from the system. In some embodiments, no more than about 30% of the therapeutic agent is released from the gastric residence system after about two hours in 40% ethanol/60% 0.1N HCl. In some embodiments, no more than about 25% of the therapeutic agent is released from the gastric residence system after about two hours in 40% ethanol/60% 0.1N HCl. In some embodiments, no more than about 20% of the therapeutic agent is released from the gastric residence system after about two hours in 40% ethanol/60% 0.1N HCl. In some embodiments, no more than about 15% of the therapeutic agent is released from the gastric residence system after about two hours in 40% ethanol/60% 0.1N HCl. In some embodiments, no more than about 10% of the therapeutic agent is released from the gastric residence system after about two hours in 40% ethanol/60% 0.1N HCl. In some embodiments, no more than about 5% of the therapeutic agent is released from the gastric residence system after about two hours in 40% ethanol/60% 0.1N HCl.

Measurement of ethanol-induced release of therapeutic agent from the gastric residence systems of the invention can also be measured by comparing release of agent in fasted-state simulated gastric fluid, fed-state simulated gastric fluid, or 0.1N HCl to the release of agent in 40% ethanol/60% fasted-state simulated gastric fluid, 40% ethanol/60% fed-state simulated gastric fluid, in 40% ethanol/60% 0.1N HCl, or 40% ethanol/60% water. In some embodiments, the release of therapeutic agent (or pharmaceutically acceptable salt of therapeutic agent) increases by no more than about 50% in 40% ethanol/60% 0.1N HCl in water versus the release over the same period of time in 0.1N HCl, or by no more than about 50% in 40% ethanol/60% simulated gastric fluid versus the release over the same period of time in simulated gastric fluid, or by no more than about 50% in 40% ethanol/60% fasted-state simulated gastric fluid versus the release over the same period of time in fasted-state simulated gastric fluid, or by no more than about 50% in 40% ethanol/60% fed-state simulated gastric fluid versus the release over the same period of time in fed-state simulated gastric fluid. In some embodiments, the release of therapeutic agent (or pharmaceutically acceptable salt of therapeutic agent) increases by no more than about 40% in 40% ethanol/60% 0.1N HCl in water versus the release over the same period of time in 0.1N HCl, or by no more than about 40% in 40% ethanol/60% simulated gastric fluid versus the release over the same period of time in simulated gastric fluid, or by no more than about 40% in 40% ethanol/60% fasted-state simulated gastric fluid versus the release over the same period of time in fasted-state simulated gastric fluid, or by no more than about 40% in 40% ethanol/60% fed-state simulated gastric fluid versus the release over the same period of time in fed-state simulated gastric fluid. In some embodiments, the release of therapeutic agent (or pharmaceutically acceptable salt of therapeutic agent) increases by no more than about 30% in 40% ethanol/60% 0.1N HCl in water versus the release over the same period of time in 0.1N HCl, or by no more than about 30% in 40% ethanol/60% simulated gastric fluid versus the release over the same period of time in simulated gastric fluid, or by no more than about 30% in 40% ethanol/60% fasted-state simulated gastric fluid versus the release over the same period of time in fasted-state simulated gastric fluid, or by no more than about 30% in 40% ethanol/60% fed-state simulated gastric fluid versus the release over the same period of time in fed-state simulated gastric fluid. In some embodiments, the release of therapeutic agent (or pharmaceutically acceptable salt of therapeutic agent) increases by no more than about 20% in 40% ethanol/60% 0.1N HCl in water versus the release over the same period of time in 0.1N HCl, or by no more than about 20% in 40% ethanol/60% simulated gastric fluid versus the release over the same period of time in simulated gastric fluid, or by no more than about 20% in 40% ethanol/60% fasted-state simulated gastric fluid versus the release over the same period of time in fasted-state simulated gastric fluid, or by no more than about 20% in 40% ethanol/60% fed-state simulated gastric fluid versus the release over the same period of time in fed-state simulated gastric fluid.

The period of time over which the comparative release is measured can be about 15 minutes, about 30 minutes, about 45 minutes, about an hour, about 90 minutes, or about two hours.

In the foregoing paragraphs regarding measurement of release in ethanol-containing solutions, "40% ethanol" can be "about 40% ethanol"; "60% simulated gastric fluid" can be "about 60% simulated gastric fluid"; "60% fasted-state simulated gastric fluid" can be "about 60% fasted-state simulated gastric fluid"; "60% fed-state simulated gastric fluid" can be "about 60% fed-state simulated gastric fluid"; and "0.1N HCl" can be "about 0.1N HCl."

Retention in Stomach; Passage of the System from the Stomach

The gastric residence system passes out of in the stomach at an appropriate time point, that is, once the useful therapeutic agent delivery lifetime of the system has been reached, or at a reasonable fraction of the useful therapeutic agent delivery lifetime of the system. This is accomplished by suitable choice of the coupling polymer components and the dimensions of the system. In its intact, uncompressed form, the gastric residence system is designed to resist passage through the pyloric sphincter. That is, in its intact form, the gastric residence system is too large to pass through the pyloric sphincter. The gastric residence system should also be resistant to being transiently re-folded by the compressive forces in the stomach, which may cause premature passage of the system. In order to prevent transient re-folding in the stomach, the gastric residence system should maintain its uncompressed form, or approximately its uncompressed form when subject to forces typically present in the stomach. Therefore, in some embodiments, the force required to fold or compress the structure is at least about 0.2 Newtons (N), at least about 0.3 N, at least about 0.4 N, at least about 0.5 N, at least about 0.75 N, at least about 1 N, at least about 1.5 N, at least about 2 N, at least about 2.5 N, at least about 3 N, at least about 4 N, or at least about 5 N. In some embodiments, the force required to fold or compress the structure is between about 0.2 N to about 5 N, between about 0.3 N to about 5 N, between about 0.4 N to about 5 N, between about 0.5 N to about 5 N, between about 0.75 N to about 5 N, between about 1 N to about 5 N, between about 1.5 N to about 5 N, between about 2 N to about 5 N, between about 2.5 N to about 5 N, between about 3 N to about 5 N, or between about 4 N to about 5 N.

The coupling polymer components are chosen such that they gradually degrade over the residence period in the stomach. When the coupling polymer components are sufficiently weakened by degradation, the gastric residence system breaks apart into smaller pieces, which are small enough to pass through the pyloric sphincter. The system then passes through the intestines and is eliminated from the patient.

Safety Elements

In its desired mode of operation, the gastric residence systems have their intact uncompressed form while resident in the stomach, and do not pass through the pylorus until they break apart after the desired residence time (residence period). If a gastric residence system passes intact into the intestine, it has the potential to result in intestinal blockage. Thus, the gastric residence systems are designed to uncouple rapidly in the intestinal environment by dissolution of one or more of the coupling polymers, within 48 hours, preferably within 24 hours, more preferably within 12 hours, yet more preferably within 1-2 hours, so as to avoid potential intestinal blockage. This is readily accomplished by using enteric polymers as some of, or all of, the coupling polymers in the systems. Enteric polymers are relatively resistant to the acidic pH levels encountered in the stomach, but dissolve rapidly at the higher pH levels found in the duodenum. Use of enteric coupling polymers as safety elements protects against undesired passage of the intact gastric residence system into the small intestine. The use of enteric coupling polymers also provides a manner of removing the gastric residence system prior to its designed residence time (residence period); should the system need to be removed, the patient can drink a mildly alkaline solution, such as a sodium bicarbonate solution, or take an antacid preparation such as hydrated magnesium hydroxide (milk of magnesia) or calcium carbonate, which will raise the pH level in the stomach and cause rapid degradation of the enteric coupling polymers. The gastric residence system will then break apart and be eliminated from the patient.

Definitions

A "carrier polymer" is a polymer suitable for blending with a therapeutic agent, such as a drug, for use in the invention.

A "hydrophilic therapeutic agent," "hydrophilic agent," or "hydrophilic drug" is an agent which readily dissolves in water. A hydrophilic agent is defined as an agent which has a solubility in water of 1 mg/ml or greater. Alternatively, a hydrophilic agent can be defined as an agent which has a log $P_{oct}$ (log partition coefficient $P_{oct}$, where $P_{oct}$=(concentration in 1-octanol)/(concentration in $H_2O$)) in a 1-octanol/water system of less than 0.5. The pH at which solubility or log $P_{oct}$ is measured is 1.6, approximating the gastric environment.

A "hydrophobic therapeutic agent," "hydrophobic agent," or "hydrophobic drug" is an agent which does not readily dissolve in water. A hydrophobic agent is defined as an agent which has a solubility in water of less than 1 mg/ml. Alternatively, a hydrophobic agent can be defined as an agent which has a log $P_{oct}$ (log partition coefficient) in a 1-octanol/water system of greater than 1. Alternatively, a hydrophobic therapeutic agent can be defined as an agent which has a higher solubility in ethanol than in water. Alternatively, a hydrophobic therapeutic agent can be defined as an agent which has a higher solubility in 40% ethanol/60% simulated gastric fluid than in 100% simulated gastric fluid.

In addition to log $P_{oct}$, where the partition coefficient of a substance is measured in a 1-octanol/water system, other systems can be used to measure partition behavior. Another such system is partitioning of a substance between a polycaprolactone phase (PCL phase) and a simulated gastric fluid phase (SGF phase), to give the partition coefficient $P_{PCL-SGF}$ between the two phases. Log $P_{PCL-SGF}$ can also be calculated. A 5:1 mixture of polycaprolactone diol (MW 530):ethyl acetate can be used as the PCL phase, and fasted-state simulated gastric fluid (FaSSGF) can be used as the SGF phase.

A "dispersant" is defined as a substance which aids in the minimization of therapeutic agent particle size and the dispersal of therapeutic agent particles in the carrier polymer matrix. That is, the dispersant helps minimize or prevent aggregation or flocculation of particles during fabrication of the systems. Thus, the dispersant has anti-aggregant activity and anti-flocculant activity, and helps maintain an even distribution of therapeutic agent particles in the carrier polymer matrix.

An "excipient" is any substance added to a formulation of therapeutic agent that is not the therapeutic agent itself. Excipients include, but are not limited to, binders, coatings, diluents, disintegrants, emulsifiers, flavorings, glidants, lubricants, and preservatives. The specific category of dispersant falls within the more general category of excipient.

An "elastic polymer" or "elastomer" (also referred to as a "tensile polymer") is a polymer that is capable of being deformed by an applied force from its original shape for a period of time, and which then substantially returns to its original shape once the applied force is removed.

A "coupling polymer" is a polymer suitable for coupling any other polymers together, such as coupling a first carrier polymer-agent component to a second carrier polymer-agent component.

"Substantially constant plasma level" refers to a plasma level that remains within plus-or-minus 25% of the average plasma level measured over the period that the gastric residence system is resident in the stomach.

The "residence time" or "residence period" is the time from deployment of the gastric residence system in the stomach to the time when the gastric residence system exits the stomach.

The "effective release period" or "effective release time" is the time over which the gastric residence system releases a therapeutically effective amount of the therapeutic agent contained in the system. For therapeutic agents released in a therapeutically effective amount only while the gastric residence system resides in the stomach, the effective release period will be less than or equal to the residence period. For therapeutic agents released in a therapeutically effective amount both while the gastric residence system resides in the stomach, and also while the components of the gastric residence system are transiting the intestinal tract subsequent to the residence period, the effective release period can be greater than the residence period.

"Biocompatible," when used to describe a material or system, indicates that the material or system does not provoke an adverse reaction, or causes only minimal, tolerable adverse reactions, when in contact with an organism, such as a human. In the context of the gastric residence systems, biocompatibility is assessed in the environment of the gastrointestinal tract.

As used herein, the singular forms "a", "an", and "the" include plural references unless indicated otherwise or the context clearly dictates otherwise.

A "patient," "individual," or "subject" refers to a mammal, preferably a human or a domestic animal such as a dog or cat. In a preferred embodiment, a patient, individual, or subject is a human.

The "diameter" of a particle as used herein refers to the longest dimension of a particle.

"Treating" a disease or disorder with the systems and methods disclosed herein is defined as administering one or more of the systems disclosed herein to a patient in need thereof, with or without additional therapeutic agents, in order to reduce or eliminate either the disease or disorder, or one or more symptoms of the disease or disorder, or to retard the progression of the disease or disorder or of one or more symptoms of the disease or disorder, or to reduce the severity of the disease or disorder or of one or more symptoms of the disease or disorder. "Suppression" of a disease or disorder with the systems and methods disclosed herein is defined as administering one or more of the systems disclosed herein to a patient in need thereof, with or without additional therapeutic agents, in order to inhibit the clinical manifestation of the disease or disorder, or to inhibit the manifestation of adverse symptoms of the disease or disorder. The distinction between treatment and suppression is that treatment occurs after adverse symptoms of the disease or disorder are manifest in a patient, while suppression occurs before adverse symptoms of the disease or disorder are manifest in a patient. Suppression may be partial, substantially total, or total. Because some diseases or disorders are inherited, genetic screening can be used to identify patients at risk of the disease or disorder. The systems and methods of the invention can then be used to treat asymptomatic patients at risk of developing the clinical symptoms of the disease or disorder, in order to suppress the appearance of any adverse symptoms.

"Therapeutic use" of the systems disclosed herein is defined as using one or more of the systems disclosed herein to treat a disease or disorder, as defined above. A "therapeutically effective amount" of a therapeutic agent is an amount of the therapeutic agent, which, when administered to a patient, is sufficient to reduce or eliminate either a disease or disorder or one or more symptoms of a disease or disorder, or to retard the progression of a disease or disorder or of one or more symptoms of a disease or disorder, or to reduce the severity of a disease or disorder or of one or more symptoms of a disease or disorder. A therapeutically effective amount can be administered to a patient as a single dose, or can be divided and administered as multiple doses.

"Prophylactic use" of the systems disclosed herein is defined as using one or more of the systems disclosed herein to suppress a disease or disorder, as defined above. A "prophylactically effective amount" of a therapeutic agent is an amount of the therapeutic agent, which, when administered to a patient, is sufficient to suppress the clinical manifestation of a disease or disorder, or to suppress the manifestation of adverse symptoms of a disease or disorder.

A prophylactically effective amount can be administered to a patient as a single dose, or can be divided and administered as multiple doses.

When numerical values are expressed herein using the term "about" or the term "approximately," it is understood that both the value specified, as well as values reasonably close to the value specified, are included. For example, the description "about 50° C." or "approximately 50° C." includes both the disclosure of 50° C. itself, as well as values close to 50° C. Thus, the phrases "about X" or "approximately X" include a description of the value X itself. If a range is indicated, such as "approximately 50° C. to 60° C." or "about 50° C. to 60° C.," it is understood that both the values specified by the endpoints are included, and that values close to each endpoint or both endpoints are included for each endpoint or both endpoints; that is, "approximately 50° C. to 60° C." (or "about 50° C. to 60° C.") is equivalent to reciting both "50° C. to 60° C." and "approximately 50° C. to approximately 60° C." (or "about 50° C. to 60° C.").

With respect to numerical ranges disclosed in the present description, any disclosed upper limit for a component may be combined with any disclosed lower limit for that component to provide a range (provided that the upper limit is greater than the lower limit with which it is to be combined). Each of these combinations of disclosed upper and lower limits are explicitly envisaged herein. For example, if ranges for the amount of a particular component are given as 10% to 30%, 10% to 12%, and 15% to 20%, the ranges 10% to 20% and 15% to 30% are also envisaged, whereas the combination of a 15% lower limit and a 12% upper limit is not possible and hence is not envisaged.

Unless otherwise specified, percentages of ingredients in compositions are expressed as weight percent, or weight/weight percent. It is understood that reference to relative weight percentages in a composition assumes that the combined total weight percentages of all components in the composition add up to 100. It is further understood that relative weight percentages of one or more components may be adjusted upwards or downwards such that the weight percent of the components in the composition combine to a total of 100, provided that the weight percent of any particular component does not fall outside the limits of the range specified for that component.

Some embodiments described herein are recited as "comprising" or "comprises" with respect to their various elements. In alternative embodiments, those elements can be recited with the transitional phrase "consisting essentially of" or "consists essentially of" as applied to those elements. In further alternative embodiments, those elements can be recited with the transitional phrase "consisting of" or "consists of" as applied to those elements. Thus, for example, if a composition or method is disclosed herein as comprising A and B, the alternative embodiment for that composition or method of "consisting essentially of A and B" and the alternative embodiment for that composition or method of "consisting of A and B" are also considered to have been disclosed herein. Likewise, embodiments recited as "consisting essentially of" or "consisting of" with respect to their various elements can also be recited as "comprising" as applied to those elements. Finally, embodiments recited as "consisting essentially of" with respect to their various elements can also be recited as "consisting of" as applied to those elements, and embodiments recited as "consisting of" with respect to their various elements can also be recited as "consisting essentially of" as applied to those elements.

When a composition or system is described as "consisting essentially of" the listed elements, the composition or system contains the elements expressly listed, and may contain other elements which do not materially affect the condition being treated (for compositions for treating conditions), or the properties of the described system (for compositions comprising a system). However, the composition or system either does not contain any other elements which do materially affect the condition being treated other than those elements expressly listed (for compositions for treating systems) or does not contain any other elements which do materially affect the properties of the system (for compositions comprising a system); or, if the composition or system does contain extra elements other than those listed which may materially affect the condition being treated or the properties of the system, the composition or system does not contain a sufficient concentration or amount of those extra elements to materially affect the condition being treated or the properties of the system. When a method is described as "consisting essentially of" the listed steps, the method contains the steps listed, and may contain other steps that do not materially affect the condition being treated by the method or the properties of the system produced by the method, but the method does not contain any other steps which materially affect the condition being treated or the system produced other than those steps expressly listed.

This disclosure provides several embodiments. It is contemplated that any features from any embodiment can be combined with any features from any other embodiment where possible. In this fashion, hybrid configurations of the disclosed features are within the scope of the present invention.

Dispersants for Modulation of Therapeutic Agent Release and Stability of Polymer Blend The use of a dispersant in the carrier polymer-agent component provides numerous advantages. The rate of elution of therapeutic agent from the carrier polymer-agent component is affected by numerous factors as previously noted, including the composition and properties of the carrier polymer (which may itself comprise multiple polymeric and non-polymeric components); the physical and chemical properties of the therapeutic agent; and the gastric environment. Avoiding burst release of therapeutic agent, especially hydrophilic agents, and maintaining sustained release of the therapeutic agent over the effective release period or residence period is an important characteristic of the systems. The use of a dispersant according to the invention enables better control of release rate and suppression of burst release. Burst release and release rate can be tuned by using varied concentrations of dispersant. Example 9 describes the effect of different dispersants and different excipients, at varying concentrations, on burst release of cetirizine in simulated gastric fluid.

Dispersants which can be used in the invention include: silicon dioxide (silica, $SiO_2$) (hydrophilic fumed); stearate salts, such as calcium stearate and magnesium stearate; microcrystalline cellulose; carboxymethylcellulose; hydrophobic colloidal silica; hypromellose; magnesium aluminum silicate; phospholipids; polyoxyethylene stearates; zinc acetate; alginic acid; lecithin; fatty acids; sodium lauryl sulfate; and non-toxic metal oxides such as aluminum oxide. Porous inorganic materials and polar inorganic materials can be used. Hydrophilic-fumed silicon dioxide is a preferred dispersant.

In addition to anti-aggregation/anti-flocculation activity, the dispersant can prevent phase separation during fabrication and/or storage of the systems. This is particularly useful for manufacture of the systems by hot melt extrusion.

The weight/weight ratio of dispersant to therapeutic agent substance can be about 0.1% to about 5%, about 0.1% to about 4%, about 0.1% to about 3%, about 0.1% to about 2%, about 0.1% to about 1%, about 1% to about 5%, about 1% to about 4%, about 1% to about 3%, about 1% to about 2%, about 2% to about 4%, about 2% to about 3%, about 3% to about 4%, about 4% to about 5%, or about 0.1%, about 0.5%, about 1%, about 2%, about 3%, about 4% or about 5%.

Dispersants can comprise about 0.1% to about 4% of the carrier polymer-agent components, such as about 0.1% to about 3.5%, about 0.1% to about 3%, about 0.1% to about 2.5%, about 0.1% to about 2%, about 0.1% to about 1.5%, about 0.1% to about 1%, about 0.1% to about 0.5%, or about 0.2% to about 0.8%.

The amount of burst release tolerable during the initial period when the gastric residence system is administered will depend on the desired effective release period or, in some circumstance, on the desired gastric residence period. In embodiments of a gastric residence system that is to be administered once weekly (that is, where the effective release period is about one week), the burst release over the approximately first six hours after initial administration is less than about 8%, preferably less than about 6%, of the total amount of drug in the system. In embodiments of a gastric residence system that is to be administered once every three days, the burst release over the approximately first six hours after initial administration is less than about 12%, preferably less than about 10%, of the total amount of drug in the system. In embodiments of a gastric residence system that is to be administered once daily, the burst release over the approximately first six hours after initial administration is less than about 40%, preferably less than about 30%, of the total amount of drug in the system. In general, if a new gastric residence system is administered every E days, and the total mass of drug is M, then the gastric residence system releases less than about [(M divided by E) times 0.5], preferably less than about [(M divided by E) multiplied by 0.4], or less than about [(M divided by E) multiplied by ⅜], more preferably less than about [(M divided by E) multiplied by 0.3], over the approximately first six hours after initial administration. In further embodiments, the gastric residence system releases at least about [(M divided by E) multiplied by 0.25] over the approximately first six hours after initial administration, that is, the system releases at least about one-quarter of the daily dosage over the first one-quarter of the first day of administration.

Stabilization of Therapeutic Agents

Many therapeutic agents are prone to oxidative degradation when exposed to reactive oxygen species, which can be present in the stomach. A therapeutic agent contained in the system may thus oxidize due to the prolonged residence in the stomach of the system, and the extended release period of therapeutic agent from the system. Accordingly, it is desirable to include stabilizers or preservatives in the systems, in order to stabilize the agent to prevent oxidative and other degradation.

Stabilizers, such as anti-oxidants including tocopherols, alpha-tocopherol, ascorbic acid, ascorbyl palmitate, butylated hydroxytoluene, butylated hydroxyanisole, and fumaric acid, can comprise about 0.1% to about 4% of the carrier polymer-agent components, such as about 0.1% to about 3.5%, about 0.1% to about 3%, about 0.1% to about 2.5%, about 0.1% to about 2%, about 0.1% to about 1.5%, about 0.1% to about 1%, about 0.1% to about 0.5%, or about 0.2% to about 0.8%.

Anti-oxidant stabilizers that can be included in the systems to reduce or prevent oxidation of the therapeutic agent include alpha-tocopherol (about 0.01 to about 0.05% v/v), ascorbic acid (about 0.01 to about 0.1% w/v), ascorbyl palmitate (about 0.01 to about 0.1% w/v), butylated hydroxytoluene (about 0.01 to about 0.1% w/w), butylated hydroxyanisole (about 0.01 to about 0.1% w/w), and fumaric acid (up to 3600 ppm).

Certain therapeutic agents can be pH-sensitive, especially at the low pH present in the gastric environment. Buffering or pH-stabilizer compounds that can be included in the systems to reduce or prevent degradation of therapeutic agent at low pH include calcium carbonate, calcium lactate, calcium phosphate, sodium phosphate, and sodium bicarbonate. They are typically used in an amount of up to about 2% w/w. The buffering or pH-stabilizer compounds can comprise about 0.1% to about 4% of the carrier polymer-agent components, such as about 0.1% to about 3.5%, about 0.1% to about 3%, about 0.1% to about 2.5%, about 0.1% to about 2%, about 0.1% to about 1.5%, about 0.1% to about 1%, about 0.1% to about 0.5%, or about 0.2% to about 0.8%.

The anti-oxidant stabilizers, pH stabilizers, and other stabilizer compounds are blended into the polymers containing the therapeutic agent by blending the stabilizer(s) into the molten carrier polymer-agent mixture. The stabilizer(s) can be blended into molten carrier polymer prior to blending the therapeutic agent into the polymer-stabilizer mixture; or the stabilizer(s) can be blended with agent prior to formulation of the blended agent-stabilizer mixture in the carrier polymer; or stabilizer(s), agent, and molten carrier polymer can be blended simultaneously. Therapeutic agent can also be blended with molten carrier polymer prior to blending the stabilizer(s) into the polymer-agent mixture.

In one embodiment, less than about 10% of the therapeutic agent remaining in the system is degraded or oxidized after a gastric residence period or effective release period of about 24 hours. In one embodiment, less than about 10% of the therapeutic agent remaining in the system is degraded or oxidized after a gastric residence period or effective release period of about 48 hours. In one embodiment, less than about 10% of the therapeutic agent remaining in the system is degraded or oxidized after a gastric residence period or effective release period of about 72 hours. In one embodiment, less than about 10% of the therapeutic agent remaining in the system is degraded or oxidized after a gastric residence period or effective release period of about 96 hours. In one embodiment, less than about 10% of the therapeutic agent remaining in the system is degraded or oxidized after a gastric residence period or effective release period of about five days. In another embodiment, less than about 10% of the therapeutic agent remaining in the system is degraded or oxidized after a gastric residence period or effective release period of about a week. In another embodiment, less than about 10% of the therapeutic agent remaining in the system is degraded or oxidized after a gastric residence period or effective release period of about two weeks. In another embodiment, less than about 10% of the therapeutic agent remaining in the system is degraded or oxidized after a gastric residence period or effective release period of about three weeks. In another embodiment, less than about 10% of the therapeutic agent remaining in the system is degraded or oxidized after a gastric residence period or effective release period of about four weeks. In another embodiment, less than about 10% of the therapeutic agent remaining in the system is degraded or oxidized after a gastric residence period or effective release period of about a month.

In one embodiment, less than about 5% of the therapeutic agent remaining in the system is degraded or oxidized after a gastric residence period or effective release period of about 24 hours. In one embodiment, less than about 5% of the therapeutic agent remaining in the system is degraded or oxidized after a gastric residence period or effective release period of about 48 hours. In one embodiment, less than about 5% of the therapeutic agent remaining in the system is degraded or oxidized after a gastric residence period or effective release period of about 72 hours. In one embodiment, less than about 5% of the therapeutic agent remaining in the system is degraded or oxidized after a gastric residence period or effective release period of about 96 hours. In one embodiment, less than about 5% of the therapeutic agent remaining in the system is degraded or oxidized after a gastric residence period or effective release period of about five days. In another embodiment, less than about 5% of the therapeutic agent remaining in the system is degraded or oxidized after a gastric residence period or effective release period of about a week. In another embodiment, less than about 5% of the therapeutic agent remaining in the system is degraded or oxidized after a gastric residence period or effective release period of about two weeks. In another embodiment, less than about 5% of the therapeutic agent remaining in the system is degraded or oxidized after a gastric residence period or effective release period of about three weeks. In another embodiment, less than about 5% of the therapeutic agent remaining in the system is degraded or oxidized after a gastric residence period or effective release period of about four weeks. In another embodiment, less than about 5% of the therapeutic agent remaining in the system is degraded or oxidized after a gastric residence period or effective release period of about a month.

Degradation and/or oxidation over time can be measured for the gastric residence systems for the specified time in any of the following: 0.1N HCl, simulated gastric fluid (fasted), simulated gastric fluid (fed), a pig stomach, a dog stomach, or a human stomach. 0.1N HCl is preferred for standardization and comparison of release rates.

Therapeutic Agent Particle Size and Milling

Control of particle size used in the gastric residence systems is important for both optimal release of therapeutic agent and mechanical stability of the systems. The particle size of the therapeutic agents affects the surface area of the agents available for dissolution when gastric fluid permeates the carrier polymer-agent components of the system. Also, as the "arms" (elongate members) of the systems are relatively thin in diameter (for example, 1 millimeter to 5 millimeters), the presence of a particle of therapeutic agent of a size in excess of a few percent of the diameter of the arms will result in a weaker arm, both before the agent elutes from the device, and after elution when a void is left in the space formerly occupied by the agent particle. Such weakening of the arms is disadvantageous, as it may lead to premature breakage and passage of the system before the end of the desired residence period.

In one embodiment, the therapeutic agent particles used for blending into the carrier polymer-agent components are smaller than about 100 microns in diameter. In another embodiment, the therapeutic agent particles are smaller than about 75 microns in diameter. In another embodiment, the therapeutic agent particles are smaller than about 50 microns in diameter. In another embodiment, the therapeutic agent particles are smaller than about 40 microns in diameter. In another embodiment, the therapeutic agent particles are smaller than about 30 microns in diameter. In another embodiment, the therapeutic agent particles are smaller than about 25 microns in diameter. In another embodiment, the therapeutic agent particles are smaller than about 20 microns in diameter. In another embodiment, the therapeutic agent particles are smaller than about 10 microns in diameter. In another embodiment, the therapeutic agent particles are smaller than about 5 microns in diameter.

In one embodiment, at least about 80% of the therapeutic agent particles used for blending into the carrier polymer-agent components are smaller than about 100 microns in diameter. In another embodiment, at least about 80% of the therapeutic agent particles are smaller than about 75 microns in diameter. In another embodiment, at least about 80% of the therapeutic agent particles are smaller than about 50 microns in diameter. In another embodiment, at least about 80% of the therapeutic agent particles are smaller than about 40 microns in diameter. In another embodiment, at least about 80% of the therapeutic agent particles are smaller than about 30 microns in diameter. In another embodiment, at least about 80% of the therapeutic agent particles are smaller than about 25 microns in diameter. In another embodiment, at least about 80% of the therapeutic agent particles are smaller than about 20 microns in diameter. In another embodiment, at least about 80% of the therapeutic agent particles are smaller than about 10 microns in diameter. In another embodiment, at least about 80% of the therapeutic agent particles are smaller than about 5 microns in diameter.

In one embodiment, at least about 80% of the mass of the therapeutic agent particles used for blending into the carrier polymer-agent components have sizes between about 1 micron and about 100 microns in diameter. In another embodiment, at least about 80% of the mass of the therapeutic agent particles have sizes between about 1 micron and about 75 microns in diameter. In another embodiment, at least about 80% of the mass of the therapeutic agent particles have sizes between about 1 micron and about 50 microns in diameter. In another embodiment, at least about 80% of the mass of the therapeutic agent particles have sizes between about 1 micron and about 40 microns in diameter. In another embodiment, at least about 80% of the mass of the therapeutic agent particles have sizes between about 1 micron and about 30 microns in diameter. In another embodiment, at least about 80% of the mass of the therapeutic agent particles have sizes between about 1 micron and about 25 microns in diameter. In another embodiment, at least about 80% of the mass of the therapeutic agent particles have sizes between about 1 micron and about 20 microns in diameter. In another embodiment, at least about 80% of the mass of the therapeutic agent particles have sizes between about 1 micron and about 10 microns in diameter. In another embodiment, at least about 80% of the mass of the therapeutic agent particles have sizes between about 1 micron and about 5 microns in diameter.

In one embodiment, at least about 80% of the mass of the therapeutic agent particles used for blending into the carrier polymer-agent components have sizes between about 2 microns and about 100 microns in diameter. In another embodiment, at least about 80% of the mass of the therapeutic agent particles have sizes between about 2 microns and about 75 microns in diameter. In another embodiment, at least about 80% of the mass of the therapeutic agent particles have sizes between about 2 microns and about 50 microns in diameter. In another embodiment, at least about 80% of the mass of the therapeutic agent particles have sizes between about 2 microns and about 40 microns in diameter. In another embodiment, at least about 80% of the mass of the therapeutic agent particles have sizes between about 2 microns and about 30 microns in diameter. In another embodiment, at least about 80% of the mass of the therapeutic agent particles have sizes between about 2 microns and about 25 microns in diameter. In another embodiment, at least about 80% of the mass of the therapeutic agent particles have sizes between about 2 microns and about 20 microns in diameter. In another embodiment, at least about 80% of the mass of the therapeutic agent particles have sizes between about 2 microns and about 10 microns in diameter. In another embodiment, at least about 80% of the mass of the therapeutic agent particles have sizes between about 2 microns and about 5 microns in diameter.

In one embodiment, at least about 80% of the mass of the therapeutic agent particles used for blending into the carrier polymer-agent components have sizes between about 5 microns and about 100 microns in diameter. In another embodiment, at least about 80% of the mass of the therapeutic agent particles have sizes between about 5 microns and about 75 microns in diameter. In another embodiment, at least about 80% of the mass of the therapeutic agent particles have sizes between about 5 microns and about 50 microns in diameter. In another embodiment, at least about 80% of the mass of the therapeutic agent particles have sizes between about 5 microns and about 40 microns in diameter. In another embodiment, at least about 80% of the mass of the therapeutic agent particles have sizes between about 5 microns and about 30 microns in diameter. In another embodiment, at least about 80% of the mass of the therapeutic agent particles have sizes between about 5 microns and about 25 microns in diameter. In another embodiment, at least about 80% of the mass of the therapeutic agent particles have sizes between about 5 microns and about 20 microns in diameter. In another embodiment, at least about 80% of the mass of the therapeutic agent particles have sizes between about 5 microns and about 10 microns in diameter.

The particle size of the therapeutic agents can be readily adjusted by milling Several milling techniques are available to reduce larger particles to smaller particles of desired size. Fluid energy milling is a dry milling technique which uses inter-particle collisions to reduce the size of particles. A type of fluid energy mill called an air jet mill shoots air into a cylindrical chamber in a manner so as to maximize collision between therapeutic agent particles. Ball milling utilizes a rolling cylindrical chamber which rotates around its principal axis. The therapeutic agent and grinding material (such as steel balls, made from chrome steel or CR—NI steel; ceramic balls, such as zirconia; or plastic polyamides) collide, causing reduction in particle size of the agent. Ball milling can be performed in either the dry state, or with liquid added to the cylinder where the therapeutic agent and the grinding material are insoluble in the liquid. Further information regarding milling is described in the chapter by R. W. Lee et al. entitled "Particle Size Reduction" in *Water-Insoluble Drug Formulation, Second Edition* (Ron Liu, editor), Boca Raton, Fla.: CRC Press, 2008; and in the chapter by A. W. Brzeczko et al. entitled "Granulation of Poorly Water-Soluble Drugs" in *Handbook of Pharmaceutical Granulation Technology, Third Edition* (Dilip M. Parikh, editor), Boca Raton, Fla.: CRC Press/Taylor & Francis Group, 2010 (and other sections of that handbook). Fluid energy milling (i.e., air jet milling) is a preferred method of milling, as it is more amenable to scale-up compared to other dry milling techniques such as ball milling.

Milling Additives

Substances can be added to the therapeutic agent material during milling to assist in obtaining particles of the desired size, and minimize aggregation during handling. Silica (silicon dioxide, SiO$_2$) is a preferred milling additive, as it is inexpensive, widely available, and non-toxic. Other additives which can be used include silica, calcium phosphate, powdered cellulose, colloidal silicon dioxide, hydrophobic colloidal silica, magnesium oxide, magnesium silicate, magnesium trisilicate, talc, polyvinylpyrrolidone, cellulose ethers, polyethylene glycol, polyvinyl alcohol, and surfactants. In particular, hydrophobic particles less than 5 microns in diameter are particularly prone to agglomeration, and hydrophilic additives are used when milling such particles. A weight/weight ratio of about 0.1% to about 5% of milling additive, such as silica, can be used for fluid milling or ball milling, or about 0.1% to about 4%, about 0.1% to about 3%, about 0.1% to about 2%, about 0.1% to about 1%, about 1% to about 5%, about 1% to about 4%, about 1% to about 3%, about 1% to about 2%, or about 0.1%, about 0.5%, about 1%, about 2%, about 3%, about 4% or about 5%.

Particle Sizing

After milling, particles can be passed through meshes of appropriate size to obtain particles of the desired size. To obtain particles of a desired maximum size, particles are passed through a mesh with holes of the maximum size desired; particles which are too large will be retained on the mesh, and particles which pass through the mesh will have the desired maximum size. To obtain particles of a desired minimum size, particles are passed through a mesh with holes of the minimum size desired; particles which pass through the mesh are too small, and the desired particles will be retained on the mesh.

System Geometry

A variety of geometrical configurations can be used for the gastric residence systems. One such configuration is shown in FIG. 1, which adopts the shape of a ring in its uncompacted form. Gastric residence system 100 is constructed from carrier polymer-agent components 102 and couplings 104 comprising coupling polymer. The system can be folded at the coupling polymer joints, or twisted into a helix for packaging into a capsule in its compacted form. Once the capsule dissolves in the stomach, system 100 unfolds to the circular shape of its uncompacted form, preventing passage through the pyloric sphincter. In this embodiment, the coupling polymer serves also as an elastomer. The carrier polymer-agent components 102 and couplings 104 are not necessarily drawn to scale; the dimensions (such as length or diameter) of the "arms" 102 and couplings 104 can vary from those shown in the figure.

Another configuration which is star-shaped (stellate) is shown in FIG. 2. Gastric residence system 200 is constructed around a central elastomer 206 which has elongate members, or "arms," projecting radially; one such arm is labeled as 208 in the figure. The arms are formed by outer carrier polymer-agent components 202, inner carrier polymer-agent components 203, and couplings 204 comprising coupling polymer. Components 202, 204, and 203 together comprise an "arm" of this "star-shaped" configuration. Elastomer 206 enables the system to be folded for packaging into a capsule. Again, the components are not necessarily drawn to scale.

FIG. 2A shows another embodiment of the system, with three arms. For the star-shaped configurations of FIG. 2 or FIG. 2A, it will be appreciated that the arms can be spaced substantially evenly around the circumference of the connecting elastomer 206. Thus, for a star-shaped device having N arms, the arms will be spaced apart by (360/N) degrees. For example, the three arms in the device of FIG. 2A are spaced apart by about 120 degrees. As for FIG. 1 and FIG. 2, the components in FIG. 2A are not necessarily drawn to scale.

FIG. 3 shows the folded state of the system of FIG. 2 or of FIG. 2A, as it would be folded for packaging into a capsule (not shown in the figure), with arms 308 comprising outer carrier polymer-agent components 302, inner carrier polymer-agent components 303, couplings 304 comprising coupling polymer, and elastomer 306, where the elastomer has been deformed from its configuration in FIG. 2 or FIG. 2A. For the sake of clarity, only two "arms" formed by outer carrier polymer-agent components 302, couplings 304, and inner carrier polymer-agent components 303 are shown in FIG. 3; additional arms may be present such as shown in the systems in FIG. 2 and FIG. 2A. Upon dissolution of the retaining capsule in the stomach, system 300 unfolds to the star-shaped configuration depicted in FIG. 2 or FIG. 2A, preventing passage through the pyloric sphincter over the residence time (residence period) of the system. The carrier polymer-agent components, couplings, and elastomer are not necessarily drawn to scale; the dimensions (such as length or diameter) of the carrier polymer-agent components, couplings, and elastomer can vary from those shown in the figure.

System Dimensions

The system must be able to adopt a compacted state with dimensions that enable the patient to swallow the system (or for the system to be introduced into the stomach by alternate means, such as a feeding tube or gastrostomy tube). Typically, the system is held in the compacted state by a container such as a capsule. Upon entry into the stomach, the system is then released from the container and adopts an uncompacted state, that is, an expanded conformation, with dimensions that prevent passage of the system through the pyloric sphincter, thus permitting retention of the system in the stomach.

Accordingly, the system should be capable of being placed inside a standard-sized capsule of the type commonly used in pharmacy. Standard capsule sizes in use in the United States are provided below in Table 1 (see "Draft Guidance for Industry on Size, Shape, and Other Physical Attributes of Generic Tablets and Capsules" at URL www.regulations.gov/#!documentDetail; D=FDA-2013-N-1434-0002). As these are the outer dimensions of the capsule, and as dimensions will vary slightly between capsule manufacturers, the system should be capable of adopting a configuration which is about 0.5 to 1 mm smaller than the outer diameter shown, and about 1 to 2 mm shorter than the length shown in Table 1.

TABLE 1

| Capsule Size | Outer Diameter (mm) | Length (mm) |
|---|---|---|
| 000 | 9.9 | 26.1 |
| 00 | 8.5 | 23.3 |
| 0 | 7.6 | 21.7 |
| 1 | 6.9 | 19.4 |
| 2 | 6.3 | 18.0 |
| 3 | 5.8 | 15.9 |
| 4 | 5.3 | 14.3 |
| 5 | 4.9 | 11.1 |

Capsules can be made of materials well-known in the art, such as gelatin or hydroxypropyl methylcellulose. In one embodiment, the capsule is made of a material that dissolves in the gastric environment, but not in the oral or esophageal environment, which prevents premature release of the system prior to reaching the stomach.

In one embodiment, the system will be folded or compressed into a compacted state in order to fit into the capsule, for example, in a manner such as that shown in FIG. 3. Once the capsule dissolves in the stomach, the system will adopt a configuration suitable for gastric retention, for example, in a manner such as that shown in FIG. 2 or FIG. 2A. Preferred capsule sizes are 00 and 00el (a 00el-size capsule has the approximate length of a 000 capsule and the approximate width of a 00 capsule), which then places constraints on the length and diameter of the folded system.

Once released from the container, the system adopts an uncompacted state with dimensions suitable to prevent passage of the gastric residence system through the pyloric sphincter. In one embodiment, the system has at least two perpendicular dimensions, each of at least 2 cm in length; that is, the gastric residence system measures at least about 2 cm in length over at least two perpendicular directions. In another embodiment, the perimeter of the system in its uncompacted state, when projected onto a plane, has two perpendicular dimensions, each of at least 2 cm in length. The two perpendicular dimensions can independently have lengths of from about 2 cm to about 7 cm, about 2 cm to about 6 cm, about 2 cm to about 5 cm, about 2 cm to about 4 cm, about 2 cm to about 3 cm, about 3 cm to about 7 cm, about 3 cm to about 6 cm, about 3 cm to about 5 cm, about 3 cm to about 4 cm, about 4 cm to about 7 cm, about 4 cm to about 6 cm, about 4 cm to about 5 cm, or about 4 cm to about 4 cm. These dimensions prevent passage of the gastric residence system through the pyloric sphincter.

Figure 2B:
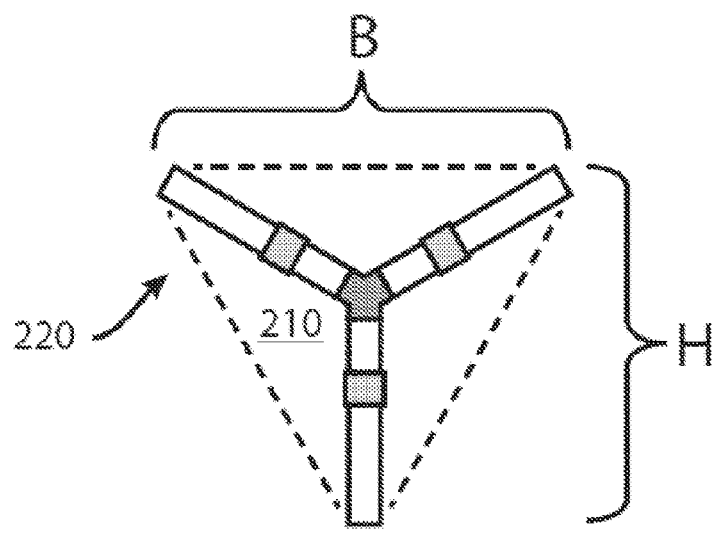
FIG. 2B shows certain dimensions of the gastric residence system of FIG. 2B.

For star-shaped polymers with N arms (where N is greater than or equal to three), the arms can have dimensions such that the system has at least two perpendicular dimensions, each of length as noted above. For example, the system of FIG. 2A can be circumscribed by a triangle, as shown in FIG. 2B, where the triangle is described by the length of its base B and height H, where B and H are perpendicular, and which comprise the two perpendicular dimensions of length as noted above. These two perpendicular dimensions are chosen as noted above in order to promote retention of the gastric residence system.

The system is designed to eventually break apart in the stomach at the end of the desired residence time (residence period). Once the coupling polymers break, the remaining components of the system are of dimensions that permit passage of the system through the pyloric sphincter, small intestine, and large intestine. Finally, the system is eliminated from the body by defecation, or by eventual complete dissolution of the system in the small and large intestines. Thus, the coupling polymers are placed in the gastric residence systems of the invention in a configuration such that, at the end of the desired residence period when the coupling polymers break or dissolve, the uncoupled components of the gastric residence system have dimensions suitable for passage through the pyloric sphincter and elimination from the digestive tract.

System Polymeric Composition

The choice of the individual polymers for the carrier polymer, coupling polymer, and elastomer influence many properties of the system, such as therapeutic agent elution rate (dependent on the carrier polymer, as well as other factors), the effective release period of the system, the residence time (residence period) of the system (dependent on the degradation of any of the polymers, principally the coupling polymers), the uncoupling time of the system if it passes into the intestine (dependent primarily on the enteric degradation rate of the coupling polymer, as discussed herein), and the shelf life of the system in its compressed form (dependent primarily on properties of the elastomer). As the systems will be administered to the gastrointestinal tract, all of the system components should be biocompatible with the gastrointestinal environment.

The rate of elution of therapeutic agent from the carrier polymer-agent component is affected by numerous factors, including the composition and properties of the carrier polymer, which may itself be a mixture of several polymeric and non-polymeric components; the properties of the therapeutic agent such as hydrophilicity/hydrophobicity, charge state, pKa, and hydrogen bonding capacity; and the properties of the gastric environment. In the aqueous environment of the stomach, avoiding burst release of a therapeutic agent (where burst release refers to a high initial delivery of active pharmaceutical ingredient upon initial deployment of the system in the stomach), particularly a hydrophilic agent, and maintaining sustained release of the agent over a period of time of days to weeks is challenging.

The residence time (residence period) of the systems in the stomach is adjusted by the choice of coupling polymers. The systems will eventually break down in the stomach, despite the use of enteric coupling polymers, as the mechanical action of the stomach and fluctuating pH will eventually weaken the enteric coupling polymers. Coupling polymers which degrade in a time-dependent manner in the stomach can also be used to adjust the time until the system breaks apart, and hence adjust the residence time. Once the system breaks apart, it passes into the intestines and is then eliminated.

The elastomer used in the systems influences the shelf life of the systems. When the systems are compressed, the elastomer is subjected to mechanical stress. The stress in turn can cause polymer creep, which, if extensive enough, can prevent the systems from returning to their uncompacted configurations when released from the capsules or other container; this in turn would lead to premature passage of the system from the stomach. Polymer creep can also be temperature dependent, and therefore the expected storage conditions of the systems also need to be considered when choosing the elastomer and other polymer components.

In some embodiments, the system components and polymers should not swell, or should have minimal swelling, in the gastric environment. The components should swell no more than about 20%, no more than about 10%, or preferably no more than about 5% when in the gastric environment over the period of residence.

In some embodiments, the system components and polymers can swell in the gastric environment.

Carrier Polymers for Carrier Polymer-Agent Component

The carrier polymer-agent component contains the therapeutic agent to be eluted from the gastric residence system in the gastric environment. Therapeutic agent is blended into the carrier polymer to form a carrier polymer-agent mixture. This mixture can be formed into the desired shape or shapes for use as carrier polymer-agent components in the systems, such as rods (cylindrical members) for the systems depicted in FIG. 1, FIG. 2, and FIG. 3. Exemplary carrier polymers suitable for use in this invention include, but are not limited to, hydrophilic cellulose derivatives (such as hydroxypropylmethyl cellulose, hydroxypropyl cellulose, hydroxymethyl cellulose, hydroxyethyl cellulose, carboxymethylcellulose, sodium-carboxymethylcellulose), cellulose acetate phthalate, poly(vinyl pyrrolidone), ethylene/vinyl alcohol copolymer, poly(vinyl alcohol), carboxyvinyl polymer (Carbomer), Carbopol® acidic carboxy polymer, polycarbophil, poly(ethyleneoxide) (Polyox WSR), polysaccharides and their derivatives, polyalkylene oxides, polyethylene glycols, chitosan, alginates, pectins, acacia, tragacanth, guar gum, locust bean gum, vinylpyrrolidonevinyl acetate copolymer, dextrans, natural gum, agar, agarose, sodium alginate, carrageenan, fucoidan, furcellaran, laminaran, hypnea, eucheuma, gum arabic, gum ghatti, gum karaya, arbinoglactan, amylopectin, gelatin, gellan, hyaluronic acid, pullulan, scleroglucan, xanthan, xyloglucan, maleic anhydride copolymers, ethylenemaleic anhydride copolymer, poly(hydroxyethyl methacrylate), ammoniomethacrylate copolymers (such as Eudragit RL or Eudragit RS), poly(ethylacrylate-methylmethacrylate) (Eudragit NE), Eudragit E (cationic copolymer based on dimethylamino ethyl methylacrylate and neutral methylacrylic acid esters), poly(acrylic acid), poly(methacrylic acid), polylactones such as poly(caprolactone), polyanhydrides such as poly[bis-(p-carboxyphenoxy)-propane anhydride], poly(terephthalic acid anhydride), polypeptides such as polylysine, polyglutamic acid, poly(ortho esters) such as copolymers of DETOSU with diols such as hexane diol, decane diol, cyclohexanedimethanol, ethylene glycol, polyethylene glycol and incorporated herein by reference those poly(ortho) esters described and disclosed in U.S. Pat. No. 4,304,767, starch, in particular pregelatinized starch, and starch-based polymers, carbomer, maltodextrins, amylomaltodextrins, dextrans, poly(2-ethyl-2-oxazoline), poly(ethyleneimine), polyurethane, poly(lactic acid), poly(glycolic acid), poly(lactic-co-glycolic acid) (PLGA), polyhydroxyalkanoates, polyhydroxybutyrate, and copolymers, mixtures, blends and combinations thereof. Polycaprolactone (PCL) is a preferred carrier polymer.

Release Enhancers and Solubilizers for Use in Gastric Residence Systems

Other excipients can be added to the carrier polymers to modulate the release of therapeutic agent. Such excipients can be added in amounts of from about 1% to about 50%, from about 1% to about 40%, from about 1% to about 30%, from about 1% to about 25%, from about 1% to about 20%, from about 1% to about 15%, from about 5% to about 10%, about 5%, or about 10%, of the carrier polymer-agent components. Examples of such excipients include Poloxamer 407 (available as Kolliphor P407, Sigma Cat #62035); Pluronic P407; Eudragit EPO (available from Evonik); hypromellose (available from Sigma, Cat #H3785), Kolliphor RH40 (available from Sigma, Cat #07076), polyvinyl caprolactam, polyvinyl acetate, polyethylene glycol, Aquaprenes, such as Aquaprene 8020 (a polydioxanone-polyethylene glycol polymer), and Soluplus (available from BASF; a copolymer of polyvinyl caprolactam, polyvinyl acetate, and polyethylene glycol).

Excipients can be added which function as solubilizers. That is, solubilizer excipients aid the dissolution of the therapeutic agent when an aqueous solution comes into contact with the gastric residence system. Such solubilizers can be added in amounts of from 1% to about 30%, from about 1% to about 25%, about 5% to about 25%, about 5% to about 20%, or about 5% to about 15%.

Excipients can be added which serve to enhance release of the therapeutic agent from the carrier polymer. Examples include pore-forming materials, which dissolve in a time-dependent manner and provide access for an aqueous solution to penetrate into the carrier polymer-therapeutic agent matrix, and wicking material which draw water into the carrier polymer-therapeutic agent matrix. Such release enhancers can be added in amounts of from about 1% to about 30%, from about 1% to about 25%, from about 1% to about 20%, from about 1% to about 15%, from about 5% to about 10%, about 5%, or about 10%. For materials which are particularly difficult to release from the carrier polymer, release enhancers can be added in larger amounts, such as from about 1% to about 50%, or from about 1% to about 40%.

Dispersants and stabilizing agents (preservatives) are also useful and are discussed in other sections herein.

Examples of solubilizing excipients, release-enhancing excipients, dispersants, and stabilizers/preservatives suitable for use in the invention are listed in Table 2.

TABLE 2

| Function | General examples | Specific examples |
| --- | --- | --- |
| Polymeric and non-polymeric solubilizers | Polyalkylene oxides<br>Polyethoxylated castor oil<br>Detergents | Kolliphor RH, Kolliphor P407, Soluplus, Cremophor, SDS |
| Release-enhancing excipient (porogen or wicking agent) | Acrylate polymers<br>Acrylate co-polymers<br>Polyvinylpyrrolidone | Eudragit RL<br>Eudragit RS<br>Eudragit E<br>Aquaprene (e.g., Aquaprene 8020) |
| Dispersant | porous inorganic material<br>polar inorganic material<br>non-toxic metal oxides<br>amphiphilic organic molecules<br>polysaccharides, cellulose, cellulose derivatives<br>fatty acids<br>detergents | silica, hydrophilic-fumed silica, hydrophobic colloidal silica, magnesium aluminum silicate, stearate salts, calcium stearate, magnesium stearate, microcrystalline cellulose, carboxymethylcellulose, hypromellose, phospholipids, polyoxyethylene stearates, zinc acetate, alginic acid, lecithin, sodium lauryl sulfate, aluminum oxide |
| Stabilizer/Preservative agent | Anti-oxidants<br>Anti-microbial agents<br>Buffering substances/pH stabilizers | Tocopherols<br>Alpha-tocopherol<br>Ascorbic acid; ascorbate salts<br>Carotenes<br>Butylated hydroxytoluene (BHT)<br>Butylated hydroxyanisole (BHA)<br>Fumaric acid<br>calcium carbonate<br>calcium lactate<br>calcium phosphate<br>sodium phosphate<br>sodium bicarbonate |

Methods of Manufacture of Carrier Polymer-Agent Components

Blending temperatures for incorporation of the therapeutic agent into polymeric matrices typically range from about 80° C. to about 120° C., although higher or lower temperatures can be used for polymers which are best blended at temperatures outside that range. When using free crystals of therapeutic agent, low blending temperatures from about 80° C. to about 100° C. can be used in order not to melt the agent particles or crystals. In certain circumstances, melting of therapeutic agent crystals during blending is acceptable when it aids in dispersing the agent in the matrix, and when the agent does not recrystallize into an undesirable form.

Blending temperatures should be used that are below the degradation temperature of the therapeutic agent, such that less than about 0.5%, 0.4%, 0.3%, 0.2%, 0.1%, 0.09%, 0.08%, 0.07%, 0.06%, 0.05%, 0.04%, 0.03%, 0.02%, 0.01%, or 0.005% of the drug degrades during blending or fabrication.

Hot melt extrusion can be used to prepare the carrier polymer-agent components. Single-screw or, preferably, twin-screw systems can be used. As noted, in some embodiments, carrier polymers should be used which can be melted at temperatures which do not melt the therapeutic agent particles blended into the polymer, since melting the particles of therapeutic agent would dramatically change the size distribution characteristics of the particles.

Plasticizers, such as triacetin, triethyl citrate, tributyl citrate, or poloxamers, can be added to the blend to reduce the temperature required for hot melt extrusion, which in turn can lower any degradation of therapeutic agent that may occur during hot melt extrusion. melt viscosity should be about 100 Pascal-second (Pa-s) to about 100,000 Pa-s for the material to be extrudable, such as between about 100 Pa-s to about 1,000 Pa-s, between about 100 Pa-s to about 10,000 Pa-s, between about 100 Pa-s to about 50,000 Pa-s, between about 1,000 Pa-s to about 10,000 Pa-s, between about 1,000 Pa-s to about 50,000 Pa-s, between about 10,000 Pa-s to about 50,000 Pa-s, between about 1,000 Pa-s to about 100,000 Pa-s, or between about 50,000 Pa-s to about 100,000 Pa-s; in some embodiments, extrusion is performed at a shear rate of about 10/s to about 1,000/s and a temperature of about 200° C. or less, such as 150° C. or less, 120° C. or less, or below the melting temperature of the therapeutic agent.

Melting and casting can also be used to prepare the carrier polymer-agent components. The carrier polymer and therapeutic agent, and any other desired components, are mixed together. The carrier polymer is melted (again, at temperatures which do not melt the particles of therapeutic agent), and the melt is mixed so that the agent particles are evenly distributed in the melt, poured into a mold, and allowed to cool.

Solvent casting can also be used to prepare the carrier polymer-agent components. The polymer is dissolved in a solvent, and particles of therapeutic agent are added. A solvent should be used which does not dissolve the agent particles, so as to avoid altering the size characteristics of the particles. The solvent-carrier polymer-agent particle mixture is then mixed to evenly distribute the particles, poured into a mold, and the solvent is evaporated.

Coupling Polymers

The coupling polymer is used to link one or more carrier polymer-agent components to one or more carrier polymer-agent components, to link one or more carrier polymer-agent components to one or more elastomer components, or to link one or more elastomer components to one or more elastomer components. In some embodiments, enteric polymers are used as coupling polymers. In some embodiments, time-dependent polymers which are pH-resistant, that is, less sensitive to changes in pH than enteric polymers, are used as coupling polymers. In some embodiments, both enteric polymers and time-dependent polymers which are less sensitive to changes in pH than enteric polymers are used as coupling polymers. Enteric polymers are relatively insoluble under acidic conditions, such as the conditions encountered in the stomach, but are soluble under the less acidic to basic conditions encountered in the small intestine. Enteric polymers which dissolve at about pH 5 or above can be used as coupling polymers, as the pH of the initial portion of the small intestine, the duodenum, ranges from about 5.4 to 6.1. If the gastric residence system passes intact through the pyloric valve, the enteric coupling polymer will dissolve and the components linked by the coupling polymer will break apart, allowing passage of the residence system through the small and large intestines. If, during treatment, the gastric residence system must be removed quickly for any reason, the patient can drink a mildly basic aqueous solution (such as a bicarbonate solution) in order to induce immediate de-coupling of the gastric residence system.

By "time-dependent polymer which are pH-resistant" (or equivalently, "pH-resistant time-dependent polymers") is meant that, under conditions where an enteric polymer would degrade to the point that it would no longer link the components together, the time-dependent polymer will still have sufficient mechanical strength to link the components together. In some embodiments, the time-dependent polymer retains about the same linking capacity, that is, about 100% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer retains at least about 90% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer retains at least about 75% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer retains at least about 60% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer retains at least about 50% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer retains at least about 25% of its linkage strength, after exposure to a solution between about pH 7 to about pH 8 as it has after exposure to a solution between about pH 2 to about pH 3, where the exposure is for about an hour, about a day, about three days, or about a week. In some embodiments, the time-dependent polymer resists breaking under a flexural force of about 0.2 Newtons (N), about 0.3 N, about 0.4 N, about 0.5 N, about 0.75 N, about 1 N, about 1.5 N, about 2 N, about 2.5 N, about 3 N, about 4 N, or about 5 N, after exposure to a solution between about pH 7 to about pH 8, where the exposure is for about an hour, about a day, about three days, or about a week. Linkage strength can be measured by any relevant test that serves to test coupling ability, such as the four-point bending flexural test (ASTM D790) described in Example 18.

Exemplary coupling polymers include, but are not limited to, cellulose acetate phthalate, cellulose acetate succinate, methylcellulose phthalate, ethylhydroxycellulose phthalate, polyvinylacetatephthalate, polyvinylbutyrate acetate, vinyl acetate-maleic anhydride copolymer, styrene-maleic mono-ester copolymer, methacrylic acid methylmethacrylate copolymer, methyl acrylate-methacrylic acid copolymer, methacrylate-methacrylic acid-octyl acrylate copolymer, and copolymers, mixtures, blends and combinations thereof. Some of the enteric polymers that can be used in the invention are listed in Table 3, along with their dissolution pH. (See Mukherji, Gour and Clive G. Wilson, "Enteric Coating for Colonic Delivery," Chapter 18 of Modified-Release Drug Delivery Technology (editors Michael J. Rathbone, Jonathan Hadgraft, Michael S. Roberts), Drugs and the Pharmaceutical Sciences Volume 126, New York: Marcel Dekker, 2002.) Preferably, enteric polymers that dissolve at a pH of no greater than about 5 or about 5.5 are used. Poly(methacrylic acid-co-ethyl acrylate) (sold under the trade name EUDRAGIT L 100-55; EUDRAGIT is a registered trademark of Evonik Röhm GmbH, Darmstadt, Germany) is a preferred enteric polymer. Cellulose acetate phthalate, cellulose acetate succinate, and hydroxypropyl methylcellulose phthalate are also suitable enteric polymers.

In one embodiment, the enteric polymers used in the gastric residence system dissolve at a pH above about 4. In another embodiment, the enteric polymers used in the gastric residence system dissolve at a pH above about 5. In another embodiment, the enteric polymers used in the gastric residence system dissolve at a pH above about 6. In another embodiment, the enteric polymers used in the gastric residence system dissolve at a pH above about 7. In another embodiment, the enteric polymers used in the gastric residence system dissolve at a pH above about 7.5. In another embodiment, the enteric polymers used in the gastric residence system dissolve at a pH between about 4 and about 5. In another embodiment, the enteric polymers used in the gastric residence system dissolve at a pH between about 4 and about 6. In another embodiment, the enteric polymers used in the gastric residence system dissolve at a pH between about 4 and about 7. In another embodiment, the enteric polymers used in the gastric residence system dissolve at a pH between about 4 and about 7.5. In another embodiment, the enteric polymers used in the gastric residence system dissolve at a pH between about 5 and about 6. In another embodiment, the enteric polymers used in the gastric residence system dissolve at a pH between about 5 and about 7. In another embodiment, the enteric polymers used in the gastric residence system dissolve at a pH between about 5 and about 7.5. In another embodiment, the enteric polymers used in the gastric residence system dissolve at a pH between about 6 and about 7. In another embodiment, the enteric polymers used in the gastric residence system dissolve at a pH between about 6 and about 7.5.

TABLE 3

| Polymer | Dissolution pH |
| --- | --- |
| Cellulose acetate phthalate | 6.0-6.4 |
| Hydroxypropyl methylcellulose phthalate 50 | 4.8 |
| Hydroxypropyl methylcellulose phthalate 55 | 5.2 |
| Polyvinylacetate phthalate | 5.0 |
| Methacrylic acid-methyl methacrylate copolymer (1:1) | 6.0 |
| Methacrylic acid-methyl methacrylate copolymer (2:1) | 6.5-7.5 |
| Methacrylic acid-ethyl acrylate copolymer (2:1) | 5.5 |
| Shellac | 7.0 |
| Hydroxypropyl methylcellulose acetate succinate | 7.0 |
| Poly (methyl vinyl ether/maleic acid) monoethyl ester | 4.5-5.0 |
| Poly (methyl vinyl ether/maleic acid) n-butyl ester | 5.4 |

Additional preferred polymers for use as coupling polymers are polymers that degrade in a time-dependent manner in the gastric environment. The liquid plasticizer triacetin releases from a polymer formulation in a time-dependent manner over seven days in simulated gastric fluid, while Plastoid B retains its strength over a seven-day period in simulated gastric fluid. Thus, a polymer that degrades in a time-dependent manner can be readily prepared by mixing Plastoid B and triacetin; the degradation time of the Plastoid B-triacetin mixture can be extended by increasing the amount of Plastoid B used in the mixture (that is, using less triacetin in the mixture), while the degradation time can be decreased by decreasing the amount of Plastoid B used in the mixture (that is using more triacetin in the mixture).

In some embodiments, the carrier polymer-agent components are elongate members comprised of segments attached by enteric polymers. In some embodiments, the carrier polymer-agent components are attached to the elastomer component of the system by enteric polymers. In any of these embodiments, when enteric polymers are used for both segment-to-segment attachments and for attachment of the elongate members to the elastomeric component, the enteric polymer used for segment-segment attachments can be the same enteric polymer as the enteric polymer used for attachment of the elongate members to the elastomeric component, or the enteric polymer used for segment-segment attachments can be a different enteric polymer than the enteric polymer used for attachment of the elongate members to the elastomeric component. The enteric polymers used for the segment-segment attachments can all be the same enteric polymer, or can all be different enteric polymers, or some enteric polymers in the segment-segment attachments can be the same and some enteric polymers in the segment-segment attachments can be different. That is, the enteric polymer(s) used for each segment-segment attachment and the enteric polymer used for attachment of the elongate members to the elastomeric component can be independently chosen.

Elastomers

Elastomers (also referred to as elastic polymers or tensile polymers) can be used as coupling polymers, and enable the gastric residence system to be compacted, such as by being folded or compressed, into a form suitable for administration to the stomach by swallowing a container or capsule containing the compacted system. Upon dissolution of the capsule in the stomach, the gastric residence system expands into a shape which prevents passage of the system through the pyloric sphincter of the patient for the desired residence time (residence period) of the system. Thus, the elastomer must be capable of being stored in a compacted configuration in a capsule for a reasonable shelf life, and of expanding to its original shape, or approximately its original shape, upon release from the capsule. In one embodiment, the elastomer is an enteric polymer, such as those listed in Table 3. In another embodiment, the coupling polymer(s) used in the system are also elastomers. FIG. 1 shows an example of a system where the coupling polymers are also elastomers, in that the circular ring is folded at the joints formed by the coupling polymers for packaging into, for example, a capsule.

In one embodiment, both the coupling polymer and elastomer are enteric polymers, which provides for more complete breakage of the system into the carrier polymer-agent pieces if the system enters the intestine, or if the patient drinks a mildly basic solution in order to induce passage of the system.

Examples of elastomers which can be used include urethane-cross-linked polycaprolactones (see Example 10, section B), poly(acryloyl 6-aminocaproic acid) (PA6ACA), poly(methacrylic acid-co-ethyl acrylate) (EUDRAGIT L 100-55), and mixtures of poly(acryloyl 6-aminocaproic acid) (PA6ACA) and poly(methacrylic acid-co-ethyl acrylate) (EUDRAGIT L 100-55) (see Example 11).

Figure 2C:
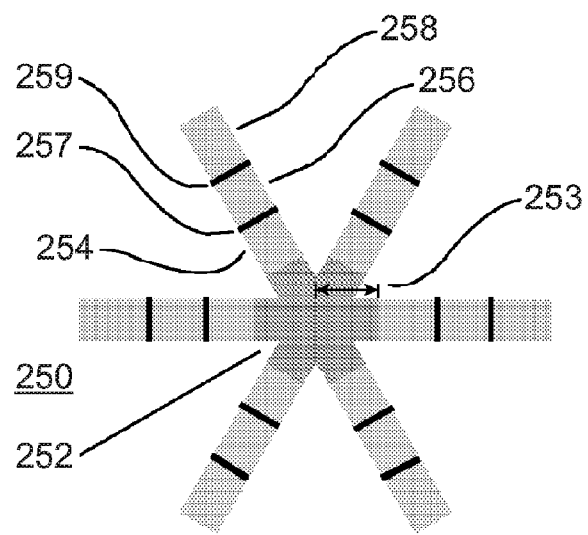
FIG. 2C shows another embodiment of a gastric residence system of the invention.

Flexible coupling polymers, i.e., elastomeric coupling polymers or elastomers, are used as the central polymer in the star-shaped or stellate design of the gastric residence systems. A particularly preferred elastomer for use as the central elastomer of the stellate or star configuration is silicone rubber. Liquid silicone rubber (LSR) can be molded easily and cured into a desired shape. The Dow Corning QP-1 series, comprising cross-linked dimethyl and methyl-vinyl siloxane copolymers and reinforcing silica, are examples of such silicone rubber polymers (see, for example, the Web site www.dowcorning.com/DataFiles/090276fe8018ed07.pdf). Elongate members comprising segments of carrier polymer-agent components can then be attached to the central silicone rubber elastomer; FIG. 2C provides one embodiment of this configuration of a gastric residence system of the invention. Another elastomer which can be used as the central elastomer in the stellate design is crosslinked polycaprolactone, such as the elastomer prepared in Example 10B.

Manufacture/Assembly of System

A stellate or star-shaped design embodiment of the gastric residence system can be assembled by preparing carrier polymer-agent components as "arms" in the shape of elongate members, where the arms are attached to a central elastomer. When the arms are prepared in the shape of a cylinder, they comprise a flat proximal end (one base of the cylinder, the first base), a distal end (the other base of the cylinder, a second base), and a curved outer surface therebetween enclosing the volume of the cylinder. The arms can also be prepared in the shape of triangular prisms, rectangular prisms, or other shapes.

The central elastomer of the gastric residence system can be prepared in the shape of an "asterisk" (or star), such as element 252 of one embodiment of the gastric residence system 250 shown in FIG. 2C. In FIG. 2C, central elastomer 252 is asterisk-shaped; the branches of the asterisk are attached to carrier polymer-agent segment 254; segment 254 is attached to carrier polymer-agent segment 256 via enteric linker 257; segment 256 is attached to carrier polymer-agent segment 258 via enteric linker 259; and the assembly of 254-257-256-259-258 forms one arm of the system 250. The elongate members (arms) comprised of segments of carrier polymer-agent components, shown as 254-257-256-259-258 in FIG. 2C, can then be attached to the ends of each branch of the asterisk by melt interfacing, adhesives, solvent welding, or other methods. The components in FIG. 2C are not necessarily drawn to scale Example 10 describes preparation of carrier polymer-agent component "arms" (Section A) and central elastomer (Section B).

Manufacture of gastric residence systems of the invention can be performed by a method comprising:

A. Forming a flexible coupling polymer component. In some embodiments, the flexible coupling polymer component is asterisk-shaped with a plurality of at least three branches (for preparation of the star configuration).

B. Forming a plurality of at least three carrier polymer-agent components, which are elongate members comprising a proximal end and a distal end.

Note that forming step A and forming step B can be performed in any order, or simultaneously.

C. Attaching the elongate members to the flexible coupling polymer component. When the elongate members are attached, and in the absence of any external constraining forces, the resulting assembly is the gastric residence system in its uncompacted form. The elongate members are attached to the flexible coupling polymer component such that, in its uncompacted form, the gastric residence system has at least two perpendicular dimensions, each dimension of at least two centimeters, that is, the gastric residence system measures at least about 2 cm in length over at least two perpendicular directions; or the perimeter of the gastric residence system in its uncompacted state, when projected onto a plane, has two perpendicular dimensions, each of at least 2 cm in length. (Further possible values for the lengths of the perpendicular dimensions are provided in the section describing System Dimensions.)

In order to place the gastric residence system into a capsule or other container for administration to a patient, a further step can be performed, comprising:

D. Compacting the gastric residence system and inserting the system into a container, such as a capsule, suitable for oral administration or administration through a gastric tube or feeding tube.

Step A, the formation of a flexible coupling polymer, can be performed by any method suitable for preparing a shaped polymer, such as by injection molding, gravity molding, compression molding, extrusion, hot melt extrusion, or three-dimensional printing. The flexible coupling polymer can be formed in the shape of a ring, a torus, a sphere, an oblate ellipsoid (also called an oblate spheroid, an ellipsoid, or an oblate sphere), or any other shape which has at least one axis of rotational symmetry, such as a cube or a rectangular cuboid. Optionally, the shape of the flexible coupling polymer can have branches, protrusions, or convexities where the carrier polymer-agent components which are elongate members can be attached. Optionally, the shape of the flexible coupling polymer can have indentations, concavities, dimples, or recesses where the carrier polymer-agent components which are elongate members can be attached.

Step B, the formation of the plurality of at least three carrier polymer-agent components, in the shape of elongate members, can likewise be performed by any suitable method for making shaped polymers, such as injection molding, gravity molding, compression molding, extrusion, hot melt extrusion, or three-dimensional printing using the carrier polymer-agent mixture. Prior to formation, the therapeutic agent is milled as described herein, and then mixed with the appropriate carrier polymer, and any desired release enhancers, solubilizers, dispersants, stabilizers, and other ingredients as described herein. The elongate members can be formed in the shape of solid rectangular prisms, solid triangular prisms, or solid cylinders. Additionally, as noted herein, the elongate members can be formed from two, three, or more segments which are coupled by coupling polymers, coupled by enteric polymers, time-dependent linkers, or by both enteric polymers and time-dependent linkers. Elongate members can be formed by joining together segments using butt joints (that is, the end of one segment can be joined to the end of another segment by adhesion, such as by a film of enteric polymer between and adhering to the ends of both of the segments), or by melting segments together, or can be formed by joining together segments using collar joints (that is, a film of an enteric polymer can be wrapped around the ends of two segments, joining them together).

Step C, attaching the carrier polymer-agent component elongate members to the flexible coupling polymer component, can be performed by various methods, such as melt interfacing, adhesives, solvent welding, or any other method suitable for attachment of polymers. If the flexible coupling polymer has branches, collar joints can be used for attaching the carrier polymer-agent component elongate members to the flexible coupling polymer component. The attachments of the carrier polymer-agent component elongate members to the flexible coupling polymer component can be formed using enteric polymers. Once the carrier polymer-agent components are attached to the flexible coupling polymer component, the gastric residence system will be in its uncompacted form in the absence of any external constraining forces.

In the stellate configuration, melt interfacing, or heat welding, of the elongate members to the flexible coupling polymer can be accomplished by providing a small portion of carrier polymer (without therapeutic agent or excipient) at various locations on the central elastomer. Local heating of the end of the elongate member to be attached to the flexible coupling polymer and of the corresponding small portion of carrier polymer on the central elastomer, followed by joining the elongate member to the small portion of carrier polymer and cooling of the system, provides a linkage between the elongate member and the central elastomer.

As described in Example 10 below, a central elastomer with small portions of carrier polymer can be prepared as follows:

providing elongate members comprising pure carrier polymer, or carrier polymer of the desired composition;

placing the elongate members in a mold for preparation of the central elastomer, and adding the pre-polymer or precursor ingredients of the central elastomer to the mold, where the elongate members are placed in a manner such that one end of the elongate members is bonded to the central elastomer after curing of the pre-polymer or precursor ingredients; in one embodiment, the mold is star-shaped with three, four, five, six, seven, or eight arms, preferably three, four, five or six arms;

curing the pre-polymer or precursor ingredients of the central elastomer such that one end of the elongate members is bonded to the central elastomer;

cutting the elongate members to leave a portion of elongate member bonded to the central elastomer sufficient for heat-welding to a different elongate member comprising carrier polymer and therapeutic agent.

Different elongate members comprising carrier polymer, therapeutic agent, and any desired excipients and/or dispersants can then be heat-welded or melt-interfaced to the central elastomer, by using the small portion of the elongate member comprising carrier polymer which remains attached to the central elastomer after cutting.

In further embodiments, the heat-welding of the portion of elongate member bonded to the central elastomer to the different elongate member comprising carrier polymer and therapeutic agent is then performed, forming a heat-welded structure. The heat-welding can be performed at any temperature that serves to provide a stable weld. In some embodiments, when the carrier polymer is polycaprolactone (such as a polycaprolactone of $M_n$ about 80 kDa), heat welding can be carried out at about 90° C., about 93° C., about 95° C., about 100° C., about 110° C., about 120° C., about 130° C., about 140° C., about 150° C., about 160° C., about 170° C., about or 180° C., or between about 90° C. to about 180° C., about 90° C. to about 170° C., between about 140° C. to about 180° C., or between about 150° C. to about 170° C., or between about 155° C. to about 165° C. After heat-welding, the heat-welded structure can be exposed to a room-temperature environment for about 24 hours, or a cooled environment between about 2° C. and about 12° C., between about 5° C. and about 15° C., between about 5° C. and about 10° C., or about 8° C., for about 24 hours.

Testing of the strength of the heat weld formed between the carrier polymer that does not comprise therapeutic agent and an elongate member comprising carrier polymer, therapeutic agent, and any desired excipients and/or dispersants was performed to ensure that the weld will not break under the compressive forces in the stomach. Example 34 to heat-welding describes such a test. In the Example, heat-welding at 160° C., followed by refrigeration of the welded structure at 8° C. for 24 hours, provided a weld that resisted a flexural force of about 100 N with none of the tested welds breaking. When testing the strength of the heat weld between the different polymer blends, the system as finally assembled can be tested for breakage strength. Alternatively, an elongate member comprising carrier polymer that does not comprise therapeutic agent and an elongate member comprising carrier polymer, therapeutic agent, and any desired excipients and/or dispersants can be welded together for easier manipulation; omitting the central polymer for such a test piece permits a single conjoined elongate member to be used in a flexural test. After heat welding, and after the welded structure cools (either at room temperature or reduced temperature, such as about 8° C.) for about 24 hours, a four-point bending flexural test, such as ASTM D790 (used below in Example 18) can be used to evaluate the strength of the arms. In some embodiments, the heat weld can resist a bending force of about 10 N without breaking. In some embodiments, the heat weld can resist a bending force of about 15 N without breaking. In some embodiments, the heat weld can resist a bending force of about 20 N without breaking. In some embodiments, the heat weld can resist a bending force of about 25 N without breaking. In some embodiments, the heat weld can resist a bending force of about 30 N without breaking. In some embodiments, the heat weld can resist a bending force of about 40 N without breaking. In some embodiments, the heat weld can resist a bending force of about 50 N without breaking. In some embodiments, the heat weld can resist a bending force of about 60 N without breaking. In some embodiments, the heat weld can resist a bending force of about 70 N without breaking. In some embodiments, the heat weld can resist a bending force of about 80 N without breaking. In some embodiments, the heat weld can resist a bending force of about 90 N without breaking. In some embodiments, the heat weld can resist a bending force of about 100 N without breaking.

Step D, compacting the gastric residence system and inserting the system into a container, can be performed either manually or mechanically, by compacting, folding, or compressing the gastric residence system into its compacted configuration, and insertion of the system into a capsule or other container of appropriate size.

Measurement of Release Rates

The nature of the solid state of the therapeutic agent blended with the carrier polymer also influences the release rate of the therapeutic agent from the gastric residence systems. The rate of release of the therapeutic agent from the systems can be measured in vitro by placing the system in simulated gastric juice (simulated gastric fluid, or SGF), as noted below in Example 3. The rate of release of the therapeutic agent from the systems can be measured in vivo by administration of the system to an experimental animal, as described below in Example 8A, or by administration of the system to a human patient, as described below in Example 8B.

Release rates of therapeutic agent, or pharmaceutically acceptable salt thereof, from the gastric residence systems can be measured in a variety of environments, including 0.1N HCl in water, simulated gastric fluid, fasted-state simulated gastric fluid, fed-state simulated gastric fluid, the stomach of an animal, the stomach of a pig, the stomach of a dog, and the stomach of a human.

Gastric Delivery Pharmacokinetics for Therapeutic Agent Gastric Residence Systems The gastric residence systems of the invention provide for high bioavailability of the therapeutic agent as measured by $AUC_{inf}$ after administration of the systems, relative to the bioavailability of a conventional oral formulation of the therapeutic agent. The systems also provide for maintenance of a substantially constant plasma level of therapeutic agent.

Relative bioavailability, $F_{REL}$, of two different formulations, formulation A and formulation B, is defined as:

$$F_{REL}=100\times(AUC_A\times Dose_B)/(AUC_B\times Dose_A)$$

where $AUC_A$ is the area under the curve for formulation A, $AUC_B$ is the area under the curve for formulation B, $Dose_A$ is the dosage of formulation A used, and $Dose_B$ is the dosage of formulation B used. AUC, the area under the curve for the plot of therapeutic agent plasma concentration versus time, is usually measured at the same time (t) after administration of each formulation, in order to provide the relative bioavailability of the formulations at the same time point. $AUC_{inf}$ refers to the AUC measured or calculated over "infinite" time, that is, over a period of time starting with initial administration, and ending where the plasma level of the therapeutic agent has dropped to a negligible amount.

In one embodiment, the substantially constant plasma level of the therapeutic agent provided by the gastric residence systems of the invention can range from at or above the trough level of the plasma level of the therapeutic agent when administered daily in a conventional oral formulation (that is, $C_{min}$ of therapeutic agent administered daily in immediate-release formulation) to at or below the peak plasma level of the therapeutic agent when administered daily in a conventional oral formulation (that is, $C_{max}$ of therapeutic agent administered daily in immediate-release formulation). In another embodiment, the substantially constant plasma level of the therapeutic agent provided by the gastric residence systems of the invention can be about 50% to about 90% of the peak plasma level of therapeutic agent when administered daily in a conventional oral formulation (that is, $C_{max}$ of the therapeutic agent administered daily in immediate-release formulation). The substantially constant plasma level of the therapeutic agent provided by the gastric residence systems of the invention can be about 75% to about 125% of the average plasma level of the therapeutic agent when administered daily in a conventional oral formulation (that is, $C_{ave}$ of the therapeutic agent administered daily in immediate-release formulation), or about 50% to about 120% of $C_{ave}$. The substantially constant plasma level of the therapeutic agent provided by the gastric residence systems of the invention can be at or above the trough level of plasma level of the therapeutic agent when administered daily in a conventional oral formulation (that is, $C_{min}$ of the therapeutic agent administered daily in immediate-release formulation), such as about 100% to about 150% of $C_{min}$, or about 50% to about 150% of $C_{min}$.

The gastric residence systems of the invention can provide bioavailability of the therapeutic agent released from the system of at least about 50%, at least about 60%, at least about 70%, or at least about 80% of that provided by an immediate release form comprising the same amount of the therapeutic agent. As indicated above, the bioavailability is measured by the area under the plasma concentration-time curve ($AUC_{inf}$).

Therapeutic Agents for Use in Gastric Residence Systems

Therapeutic agents which can be administered to or via the gastrointestinal tract can be used in the gastric residence systems of the invention. Therapeutic agents include, but are not limited to, drugs, pro-drugs, biologics, and any other substance which can be administered to produce a beneficial effect on an illness or injury. Therapeutic agents that can be used in the gastric residence systems of the invention include statins, such as rosuvastatin; nonsteroidal anti-inflammatory drugs (NSAIDs) such as meloxicam; selective serotonin reuptake inhibitors (SSRIs) such as escitalopram and citalopram; blood thinners, such as clopidogrel; steroids, such as prednisone; antipsychotics, such as aripiprazole and risperidone; analgesics, such as buprenorphine; opioid antagonists, such as naloxone; anti-asthmatics such as montelukast; anti-dementia drugs, such as memantine; cardiac glycosides such as digoxin; alpha blockers such as tamsulosin; cholesterol absorption inhibitors such as ezetimibe; anti-gout treatments, such as colchicine; antihistamines, such as loratadine and cetirizine, opioids, such as loperamide; proton-pump inhibitors, such as omeprazole; antiviral agents, such as entecavir; antibiotics, such as doxycycline, ciprofloxacin, and azithromycin; anti-malarial agents; levothyroxine; substance abuse treatments, such as methadone and varenicline; contraceptives; stimulants, such as caffeine; and nutrients such as folic acid, calcium, iodine, iron, zinc, thiamine, niacin, vitamin C, vitamin D, biotin, plant extracts, phytohormones, and other vitamins or minerals. Biologics that can be used as therapeutic agents in the gastric residence systems of the invention include proteins, polypeptides, polynucleotides, and hormones. Exemplary classes of therapeutic agents include, but are not limited to, analgesics; anti-analgesics; anti-inflammatory drugs; antipyretics; antidepressants; antiepileptics; antipsychotic agents; neuroprotective agents; anti-proliferatives, such as anti-cancer agents; antihistamines; antimigraine drugs; hormones; prostaglandins; antimicrobials, such as antibiotics, antifungals, antivirals, and antiparasitics; anti-muscarinics; anxiolytics; bacteriostatics; immunosuppressant agents;

sedatives; hypnotics; antipsychotics; bronchodilators; anti-asthma drugs; cardiovascular drugs; anesthetics; anti-coagulants; enzyme inhibitors; steroidal agents; steroidal or non-steroidal anti-inflammatory agents; corticosteroids; dopaminergics; electrolytes; gastro-intestinal drugs; muscle relaxants; nutritional agents; vitamins; parasympathomimetics; stimulants; anorectics; anti-narcoleptics; and antimalarial drugs, such as quinine, lumefantrine, chloroquine, amodiaquine, pyrimethamine, proguanil, chlorproguanil-dapsone, sulfonamides (such as sulfadoxine and sulfamethoxypyridazine), mefloquine, atovaquone, primaquine, halofantrine, doxycycline, clindamycin, artemisinin, and artemisinin derivatives (such as artemether, dihydroartemisinin, arteether and artesunate). The term "therapeutic agent" includes salts, solvates, polymorphs, and co-crystals of the aforementioned substances. In certain embodiments, the therapeutic agent is selected from the group consisting of cetirizine, rosuvastatin, escitalopram, citalopram, risperidone, olanzapine, donezepil, and ivermectin. In another embodiment, the therapeutic agent is one that is used to treat a neuropsychiatric disorder, such as an anti-psychotic agent or an anti-dementia drug such as memantine.

In some embodiments of the invention disclosed herein, the therapeutic agent can exclude adamantane-class drugs. In some embodiments of the invention disclosed herein, the therapeutic agent can exclude any one or more of memantine; amantadine; adapromine; nitromemantine; rimantadine; bromantane; neramexane; or tromantadine; or a pharmaceutically acceptable salt of memantine, amantadine, adapromine, nitromemantine, rimantadine, bromantane, or tromantadine. In some embodiments of the invention disclosed herein, the therapeutic agent can exclude memantine. In some embodiments of the invention disclosed herein, the therapeutic agent can exclude a salt of memantine or a pharmaceutically acceptable salt of memantine.

Crystalline and Amorphous Forms of Therapeutic Agents

Therapeutic agents can be used in the gastric residence systems of the invention in any suitable crystalline form, or in amorphous form, or in both crystalline form or forms and amorphous forms. That is, therapeutic agent or drug particles contained in the gastric residence systems can be used in crystalline form, in amorphous form, or in a mixture of crystalline forms (either a single crystalline form, or multiple crystalline forms) and amorphous forms, so as to provide a desired rate of release or desired physical or chemical properties.

Therapeutic Agent Classes of Interest

Gastric residence systems are well-suited for use in treatment of diseases and disorders which present difficulties with patient compliance, and thus in some embodiments, the gastric residence systems are used to treat a disease or disorder where patient compliance with a medication regimen is problematic. Such diseases and disorders include neuropsychiatric diseases and disorders, dementia and other diseases and disorders which affect memory, Alzheimer's disease, psychoses, schizophrenia, and paranoia. Accordingly, therapeutic agents which can be used in the gastric residence systems include, but are not limited to, anti-dementia agents, anti-Alzheimer's disease agents, and antipsychotics.

Hydrophilic Therapeutic Agents

Exemplary hydrophilic therapeutic agents which can be used in the systems include risperidone, cetirizine, memantine, and olanzapine.

Hydrophobic Therapeutic Agents

Exemplary hydrophobic therapeutic agents which can be used in the systems include aripiprazole, ivermectin, rosuvastatin, citalopram, and escitalopram.

Physical-Chemical Classes of Drugs

Example 27 herein shows partition coefficients for different therapeutic agents between a polycaprolactone (PCL) phase and a fasted simulated gastric fluid (FasSGF) phase ($P_{PCL}$) and between octanol and water ($P_{OCT}$). Such partition coefficients can be used to guide selection of excipients and dispersants for use in gastric residence systems comprising those therapeutic agents. A higher $P_{PCL}$ (or log $P_{PCL}$) indicates a greater affinity of the therapeutic agent for the PCL matrix. Consequently, the amount of release enhancer, solubilizer, or both release enhancer and solubilizer can be increased to promote release of the therapeutic agent from the PCL matrix.

In some embodiments, in gastric residence systems where the carrier polymer-agent components comprise a therapeutic agent having a $P_{PCL}$ lower than about 0, a solubilizer can be used in an amount of about 1% to about 30%; or a release enhancer can be used in an amount of about 1% to about 30%, or both a solubilizer can be used in an amount of about 1% to about 30% and a release enhancer can be used in an amount of about 1% to about 30% can be used; in further embodiments, a proviso is added that the total amount of solubilizer and release enhancer does not comprise more than about 30% of the carrier polymer-agent components. In some embodiments, in gastric residence systems where the carrier polymer-agent components comprise a therapeutic agent having a $P_{PCL}$ lower than about 1, a solubilizer can be used in an amount of about 1% to about 30%; or a release enhancer can be used in an amount of about 1% to about 30%, or both a solubilizer can be used in an amount of about 1% to about 30% and a release enhancer can be used in an amount of about 1% to about 30% can be used; in further embodiments, a proviso is added that the total amount of solubilizer and release enhancer does not comprise more than about 30% of the carrier polymer-agent components. In some embodiments, in gastric residence systems where the carrier polymer-agent components comprise a therapeutic agent having a $P_{PCL}$ lower than about 2, a solubilizer can be used in an amount of about 1% to about 30%; or a release enhancer can be used in an amount of about 1% to about 30%, or both a solubilizer can be used in an amount of about 1% to about 30% and a release enhancer can be used in an amount of about 1% to about 30% can be used; in further embodiments, a proviso is added that the total amount of solubilizer and release enhancer does not comprise more than about 30% of the carrier polymer-agent components. In some embodiments, in gastric residence systems where the carrier polymer-agent components comprise a therapeutic agent having a $P_{PCL}$ lower than about 5, a solubilizer can be used in an amount of about 1% to about 30%; or a release enhancer can be used in an amount of about 1% to about 30%, or both a solubilizer can be used in an amount of about 1% to about 30% and a release enhancer can be used in an amount of about 1% to about 30% can be used; in further embodiments, a proviso is added that the total amount of solubilizer and release enhancer does not comprise more than about 30% of the carrier polymer-agent components. In some embodiments, in gastric residence systems where the carrier polymer-agent components comprise a therapeutic agent having a $P_{PCL}$ lower than about 10, a solubilizer can be used in an amount of about 1% to about 30%; or a release enhancer can be used in an amount of about 1% to about 30%, or both a solubilizer can be used in an amount of about 1% to about 30% and a release enhancer can be used in an amount of about 1% to about 30% can be used; in further embodiments, a proviso is added that the total amount of solubilizer and release enhancer does not comprise more than about 30% of the carrier polymer-agent components.

In some embodiments, in gastric residence systems where the carrier polymer-agent components comprise a therapeutic agent having a solubility higher than about 1 mg/ml in 0.1N HCl, a solubilizer can be used in an amount of about 1% to about 30%; or a release enhancer can be used in an amount of about 1% to about 30%, or both a solubilizer can be used in an amount of about 1% to about 30% and a release enhancer can be used in an amount of about 1% to about 30% can be used; in further embodiments, a proviso is added that the total amount of solubilizer and release enhancer does not comprise more than about 30% of the carrier polymer-agent components. In some embodiments, in gastric residence systems where the carrier polymer-agent components comprise a therapeutic agent having a solubility higher than about 5 mg/ml in 0.1N HCl, a solubilizer can be used in an amount of about 1% to about 30%; or a release enhancer can be used in an amount of about 1% to about 30%, or both a solubilizer can be used in an amount of about 1% to about 30% and a release enhancer can be used in an amount of about 1% to about 30% can be used; in further embodiments, a proviso is added that the total amount of solubilizer and release enhancer does not comprise more than about 30% of the carrier polymer-agent components. In some embodiments, in gastric residence systems where the carrier polymer-agent components comprise a therapeutic agent having a solubility higher than about 10 mg/ml in 0.1N HCl, a solubilizer can be used in an amount of about 1% to about 30%; or a release enhancer can be used in an amount of about 1% to about 30%, or both a solubilizer can be used in an amount of about 1% to about 30% and a release enhancer can be used in an amount of about 1% to about 30% can be used; in further embodiments, a proviso is added that the total amount of solubilizer and release enhancer does not comprise more than about 30% of the carrier polymer-agent components. In some embodiments, in gastric residence systems where the carrier polymer-agent components comprise a therapeutic agent having a solubility higher than about 20 mg/ml in 0.1N HCl, a solubilizer can be used in an amount of about 1% to about 30%; or a release enhancer can be used in an amount of about 1% to about 30%, or both a solubilizer can be used in an amount of about 1% to about 30% and a release enhancer can be used in an amount of about 1% to about 30% can be used; in further embodiments, a proviso is added that the total amount of solubilizer and release enhancer does not comprise more than about 30% of the carrier polymer-agent components.

In some embodiments, in gastric residence systems where the carrier polymer-agent components comprise a therapeutic agent having a $P_{PCL}$ higher than about 10, a solubilizer can be used in an amount of about 1% to about 30%; or a release enhancer can be used in an amount of about 1% to about 30%, or both a solubilizer can be used in an amount of about 1% to about 30% and a release enhancer can be used in an amount of about 1% to about 30% can be used; in further embodiments, a proviso is added that the total amount of solubilizer and release enhancer does not comprise more than about 50% of the carrier polymer-agent components. In some embodiments, in gastric residence systems where the carrier polymer-agent components comprise a therapeutic agent having a $P_{PCL}$ higher than about 20, a solubilizer can be used in an amount of about 1% to about 30%; or a release enhancer can be used in an amount of about 1% to about 30%, or both a solubilizer can be used in an amount of about 1% to about 30% and a release enhancer can be used in an amount of about 1% to about 30% can be used; in further embodiments, a proviso is added that the total amount of solubilizer and release enhancer does not comprise more than about 50% of the carrier polymer-agent components. In some embodiments, in gastric residence systems where the carrier polymer-agent components comprise a therapeutic agent having a $P_{PCL}$ higher than about 30, a solubilizer can be used in an amount of about 1% to about 30%; or a release enhancer can be used in an amount of about 1% to about 30%, or both a solubilizer can be used in an amount of about 1% to about 30% and a release enhancer can be used in an amount of about 1% to about 30% can be used; in further embodiments, a proviso is added that the total amount of solubilizer and release enhancer does not comprise more than about 50% of the carrier polymer-agent components. In some embodiments, in gastric residence systems where the carrier polymer-agent components comprise a therapeutic agent having a $P_{PCL}$ higher than about 40, a solubilizer can be used in an amount of about 1% to about 30%; or a release enhancer can be used in an amount of about 1% to about 30%, or both a solubilizer can be used in an amount of about 1% to about 30% and a release enhancer can be used in an amount of about 1% to about 30% can be used; in further embodiments, a proviso is added that the total amount of solubilizer and release enhancer does not comprise more than about 50% of the carrier polymer-agent components. In some embodiments, in gastric residence systems where the carrier polymer-agent components comprise a therapeutic agent having a $P_{PCL}$ higher than about 50, a solubilizer can be used in an amount of about 1% to about 30%; or a release enhancer can be used in an amount of about 1% to about 30%, or both a solubilizer can be used in an amount of about 1% to about 30% and a release enhancer can be used in an amount of about 1% to about 30% can be used; in further embodiments, a proviso is added that the total amount of solubilizer and release enhancer does not comprise more than about 50% of the carrier polymer-agent components.

In some embodiments, in gastric residence systems where the carrier polymer-agent components comprise a therapeutic agent having a solubility lower than about 1 mg/ml in 0.1N HCl, a solubilizer can be used in an amount of about 1% to about 30%; or a release enhancer can be used in an amount of about 1% to about 30%, or both a solubilizer can be used in an amount of about 1% to about 30% and a release enhancer can be used in an amount of about 1% to about 30% can be used; in further embodiments, a proviso is added that the total amount of solubilizer and release enhancer does not comprise more than about 50% of the carrier polymer-agent components. In some embodiments, in gastric residence systems where the carrier polymer-agent components comprise a therapeutic agent having a solubility lower than about 0.5 mg/ml in 0.1N HCl, a solubilizer can be used in an amount of about 1% to about 30%; or a release enhancer can be used in an amount of about 1% to about 30%, or both a solubilizer can be used in an amount of about 1% to about 30% and a release enhancer can be used in an amount of about 1% to about 30% can be used; in further embodiments, a proviso is added that the total amount of solubilizer and release enhancer does not comprise more than about 50% of the carrier polymer-agent components. In some embodiments, in gastric residence systems where the carrier polymer-agent components comprise a therapeutic agent having a solubility lower than about 0.1 mg/ml in 0.1N HCl, a solubilizer can be used in an amount of about 1% to about 30%; or a release enhancer can be used in an amount of about 1% to about 30%, or both a solubilizer can be used in an amount of about 1% to about 30% and a release enhancer can be used in an amount of about 1% to about 30% can be used; in further embodiments, a proviso is added that the total amount of solubilizer and release enhancer does not comprise more than about 50% of the carrier polymer-agent components. In some embodiments, in gastric residence systems where the carrier polymer-agent components comprise a therapeutic agent having a solubility lower than about 0.05 mg/ml in 0.1N HCl, a solubilizer can be used in an amount of about 1% to about 30%; or a release enhancer can be used in an amount of about 1% to about 30%, or both a solubilizer can be used in an amount of about 1% to about 30% and a release enhancer can be used in an amount of about 1% to about 30% can be used; in further embodiments, a proviso is added that the total amount of solubilizer and release enhancer does not comprise more than about 50% of the carrier polymer-agent components.

Granulation

Granulation of drugs can be used to enhance solubility, particularly for hydrophobic drugs which are poorly soluble in water. Drugs can be granulated with solutions of solubilizers such as polyalkylene oxides (for example, polyethylene glycol (PEG), polypropylene glycol (PPG), PEG-PPG co-polymers, PEG-PPG block co-polymers), polyethoxylated castor oil, and detergents. In some embodiments, where the carrier polymer-agent components comprise a therapeutic agent having a solubility lower than about 1 mg/ml, 0.5 mg/ml, 0.1 mg/ml, or 0.05 mg/ml in 0.1N HCl, the therapeutic agent is granulated with one or more solubilizers, such as one of the foregoing solubilizers (polyalkylene oxides (for example, polyethylene glycol (PEG), polypropylene glycol (PPG), PEG-PPG co-polymers, PEG-PPG block co-polymers), polyethoxylated castor oil, and detergents) prior to blending with the carrier polymer. In some embodiments, where the carrier polymer-agent components comprise a therapeutic agent having a $P_{PCL}$ higher than about 10, about 20, about 30, about 40, or about 50, the therapeutic agent is granulated with one or more solubilizers, such as one of the foregoing solubilizers (polyalkylene oxides (for example, polyethylene glycol (PEG), polypropylene glycol (PPG), PEG-PPG co-polymers, PEG-PPG block co-polymers), polyethoxylated castor oil, and detergents) prior to blending with the carrier polymer.

Aripiprazole is a particularly difficult drug to solubilize, and in some embodiments, aripiprazole is granulated with one or more solubilizers prior to blending with the carrier polymer. Aripiprazole can be granulated with CAPROL 3GO, CAPTEX 355, CAPMUL MCM, Kolliphor P407, PVP, Kolliphor RH-40, SOLUPLUS, Kolliphor EL, and/or SDS to increase solubility and release from a gastric residence system. Kolliphor EL and SDS are preferred solubilizers for aripiprazole.

Granulation for hydrophobic drugs is preferably used in combination with relatively small drug particle sizes, such as embodiments where the therapeutic agent particles are smaller than about 20 microns in diameter, embodiments where the therapeutic agent particles are smaller than about 10 microns in diameter, embodiments where the therapeutic agent particles are smaller than about 5 microns in diameter, embodiments where at least about 80% of the therapeutic agent particles are smaller than about 20 microns in diameter, embodiments where at least about 80% of the therapeutic agent particles are smaller than about 10 microns in diameter, embodiments where at least about 80% of the therapeutic agent particles are smaller than about 5 microns in diameter, embodiments where at least about 80% of the mass of the therapeutic agent particles have sizes between about 1 micron and about 20 microns in diameter, embodiments where at least about 80% of the mass of the therapeutic agent particles have sizes between about 1 micron and about 10 microns in diameter, embodiments where at least about 80% of the mass of the therapeutic agent particles have sizes between about 1 micron and about 5 microns in diameter, embodiments where at least about 80% of the mass of the therapeutic agent particles have sizes between about 2 microns and about 20 microns in diameter, embodiments where at least about 80% of the mass of the therapeutic agent particles have sizes between about 2 microns and about 10 microns in diameter, embodiments where at least about 80% of the mass of the therapeutic agent particles have sizes between about 2 microns and about 5 microns in diameter, embodiments where at least about 80% of the mass of the therapeutic agent particles have sizes between about 5 microns and about 20 microns in diameter, or embodiments where at least about 80% of the mass of the therapeutic agent particles have sizes between about 5 microns and about 10 microns in diameter.

Low Dosage Agents

Drugs and other therapeutic agents which are administered at relatively low dosages, such as equal to or less than about 1 mg/day, about 0.5 mg/day, or about 0.1 mg/day, are also well-suited for use in the gastric residence systems of the invention. Examples of such agents which can be used in the gastric residence systems include, but are not limited to, levothyroxine, low dose contraceptives, and vitamins and other nutrients such as Vitamin A, Vitamin D, Vitamin K, folate, Vitamin B12, and biotin.

Cetirizine

Cetirizine, a hydrophilic drug, is a second-generation antihistamine (sgAH). Cetirizine is sold under the trade name Zyrtec® and other trade names Cetirizine is available in a variety of dosage forms. Typically, cetirizine is administered once daily, at a dosage of 5 mg or 10 mg. An extended-release formulation is available as Zyrtec D®, which combines cetirizine hydrochloride and pseudoephedrine hydrochloride. However, this "extended release" combination is administered more frequently (every twelve hours) than cetirizine alone, as the extended release refers primarily to pseudoephedrine release.

Cetirizine can be used to treat various allergic disorders and histamine-mediated (histamine-induced) disorders. Cetirizine is used to treat allergic rhinitis, allergic conjunctivitis, dermatitis, acute urticaria, chronic urticaria, pollen-induced asthma, pruritis, anaphylaxis, angioedema, Kimura's disease, and angiolymphoid hyperplasia with eosinophilia (ALHE).

Cetirizine has been formulated into pharmaceuticals as a racemic mixture of the dihydrochloride salts of (S)-cetirizine and (R)-cetirizine, and sold under the brand name Zyrtec® (ZYRTEC is a registered trademark of Johnson & Johnson Corporation, New Brunswick, N.J.). The melting point of the dihydrochloride is 225° C. (decomp.), while crystals of free cetirizine (the non-salt form, which exists as a zwitterion) melt at 110-115° C. (U.S. Pat. No. 4,525,358). (R)-cetirizine, known as levocetirizine, is the more active enantiomer, and pharmaceuticals containing levocetirizine dihydrochloride are sold under the brand name Xyzal® (XYZAL is a registered trademark of UCB Pharma, Brussels, Belgium). (S)-cetirizine is known as dextrocetirizine.

The relatively low melting point of cetirizine crystals in the free (non-salt) form, of about 110-115° C., poses particular challenges for formulating a polymeric matrix containing such crystals. Many polymers must be heated above 115° C. in order to soften and blend them with a drug, and/or in order to extrude or shape the polymer. Accordingly, formulating a mixture of free cetirizine crystals with a polymer requires judicious selection of the polymer and the blending conditions, in order to ensure that the cetirizine contained in the polymer is in the desired form, which in turn will affect the release rate of the drug from the polymer-drug blend.

Cetirizine is also known to oxidize (Dyakonov et al., Pharm. Res. 27(7):1318-24 (2010)), which is another challenge facing the development of extended-release formulations. Thus, formulations of cetirizine must also be resistant to oxidation or other degradation reactions over the period of extended release.

In any of the embodiments set forth herein where cetirizine is provided in the gastric residence system, the cetirizine present in the gastric residence system can be protected against oxidation, such that less than about 5% of the cetirizine in the carrier polymer-drug components of the system is oxidized after retention in the stomach for about 5 days.

In any of the embodiments set forth herein where cetirizine is provided in the gastric residence system, the gastric residence system can release between about 5 to 15 mg of cetirizine per day in the stomach.

In any of the embodiments set forth herein where cetirizine is provided in the gastric residence system, the gastric residence system provides bioavailability of cetirizine released from the system which is at least about 50% of the bioavailability provided by an immediate release form comprising the same amount of cetirizine. The bioavailability can be measured by the area under the plasma concentration-time curve ($AUC_{inf}$).

In any of the embodiments set forth herein where cetirizine is provided in the gastric residence system, the gastric residence system can comprise between about 40 mg to about 120 mg of cetirizine.

In one embodiment, the substantially constant plasma level of cetirizine provided by the gastric residence systems of the invention can range from at or above the trough level of the plasma level of cetirizine when administered daily in a conventional oral formulation (that is, $C_{min}$ of cetirizine administered daily in immediate-release formulation) to at or below the peak plasma level of cetirizine when administered daily in a conventional oral formulation (that is, $C_{max}$ of cetirizine administered daily in immediate-release formulation). In another embodiment, the substantially constant plasma level of cetirizine provided by the gastric residence systems of the invention can be about 50% to about 90% of the peak plasma level of cetirizine when administered daily in a conventional oral formulation (that is, $C_{max}$ of cetirizine administered daily in immediate-release formulation). The substantially constant plasma level of cetirizine provided by the gastric residence systems of the invention can be about 75% to about 125% of the average plasma level of cetirizine when administered daily in a conventional oral formulation (that is, $C_{ave}$ of cetirizine administered daily in immediate-release formulation). The substantially constant plasma level of cetirizine provided by the gastric residence systems of the invention can be at or above the trough level of plasma level of cetirizine when administered daily in a conventional oral formulation (that is, $C_{min}$ of cetirizine administered daily in immediate-release formulation), such as about 100% to about 150% of $C_{min}$.

The substantially constant plasma level of cetirizine provided by the gastric residence systems of the invention can be about 150 ng/ml to about 250 ng/ml in adults.

The gastric residence systems of the invention can release cetirizine at a rate of about 8.4 mg/day to about 11 mg/day, or about 10 mg/day, or about 0.35 mg/hour to about 0.45 mg/hour.

The gastric residence systems of the invention can provide bioavailability of cetirizine released from the system of at least about 50%, at least about 60%, at least about 70%, or at least about 80% of that provided by an immediate release form comprising the same amount of cetirizine. As indicated above, the bioavailability is measured by the area under the plasma concentration-time curve ($AUC_{inf}$).

Rosuvastatin

Rosuvastatin, a hydrophobic drug, is a selective and competitive inhibitor of 3-hydroxy-3-methylglutaryl coenzyme A (HMG-CoA) reductase. Rosuvastatin is the active ingredient of CRESTOR®. HMG-CoA reductase converts HMG-CoA to mevalonate, which is a precursor of cholesterol and as a result of its mechanism of action, rosuvastatin is primarily indicated in the treatment of dyslipidemia, a condition characterized by an abnormal level of lipids (e.g. cholesterol and/or triglycerides) in the blood. Rosuvastatin was developed by Shionogi & Co., Ltd. and described inter alia in U.S. Pat. Nos. RE37314 and 6,316,460.

Rosuvastatin and other statin HMG-CoA inhibitors have been linked to undesirable side effects, including muscle pain. A rare side effect is severe myopathy and rhabdomyolysis—a condition in which damaged muscles break down rapidly, leading to the production of compounds harmful to the kidneys and potentially resulting in kidney damage and kidney failure. Rosuvastatin is also associated with incidences of myalgia. While these complications can occur at any dose level, the risk is increased at high doses of the drug.

Rosuvastatin is typically administered orally once daily and has an elimination half-life of approximately 19 hours. The plasma concentration of periodically-administered drug will oscillate between a maximum ($C_{max}$) shortly after periodic administration and a minimum ($C_{min}$) before each periodic administration. Both in vitro and in vivo studies have shown the primary location of rosuvastatin uptake to be the liver, the main target organ for therapies aimed at lowering cholesterol and triglycerides. Some undesirable side effects, such as myopathy, are thought to be related in a dose-dependent way to systemic drug exposure in the serum. Therefore, methods of administration that favor higher uptake in the liver with respect to systemic exposure could have favorable risk-benefit profiles.

Administration of rosuvastatin via the gastric residence systems of the invention allows a relatively low, relatively constant level of rosuvastatin to enter the hepatic portal circulation, as opposed to periodic administration. This lower, continual level results in greater absorption of the drug in the liver (the target organ where the drug provides its therapeutic effect) and a lower maximum amount of drug in the general circulation (where the drug causes undesirable side effects).

In any of the embodiments set forth herein, rosuvastatin can be provided in the gastric residence system in the form of rosuvastatin calcium, or can be provided in its free base (non-salt) form.

In any of the embodiments set forth herein where rosuvastatin is provided in the gastric residence system, the rosuvastatin present in the gastric residence system can be protected against degradation (such as acid degradation), such that less than about 5% of the rosuvastatin remaining in the system is degraded after a gastric residence period or effective release period of about 24 hours. In some embodiments, less than about 5% of the rosuvastatin remaining in the system is degraded after a gastric residence period or effective release period of about 48 hours. In some embodiments, less than about 5% of the rosuvastatin remaining in the system is degraded after a gastric residence period or effective release period of about 72 hours. In some embodiments, less than about 5% of the rosuvastatin remaining in the system is degraded after a gastric residence period or effective release period of about 96 hours. In some embodiments, less than about 5% of the rosuvastatin remaining in the system is degraded after a gastric residence period or effective release period of about five days. In some embodiments, less than about 5% of the rosuvastatin remaining in the system is degraded after a gastric residence period or effective release period of about a week. In some embodiments, less than about 5% of the rosuvastatin remaining in the system is degraded after a gastric residence period or effective release period of about two weeks. In some embodiments, less than about 5% of the rosuvastatin remaining in the system is degraded after a gastric residence period or effective release period of about three weeks. In some embodiments, less than about 5% of the rosuvastatin remaining in the system is degraded after a gastric residence period or effective release period of about four weeks. In some embodiments, less than about 5% of the rosuvastatin remaining in the system is degraded after a gastric residence period or effective release period of about a month.

In any of the embodiments set forth herein where rosuvastatin is provided in the gastric residence system, the gastric residence system can release between about 5 to about 40 mg of rosuvastatin per day in the stomach over its period of residence, or over its effective release period. In any of the embodiments set forth herein, the gastric residence system can release between about 5 to about 20 mg of rosuvastatin per day in the stomach over its period of residence, or over its effective release period.

In any of the embodiments set forth herein where rosuvastatin is provided in the gastric residence system, the reduction of LDL cholesterol by the gastric residence system is about 90% to 150% of the reduction of LDL cholesterol by an approximately equal amount of an immediate release formulation of rosuvastatin administered over about the same period of time, such as a period of time of about one week. The carrier polymer used in the gastric residence system can comprise polycaprolactone, such as linear polycaprolactone with a number-average molecular weight range between about 45 kDa and about 55 kDa, between about 60 kDa to about 100 kDa; between about 75 kDa to about 85 kDa; or about 80 kDa.

In any of the embodiments set forth herein where rosuvastatin is provided in the gastric residence system, the gastric residence system comprises between about 25 mg to about 300 mg of rosuvastatin.

In any of the embodiments set forth herein where rosuvastatin is provided in the gastric residence system, the carrier polymer-drug components of the gastric residence system further comprise a buffering substance. The buffering substance can be one or more compounds selected from the group consisting of calcium carbonate, calcium lactate, calcium phosphate, sodium phosphate, and sodium bicarbonate. The buffering substance is typically used in an amount of up to about 2% w/w.

In further embodiments, the invention embraces a method of treating a patient having high cholesterol or triglyceride levels, comprising administering any embodiment of the gastric residence systems disclosed herein to the patient, where the gastric residence system contains rosuvastatin (in free base form, rosuvastatin calcium salt form, or other pharmaceutically acceptable salt form of rosuvastatin). The gastric residence system can administered to the patient at intervals, such as once a week. A new gastric residence system can be administered to the patient at intervals of E days, where E days is the effective release period of the system; this administration can be performed every E days over a total desired treatment period.

Myalgia is of particular concern when treating patients with rosuvastatin. In some embodiments, administration of rosuvastatin using the gastric residence device comprising a dispersant (such as silica) can reduce self-reported incidences of myalgia by at least 5% compared to an immediate-release oral administration of rosuvastatin with an approximately equivalent therapeutic effect. In some embodiments, administration of rosuvastatin using the gastric residence device comprising a dispersant can reduce self-reported incidences of myalgia by at least 10%, at least 15%, at least 20%, at least 25%, at least 30%, at least 35%, at least 40%, at least 45%, or at least 50% compared an immediate-release oral administration of rosuvastatin with an approximately equivalent therapeutic effect. In some embodiments, administration of rosuvastatin using the gastric residence device comprising a dispersant can reduce self-reported incidences of myalgia by about 5% to about 50% compared to an immediate-release oral administration of rosuvastatin with an approximately equivalent therapeutic effect. In some embodiments, administration of rosuvastatin using the gastric residence device comprising a dispersant can reduce self-reported incidences of myalgia by about 10% to about 40%, or about 15% to about 30% compared to an immediate-release oral administration of rosuvastatin with an approximately equivalent therapeutic effect.

Stabilizing drug plasma levels, particularly limiting initial burst phase and induced burst release, is particularly challenging for rosuvastatin using a gastric residence system. Rosuvastatin is relatively hydrophobic, and has the potential to elute rapidly from a gastric residence system after the consumption of high-fat foods or alcoholic beverages, as rosuvastatin is more soluble in ethanol than in water. Consumption of other hydrophobic substances, such as a medicament administered in vegetable oil, also have the potential to cause burst release of a hydrophobic drug from the gastric residence system. The burst of drug is absorbed by the patient, resulting in a sudden rise in blood plasma levels. Burst release results in an undesired peak level of drug, and may also result in insufficient drug delivery during the remaining effective release time or residence time of the system. The inclusion of a dispersant, as described herein, in the gastric residence system limits the sudden induced burst release of rosuvastatin due to the consumption of hydrophobic substances (such as alcoholic beverages). The combination of the dispersant, rosuvastatin, and a carrier polymer provides more stable drug release compared to the combination of rosuvastatin and the carrier polymer without the dispersant. Milling as described herein can also ensure smaller drug particle size, and thus greater surface area of the rosuvastatin, in the carrier polymer, thereby increasing exposure of the drug to the gastric environment and promoting efficient drug elution.

In order to ensure efficacy of treatment at the lower systemic exposure levels provided by the gastric release systems comprising rosuvastatin, patients are monitored via periodic lipid panels. Such lipid panel tests include assays for total cholesterol, high-density lipoprotein (HDL) cholesterol (sometimes referred to as "good" cholesterol), low-density lipoprotein (LDL) cholesterol (sometimes referred to as "bad" cholesterol), and triglycerides. Other specialized tests can be used, such as LDL receptor density. Patients can also be monitored for normal liver function using standard liver panel testing, including standard clinical chemistry tests for alanine transaminase (ALT), aspartate transaminase (AST), alkaline phosphatase (ALP), albumin, total protein, bilirubin, gamma-glutamyltransferase (GGT), L-lactate dehydrogenase (LD), and prothrombin time (PT).

In one embodiment, the reduction of LDL cholesterol by a gastric residence system of the invention comprising rosuvastatin is about 75% to 150% of the reduction of LDL cholesterol by an immediate release formulation of rosuvastatin, where approximately equal amounts of rosuvastatin are administered by each delivery method over the same period of time. For example, the reduction of LDL cholesterol by a gastric residence system of the invention, with an effective release period or residence period of one week, and containing 70 mg of rosuvastatin released at about 10 mg/day, is about 75% to 150% of the reduction of LDL cholesterol by an immediate release formulation of rosuvastatin administered at a dose of 10 mg/day over seven days. The reduction of LDL cholesterol by a gastric residence system of the invention, with an effective release period or residence period of one week, and containing 140 mg of rosuvastatin released at about 20 mg/day, where a gastric residence system is administered to the patient once a week for four consecutive weeks, is about 75% to 150% of the reduction of LDL cholesterol by an immediate release formulation of rosuvastatin administered at a dose of 20 mg/day over 28 days. The approximately equal amounts can be 10 mg/day, 20 mg/day, 30 mg/day, or 40 mg/day. The period of time can be 3 days, 4 days, 5 days, 6 days, 1 week, 10 days, 2 weeks, 3 weeks, 4 weeks, or one month. In further embodiments, the reduction of LDL cholesterol by a gastric residence system of the invention is at least about 50%, at least about 75%, at least about 90%, at least about 100%, at least about 125%, at least about 140%, at least about 150%, about 50% to 150%, about 75% to 150%, about 90% to about 150%, about 100% to 150%, or about 125% to 150% of the reduction of LDL cholesterol by an immediate release formulation of rosuvastatin, where approximately equal amounts of rosuvastatin are administered by each delivery method over the same period of time.

Effective Release Period; Residence Period

The effective release period (or effective release time) of the gastric residence system is defined as the time during which the gastric residence system releases a therapeutically effective amount of the therapeutic agent in the gastric residence system. A preferred effective release period is one week or about one week; another preferred effective release period is 3 days or about 3 days. In one embodiment, the gastric residence system has an effective release period of about 24 hours, or up to about 24 hours. In one embodiment, the gastric residence system has an effective release period of about 48 hours, or up to about 48 hours. In one embodiment, the gastric residence system has an effective release period of about 72 hours, or up to about 72 hours. In one embodiment, the gastric residence system has an effective release period of about 96 hours, or up to about 96 hours. In one embodiment, the gastric residence system has an effective release period of about 5 days, or up to about 5 days. In one embodiment, the gastric residence system has an effective release period of about 6 days, or up to about 6 days. In one embodiment, the gastric residence system has an effective release period of about 7 days, or up to about 7 days. In one embodiment, the gastric residence system has an effective release period of about 10 days, or up to about 10 days. In one embodiment, the gastric residence system has an effective release period of about 14 days, or up to about 14 days. In one embodiment, the gastric residence system has an effective release period of about 3 weeks, or up to about 3 weeks. In one embodiment, the gastric residence system has an effective release period of about 4 weeks, or up to about 4 weeks. In one embodiment, the gastric residence system has an effective release period of about one month, or up to about one month.

In one embodiment, the gastric residence system has an effective release period between about 24 hours and about 7 days. In one embodiment, the gastric residence system has an effective release period between about 48 hours and about 7 days. In one embodiment, the gastric residence system has an effective release period between about 72 hours and about 7 days. In one embodiment, the gastric residence system has an effective release period between about 96 hours and about 7 days. In one embodiment, the gastric residence system has an effective release period between about 5 days and about 7 days. In one embodiment, the gastric residence system has an effective release period between about 6 days and about 7 days.

In one embodiment, the gastric residence system has an effective release period between about 24 hours and about 10 days. In one embodiment, the gastric residence system has an effective release period between about 48 hours and about 10 days. In one embodiment, the gastric residence system has an effective release period between about 72 hours and about 10 days. In one embodiment, the gastric residence system has an effective release period between about 96 hours and about 10 days. In one embodiment, the gastric residence system has an effective release period between about 5 days and about 10 days. In one embodiment, the gastric residence system has an effective release period between about 6 days and about 10 days. In one embodiment, the gastric residence system has an effective release period between about 7 days and about 10 days.

In one embodiment, the gastric residence system has an effective release period between about 24 hours and about 14 days. In one embodiment, the gastric residence system has an effective release period between about 48 hours and about 14 days. In one embodiment, the gastric residence system has an effective release period between about 72 hours and about 14 days. In one embodiment, the gastric residence system has an effective release period between about 96 hours and about 14 days. In one embodiment, the gastric residence system has an effective release period between about 5 days and about 14 days. In one embodiment, the gastric residence system has an effective release period between about 6 days and about 14 days. In one embodiment, the gastric residence system has an effective release period between about 7 days and about 14 days. In one embodiment, the gastric residence system has an effective release period between about 10 days and about 14 days.

In one embodiment, the gastric residence system has an effective release period between about 24 hours and about three weeks. In one embodiment, the gastric residence system has an effective release period between about 48 hours and about three weeks. In one embodiment, the gastric residence system has an effective release period between about 72 hours and about three weeks. In one embodiment, the gastric residence system has an effective release period between about 96 hours and about three weeks. In one embodiment, the gastric residence system has an effective release period between about 5 days and about three weeks. In one embodiment, the gastric residence system has an effective release period between about 6 days and about three weeks. In one embodiment, the gastric residence system has an effective release period between about 7 days and about three weeks. In one embodiment, the gastric residence system has an effective release period between about 10 days and about three weeks. In one embodiment, the gastric residence system has an effective release period between about 14 days and about three weeks.

In one embodiment, the gastric residence system has an effective release period between about 24 hours and about four weeks. In one embodiment, the gastric residence system has an effective release period between about 48 hours and about four weeks. In one embodiment, the gastric residence system has an effective release period between about 72 hours and about four weeks. In one embodiment, the gastric residence system has an effective release period between about 96 hours and about four weeks. In one embodiment, the gastric residence system has an effective release period between about 5 days and about four weeks. In one embodiment, the gastric residence system has an effective release period between about 6 days and about four weeks. In one embodiment, the gastric residence system has an effective release period between about 7 days and about four weeks. In one embodiment, the gastric residence system has an effective release period between about 10 days and about four weeks. In one embodiment, the gastric residence system has an effective release period between about 14 days and about four weeks. In one embodiment, the gastric residence system has an effective release period between about three weeks and about four weeks.

In one embodiment, the gastric residence system has an effective release period between about 24 hours and about one month. In one embodiment, the gastric residence system has an effective release period between about 48 hours and about one month. In one embodiment, the gastric residence system has an effective release period between about 72 hours and about one month. In one embodiment, the gastric residence system has an effective release period between about 96 hours and about one month. In one embodiment, the gastric residence system has an effective release period between about 5 days and about one month. In one embodiment, the gastric residence system has an effective release period between about 6 days and about one month. In one embodiment, the gastric residence system has an effective release period between about 7 days and about one month. In one embodiment, the gastric residence system has an effective release period between about 10 days and about one month. In one embodiment, the gastric residence system has an effective release period between about 14 days and about one month. In one embodiment, the gastric residence system has an effective release period between about three weeks and about one month.

The residence time (or residence period) of the gastric residence system is defined as the time between administration of the system to the stomach and exit of the system from the stomach. In one embodiment, the gastric residence system has a residence time (residence period) of about 24 hours, or up to about 24 hours. In one embodiment, the gastric residence system has a residence time (residence period) of about 48 hours, or up to about 48 hours. In one embodiment, the gastric residence system has a residence time (residence period) of about 72 hours, or up to about 72 hours. In one embodiment, the gastric residence system has a residence time (residence period) of about 96 hours, or up to about 96 hours. In one embodiment, the gastric residence system has a residence time (residence period) of about 5 days, or up to about 5 days. In one embodiment, the gastric residence system has a residence time (residence period) of about 6 days, or up to about 6 days. In one embodiment, the gastric residence system has a residence time (residence period) of about 7 days, or up to about 7 days. In one embodiment, the gastric residence system has a residence time (residence period) of about 10 days, or up to about 10 days. In one embodiment, the gastric residence system has a residence time (residence period) of about 14 days, or up to about 14 days. In one embodiment, the gastric residence system has a residence time (residence period) of about 3 weeks, or up to about 3 weeks. In one embodiment, the gastric residence system has a residence time (residence period) of about 4 weeks, or up to about 4 weeks. In one embodiment, the gastric residence system has a residence time (residence period) of about one month, or up to about one month.

In one embodiment, the gastric residence system has a residence time (residence period) between about 24 hours and about 7 days. In one embodiment, the gastric residence system has a residence time (residence period) between about 48 hours and about 7 days. In one embodiment, the gastric residence system has a residence time (residence period) between about 72 hours and about 7 days. In one embodiment, the gastric residence system has a residence time (residence period) between about 96 hours and about 7 days. In one embodiment, the gastric residence system has a residence time (residence period) between about 5 days and about 7 days. In one embodiment, the gastric residence system has a residence time (residence period) between about 6 days and about 7 days.

In one embodiment, the gastric residence system has a residence time (residence period) between about 24 hours and about 10 days. In one embodiment, the gastric residence system has a residence time (residence period) between about 48 hours and about 10 days. In one embodiment, the gastric residence system has a residence time (residence period) between about 72 hours and about 10 days. In one embodiment, the gastric residence system has a residence time (residence period) between about 96 hours and about 10 days. In one embodiment, the gastric residence system has a residence time (residence period) between about 5 days and about 10 days. In one embodiment, the gastric residence system has a residence time (residence period) between about 6 days and about 10 days. In one embodiment, the gastric residence system has a residence time (residence period) between about 7 days and about 10 days.

In one embodiment, the gastric residence system has a residence time (residence period) between about 24 hours and about 14 days. In one embodiment, the gastric residence system has a residence time (residence period) between about 48 hours and about 14 days. In one embodiment, the gastric residence system has a residence time (residence period) between about 72 hours and about 14 days. In one embodiment, the gastric residence system has a residence time (residence period) between about 96 hours and about 14 days. In one embodiment, the gastric residence system has a residence time (residence period) between about 5 days and about 14 days. In one embodiment, the gastric residence system has a residence time (residence period) between about 6 days and about 14 days. In one embodiment, the gastric residence system has a residence time (residence period) between about 7 days and about 14 days. In one embodiment, the gastric residence system has a residence time (residence period) between about 10 days and about 14 days.

In one embodiment, the gastric residence system has a residence time (residence period) between about 24 hours and about three weeks. In one embodiment, the gastric residence system has a residence time (residence period)

between about 48 hours and about three weeks. In one embodiment, the gastric residence system has a residence time (residence period) between about 72 hours and about three weeks. In one embodiment, the gastric residence system has a residence time (residence period) between about 96 hours and about three weeks. In one embodiment, the gastric residence system has a residence time (residence period) between about 5 days and about three weeks. In one embodiment, the gastric residence system has a residence time (residence period) between about 6 days and about three weeks. In one embodiment, the gastric residence system has a residence time (residence period) between about 7 days and about three weeks. In one embodiment, the gastric residence system has a residence time (residence period) between about 10 days and about three weeks. In one embodiment, the gastric residence system has a residence time (residence period) between about 14 days and about three weeks.

In one embodiment, the gastric residence system has a residence time (residence period) between about 24 hours and about four weeks. In one embodiment, the gastric residence system has a residence time (residence period) between about 48 hours and about four weeks. In one embodiment, the gastric residence system has a residence time (residence period) between about 72 hours and about four weeks. In one embodiment, the gastric residence system has a residence time (residence period) between about 96 hours and about four weeks. In one embodiment, the gastric residence system has a residence time (residence period) between about 5 days and about four weeks. In one embodiment, the gastric residence system has a residence time (residence period) between about 6 days and about four weeks. In one embodiment, the gastric residence system has a residence time (residence period) between about 7 days and about four weeks. In one embodiment, the gastric residence system has a residence time (residence period) between about 10 days and about four weeks. In one embodiment, the gastric residence system has a residence time (residence period) between about 14 days and about four weeks. In one embodiment, the gastric residence system has a residence time (residence period) between about three weeks and about four weeks.

In one embodiment, the gastric residence system has a residence time (residence period) between about 24 hours and about one month. In one embodiment, the gastric residence system has a residence time (residence period) between about 48 hours and about one month. In one embodiment, the gastric residence system has a residence time (residence period) between about 72 hours and about one month. In one embodiment, the gastric residence system has a residence time (residence period) between about 96 hours and about one month. In one embodiment, the gastric residence system has a residence time (residence period) between about 5 days and about one month. In one embodiment, the gastric residence system has a residence time (residence period) between about 6 days and about one month. In one embodiment, the gastric residence system has a residence time (residence period) between about 7 days and about one month. In one embodiment, the gastric residence system has a residence time (residence period) between about 10 days and about one month. In one embodiment, the gastric residence system has a residence time (residence period) between about 14 days and about one month. In one embodiment, the gastric residence system has a residence time (residence period) between about three weeks and about one month.

The gastric residence system releases a therapeutically effective amount of therapeutic agent during at least a portion of the residence time or residence period. In one embodiment, the system releases a therapeutically effective amount of therapeutic agent during at least about 25% of the residence period (that is, the effective release period is at least about 25% of the residence period). In one embodiment, the system releases a therapeutically effective amount of therapeutic agent during at least about 50% of the residence period (that is, the effective release period is at least about 50% of the residence period). In one embodiment, the system releases a therapeutically effective amount of therapeutic agent during at least about 60% of the residence period (that is, the effective release period is at least about 60% of the residence period). In one embodiment, the system releases a therapeutically effective amount of therapeutic agent during at least about 70% of the residence period (that is, the effective release period is at least about 70% of the residence period). In one embodiment, the system releases a therapeutically effective amount of therapeutic agent during at least about 75% of the residence period (that is, the effective release period is at least about 75% of the residence period). In one embodiment, the system releases a therapeutically effective amount of therapeutic agent during at least about 80% of the residence period (that is, the effective release period is at least about 80% of the residence period). In one embodiment, the system releases a therapeutically effective amount of therapeutic agent during at least about 85% of the residence period (that is, the effective release period is at least about 85% of the residence period). In one embodiment, the system releases a therapeutically effective amount of therapeutic agent during at least about 90% of the residence period (that is, the effective release period is at least about 90% of the residence period). In one embodiment, the system releases a therapeutically effective amount of therapeutic agent during at least about 95% of the residence period (that is, the effective release period is at least about 95% of the residence period). In one embodiment, the system releases a therapeutically effective amount of therapeutic agent during at least about 98% of the residence period (that is, the effective release period is at least about 98% of the residence period). In one embodiment, the system releases a therapeutically effective amount of therapeutic agent during at least about 99% of the residence period (that is, the effective release period is at least about 99% of the residence period).

The gastric residence system releases a therapeutically effective amount of therapeutic agent during at least a portion of the residence time or residence period. When the gastric residence system breaks apart and passes out of the stomach into the small intestine, the components of the gastric residence system may cease to release a therapeutically effective amount of therapeutic agent, in which case the effective release period has terminated. In some cases, however, the components of the gastric residence system may continue to release a therapeutically effective amount of therapeutic agent. Thus, the period of release of a therapeutically effective amount of therapeutic agent (the effective release period) may last longer than the residence period in the stomach. In one embodiment, the system releases a therapeutically effective amount of therapeutic agent during at least about 25% of the (residence period plus about 24 hours) (that is, the effective release period is at least about 25% of the (residence period plus about 24 hours)). In one embodiment, the system releases a therapeutically effective amount of therapeutic agent during at least about 50% of the (residence period plus about 24 hours) (that is, the effective release period is at least about 50% of the (residence period plus about 24 hours)). In one embodiment, the system releases a therapeutically effective amount of therapeutic agent during at least about 60% of the (residence period plus about 24 hours) (that is, the effective release period is at least about 60% of the (residence period plus about 24 hours)). In one embodiment, the system releases a therapeutically effective amount of therapeutic agent during at least about 70% of the (residence period plus about 24 hours) (that is, the effective release period is at least about 70% of the (residence period plus about 24 hours)). In one embodiment, the system releases a therapeutically effective amount of therapeutic agent during at least about 75% of the (residence period plus about 24 hours) (that is, the effective release period is at least about 75% of the (residence period plus about 24 hours)). In one embodiment, the system releases a therapeutically effective amount of therapeutic agent during at least about 80% of the (residence period plus about 24 hours) (that is, the effective release period is at least about 80% of the (residence period plus about 24 hours)). In one embodiment, the system releases a therapeutically effective amount of therapeutic agent during at least about 85% of the (residence period plus about 24 hours) (that is, the effective release period is at least about 85% of the (residence period plus about 24 hours)). In one embodiment, the system releases a therapeutically effective amount of therapeutic agent during at least about 90% of the (residence period plus about 24 hours) (that is, the effective release period is at least about 90% of the (residence period plus about 24 hours)). In one embodiment, the system releases a therapeutically effective amount of therapeutic agent during at least about 95% of the (residence period plus about 24 hours) (that is, the effective release period is at least about 95% of the (residence period plus about 24 hours)). In one embodiment, the system releases a therapeutically effective amount of therapeutic agent during at least about 98% of the (residence period plus about 24 hours) (that is, the effective release period is at least about 98% of the (residence period plus about 24 hours)). In one embodiment, the system releases a therapeutically effective amount of therapeutic agent during at least about 99% of the (residence period plus about 24 hours) (that is, the effective release period is at least about 99% of the (residence period plus about 24 hours)).

In one embodiment, the system releases a therapeutically effective amount of therapeutic agent during at least about 25% of the (residence period plus about 48 hours) (that is, the effective release period is at least about 25% of the (residence period plus about 48 hours)). In one embodiment, the system releases a therapeutically effective amount of therapeutic agent during at least about 50% of the (residence period plus about 48 hours) (that is, the effective release period is at least about 50% of the (residence period plus about 48 hours)). In one embodiment, the system releases a therapeutically effective amount of therapeutic agent during at least about 60% of the (residence period plus about 48 hours) (that is, the effective release period is at least about 60% of the (residence period plus about 48 hours)). In one embodiment, the system releases a therapeutically effective amount of therapeutic agent during at least about 70% of the (residence period plus about 48 hours) (that is, the effective release period is at least about 70% of the (residence period plus about 48 hours)). In one embodiment, the system releases a therapeutically effective amount of therapeutic agent during at least about 75% of the (residence period plus about 48 hours) (that is, the effective release period is at least about 75% of the (residence period plus about 48 hours)). In one embodiment, the system releases a therapeutically effective amount of therapeutic agent during at least about 80% of the (residence period plus about 48 hours) (that is, the effective release period is at least about 80% of the (residence period plus about 48 hours)). In one embodiment, the system releases a therapeutically effective amount of therapeutic agent during at least about 85% of the (residence period plus about 48 hours) (that is, the effective release period is at least about 85% of the (residence period plus about 48 hours)). In one embodiment, the system releases a therapeutically effective amount of therapeutic agent during at least about 90% of the (residence period plus about 48 hours) (that is, the effective release period is at least about 90% of the (residence period plus about 48 hours)). In one embodiment, the system releases a therapeutically effective amount of therapeutic agent during at least about 95% of the (residence period plus about 48 hours) (that is, the effective release period is at least about 95% of the (residence period plus about 48 hours)). In one embodiment, the system releases a therapeutically effective amount of therapeutic agent during at least about 98% of the (residence period plus about 48 hours) (that is, the effective release period is at least about 98% of the (residence period plus about 48 hours)). In one embodiment, the system releases a therapeutically effective amount of therapeutic agent during at least about 99% of the (residence period plus about 48 hours) (that is, the effective release period is at least about 99% of the (residence period plus about 48 hours)).

In one embodiment, the system releases a therapeutically effective amount of therapeutic agent during at least about 25% of the (residence period plus about 72 hours) (that is, the effective release period is at least about 25% of the (residence period plus about 72 hours)). In one embodiment, the system releases a therapeutically effective amount of therapeutic agent during at least about 50% of the (residence period plus about 72 hours) (that is, the effective release period is at least about 50% of the (residence period plus about 72 hours)). In one embodiment, the system releases a therapeutically effective amount of therapeutic agent during at least about 60% of the (residence period plus about 72 hours) (that is, the effective release period is at least about 60% of the (residence period plus about 72 hours)). In one embodiment, the system releases a therapeutically effective amount of therapeutic agent during at least about 70% of the (residence period plus about 72 hours) (that is, the effective release period is at least about 70% of the (residence period plus about 72 hours)). In one embodiment, the system releases a therapeutically effective amount of therapeutic agent during at least about 75% of the (residence period plus about 72 hours) (that is, the effective release period is at least about 75% of the (residence period plus about 72 hours)). In one embodiment, the system releases a therapeutically effective amount of therapeutic agent during at least about 80% of the (residence period plus about 72 hours) (that is, the effective release period is at least about 80% of the (residence period plus about 72 hours)). In one embodiment, the system releases a therapeutically effective amount of therapeutic agent during at least about 85% of the (residence period plus about 72 hours) (that is, the effective release period is at least about 85% of the (residence period plus about 72 hours)). In one embodiment, the system releases a therapeutically effective amount of therapeutic agent during at least about 90% of the (residence period plus about 72 hours) (that is, the effective release period is at least about 90% of the (residence period plus about 72 hours)). In one embodiment, the system releases a therapeutically effective amount of therapeutic agent during at least about 95% of the (residence period plus about 72 hours) (that is, the effective release period is at least about 95% of the (residence period plus about 72 hours)). In one embodiment, the system releases a therapeutically effective amount of therapeutic agent during at least about 98% of the (residence period plus about 72 hours) (that is, the effective release period is at least about 98% of the (residence period plus about 72 hours)). In one embodiment, the system releases a therapeutically effective amount of therapeutic agent during at least about 99% of the (residence period plus about 72 hours) (that is, the effective release period is at least about 99% of the (residence period plus about 72 hours)).

Radiopacity

The systems are optionally radiopaque, so that they can be located via abdominal X-ray if necessary. In some embodiments, one or more of the materials used for construction of the system is sufficiently radiopaque for X-ray visualization. In other embodiments, a radiopaque substance is added to one or more materials of the system, or coated onto one or more materials of the system, or placed on a small portion of the system, or added to a small portion of the system. Examples of suitable radiopaque substances are barium sulfate, bismuth subcarbonate, bismuth oxychloride, and bismuth trioxide. It is preferable that these materials should not be blended into the polymers used to construct the gastric residence system, so as not to alter therapeutic agent release from the carrier polymer, or desired properties of other system polymers. Metal striping or metal tips on a small portion of the system components can also be used, using metals such as tungsten.

Methods of Treatment Using the Gastric Residence Systems

The gastric residence systems can be used to treat conditions requiring administration of a therapeutic agent over an extended period of time. For long-term administration of a therapeutic agent, which may be taken for months, years, or indefinitely, administration of a gastric residence system once weekly, once every two weeks, or once a month can provide substantial advantages in patient compliance and convenience.

Once a gastric residence system has been administered to a patient, the system provides sustained release of therapeutic agent over the effective release period. After the gastric residence period, the system degrades and passes out of the stomach. Thus, for a system with an effective release period of one week, the patient will swallow (or have administered to the stomach via other means) a new system every week. Accordingly, in one embodiment, a method of treatment of a patient with a gastric residence system of the invention having an effective release period of a number of days E (where E-days is the effective release period in days), over a total desired treatment period T-total (where T-total is the desired length of treatment in days) with the therapeutic agent in the system, comprises introducing a new gastric residence system every E-days into the stomach of the patient, by oral administration or other means, over the total desired treatment period. The number of gastric residence systems administered to the patient will be (T-total) divided by (E-days). For example, if treatment of a patient for a year (T-total=365 days) is desired, and the effective release period of the system is 7 days (E-days=7 days), approximately 52 gastric residence systems will be administered to the patient over the 365 days, as a new system will be administered once every seven days.

Kits and Articles of Manufacture

Also provided herein are kits for treatment of patients with the gastric residence systems of the invention. The kit may contain, for example, a sufficient number of gastric residence systems for periodic administration to a patient over a desired total treatment time period. If the total treatment time in days is (T-total), and the gastric residence systems have an effective release period of (E-days), then the kit will contain a number of gastric residence systems equal to ((T-total) divided by (E-days)) (rounded to an integral number), for administration every E-days. The kit may contain, for example, several gastric residence systems in containers (where the containers may be capsules) and may optionally also contain printed or computer readable instructions for dosing regimens, duration of treatment, or other information pertinent to the use of the gastric residence systems and/or the therapeutic agent contained in the gastric residence systems. For example, if the total treatment period prescribed for the patient is one year, and the gastric residence system has an effective release period of one week, the kit may contain 52 capsules, each capsule containing one gastric residence system, with instructions to swallow one capsule once a week on the same day (e.g., every Saturday).

Articles of manufacture, comprising a sufficient number of gastric residence systems for periodic administration to a patient over a desired total treatment time period, and optionally comprising instructions for dosing regimens, duration of treatment, or other information pertinent to the use of the gastric residence systems and/or the therapeutic agent contained in the gastric residence systems, are also included in the invention. The articles of manufacture may be supplied in appropriate packaging, such as dispensers, trays, or other packaging that assists the patient in administration of the gastric residence systems at the prescribed interval.

EXEMPLARY EMBODIMENTS

The invention is further described by the following embodiments. The features of each of the embodiments are combinable with any of the other embodiments where appropriate and practical.

Embodiment 1

A gastric residence system for administration to a patient, comprising:
a plurality of carrier polymer-agent components comprising:
i) a carrier polymer,
ii) a dispersant, and
iii) a therapeutic agent or a salt thereof,
wherein the plurality of carrier polymer-agent components are linked together by one or more coupling polymer components, wherein at least one of the one or more coupling polymer components is an elastomer;
wherein the gastric residence system is configured to have a compacted form in a container, suitable for administration orally or through a feeding tube; and an uncompacted form when released from the container in the stomach of the patient;
wherein the gastric residence system is retained in the stomach for a period of at least about 24 hours; and
wherein the system releases a therapeutically effective amount of the therapeutic agent over at least a portion of the period in which the system is retained in the stomach.

Embodiment 2

The gastric residence system of embodiment 1, wherein the dispersant comprises a compound selected from the group consisting of: a porous inorganic material, a polar inorganic material, silica, hydrophilic-fumed silica, stearate salts, calcium stearate, magnesium stearate, microcrystalline cellulose, carboxymethylcellulose, hydrophobic colloidal silica, hypromellose, magnesium aluminum silicate, phospholipids, polyoxyethylene stearates, zinc acetate, alginic acid, lecithin, fatty acids, sodium lauryl sulfate, non-toxic metal oxides, and aluminum oxide.

Embodiment 3

The gastric residence system of embodiment 1, wherein the dispersant comprises silica.

Embodiment 4

The gastric residence system of any one of embodiments 1-3, wherein the therapeutic agent or salt thereof is comprised of particles dispersed throughout the carrier polymer.

Embodiment 5

The gastric residence system of embodiment 4, wherein at least about 80% of the mass of the therapeutic agent particles are between about 2 microns and about 50 microns in diameter.

Embodiment 6

The gastric residence system of any one of embodiments 1-5, wherein the therapeutic agent or a salt thereof is a hydrophilic therapeutic agent or a salt thereof, and wherein less than about 10% of the hydrophilic therapeutic agent contained in the system elutes within about the first six hours of exposure to gastric fluid.

Embodiment 7

The gastric residence system of any one of embodiments 1-5, wherein the therapeutic agent or a salt thereof is a hydrophilic therapeutic agent or a salt thereof, and wherein the amount of hydrophilic therapeutic agent eluted from the system within about the first six hours of exposure to gastric fluid is about 50% or less than the amount of therapeutic agent eluted from the system without the dispersant.

Embodiment 8

The gastric residence system of embodiment 6 or embodiment 7, wherein the carrier polymer-agent component comprises between about 1% to about 30% hydrophilic therapeutic agent or salt thereof, about 0.5% to about 2.5% of dispersant, and about 67.5% to about 98.5% carrier polymer.

Embodiment 9

The gastric residence system of any one of embodiments 6-8, wherein the hydrophilic therapeutic agent has a log P less than or equal to about 0.5. In this embodiment, log P is measured in a 1-octanol/water system.

Embodiment 10

The gastric residence system of any one of embodiments 6-8, wherein the solubility of the hydrophilic therapeutic agent in water is at least about 1 mg/ml.

Embodiment 11

The gastric residence system of any one of embodiments 1-5, wherein the therapeutic agent or a salt thereof is a hydrophobic therapeutic agent or a salt thereof.

Embodiment 12

The gastric residence system of embodiment 11, wherein the carrier polymer-agent component comprises between about 1% to about 30% hydrophobic therapeutic agent or salt thereof, about 0.5% to about 2.5% of dispersant, and about 67.5% to about 98.5% carrier polymer.

Embodiment 13

The gastric residence system of embodiment 11 or embodiment 12, wherein the hydrophobic therapeutic agent has a log P greater than or equal to about 1. In this embodiment, log P is measured in a 1-octanol/water system.

Embodiment 14

The gastric residence system of embodiment 11 or embodiment 12, wherein the solubility of the hydrophobic therapeutic agent in water is less than about 1 mg/ml.

Embodiment 15

The gastric residence system of any one of embodiments 1-14, wherein the carrier polymer comprises polycaprolactone.

Embodiment 16

The gastric residence system of embodiment 15, wherein the polycaprolactone comprises linear polycaprolactone with a number-average molecular weight range between about 45 kDa and about 55 kDa.

Embodiment 16A

The gastric residence system of embodiment 15, wherein the polycaprolactone comprises linear polycaprolactone with a number-average molecular weight ($M_n$) range between about 60 kiloDalton (kDa) to about 100 kDa; 75 kDa to 85 kDa; or about 80 kDa.

Embodiment 17

The gastric residence system of any one of embodiments 1-16, wherein the plurality of carrier polymer-agent components are linked together by two or more coupling polymer components, wherein at least one of the two or more coupling polymer components is an elastomer and at least another one of the two or more coupling polymer components is an enteric polymer.

Embodiment 18

The gastric residence system of embodiment 17, wherein each enteric polymer is independently selected from the group consisting of poly(methacrylic acid-co-ethyl acrylate), cellulose acetate phthalate, cellulose acetate succinate, and hydroxypropyl methylcellulose phthalate.

Embodiment 18A

The gastric residence system of embodiment 17, wherein each enteric polymer is independently selected from the group consisting of poly(methacrylic acid-co-ethyl acrylate), cellulose acetate phthalate, cellulose acetate succinate, hydroxypropyl methylcellulose phthalate, and hypromellose acetate succinate (HPMCAS).

Embodiment 19

The gastric residence system of any one of embodiments 1-18, wherein the gastric residence system is retained in the stomach for about 5 days to about 7 days.

Embodiment 20

A method of making a gastric residence system of any one of embodiments 1-19, comprising:
  forming a flexible coupling polymer component;
  forming a plurality of at least three carrier polymer-agent components, which are elongate members comprising a proximal end and a distal end; and
  attaching the elongate members to the flexible coupling polymer component.

Embodiment 21

The method of embodiment 20, further comprising compacting the gastric residence system and inserting the system into a container suitable for oral administration or administration through a gastric tube or feeding tube.

Embodiment 22

The method of embodiment 20 or embodiment 21, wherein the carrier polymer-agent components are formed by milling the therapeutic agent or salt thereof, and blending the milled therapeutic agent or salt thereof, the dispersant, and the carrier polymer.

Embodiment 23

The method of embodiment 22, wherein the therapeutic agent or salt thereof is milled with a compound selected from the group consisting of silica, calcium phosphate, powdered cellulose, colloidal silicon dioxide, hydrophobic colloidal silica, magnesium oxide, magnesium silicate, magnesium trisilicate, talc, polyvinylpyrrolidone, cellulose ethers, polyethylene glycol, polyvinyl alcohol, and surfactants.

Embodiment 24

The method of embodiment 22 or embodiment 23, wherein the therapeutic agent or a salt thereof comprises particles, wherein at least about 80% of the mass of particles have sizes between about 2 microns and about 50 microns in diameter.

Embodiment 25

The method of embodiment 22, wherein the blending is performed by hot melt extrusion.

Embodiment 26

The method of any one of embodiments 20-25, wherein forming a plurality of at least three carrier polymer-agent components which are elongate members comprises forming the elongate members from at least two segments.

Embodiment 27

The method of embodiment 26, wherein forming the elongate members from at least two segments comprises forming a collar joint between the segments.

Embodiment 28

The method of any one of embodiments 20-27, wherein the flexible coupling polymer component is asterisk-shaped with a plurality of at least three branches.

Embodiment 29

The method of any one of embodiments 20-28, wherein attaching the elongate members to the flexible coupling polymer component comprises adhering the elongate members to the flexible coupling polymer component.

Embodiment 30

The method of embodiment 28, wherein attaching the elongate members to the asterisk-shaped flexible coupling polymer component comprises forming a collar joint between the elongate members and the branches of the flexible coupling polymer component.

Embodiment 31

A method of administering a therapeutic agent to a patient, comprising administering a gastric residence system of any one of embodiments 1-19 to the patient.

Embodiment 32

The method of embodiment 31, wherein the gastric residence system has a gastric retention period of D days, and a new gastric residence system is administered to the patient every D days over a total desired treatment period.

Embodiment 33

The method of embodiment 32, wherein the gastric retention period is seven days.

Embodiment 34

A gastric residence system for administration to a patient, comprising:
  a plurality of carrier polymer-agent components comprising:
    i) a carrier polymer, and
    ii) a therapeutic agent or a pharmaceutically-acceptable salt thereof,
  wherein the carrier polymer-agent components are linked together by one or more coupling polymer components, wherein at least one of the one or more coupling polymer components is an elastomer;
  wherein the gastric residence system is configured to have a compacted form in a container, suitable for administration orally or through a feeding tube; and an uncompacted form when released from the container;

wherein the gastric residence system is retained in the stomach for a residence period of between at least about 24 hours and about one month; and wherein:

the system releases a therapeutically effective amount of the therapeutic agent over at least a portion of the period in which the system is retained in the stomach; and the system releases less than about 20% of the therapeutic agent or pharmaceutically-acceptable salt thereof within a six-hour period.

Embodiment 35

The gastric residence system of embodiment 34, wherein the system releases about 30% to about 70% of the therapeutic agent or pharmaceutically-acceptable salt thereof within a period of about 40% to 60% of the residence period.

Embodiment 36

The gastric residence system of embodiment 34 or embodiment 35, wherein the system releases greater than about 70% of the therapeutic agent or pharmaceutically-acceptable salt thereof within a period of about 90% of the residence period.

Embodiment 37

The gastric residence system of any one of embodiments 34-36, wherein the release of the therapeutic agent or pharmaceutically-acceptable salt thereof is measured in an aqueous environment selected from the group consisting of: 0.1N HCl in water, simulated gastric fluid, fasted-state simulated gastric fluid, fed-state simulated gastric fluid, the stomach of an animal, the stomach of a pig, the stomach of a dog, and the stomach of a human.

Embodiment 38

The gastric residence system of any one of embodiments 34-37, wherein the release of the therapeutic agent or pharmaceutically-acceptable salt thereof is measured in 0.1N HCl.

Embodiment 39

The gastric residence system of any one of embodiments 34-37, wherein the release of the therapeutic agent or pharmaceutically-acceptable salt thereof is measured in fasted-state simulated gastric fluid.

Embodiment 40

The gastric residence system of any one of embodiments 34-37, wherein the release of the therapeutic agent or pharmaceutically-acceptable salt thereof is measured in fed-state simulated gastric fluid.

Embodiment 41

The gastric residence system of any one of embodiments 34-40, wherein the release of the therapeutic agent or pharmaceutically-acceptable salt thereof increases by no more than about 40% in 40% ethanol/60% 0.1N HCl in water versus the release over the same period of time in 0.1N HCl, or by no more than about 40% in 40% ethanol/60% simulated gastric fluid versus the release over the same period of time in simulated gastric fluid, or by no more than about 40% in 40% ethanol/60% fasted-state simulated gastric fluid versus the release over the same period of time in fasted-state simulated gastric fluid, or by no more than about 40% in 40% ethanol/60% fed-state simulated gastric fluid versus the release over the same period of time in fed-state simulated gastric fluid.

Embodiment 42

The gastric residence system of any one of embodiments 34-41, wherein: ii) the therapeutic agent or a pharmaceutically-acceptable salt thereof comprises about 10% to about 35% of the carrier polymer-agent components.

Embodiment 43

The gastric residence system of any one of embodiments 34-42, wherein the therapeutic agent or a pharmaceutically-acceptable salt thereof is selected from the group consisting of doxycycline, donepezil, ivermectin, risperidone, cetirizine, and rosuvastatin.

Embodiment 44

The gastric residence system of any one of embodiments 34-43, wherein the carrier polymer-agent components further comprise iii) a release enhancer.

Embodiment 45

The gastric residence system of any one of embodiments 34-44, wherein the release enhancer comprises about 2% to about 30% of the carrier polymer-agent components.

Embodiment 46

The gastric residence system of any one of embodiments 34-45, wherein the release enhancer is selected from the group consisting of an acrylate polymer, an acrylate copolymer, a polydioxanone-polyethylene glycol polymer, and polyvinylpyrrolidone.

Embodiment 47

The gastric residence system of any one of embodiments 34-46, wherein the carrier polymer-agent components further comprise iv) a dispersant.

Embodiment 48

The gastric residence system of any one of embodiments 34-47, wherein the dispersant comprises about 0.1% to about 4% of the carrier polymer-agent components.

Embodiment 49

The gastric residence system of any one of embodiments 34-48, wherein the dispersant is selected from the group consisting of a porous inorganic material, a polar inorganic material, a non-toxic metal oxide, an amphiphilic organic molecule, a polysaccharide, cellulose, a cellulose derivative, a fatty acid, a detergent, silica, hydrophilic-fumed silica, hydrophobic colloidal silica, magnesium aluminum silicate, a stearate salt, calcium stearate, magnesium stearate, microcrystalline cellulose, carboxymethylcellulose, hypromellose, a phospholipid, a polyoxyethylene stearate, zinc acetate, alginic acid, lecithin, sodium lauryl sulfate, and aluminum oxide.

Embodiment 50

The gastric residence system of any one of embodiments 34-48, wherein the dispersant comprises silica.

Embodiment 51

The gastric residence system of any one of embodiments 34-50, wherein the carrier polymer-agent components further comprise: v) a solubilizer.

Embodiment 52

The gastric residence system of any one of embodiments 34-51, wherein the solubilizer comprises about 1% to about 10% of the carrier polymer-agent components.

Embodiment 53

The gastric residence system of any one of embodiments 34-52, wherein the solubilizer is selected from the group consisting of a polyalkylene oxide, a polyethoxylated castor oil, and a detergent.

Embodiment 54

The gastric residence system of any one of embodiments 34-53, wherein the carrier polymer-agent components further comprise: vi) a stabilizer.

Embodiment 55

The gastric residence system of any one of embodiments 34-54, wherein the stabilizer comprises about 0.1% to about 2% of the carrier polymer-agent components.

Embodiment 56

The gastric residence system of any one of embodiments 34-55, wherein the stabilizer is an anti-oxidant selected from the group consisting of an anti-oxidant, a tocopherol, alpha-tocopherol, ascorbic acid, an ascorbate salt, a carotene, butylated hydroxyanisole, butylated hydroxytoluene, fumaric acid, an anti-microbial, a buffering substance, calcium carbonate, calcium lactate, calcium phosphate, sodium phosphate, and sodium bicarbonate.

Embodiment 57

The gastric residence system of any one of embodiments 34-56, wherein the carrier polymer comprises a polylactone.

Embodiment 58

The gastric residence system of embodiment 57, wherein the polylactone comprises polycaprolactone.

Embodiment 59

The gastric residence system of embodiment 58, wherein the polycaprolactone has an average $M_n$ of about 60,000 to 100,000.

Embodiment 60

The gastric residence system of embodiment 58, wherein the polycaprolactone has an average $M_n$ of about 75,000 to 85,000.

Embodiment 61

The gastric residence system of embodiment 58, wherein the polycaprolactone has an average $M_n$ of about 80,000.

Embodiment 62

The gastric residence system of any one of embodiments 34-61, wherein if a solublizer is present, the solubilizer comprises no more than about 5% of the carrier polymer-agent components; and if one or more of a solubilizer, release enhancer, disperant, or stabilizer is present, the total combined amount of any solubilizer, release enhancer, dispersant, and stabilizer present comprises no more than about 30% of the carrier polymer-agent components.

Embodiment 63

An extended release formulation for a therapeutic agent, comprising: i) a polylactone; wherein ii) the therapeutic agent is selected from the group consisting of doxycycline, donepezil, ivermectin, risperidone, rosuvastatin, cetirizine, or a pharmaceutically acceptable salt thereof.

Embodiment 64

The formulation of embodiment 63, wherein the polylactone comprises polycaprolactone.

Embodiment 65

The formulation of embodiment 63, wherein the polycaprolactone has an average $M_n$ of about 60,000 to 100,000.

Embodiment 66

The formulation of embodiment 63, wherein the polycaprolactone has an average $M_n$ of about 75,000 to 85,000.

Embodiment 67

The formulation of embodiment 63, wherein the polycaprolactone has an average $M_n$ of about 80,000.

Embodiment 68

The formulation of any one of embodiments 63-67, further comprising: iii) a release enhancer.

Embodiment 69

The formulation of embodiment 68, wherein the release enhancer comprises about 2% to 30% of the formulation.

Embodiment 70

The formulation of embodiment 68 or embodiment 69, wherein the release enhancer is selected from the group consisting of acrylate polymers, acrylate co-polymers, polydioxanone-polyethylene glycol polymers, and polyvinylpyrrolidone.

Embodiment 71

The formulation of embodiment 68 or embodiment 69, wherein the release enhancer comprises polyvinylpyrrolidone, and the polyvinylpyrrolidone comprises about 2% to about 8% of the formulation.

Embodiment 72

The formulation of embodiment 68 or embodiment 69, wherein the release enhancer comprises an acrylate polymer or an acrylate co-polymer, and the acrylate polymer or acrylate co-polymer comprises about 5% to about 30% of the formulation.

Embodiment 73

The formulation of embodiment 70 or embodiment 72, wherein the acrylate polymer or acrylate co-polymer comprises a co-polymer of ethyl acrylate, methyl methacrylate and trimethylammonioethyl methacrylate, optionally in a molar ratio of about 1:2:0.1, about 1:2:0.2, or between about 1:2:0.1 to about 1:2:0.2; or the acrylate polymer or acrylate co-polymer comprises a co-polymer of dimethylaminoethyl methacrylate, butyl methacrylate, and methyl methacrylate, optionally in a molar ratio of from about 2:1:1 to about 1:1:1.

Embodiment 74

The formulation of any one of embodiments 63-73, further comprising: iv) a dispersant.

Embodiment 75

The formulation of embodiment 74, wherein the dispersant comprises about 0.1% to about 4% of the formulation.

Embodiment 76

The formulation of embodiment 74 or embodiment 75, wherein the dispersant is selected from the group consisting of a porous inorganic material, a polar inorganic material, a non-toxic metal oxide, an amphiphilic organic molecule, a polysaccharide, cellulose, a cellulose derivative, a fatty acid, a detergent, silica, hydrophilic-fumed silica, hydrophobic colloidal silica, magnesium aluminum silicate, a stearate salt, calcium stearate, magnesium stearate, microcrystalline cellulose, carboxymethylcellulose, hypromellose, a phospholipid, a polyoxyethylene stearate, zinc acetate, alginic acid, lecithin, sodium lauryl sulfate, and aluminum oxide.

Embodiment 77

The formulation of embodiment 74 or embodiment 75, wherein the dispersant comprises silica.

Embodiment 78

The formulation of embodiment 77, wherein the silica comprises hydrophilic fumed silica.

Embodiment 79

The formulation of any one of embodiments 63-78, wherein the formulation further comprises: v) a solubilizer.

Embodiment 80

The formulation of embodiment 79, wherein the solubilizer comprises about 0.2% to about 10% of the formulation.

Embodiment 81

The formulation of embodiment 79 or embodiment 80, wherein the solubilizer is selected from the group consisting of a polyalkylene oxide, a polyethoxylated castor oil, and a detergent.

Embodiment 82

The formulation of any one of embodiments 79-81, wherein the solubilizer comprises a polyalkylene glycol.

Embodiment 83

The formulation of any one of embodiments 79-82, wherein the solubilizer is selected from the group consisting of polyethylene glycol (PEG), polypropylene glycol (PPG), and a block copolymer of PEG and PPG.

Embodiment 84

The formulation of any one of embodiments 79-83, wherein the solubilizer is a block copolymer of PEG and PPG, optionally of the formula H—$(OCH_2CH_2)_x$—(O—CH$(CH_3)CH_2)_y$—$(OCH_2CH_2)_z$—OH, where x and z are about 101 and y is about 56.

Embodiment 85

The formulation of any one of embodiments 63-84, wherein the formulation further comprises: vi) a stabilizer.

Embodiment 86

The formulation of embodiment 85, wherein the stabilizer comprises about 0.1% to about 2% of the formulation.

Embodiment 87

The formulation of embodiment 85 or embodiment 86, wherein the stabilizer comprises one or more compounds selected from the group consisting of an anti-oxidant, a tocopherol, alpha-tocopherol, ascorbic acid, an ascorbate salt, a carotene, butylated hydroxyanisole, butylated hydroxytoluene, fumaric acid, an anti-microbial, a buffering substance, calcium carbonate, calcium lactate, calcium phosphate, sodium phosphate, and sodium bicarbonate.

Embodiment 88

The formulation of embodiment 85 or embodiment 86, wherein the stabilizer comprises alpha-tocopherol.

Embodiment 89

The formulation of any one of embodiments 63-88, wherein the therapeutic agent or a pharmaceutically acceptable salt thereof comprises about 15% to about 35% of the formulation.

Embodiment 90

The formulation of any one of embodiments 63-89, wherein if a solublizer is present, the solubilizer comprises no more than about 5% of the carrier polymer-agent components; and if one or more of a solubilizer, release enhancer, dispersant, or stabilizer is present, the total combined amount of any solubilizer, release enhancer, dispersant, and stabilizer present comprises no more than about 30% of the carrier polymer-agent components.

Embodiment 91

The formulation of any one of embodiments 63-90, wherein the therapeutic agent is doxycycline or a pharmaceutically acceptable salt thereof.

Embodiment 92

The formulation of any one of embodiments 63-90, wherein the therapeutic agent is donepezil or a pharmaceutically acceptable salt thereof.

Embodiment 93

The formulation of any one of embodiments 63-90, wherein the therapeutic agent is ivermectin or a pharmaceutically acceptable salt thereof.

Embodiment 94

The formulation of any one of embodiments 63-90, wherein the therapeutic agent is risperidone or a pharmaceutically acceptable salt thereof.

Embodiment 95

The formulation of any one of embodiments 63-90, wherein the therapeutic agent is rosuvastatin or a pharmaceutically acceptable salt thereof.

Embodiment 96

The formulation of any one of embodiments 63-90, wherein the therapeutic agent is cetirizine or a pharmaceutically acceptable salt thereof.

Embodiment 97

The formulation of any one of embodiments 63-96, wherein the formulation meets any one, any two, or any three of the following criteria:
the formulation releases less than about 20% of the therapeutic agent or pharmaceutically-acceptable salt thereof within a six-hour period in an aqueous environment; the formulation releases about 30% to about 70% of the therapeutic agent or pharmaceutically-acceptable salt thereof within a period of about three days in the aqueous environment; and the formulation releases greater than about 70% of the therapeutic agent or pharmaceutically-acceptable salt thereof within a period of about seven days in the aqueous environment.

Embodiment 98

The gastric residence system of embodiment 97, wherein the aqueous environment is selected from the group consisting of: 0.1N HCl, simulated gastric fluid, fasted-state simulated gastric fluid, fed-state simulated gastric fluid, the stomach of an animal, the stomach of a pig, the stomach of a dog, and the stomach of a human.

Embodiment 99

The gastric residence system of embodiment 97, wherein the aqueous environment is 0.1N HCl.

Embodiment 100

The gastric residence system of embodiment 97, wherein the aqueous environment is fasted-state simulated gastric fluid.

Embodiment 101

The gastric residence system of embodiment 97, wherein the aqueous environment is fed-state simulated gastric fluid.

Embodiment 102

A gastric residence system for administration of a therapeutic agent or pharmaceutically-acceptable salt thereof to a patient, comprising a plurality of carrier polymer-agent components comprising a formulation of any one of embodiments 63-96;
wherein the carrier polymer-agent components are linked together by one or more coupling polymer components, wherein at least one of the one or more coupling polymer components is an elastomer;
wherein the gastric residence system is configured to have a compacted form in a container, suitable for administration orally or through a feeding tube; and an uncompacted form when released from the container;
wherein the gastric residence system is retained in the stomach for a residence period of between at least about 24 hours and about one month; and wherein:
the system releases a therapeutically effective amount of the therapeutic agent over an effective release period which is less than or equal to the residence period in which the system is retained in the stomach; and the system releases less than about 20% of the therapeutic agent or pharmaceutically-acceptable salt thereof within a six-hour period.

Embodiment 103

The gastric residence system of embodiment 102, wherein the system releases about 30% to about 70% of the therapeutic agent or pharmaceutically-acceptable salt thereof within a period of about 40% to 60% of the effective release period.

Embodiment 104

The gastric residence system of embodiment 102 or embodiment 103, wherein the system releases greater than about 70% of the therapeutic agent or pharmaceutically-acceptable salt thereof within a period of about 90% of the effective release period.

Embodiment 105

The gastric residence system of any one of embodiments 102-104, wherein the release of the therapeutic agent or pharmaceutically-acceptable salt thereof is measured in an aqueous environment selected from the group consisting of: 0.1N HCl in water, simulated gastric fluid, fasted-state simulated gastric fluid, fed-state simulated gastric fluid, the stomach of an animal, the stomach of a pig, the stomach of a dog, and the stomach of a human.

Embodiment 106

The gastric residence system of any one of embodiments 102-104, wherein the release of the therapeutic agent or pharmaceutically-acceptable salt thereof is measured in 0.1N HCl.

Embodiment 107

The gastric residence system of any one of embodiments 102-104, wherein the release of the therapeutic agent or pharmaceutically-acceptable salt thereof is measured in fasted-state simulated gastric fluid.

Embodiment 108

The gastric residence system of any one of embodiments 102-104, wherein the release of the therapeutic agent or pharmaceutically-acceptable salt thereof is measured in fed-state simulated gastric fluid.

Embodiment 109

The gastric residence system of any one of embodiments 102-108, wherein the release of the therapeutic agent or pharmaceutically-acceptable salt thereof increases by no more than about 40% in 40% ethanol/60% 0.1N HCl in water versus the release over the same period of time in 0.1N HCl, or by no more than about 40% in 40% ethanol/60% simulated gastric fluid versus the release over the same period of time in simulated gastric fluid, or by no more than about 40% in 40% ethanol/60% fasted-state simulated gastric fluid versus the release over the same period of time in fasted-state simulated gastric fluid, or by no more than about 40% in 40% ethanol/60% fed-state simulated gastric fluid versus the release over the same period of time in fed-state simulated gastric fluid.

Embodiment 110

The gastric residence system of any one of embodiments 102-108, wherein less than about 20% of the therapeutic agent is released from the system after about 2 hours in 40% ethanol/60% 0.1N HCl.

Embodiment 111

An elongate member formed from a material comprising a formulation according to any one of embodiments 63-96.

Embodiment 112

A gastric residence system comprising at least one elongate member according to embodiment 111.

Embodiment 113

The gastric residence system according to any one of embodiments 1-19, 34-62, or 98-101, comprising at least one elongate member according to embodiment 111.

Embodiment 114

A gastric residence system for administration to the stomach of a patient, comprising: a plurality of carrier polymer-drug components comprising a carrier polymer and cetirizine or a salt thereof, wherein the plurality of carrier polymer-drug components are linked together by coupling polymers; wherein the gastric residence system is configured to have a compacted form in a container, suitable for administration orally or through a feeding tube; and an uncompacted form when released from the container in the stomach of the patient; wherein the gastric residence system is retained in the stomach for at least about 24 hours; and wherein the system releases a therapeutically effective amount of cetirizine over the period in which the system is retained in the stomach.

Embodiment 115

The gastric residence system of embodiment 114, wherein the cetirizine is in the form of cetirizine hydrochloride.

Embodiment 116

The gastric residence system of embodiment 114, wherein the cetirizine is in non-salt form.

Embodiment 117

The gastric residence system of any one of embodiments 114-116, wherein the carrier polymer is polycaprolactone.

Embodiment 118

The gastric residence system of any one of embodiments 114-117, wherein the coupling polymers are enteric polymers.

Embodiment 119

The gastric residence system of embodiment 118, wherein the coupling polymers are enteric polymers which dissolve at a pH at or above about 5.

Embodiment 120

The gastric residence system of embodiment 118, wherein the enteric polymers dissolve at a pH between about 5 and about 7.

Embodiment 121

The gastric residence system of any one of embodiments 114-120, wherein the coupling polymer is poly(methacrylic acid-co-ethyl acrylate).

Embodiment 122

The gastric residence system of any one of embodiments 114-121, wherein the system is retained in the stomach for at least about five days.

Embodiment 123

The gastric residence system of any one of embodiments 114-122, wherein less than about 5% of the cetirizine present in the system is oxidized after retention in the stomach for about 5 days.

Embodiment 124

The gastric residence system of any one of embodiments 114-123, wherein the system releases between about 5 to 15 mg of cetirizine per day in the stomach.

Embodiment 125

The gastric residence system of any one of embodiments 114-124, wherein the bioavailability of cetirizine released from the system is at least about 50% of that provided by an immediate release form comprising the same amount of cetirizine, wherein the bioavailability is measured by the area under the plasma concentration-time curve (AUCinf).

Embodiment 126

The gastric residence system of any one of embodiments 114-125, wherein the system comprises between about 40 mg to about 120 mg of cetirizine.

Embodiment 127

The gastric residence system of any one of embodiments 114-126, wherein the system adopts its uncompacted form upon release from the container.

Embodiment 128

The gastric residence system of any one of embodiments 114-127, wherein the container is a capsule.

Embodiment 129

The gastric residence system of any one of embodiments 114-128, wherein the gastric residence system further comprises a radiopaque substance.

Embodiment 130

The gastric residence system of any one of embodiments 114-129, wherein the carrier polymer-drug components further comprise an anti-oxidant.

Embodiment 131

A method of treating a patient having an allergic reaction, comprising administering a gastric residence system of any one of embodiments 114-130 to the patient.

Embodiment 132

The method of embodiment 131, wherein the allergic reaction is allergic rhinitis.

Embodiment 133

The method of embodiment 131, wherein the allergic reaction is dermatitis.

Embodiment 134

The method of embodiment 131, wherein the allergic reaction is acute urticaria or chronic urticaria.

Embodiment 135

The method of any one of embodiments 131-134, wherein the gastric residence system is administered to the patient once a week.

Embodiment 136

The method of any one of embodiments 131-134, wherein the gastric residence system has a gastric retention period of D days, and a new gastric residence system is administered to the patient every D days over a total desired treatment period.

Embodiment 137

A gastric residence system for administration to a patient, comprising a plurality of carrier polymer-drug components comprising i) a carrier polymer, ii) a dispersant, and iii) cetirizine or a salt thereof, wherein the plurality of carrier polymer-drug components are linked together by one or more coupling polymer components, wherein at least one of the one or more coupling polymer components is an elastomer; wherein the gastric residence system is configured to have a compacted form in a container, suitable for administration orally or through a feeding tube; and an uncompacted form when released from the container in the stomach of the patient; wherein the gastric residence system is retained in the stomach for a period of at least about 24 hours; and wherein the system releases a therapeutically effective amount of the drug over at least a portion of the period in which the system is retained in the stomach.

Embodiment 138

The gastric residence system of embodiment 137, wherein the dispersant comprises a compound selected from the group consisting of: a porous inorganic material, a polar inorganic material, silica, hydrophilic-fumed silica, stearate salts, calcium stearate, magnesium stearate, microcrystalline cellulose, carboxymethylcellulose, hydrophobic colloidal silica, hypromellose, magnesium aluminum silicate, phospholipids, polyoxyethylene stearates, zinc acetate, alginic acid, lecithin, fatty acids, sodium lauryl sulfate, non-toxic metal oxides, and aluminum oxide.

Embodiment 139

The gastric residence system of embodiment 137, wherein the dispersant comprises silica.

Embodiment 140

The gastric residence system of any one of embodiments 137-139, wherein the cetirizine or salt thereof is comprised of particles dispersed throughout the carrier polymer.

Embodiment 141

The gastric residence system of embodiment 140, wherein at least about 80% of the cetirizine or cetirizine salt particles are between about 2 microns and about 50 microns in diameter.

Embodiment 142

The gastric residence system of any one of embodiments 137-141, wherein less than about 10% of the cetirizine or salt thereof contained in the system elutes within about the first six hours of exposure to gastric fluid.

Embodiment 143

The gastric residence system of any one of embodiments 137-141, wherein the amount of cetirizine or salt thereof eluted from the system within about the first six hours of exposure to gastric fluid is about 50% or less than the amount of cetirizine eluted from the system without the dispersant.

Embodiment 144

The gastric residence system of embodiment 142 or embodiment 143, wherein the carrier polymer-drug component comprises between about 1% to about 30% cetirizine or salt thereof, about 0.5% to about 2.5% of dispersant, and about 67.5% to about 98.5% carrier polymer.

Embodiment 145

The gastric residence system of any one of embodiments 137-144, wherein the carrier polymer comprises polycaprolactone.

Embodiment 146

The gastric residence system of embodiment 145, wherein the polycaprolactone comprises linear polycaprolactone with a number-average molecular weight range between about 45 kDa and about 55 kDa.

Embodiment 147

The gastric residence system of any one of embodiments 137-146, wherein the plurality of carrier polymer-drug components are linked together by two or more coupling polymer components, wherein at least one of the two or more coupling polymer components is an elastomer and at least another one of the two or more coupling polymer components is an enteric polymer.

Embodiment 148

The gastric residence system of embodiment 147, wherein the enteric polymer is selected from the group consisting of poly(methacrylic acid-co-ethyl acrylate), cellulose acetate phthalate, cellulose acetate succinate, and hydroxypropyl methylcellulose phthalate.

Embodiment 149

The gastric residence system of any one of embodiments 136-148, wherein the gastric residence system is retained in the stomach for about 5 days to about 7 days.

Embodiment 150

A gastric residence system for administration to the stomach of a patient, comprising cetirizine or a salt thereof, wherein the plurality of carrier polymer-drug components are linked together by coupling polymers; wherein the gastric residence system is configured to have a compacted form in a container, suitable for administration orally or through a feeding tube; and an uncompacted form when released from the container in the stomach of the patient; wherein the gastric residence system is retained in the stomach for at least about 24 hours; and wherein the system releases a therapeutically effective amount of cetirizine over the period in which the system is retained in the stomach.

Embodiment 151

The gastric residence system of embodiment 150, wherein the cetirizine is in the form of cetirizine hydrochloride.

Embodiment 152

The gastric residence system of embodiment 150, wherein the cetirizine is in non-salt form.

Embodiment 153

The gastric residence system of any one of embodiments 150-152, wherein the carrier polymer is polycaprolactone.

Embodiment 154

The gastric residence system of any one of embodiments 150-153, wherein the coupling polymers are enteric polymers.

Embodiment 155

The gastric residence system of embodiment 154, wherein the coupling polymers are enteric polymers which dissolve at a pH at or above about 5.

Embodiment 156

The gastric residence system of embodiment 154, wherein the enteric polymers dissolve at a pH between about 5 and about 7.

Embodiment 157

The gastric residence system of any one of embodiments 150-156, wherein the coupling polymer is poly(methacrylic acid-co-ethyl acrylate).

Embodiment 158

The gastric residence system of any one of embodiments 150-157, wherein the system is retained in the stomach for at least about five days.

Embodiment 159

The gastric residence system of any one of embodiments 150-158, wherein less than about 5% of the cetirizine present in the system is oxidized after retention in the stomach for about 5 days.

Embodiment 160

The gastric residence system of any one of embodiments 150-159, wherein the system releases between about 5 to 15 mg of cetirizine per day in the stomach.

Embodiment 161

The gastric residence system of any one of embodiments 150-160, wherein the bioavailability of cetirizine released from the system is at least about 50% of that provided by an immediate release form comprising the same amount of cetirizine, wherein the bioavailability is measured by the area under the plasma concentration-time curve (AUCinf).

Embodiment 162

The gastric residence system of any one of embodiments 150-161, wherein the system comprises between about 40 mg to about 120 mg of cetirizine.

Embodiment 163

The gastric residence system of any one of embodiments 150-162, wherein the system adopts its uncompacted form upon release from the container.

Embodiment 164

The gastric residence system of any one of embodiments 150-163, wherein the container is a capsule.

Embodiment 165

The gastric residence system of any one of embodiments 150-164, wherein the gastric residence system further comprises a radiopaque substance.

Embodiment 166

The gastric residence system of any one of embodiments 150-165, wherein the carrier polymer-drug components further comprise an anti-oxidant.

Embodiment 167

A method of treating a patient having an allergic reaction, comprising administering a gastric residence system of any one of embodiments 137-166 to the patient.

Embodiment 168

The method of embodiment 167, wherein the allergic reaction is allergic rhinitis.

Embodiment 169

The method of embodiment 167, wherein the allergic reaction is dermatitis.

Embodiment 170

The method of embodiment 167, wherein the allergic reaction is acute urticaria or chronic urticaria.

Embodiment 171

The method of any one of embodiments 167-170, wherein the gastric residence system is administered to the patient once a week.

Embodiment 172

The method of any one of embodiments 167-170, wherein the gastric residence system has a gastric retention period of D days, and a new gastric residence system is administered to the patient every D days over a total desired treatment period.

Embodiment 173

A method of making a gastric residence system of any one of embodiments 137-166, comprising forming a coupling polymer component; forming a plurality of at least three carrier polymer-drug components, which are elongate members comprising a proximal end and a distal end, wherein the drug is cetirizine or a salt thereof; and attaching the elongate members to the coupling polymer component.

Embodiment 174

The method of embodiment 173, further comprising compacting the gastric residence system and inserting the system into a container suitable for oral administration or administration through a gastric tube or feeding tube.

Embodiment 175

The method of embodiment 173 or embodiment 174, wherein the carrier polymer-drug components are formed by milling cetirizine or a salt thereof, and blending the milled cetirizine or salt thereof, the dispersant, and the carrier polymer.

Embodiment 176

The method of embodiment 175, wherein the blending is performed by hot melt extrusion.

Embodiment 177

The method of any one of embodiments 173-176, wherein forming a plurality of at least three carrier polymer-drug components which are elongate members comprises forming the elongate members from at least two segments.

Embodiment 178

The method of embodiment 177, wherein forming the elongate members from at least two segments comprises forming a collar joint between the segments.

Embodiment 179

The method of any one of embodiments 173-178, wherein the coupling polymer component is asterisk-shaped with a plurality of at least three branches.

Embodiment 180

The method of any one of embodiments 173-179, wherein attaching the elongate members to the coupling polymer component comprises adhering the elongate members to the coupling polymer component.

Embodiment 181

The method of embodiment 179, wherein attaching the elongate members to the asterisk-shaped coupling polymer component comprises forming a collar joint between the elongate members and the branches of the coupling polymer component.

Embodiment 182

A gastric residence system for administration to the stomach of a patient, comprising a plurality of carrier polymer-drug components comprising a carrier polymer and rosuvastatin or a salt thereof, wherein the plurality of carrier polymer-drug components are linked together by coupling polymers; wherein the gastric residence system is configured to have a compacted form in a container, suitable for administration orally or through a feeding tube; and an uncompacted form when released from the container in the stomach of the patient; wherein the gastric residence system is retained in the stomach for at least about 24 hours; and wherein the system releases a therapeutically effective amount of rosuvastatin over the period in which the system is retained in the stomach.

Embodiment 183

The gastric residence system of embodiment 182, wherein the rosuvastatin is in the form of rosuvastatin calcium.

Embodiment 284

The gastric residence system of embodiment 182 or embodiment 183, wherein the carrier polymer is polycaprolactone.

Embodiment 185

The gastric residence system of any one of embodiments 182-185, wherein the coupling polymers are enteric polymers.

Embodiment 186

The gastric residence system of embodiment 185, wherein the coupling polymers are enteric polymers which dissolve at a pH at or above about 5.

Embodiment 187

The gastric residence system of embodiment 185, wherein the enteric polymers dissolve at a pH between about 5 and about 7.

Embodiment 188

The gastric residence system of any one of embodiments 182-187, wherein the coupling polymer is poly(methacrylic acid-co-ethyl acrylate).

Embodiment 189

The gastric residence system of any one of embodiments 182-188, wherein the system is retained in the stomach for at least about five days.

Embodiment 190

The gastric residence system of any one of embodiments 182-189, wherein less than about 5% of the rosuvastatin present in the system is degraded after retention in the stomach for about 5 days.

Embodiment 191

The gastric residence system of any one of embodiments 182-190, wherein the system releases between about 5 to 40 mg of rosuvastatin per day in the stomach.

Embodiment 192

The gastric residence system of any one of embodiments 182-191, wherein the reduction of LDL cholesterol by the system is about 90% to 150% of the reduction of LDL cholesterol by an approximately equal amount of an immediate release formulation of rosuvastatin administered over about the same period of time.

Embodiment 193

The gastric residence system of embodiment 192, wherein the period of time is about one week.

Embodiment 194

The gastric residence system of any one of embodiments 182-193, wherein the system comprises between about 25 mg to about 300 mg of rosuvastatin.

Embodiment 195

The gastric residence system of any one of embodiments 182-194, wherein the system adopts its uncompacted form upon release from the container.

Embodiment 196

The gastric residence system of any one of embodiments 182-195, wherein the container is a capsule.

Embodiment 197

The gastric residence system of any one of embodiments 182-196, wherein the gastric residence system further comprises a radiopaque substance.

Embodiment 198

The gastric residence system of any one of embodiments 182-197, wherein the carrier polymer-drug components further comprise a buffering substance.

Embodiment 199

A method of treating a patient having high cholesterol or triglyceride levels, comprising administering a gastric residence system of any one of embodiments 182-198 to the patient.

Embodiment 200

The method of embodiment 199, wherein the gastric residence system is administered to the patient once a week.

Embodiment 201

The method of embodiment 199, wherein the gastric residence system has a gastric retention period of D days, and a new gastric residence system is administered to the patient every D days over a total desired treatment period.

Embodiment 202

A gastric residence system for administration to a patient, comprising a plurality of carrier polymer-drug components comprising i) a carrier polymer, ii) a dispersant, and iii) rosuvastatin or a salt thereof, wherein the plurality of carrier polymer-drug components are linked together by one or more coupling polymer components, wherein at least one of the one or more coupling polymer components is an elastomer; wherein the gastric residence system is configured to

87 have a compacted form in a container, suitable for administration orally or through a feeding tube; and an uncompacted form when released from the container in the stomach of the patient; wherein the gastric residence system is retained in the stomach for a period of at least about 24 hours; and wherein the system releases a therapeutically effective amount of the drug over at least a portion of the period in which the system is retained in the stomach.

Embodiment 203

The gastric residence system of embodiment 202, wherein the dispersant comprises a compound selected from the group consisting of: a porous inorganic material, a polar inorganic material, silica, hydrophilic-fumed silica, stearate salts, calcium stearate, magnesium stearate, microcrystalline cellulose, carboxymethylcellulose, hydrophobic colloidal silica, hypromellose, magnesium aluminum silicate, phospholipids, polyoxyethylene stearates, zinc acetate, alginic acid, lecithin, fatty acids, sodium lauryl sulfate, non-toxic metal oxides, and aluminum oxide.

Embodiment 204

The gastric residence system of embodiment 202, wherein the dispersant comprises silica.

Embodiment 205

The gastric residence system of any one of embodiments 202-204, wherein the rosuvastatin or salt thereof is comprised of particles dispersed throughout the carrier polymer.

Embodiment 206

The gastric residence system of embodiment 205, wherein at least about 80% of the rosuvastatin or rosuvastatin salt particles are between about 2 microns and about 50 microns in diameter.

Embodiment 207

The gastric residence system of any one of embodiments 202-206, wherein less than about 10% of the rosuvastatin or salt thereof contained in the system elutes within about the first six hours of exposure to gastric fluid.

Embodiment 208

The gastric residence system of any one of embodiments 202-207, wherein the amount of rosuvastatin or salt thereof eluted from the system within about the first six hours of exposure to gastric fluid is about 50% or less than the amount of rosuvastatin eluted from the system without the dispersant.

Embodiment 209

The gastric residence system of embodiment 207 or embodiment 208, wherein the carrier polymer-drug component comprises between about 1% to about 30% rosuvastatin or salt thereof, about 0.5% to about 2.5% of dispersant, and about 67.5% to about 98.5% carrier polymer.

88

Embodiment 210

The gastric residence system of any one of embodiments 202-209, wherein the carrier polymer comprises polycaprolactone.

Embodiment 211

The gastric residence system of embodiment 210, wherein the polycaprolactone comprises linear polycaprolactone with a number-average molecular weight range between about 45 kDa and about 55 kDa.

Embodiment 212

The gastric residence system of any one of embodiments 202-221, wherein the plurality of carrier polymer-drug components are linked together by two or more coupling polymer components, wherein at least one of the two or more coupling polymer components is an elastomer and at least another one of the two or more coupling polymer components is an enteric polymer.

Embodiment 213

The gastric residence system of embodiment 212, wherein the enteric polymer is selected from the group consisting of poly(methacrylic acid-co-ethyl acrylate), cellulose acetate phthalate, cellulose acetate succinate, and hydroxypropyl methylcellulose phthalate.

Embodiment 214

The gastric residence system of any one of embodiments 202-213, wherein the gastric residence system is retained in the stomach for about 5 days to about 7 days.

Embodiment 215

A gastric residence system for administration to the stomach of a patient, comprising a plurality of carrier polymer-drug components comprising a carrier polymer and rosuvastatin or a salt thereof, wherein the plurality of carrier polymer-drug components are linked together by coupling polymers; wherein the gastric residence system is configured to have a compacted form in a container, suitable for administration orally or through a feeding tube; and an uncompacted form when released from the container in the stomach of the patient; wherein the gastric residence system is retained in the stomach for at least about 24 hours; and wherein the system releases a therapeutically effective amount of rosuvastatin over the period in which the system is retained in the stomach.

Embodiment 216

The gastric residence system of embodiment 215, wherein the rosuvastatin is in the form of rosuvastatin calcium.

Embodiment 217

The gastric residence system of embodiment 215 or embodiment 216, wherein the carrier polymer comprises polycaprolactone.

Embodiment 218

The gastric residence system of any one of embodiments 215-217, wherein the coupling polymers are enteric polymers.

Embodiment 219

The gastric residence system of embodiment 218, wherein the coupling polymers are enteric polymers which dissolve at a pH at or above about 5.

Embodiment 220

The gastric residence system of embodiment 218, wherein the enteric polymers dissolve at a pH between about 5 and about 7.

Embodiment 221

The gastric residence system of any one of embodiments 215-220, wherein the coupling polymer is poly(methacrylic acid-co-ethyl acrylate).

Embodiment 222

The gastric residence system of any one of embodiments 215-221, wherein the system is retained in the stomach for at least about five days.

Embodiment 223

The gastric residence system of any one of embodiments 215-222, wherein less than about 5% of the rosuvastatin present in the system is degraded after retention in the stomach for about 5 days.

Embodiment 224

The gastric residence system of any one of embodiments 215-223, wherein the system releases between about 5 to 40 mg of rosuvastatin per day in the stomach.

Embodiment 225

The gastric residence system of any one of embodiments 215-224, wherein the reduction of LDL cholesterol by the system is about 90% to 150% of the reduction of LDL cholesterol by an approximately equal amount of an immediate release formulation of rosuvastatin administered over about the same period of time.

Embodiment 226

The gastric residence system of embodiment 225, wherein the period of time is about one week.

Embodiment 227

The gastric residence system of any one of embodiments 215-226, wherein the system comprises between about 25 mg to about 300 mg of rosuvastatin.

Embodiment 228

The gastric residence system of any one of embodiments 215-227, wherein the system adopts its uncompacted form upon release from the container.

Embodiment 229

The gastric residence system of any one of embodiments 215-228, wherein the container is a capsule.

Embodiment 230

The gastric residence system of any one of embodiments 215-229, wherein the gastric residence system further comprises a radiopaque substance.

Embodiment 231

The gastric residence system of any one of embodiments 215-230, wherein the carrier polymer-drug components further comprise a buffering substance.

Embodiment 232

A method of treating a patient having high cholesterol or triglyceride levels, comprising administering a gastric residence system of any one of embodiments 1-30 to the patient.

Embodiment 233

The method of embodiment 232, wherein the gastric residence system is administered to the patient once a week.

Embodiment 234

The method of embodiment 232, wherein the gastric residence system has a gastric retention period of D days, and a new gastric residence system is administered to the patient every D days over a total desired treatment period.

Embodiment 235

A method of making a gastric residence system of any one of embodiments 182-231, comprising forming a coupling polymer component; forming a plurality of at least three carrier polymer-drug components, which are elongate members comprising a proximal end and a distal end, wherein the drug is rosuvastatin or a salt thereof; and attaching the elongate members to the coupling polymer component.

Embodiment 236

The method of embodiment 235, further comprising compacting the gastric residence system and inserting the system into a container suitable for oral administration or administration through a gastric tube or feeding tube.

Embodiment 237

The method of embodiment 235 or embodiment 236, wherein the carrier polymer-drug components are formed by milling rosuvastatin or a salt thereof, and blending the milled rosuvastatin or salt thereof, the dispersant, and the carrier polymer.

Embodiment 238

The method of embodiment 237, wherein the blending is performed by hot melt extrusion.

Embodiment 239

The method of any one of embodiments 235-238, wherein forming a plurality of at least three carrier polymer-drug components which are elongate members comprises forming the elongate members from at least two segments.

Embodiment 240

The method of embodiment 239, wherein forming the elongate members from at least two segments comprises forming a collar joint between the segments.

Embodiment 241

The method of any one of embodiments 235-240, wherein the coupling polymer component is asterisk-shaped with a plurality of at least three branches.

Embodiment 242

The method of any one of embodiments 235-241, wherein attaching the elongate members to the coupling polymer component comprises adhering the elongate members to the coupling polymer component.

Embodiment 243

The method of embodiment 241, wherein attaching the elongate members to the asterisk-shaped coupling polymer component comprises forming a collar joint between the elongate members and the branches of the coupling polymer component.

EXAMPLES

The invention is further illustrated by the following non-limiting examples.

Example 1

Formulation

Cetirizine hydrochloride powder was weighed and blended with dry powder of hydrophilic excipient polymers in a glass vial. Polycaprolactone (PCL) beads were added and the vial was heated in an oven to 90° C. for 10-20 min or until PCL was completely melted. The vial was then transferred to a dry heating block at 90° C. where the ingredients were mixed thoroughly using a spatula. The mixture was then transferred to the desired mold, which was returned to the 90° C. oven for 20-30 min for gravity molding. The mold was then removed from the oven and allowed to cool to room temperature.

Example 2

Liquid Chromatography/Mass Spectrometry Analysis

Drug concentrations in media used for in vitro release experiments were determined using an Agilent 1100 series HPLC with an Agilent Eclipse XDB C18 column, or a Waters Acquity UPLC with a Xevo QToF LC/MS. Samples were run on the Agilent system using either a gradient of 5%-95% acetonitrile in water over 10 min or an isocratic method at 40% acetonitrile:water over 10 min, or on the Waters system using a Waters Acuity C18 column with a gradient of 5%-95% (acetonitrile with 0.1% formic acid):(water with 0.1% formic acid) in 3 min. A standard curve for determination of cetirizine concentration was developed by integration of the UV absorbance trace. The column eluent can be fed into a mass spectrometer for further analysis.

Example 3

In Vitro Release in Simulated Gastric Fluid

Formulations of 25% cetirizine, 5-20% other excipients, and the balance PCL were prepared as described in Example 1. Formulations were gravity molded into rod-shaped pieces.

Fasted state simulated gastric fluid (FaSSGF, also referred to as SGF) was prepared according to the vendor's instructions (Biorelevant.com, London, United Kingdom). A NaCl/HCl solution was prepared by dissolving 2.0 g of NaCl in about 0.9 L of purified water. The pH was adjusted to 1.6 with HCl. The volume was made up to 1.0 L with purified water at room temperature. 0.060 g of FaSSIF, FeSSIF & FaSSGF Powder was added to about 0.5 L HCl/NaCl solution, and the volume was made up to 1.0 L with HCl/NaCl solution at room temperature to make FaSSGF (also referred to herein as SGF).

Polymer-agent pieces were submerged in 20 mL FaSSGF in glass vials with small stir bars. Vials were heated to 37° C. in a dry heating block and stirred at a rate of ~200 rpm. At each time point, release media was sampled for LCMS or HPLC analysis as per Example 2, and the entire volume of release media was replaced with fresh FaSSGF.

Figure 5A:
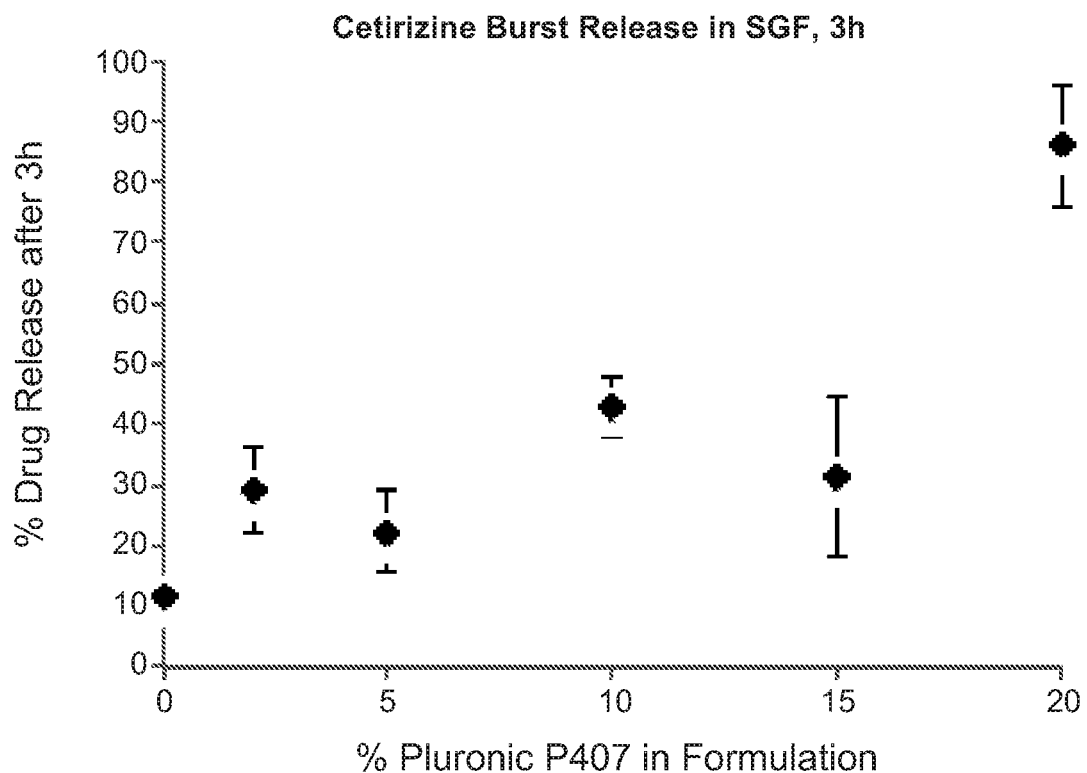
FIG. 5 shows burst release of cetirizine from a polycaprolactone carrier polymer formulation with varying amounts of Pluronic P407 excipient polymer. Panel A shows release into simulated gastric fluid after 3 hours, while panel B shows release into simulated gastric fluid after 6 hours.
Figure 5B:
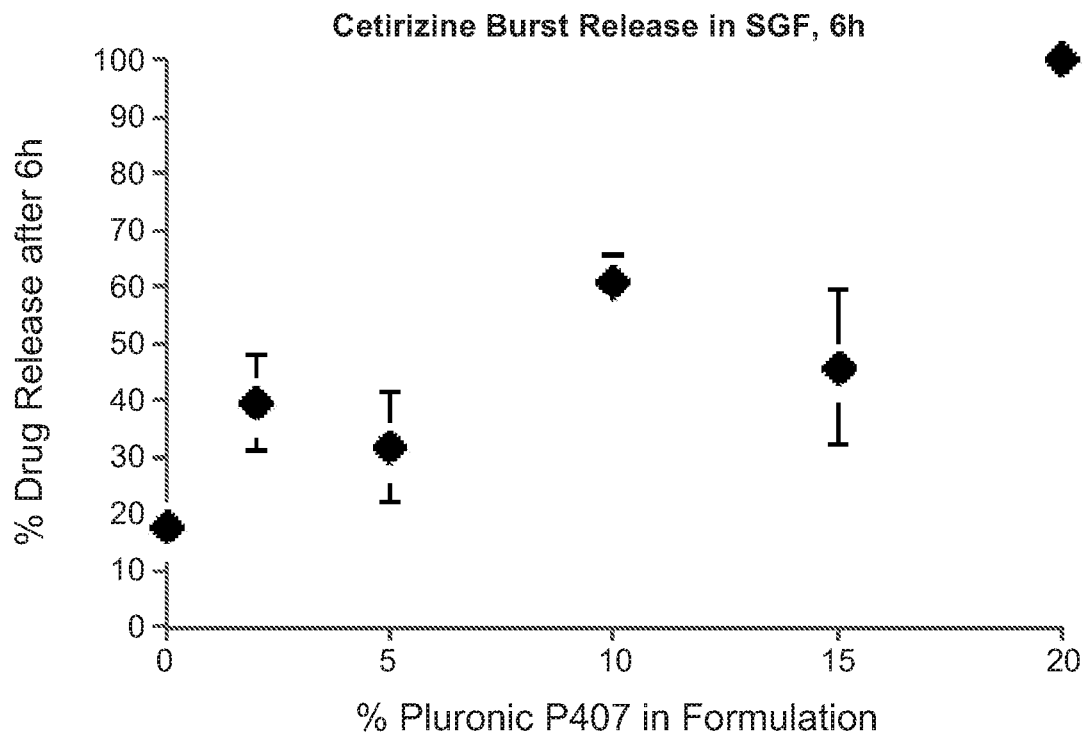

Cetirizine burst release, the percentage of the drug load released from a formulation in the first 6 hours of incubation in SGF, is shown in FIG. 5 for formulations of cetirizine in polycaprolactone (PCL) with varying amounts of Pluronic P407 as polymer excipient. Panel A shows release after 3 hours in SGF, while panel B of FIG. 5 shows release after 6 hours in SGF. Cetirizine is a very hydrophilic drug, and was released rapidly from the PCL formulations in SGF. Reducing the amount of hydrophilic excipient polymer (Pluronic P407 in this case) in the formulation reduced the release rate of cetirizine from the formulation.

Example 4

Testing Release Variability with Respect to Different Solvents In Vitro

Formulations are prepared as described and molded into 200-mg discs. The discs are submerged in 10 mL FaSSGF, heated to 37° C. in a dry heating block and stirred at a rate of ~200 rpm for 24 h. After 24 h, the FaSSGF is removed and 10 mL of warm (50° C.) water, 40% ethanol, or fresh FaSSGF (control) are added to the vials. After one more hour, release media is sampled and analyzed by LCMS or HPLC to determine cetirizine concentration and calculate total drug release in the 1-hour time frame as compared to the control formulation (which is incubated in 10 mL FaSSGF at 37° C. for 1 h).

Example 5

Testing Therapeutic Agent Stability Under Different Solution and Heat Conditions In Vitro Cetirizine was subjected to various forced degradation conditions both in solution and in PCL formulation. 50 mg pieces of formulation (25% cetirizine, 5% Pluronic P407, 70% PCL) were soaked in 30% $H_2O_2$ at 37° C. At the specified time points, the formulations were removed from the peroxide solution and remaining drug was extracted and analyzed by HPLC. FIG. 4 shows the analytical results. The first trace (A) shows intact cetirizine extracted from formulation before any exposure to peroxide. The second trace (B) shows cetirizine, without any polymer formulation, degraded by dissolution in 30% $H_2O_2$ at 37° C. for 20 hours. The remaining traces show cetirizine extracted from formulation after the specified time (trace C, 4 hours; trace D, 8 hours; trace E, 20 hours) in 30% $H_2O_2$ at 37° C. The decreasing peak size from traces C to E is due to elution of drug from the carrier polymer matrix. Traces C, D, and E show that the cetirizine remaining in the PCL formulation (i.e., the drug that is not eluted during the time period) was protected against oxidative degradation.

Example 6

Microscopy

Samples are imaged using an EVOS fluorescence microscope. Cetirizine hydrochloride powder, pure PCL, and drug-polymer formulations are imaged using both bright field and red fluorescent protein settings.

Example 7

In Vitro Estimation of Uncoupling Time

The uncoupling time of the systems caused by weakening and dissolution of the coupling polymer can be estimated by placing the systems in simulated gastric fluid (SGF) and in simulated intestinal fluid. Simulated gastric fluid (SGF) and simulated intestinal fluid (SIF) are prepared using Biorelevant.com FaSSIF, FeSSIF & FaSSGF Powder according to the manufacturer's instructions for SGF (see Example 3) and SIF at the URL biorelevant.com/fassif-fessif-fassgf-dissolution-media/fasted-fed-state-simulated-intestinal-gastric-fluid/how-to-make. Instructions for preparation of SIF are as follows: buffer is prepared by dissolving 0.420 g of NaOH pellets, 3.438 g of anhydrous $NaH_2PO_4$, and 6.186 g of NaCl in about 0.900 L of purified water. The pH is adjusted to 6.5 with either 1 N NaOH or 1 N HCl, and the volume made up to 1.000 L with purified water at room temperature. 2.240 g of FaSSIF, FeSSIF & FaSSGF Powder is added to about 0.5 L of buffer and the mixture stirred until the powder is completely dissolved. The volume is made up to 1.000 L with buffer at room temperature. The SIF is allowed to stand for 2 hours before use.

A system is placed in SGF. Another, identical system is placed in SIF. Gentle periodic agitation is provided to simulate the stomach or intestinal environment. The time at which the first coupling polymer junction separates is designated as an initial or first uncoupling time, while the times at which subsequent coupling polymer junctions separate is designated as a second, third, etc. uncoupling time. The time required for all polymer junctions to separate is the final uncoupling time. Ideally, the uncoupling time in SGF is about 7 days to about 12 days, while the uncoupling time in SIF is about 1 hour to about 48 hours.

Example 8A

In Vivo Evaluation of Gastric Residence Systems: Pigs

In vivo testing of gastric residence systems can be performed in a pig model. Experimental animals are used in compliance with applicable laws and institutional guidelines. Yorkshire pigs have similar gastric and intestinal anatomy as humans, and have been used for evaluation of systems and systems used in the GI tract. Yorkshire pigs weighing 45-55 kg are sedated and capsules are introduced into the stomach via the esophagus under endoscopic visualization. Pigs are monitored over the period of time from several days prior to introduction of the system until several days after passage of the system. The feeding and elimination patterns of the pigs are noted. X-rays and/or endoscopic images are taken periodically to determine the position and condition of the gastric residence system. Blood samples are drawn periodically to determine plasma levels delivered by the gastric residence system.

Example 8B

In Vivo Evaluation of Gastric Residence Systems: Humans

In vivo testing of gastric residence systems is performed in human subjects. Testing is performed in subjects in compliance with applicable laws and institutional guidelines. The subjects swallow a capsule, and are monitored over the period of time from several days prior to introduction of the system until several days after passage of the system. Digestive function and elimination patterns of the subjects are noted. The subjects complete questionnaires at periodic intervals to report any unusual events. X-rays and/or endoscopic images are taken periodically to determine the position and condition of the gastric residence system. Blood samples are drawn periodically to determine plasma levels delivered by the gastric residence system.

Example 9

Excipient Effect on Therapeutic Agent Elution Rate; Dispersant Effect on Cetirizine Burst Release The effect of different excipients on the elution rate of cetirizine from carrier polymer-agent formulations was studied. The carrier polymer-agent formulations were in the shape of triangular prisms ("star arms") suitable for use in a system such as that depicted in FIG. 2 or FIG. 2A. The star arms were placed in simulated gastric fluid prepared as described in Example 3. The amount of drug released was assayed at 3 hours of immersion in SGF and 6 hours of immersion in SGF.

Figure 6:
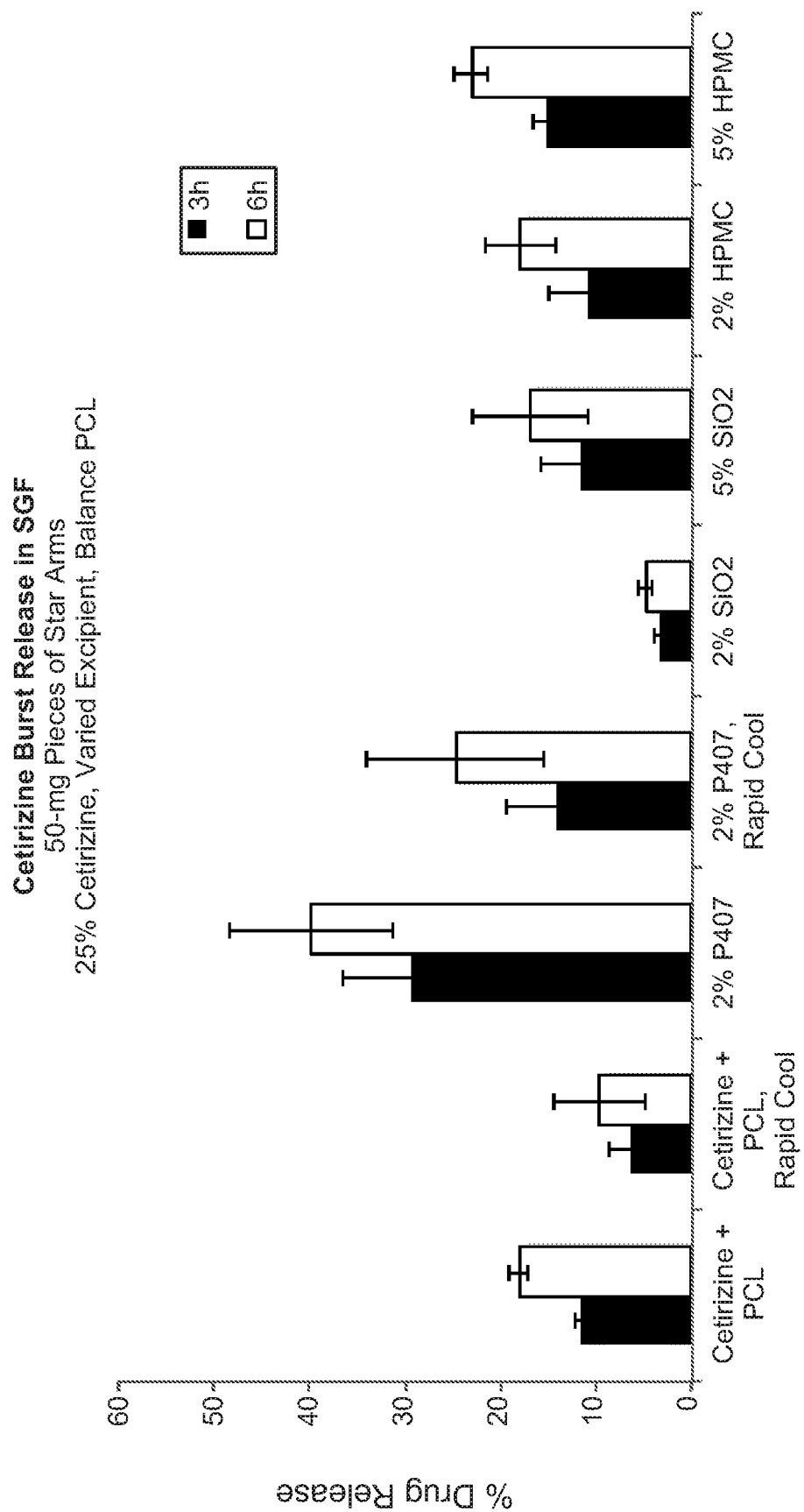
FIG. 6 shows burst release of cetirizine from a polycaprolactone carrier polymer-agent formulation with no additional excipients or dispersants and with varying amounts of excipient or dispersant. Black (filled) bars, release after 3 hours; white (unfilled) bars, release after 6 hours.

FIG. 6 shows the results of testing burst release of cetirizine. From left to right, the pairs of bars show: cetirizine (25%)+polycaprolactone (75%) (bars labeled cetirizine+PCL); cetirizine (25%)+polycaprolactone (75%) with rapid cooling of polymer melt (bars labeled cetirizine+PCL, rapid cool); cetirizine (25%)+Pluronic P407 (2%)+polycaprolactone (73%) (bars labeled 2% P407); cetirizine (25%)+Pluronic P407 (2%)+polycaprolactone (73%) with rapid cooling of polymer melt (bars labeled 2% P407, rapid cool); cetirizine (25%)+$SiO_2$ (2%)+polycaprolactone (73%) (bars labeled 2% $SiO_2$); cetirizine (25%)+$SiO_2$ (5%)+polycaprolactone (70%) (bars labeled 5% $SiO_2$); cetirizine (25%)+hydroxypropyl methylcellulose (2%)+polycaprolactone (73%) (bars labeled 2% HPMC); cetirizine (25%)+hydroxypropyl methylcellulose (5%)+polycaprolactone (70%) (bars labeled 5% HPMC). The black (filled) bars show release after 3 hours, while the white (unfilled) bars show release after 6 hours.

When cetirizine was formulated in polycaprolactone (PCL), at a ratio of 25% drug to 75% PCL, about 12% of the drug is released within 3 hours, while about 18% of the drug is released within 6 hours, as shown in the leftmost bars of FIG. 6 labeled "Cetirizine+PCL." Rapid cooling of the polymer-agent melt results in a significant lowering of burst release, as shown in the bars labeled "Cetirizine+PCL, rapid cool" in FIG. 6. The largest decrease in burst release is demonstrated by using silicon dioxide as an excipient. Accordingly, the effect of using different amounts of $SiO_2$ in the carrier polymer-agent component was studied.

Figure 7:
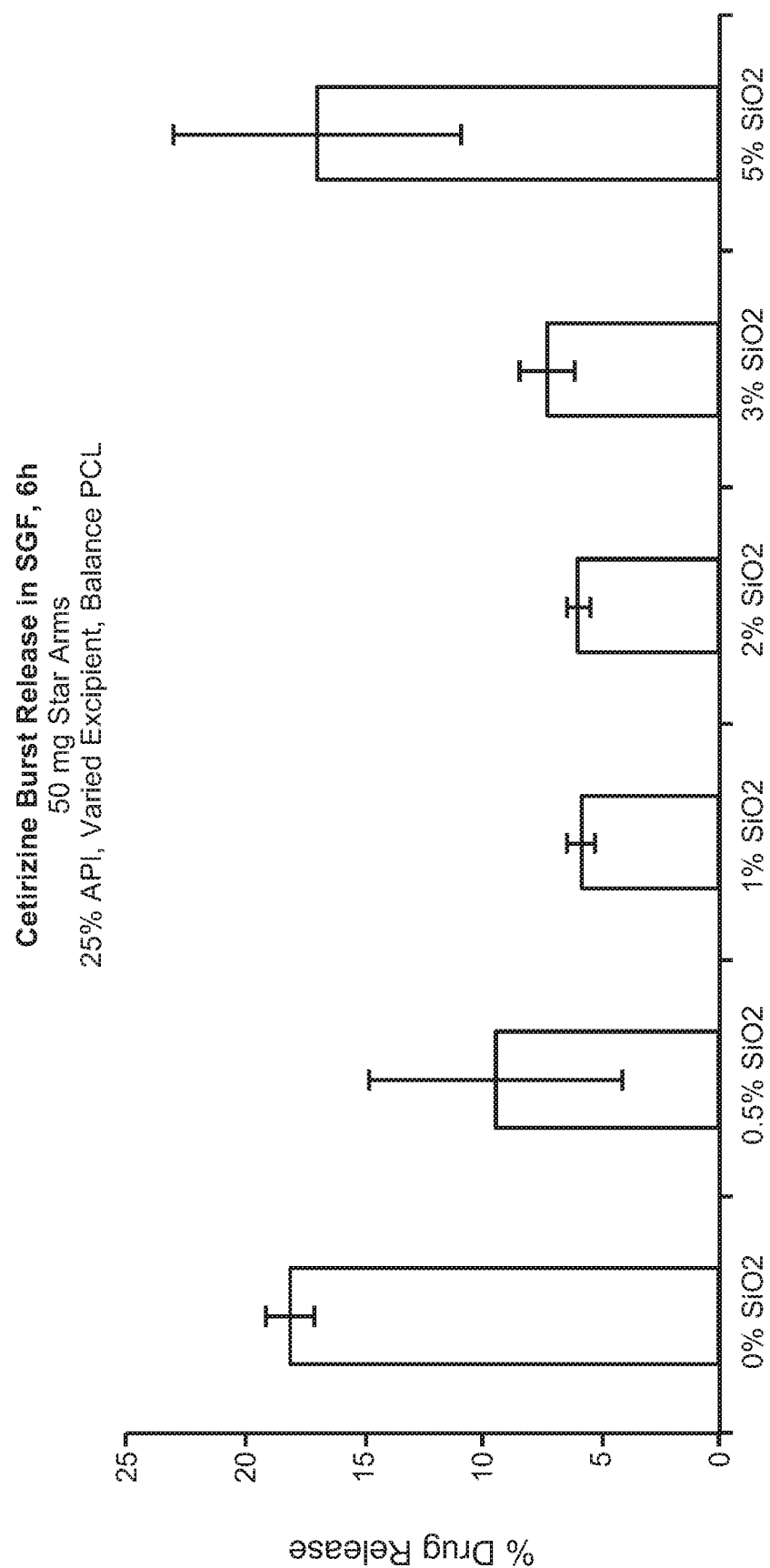
FIG. 7 shows burst release of cetirizine from a polycaprolactone carrier polymer-agent formulation with no additional dispersants and with varying amounts of $SiO_2$ dispersant.
Figure 8:
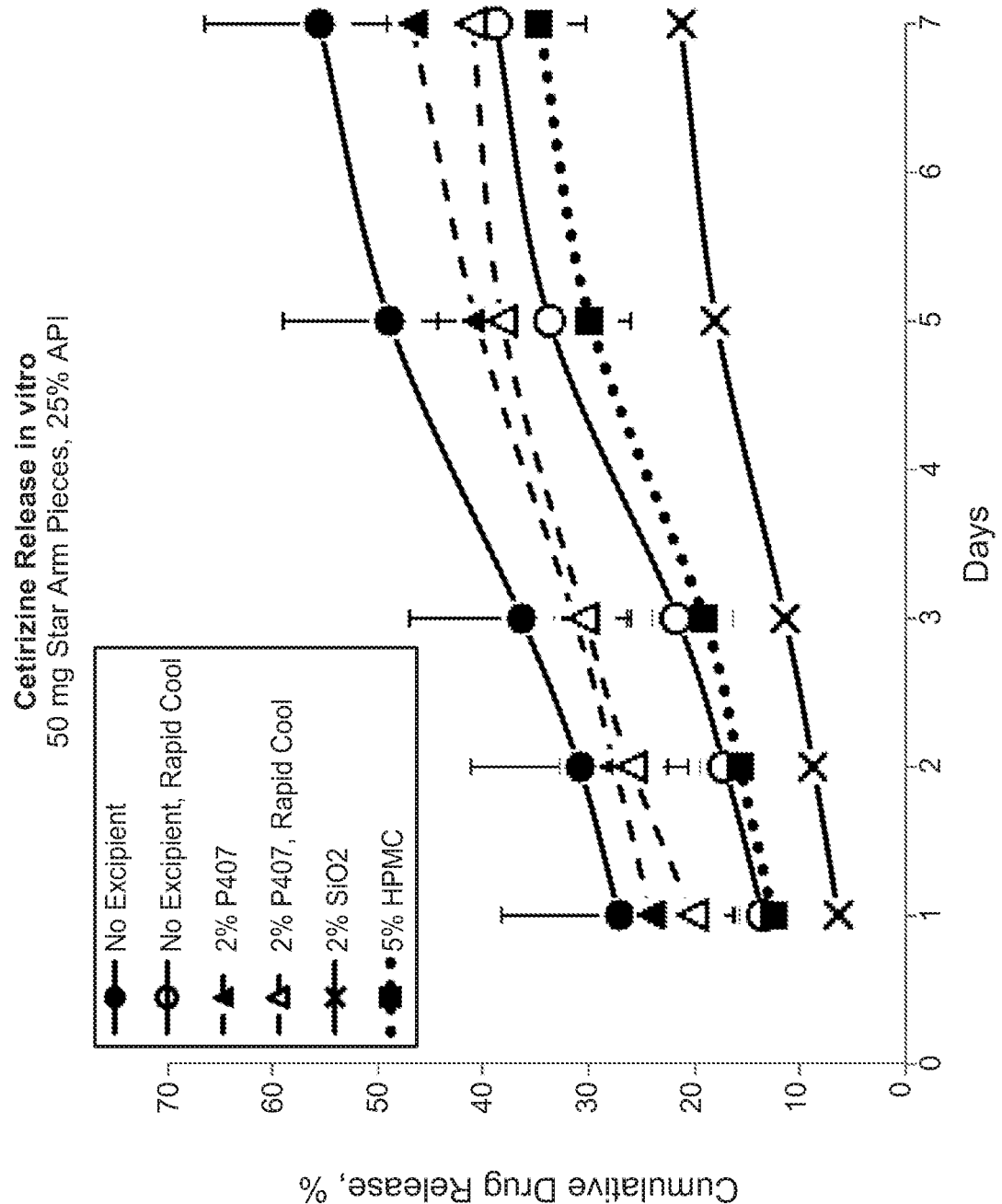
FIG. 8 shows cumulative release of cetirizine over a seven-day period from different polycaprolactone carrier polymer-agent formulations. At seven days, PCL-cetirizine formulation with no additional excipients or dispersants (filled circles) showed the most cetirizine release, followed by PCL-cetirizine formulation with 2% P407 (filled triangles), PCL-cetirizine formulation with 2% P407 and rapid cooling (open triangles), PCL-cetirizine formulation with 5% hydroxypropylmethylcellulose (HMPC) (filled squares), while PCL-cetirizine formulation with 2% $SiO_2$ (marked by X's) showed the lowest release after seven days and for every day over the seven day period.
Figure 9C:
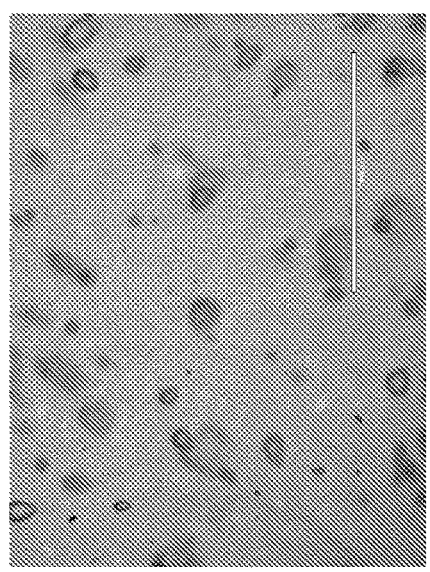
FIG. 9 shows images of unprocessed ivermectin (A), ivermectin milled for 1 hour (B), and ivermectin milled for 1 hour with 1% $SiO_2$ (C); PCL formulation with unprocessed ivermectin (AA), PCL formulation with ivermectin milled for 1 hour (BB), and PCL formulation with ivermectin milled for 1 hour with 1% $SiO_2$ (CC).
Figure 9C:
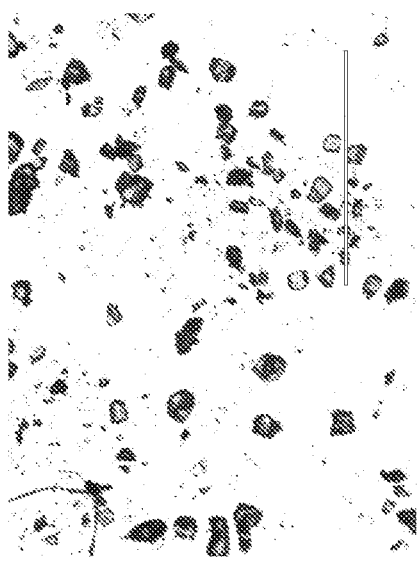
Figure 9B:
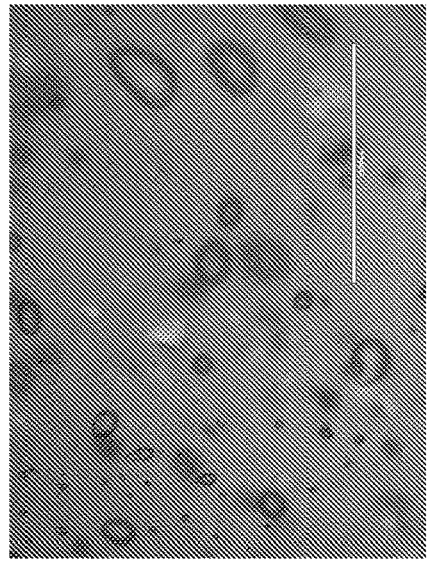
Figure 9B:
Figure 9A:
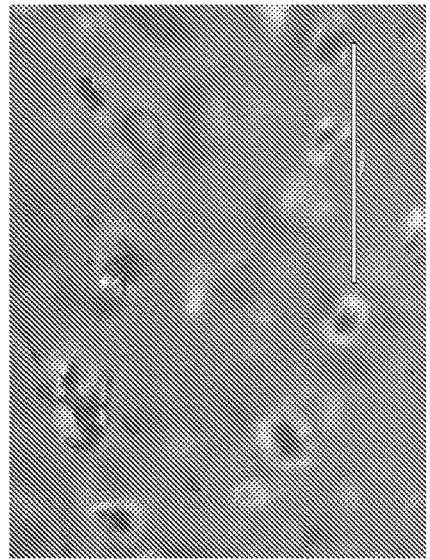
Figure 9A:
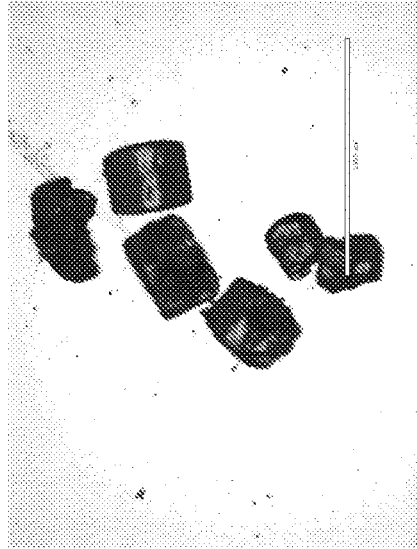
Figure 10C:
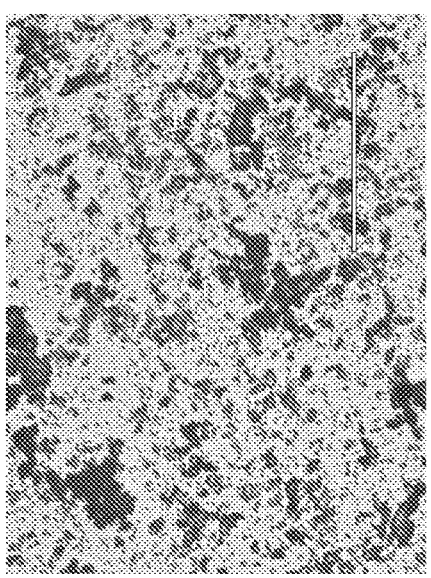
FIG. 10 shows images of unprocessed risperidone (A), risperidone milled with 1% $SiO_2$ (B, 2× magnification; C, 40× magnification); PCL formulation with unprocessed risperidone (AA), PCL formulation with risperidone milled with 1% $SiO_2$ (BB, 2× magnification; CC, 40× magnification).
Figure 10C:
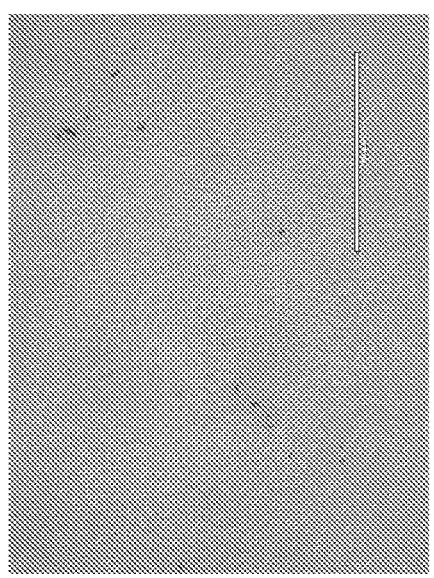
Figure 10B:
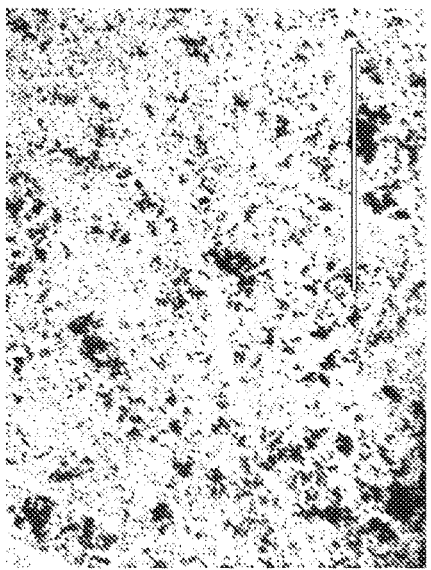
Figure 10B:
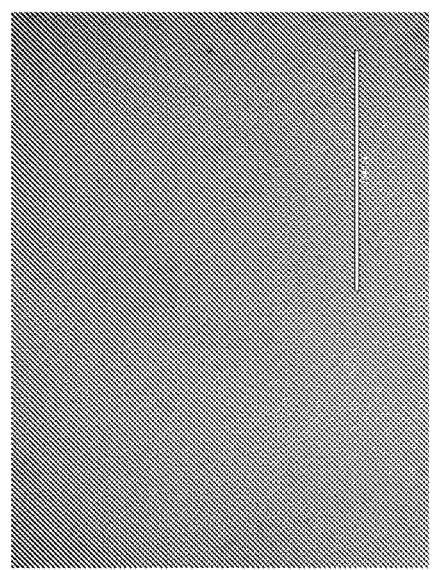
Figure 10A:
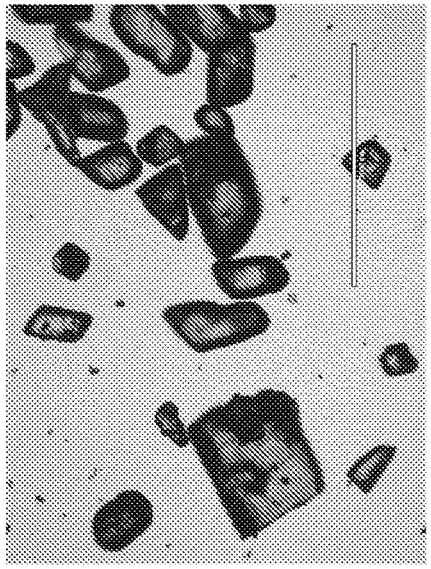
Figure 10A:
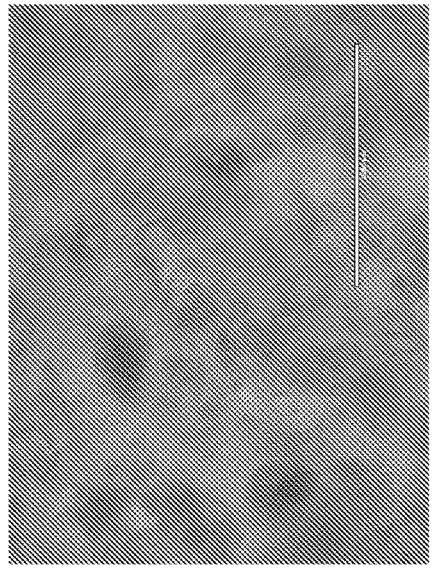
Figure 11:
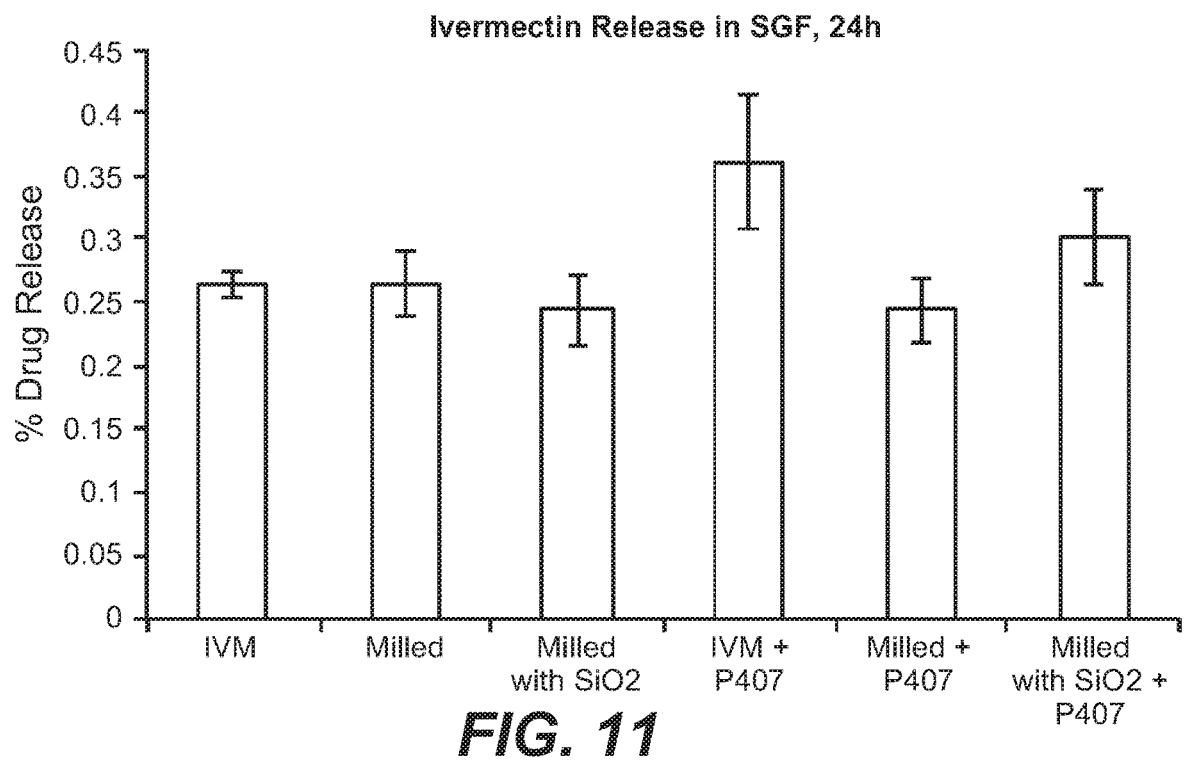
FIG. 11 shows release from ivermectin formulations in simulated gastric fluid over 24 hours.
Figure 12:
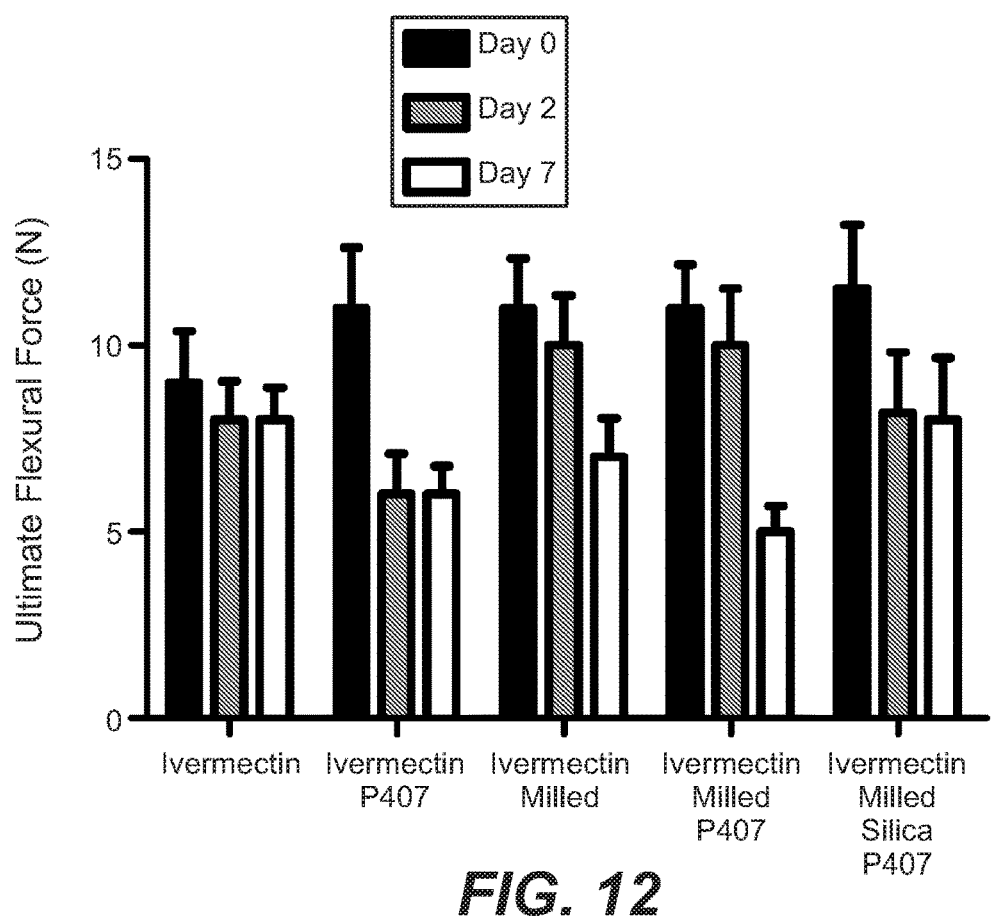
FIG. 12 shows four-point flexural tests of ivermectin drug-loaded arms.

FIG. 7 shows burst release of cetirizine from polycaprolactone carrier polymer-agent formulations with either no additional excipients, or with varying amounts of $SiO_2$ excipient. The formulation comprised 25% cetirizine and the indicated amount of $SiO_2$, while the remaining amount was made up by polycaprolactone. From left to right in FIG. 7, the percentages of $SiO_2$ used were 0%, 0.5%, 1%, 2%, 3%, and 5%. An amount of $SiO_2$ of from 1% to 2% showed the lowest amount of burst release (about 5%-7%) after 6 hours in simulated gastric fluid.

Example 10

Preparation of Elastomer for Use in Systems

A. Preparation of 80 k PCL Star Arms for Elastomer Interfacing:

Polycaprolactone (PCL) beads (Mn~80 k, Sigma Cat #440744) were loaded into a 00e1-sized, star-shaped polydimethylsiloxane (PDMS) mold. The beads were melted in an oven 90-100° C. for 20-30 min or until fully melted. Additional polymer beads were added and melted as needed to completely fill the mold. Once filled and completely molten, the mold was removed from the oven and covered with a Teflon sheet. A weight was placed on top of the Teflon sheet to ensure a flat upper surface to the molded shape. Stars were allowed to cool at room temperature for at least 1 h.

After cooling, the PCL stars were removed from the mold and trimmed of any excess PCL using a scalpel or razor blade. Star arms were then cut away from the center portion of the star. Cuts were made along the arms at a position 1-5 mm from the point at which star arms meet. The six star arms were then replaced in the PDMS mold and the central portion was discarded, leaving a space in the center of the mold for formation of the elastic crosslinked PCL element.

B. Preparation of Elastic Crosslinked PCL:

Polycaprolactone (PCL) diol (3.2 g, Mn~900: Sigma Cat #189405), PCL triol (1.2 g. Mn~530: Sigma Cat #200409), and linear PCL (Mn~14 k, Sigma Cat #440752; or Mn~45 k, Sigma Cat #704105; or Mn~55 k, Scientific Polymer Products Cat #1029; 1.2 g) were loaded into a 20-mL glass vial with a magnetic stir bar and heated to 70° C. The mixture was stirred gently at a rate of 100-150 rpm for at least two hours. Crosslinker (1.573 mL of hexamethylene diisocyanate, Sigma Cat #52649) was then added and the mixture was stirred at 70° C. for an additional 20-40 min. The prepolymer mixture was then degassed under vacuum for 2-5 minutes. The prepolymer was then transferred to the desired mold, a 00e1-sized star shape in which the star arms were previously filled with 80 k PCL as described above. The prepolymer was then cured in the presence of the 80 k PCL arms to ensure strong interfacing of the elastomer to the PCL arms. The polymer was cured for 48 hours at 70° C., then removed from the oven and allowed to set for at least 2 days at room temperature. The 80 k PCL arms were then cut at a position 0.5-3 mm from the interface of the PCL with the crosslinked elastomer. This produced an elastic central asterisk shape, with arms capped with thin layers of PCL at their ends. The thin layers of PCL allow for later melt interfacing to agent-loaded arms (carrier polymer-agent components), such as those prepared in Section A of this Example.

Mixing temperatures, curing temperatures, and curing times may be varied for other crosslinking agents, such as toluene diisocyanate (Sigma Cat #T3985) or cyclohexylene diisocyanate (Sigma Cat #269360).

Example 11

Preparation of Enteric Elastomer for Use in Systems

An enteric elastomer suitable for use in the systems is prepared from poly(acryloyl 6-aminocaproic acid) (PA6ACA) and poly(methacrylic acid-co-ethyl acrylate) (EUDRAGIT L 100-55), as described in Zhang et al., "A pH-responsive supramolecular polymer gel as an enteric elastomer for use in gastric devices," Nature Materials 14(10):1065-71 (epub Jul. 27, 2015). Briefly, the enteric elastomer is prepared by co-precipitation of a solution of PA6ACA sodium salt and L 100-55 sodium salt in polymer weight ratios of 1:0, 1:1 and 1:2 via addition of 6M HCl solution. The polymer is then compacted by ultracentrifugation, and cut into the desired shape for the system.

Example 12

Burst Release of Risperidone from PCL Formulation

Preparation and Molding of Agent-Polymer Blends.

1.5 g of agent-polymer blend was prepared as follows: 375 mg of either unprocessed risperidone, or ball milled and sifted risperidone, were weighed in a 20-mL glass vial for each formulation. Silicon dioxide (fumed silica: CAB-O-SIL® M-5P (CAS #112945-52-5); 0-7.5 mg, corresponding to 0-5% of the total formulation) was added to the drug powder. The drug powder and silicon dioxide excipient were blended with a spatula for about one minute. Polycaprolactone (PCL) pellets (1.05 g-1.125 g; Mn~45 k, Sigma Cat #704105; or Mn~55 k, Scientific Polymer Products Cat #1029 (CAS #24980-41-4)) were added to the drug-silica blend and the vials were placed in a 90° C. convection oven for 20-30 minutes or until the PCL was melted. Each formulation was blended with a metal spatula until all of the drug powder was evenly distributed within the molten polymer. After mixing, the formulations were returned to the oven for 20-30 minutes at 90° C. Formulations were then removed from the oven and the drug-polymer blend was loaded into PDMS molds of the desired geometry (00e1 size stars). Filled molds were heated in the oven at 90° C. for 30 min. They were then removed from the oven, and covered with a Teflon sheet and a weight to achieve a flat upper surface. Covered molds were allowed to cool to room temperature for 1 h.

Drug Release Assay.

Simulated gastric fluid (FaSSGF) and simulated intestinal fluid (FaSSIF) were prepared according to the manufacturer's instructions (biorelevant.com). Molded stars of drug-polymer formulation were cut into 50-mg pieces. Each piece was loaded into a 15-mL Falcon centrifuge tube, along with 5 mL of release media (FaSSGF or FaSSIF). Racks of tubes were placed into a 37° C. orbital shaker and shaken at 180-250 rpm for the desired release time. Samples of release media were analyzed by HPLC to determine drug concentration.

Figure 13:
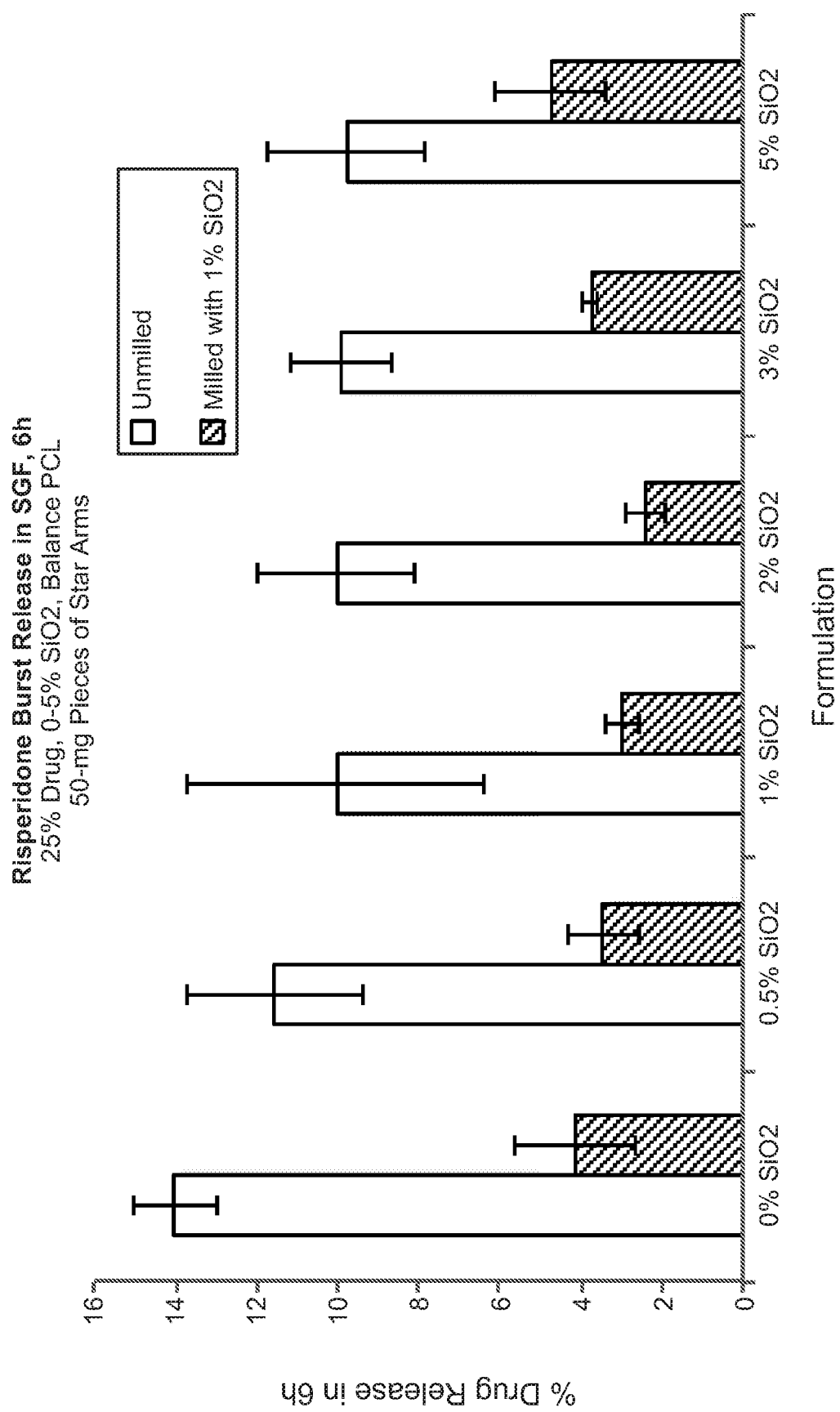
FIG. 13 shows burst release of various risperidone formulations in simulated gastric fluid over 6 hours.
Figure 14:
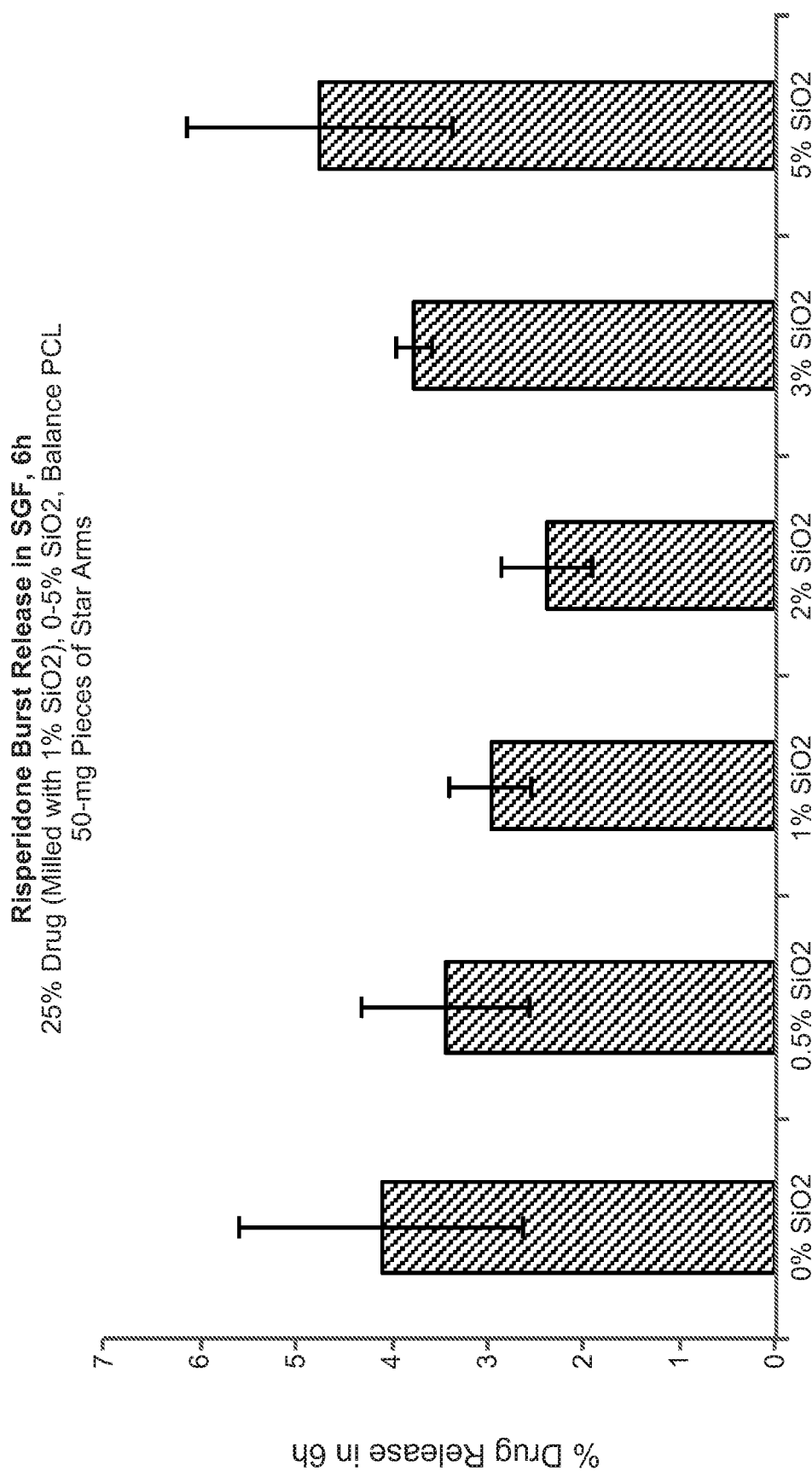
FIG. 14 shows burst release of various risperidone formulations in simulated gastric fluid over 6 hours, on an expanded vertical scale.
Figure 15:
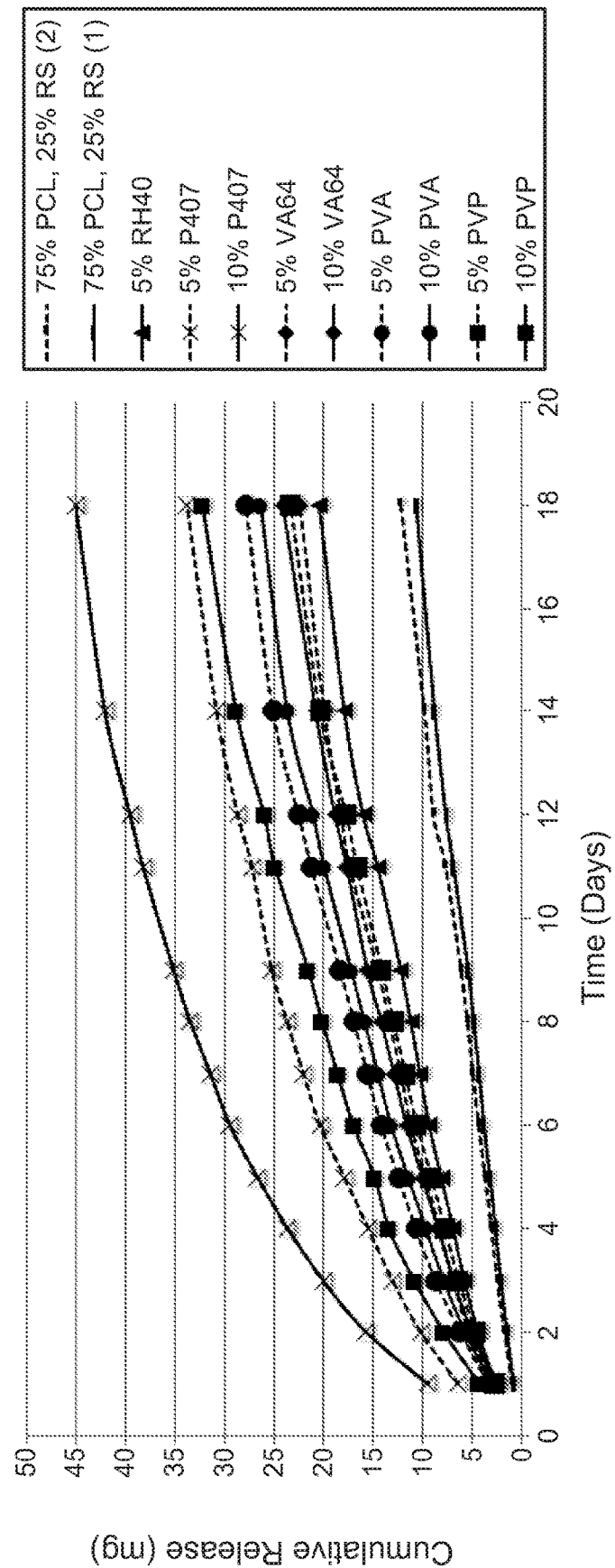
FIG. 15 shows in vitro release rates of rosuvastatin (RS) from various blends of polycaprolactone and additional excipients (25% rosuvastatin, plus indicated percentage of additional excipient; balance polycaprolactone). Abbreviations: PCL, polycaprolactone; RH40, Kolliphor RH 40; P407, Pluronic P407; VA74, Kollidon VA 64; PVA, polyvinylacetate; PVP, polyvinylpyrrolidone.

FIG. 13 shows the results of risperidone burst release tests in simulated gastric fluid, both for unmilled and milled risperidone formulations containing 25% risperidone, 0-5% $SiO_2$, and the balance PCL. For unmilled risperidone, addition of $SiO_2$ dispersant decreased burst release up to about 1% $SiO_2$; increasing the amount of $SiO_2$ up to 5% showed no additional effect. For milled risperidone, addition of $SiO_2$ dispersant decreased burst release up to about 2% $SiO_2$; burst release began increasing at 3% $SiO_2$. $SiO_2$ decreased the burst release of risperidone in a similar manner to that seen for cetirizine. Much more significant, however, is the dramatic decrease in burst release between unmilled and milled risperidone seen in FIG. 13. FIG. 14 shows the data for milled risperidone on an expanded axis; with 2% $SiO_2$, burst release of risperidone was reduced below 3% for the first six hours in simulated gastric fluid.

Example 13

Ivermectin Milling

Ivermectin was ball milled with and without 1% silica and sifted through a 180-micron sieve. Drug-polymer blends were prepared as described in Example 12, using either unmilled ivermectin, milled ivermectin, or ivermectin milled with 1% silica. FIG. 9 shows the resulting drug particle size and homogeneity; view (A) shows unprocessed ivermectin, view (B) shows ivermectin milled for 1 hour, and view (C) shows ivermectin milled for 1 hour with 1% $SiO_2$.

Example 14

Assessment of Ivermectin Formulation Homogeneity by Light Microscopy

Polycaprolactone formulations of ivermectin were prepared using unprocessed ivermectin or ivermectin as milled in Example 13. Additional silicon dioxide was added to the drug during formulation, along with other excipients. Final formulations consisted of 15% ivermectin, 0.5% silicon dioxide, 0.5% alpha tocopherol, 0.5 or 8.5% poloxamer 407, and the balance PCL. (The 15% ivermectin included milling agent; thus, when ivermectin was milled with 1% silica and 15% milled ivermectin was added to the formulation, 1% of the milled ivermectin was silica. Thus, addition of 0.5% silicon dioxide resulted in a total amount of silica in the formulation of 0.65%, as 1%×15% provides an additional 0.15% of silica.)

Approximately 20 mg of drug-polymer formulation was placed on a glass microscope slide and heated in a 70° C. oven for 10 minutes. The glass slide was removed from the oven and covered with a Teflon sheet. A weight was placed on top of the Teflon sheet, pressing the softened formulation into a film of less than 1 mm in thickness. These formulation sheets were observed under an Evos light microscope using either the bright field or phase contrast settings.

FIG. 9 shows microscopic examination of formulations of ivermectin with PCL. View (AA) shows PCL formulation with unprocessed ivermectin, view (BB) shows PCL formulation with ivermectin milled for 1 hour, and view (CC) shows PCL formulation with ivermectin milled for 1 hour with 1% $SiO_2$ (CC).

Example 15

Risperidone Milling

Risperidone drug substance was examined in the unprocessed state and after milling with 1% $SiO_2$. FIG. 10, view (A) shows unprocessed risperidone; FIG. 10, view (B) shows risperidone milled with 1% SiO2 at 2× magnification, while view (C) shows risperidone milled with 1% SiO2 at 40× magnification.

Example 16

Assessment of Risperidone Formulation Homogeneity by Light Microscopy

Formulations containing the risperidone milled in Example 15 were prepared in a similar manner as for ivermectin in Example 14. FIG. 10, view (AA) shows formulation with unprocessed risperidone; FIG. 10, view (BB) shows formulation with risperidone milled with 1% SiO2 at 2× magnification, while view (CC) shows formulation with risperidone milled with 1% SiO2 at 40× magnification.

Example 17

Ivermectin Release in Simulated Gastric Fluid

Figure 22:
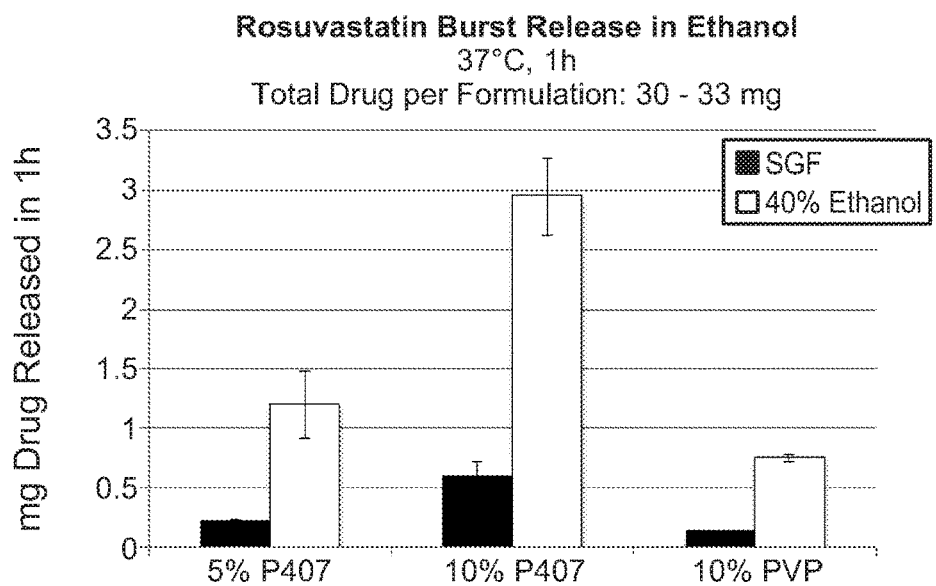
FIG. 22 shows burst release of rosuvastatin when exposed to 40% ethanol/60% simulated gastric fluid versus simulated gastric fluid.
Figure 23A:
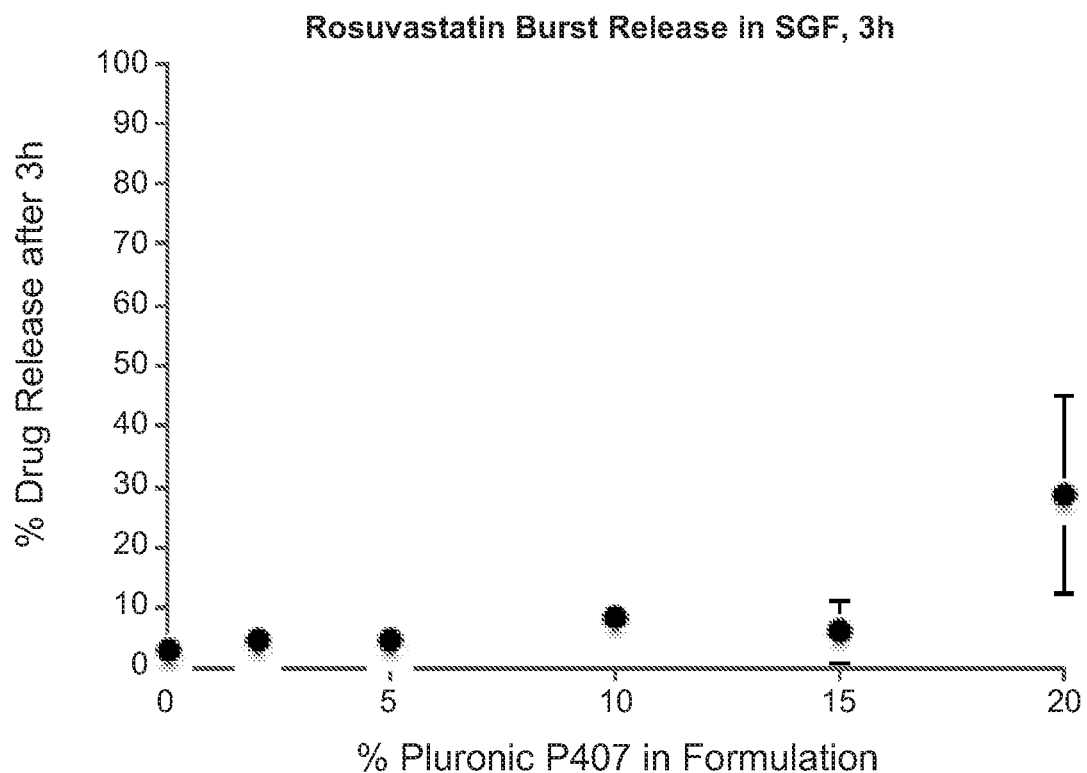
FIG. 23 shows burst release of rosuvastatin from a polycaprolactone carrier polymer formulation with varying amounts of Pluronic P407 excipient polymer. Panel A shows release into simulated gastric fluid after 3 hours, while panel B shows release into simulated gastric fluid after 6 hours.
Figure 23B:
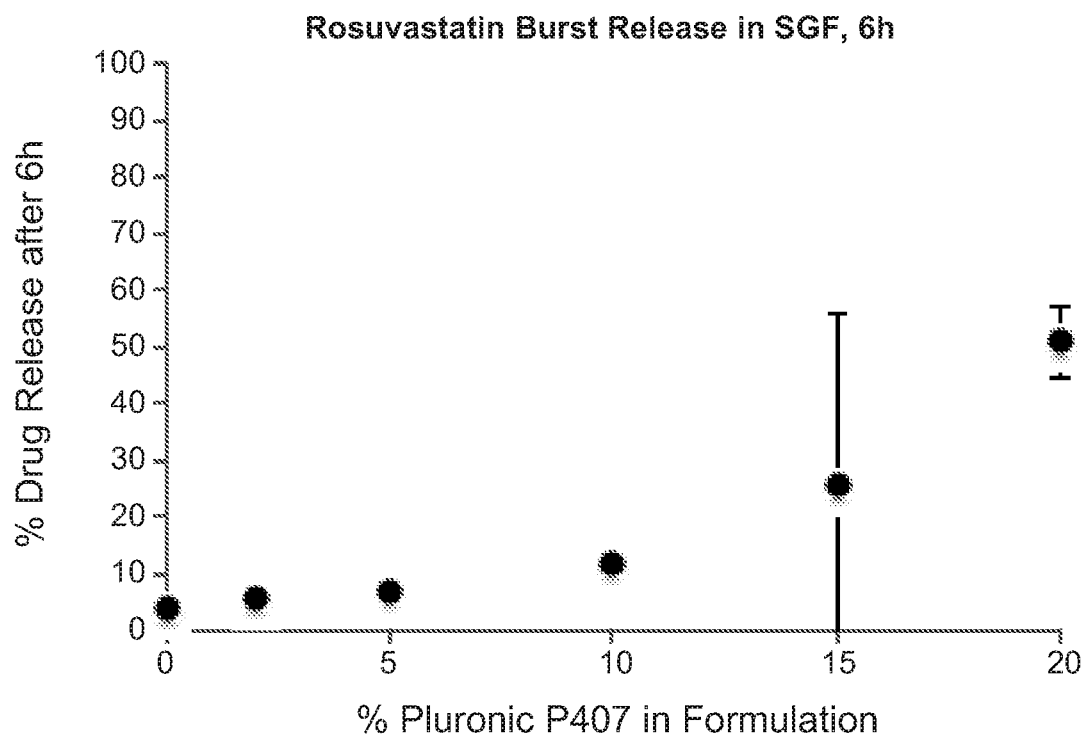
Figure 24:
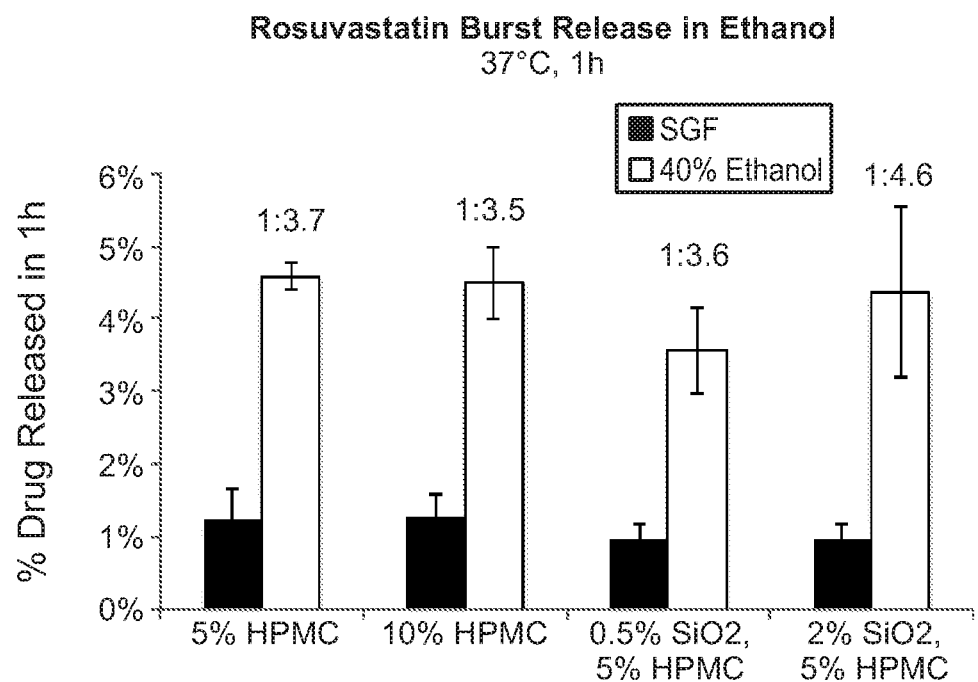
FIG. 24 shows burst release of rosuvastatin from a polycaprolactone carrier polymer-drug formulation with varying amounts of $SiO_2$ dispersant and hydroxypropyl methylcellulose (HMPC) after 1 hour at 37° C. in either simulated gastric fluid (SGF) (black bars) or 40% ethanol/60% simulated gastric fluid (white bars).
Figure 25:
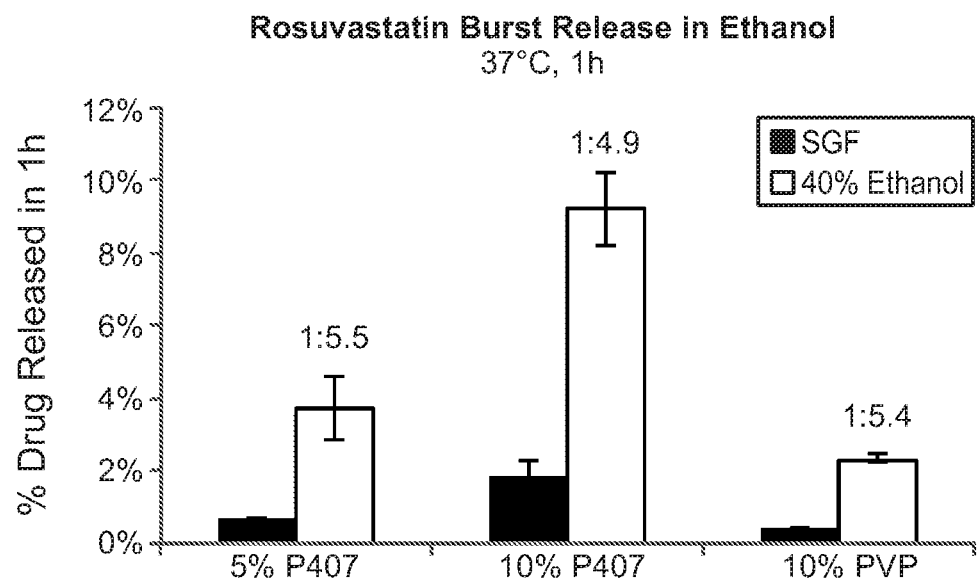
FIG. 25 shows burst release of rosuvastatin from a polycaprolactone carrier polymer-drug formulation with 5% Pluronic P407 (5% P407), 10% Pluronic P407 (10% P407), or 10% polyvinylpyrrolidone (PVP) after 1 hour at 37° C. in either simulated gastric fluid (SGF) (black bars) or 40% ethanol/60% simulated gastric fluid (white bars).

Agent-loaded PCL arms containing ivermectin were prepared. Various forms and formulations of ivermectin (IVM) were used: unprocessed IVM (15% unmilled drug, 0.5% $SiO_2$, 0.5% alpha-tocopherol, 0.5% Pluronic P407, balance PCL), milled IVM (15% drug milled with no milling additive/glidant, 0.5% $SiO_2$, 0.5% alpha-tocopherol, 0.5% Pluronic P407, balance PCL), IVM milled with $SiO_2$ (15% drug milled with 1% $SiO_2$, percentage of SiO2 as w/w of the milled drug; an additional 0.5% SiO2 added w/w to total formulation weight, 0.5% alpha-tocopherol, 0.5% Pluronic P407, balance PCL), IVM plus P407 (15% unmilled drug, 0.5% $SiO_2$, 0.5% alpha-tocopherol, 8.5% Pluronic P407, balance PCL), milled IVM formulated with P407 (15% drug milled with no milling additive/glidant, 0.5% $SiO_2$, 0.5% alpha-tocopherol, 8.5% Pluronic P407, balance PCL), and IVM milled with $SiO_2$ and formulated with P407 (15% drug milled with 1% $SiO_2$, percentage of SiO2 as w/w of the milled drug; an additional 0.5% SiO2 added w/w to total formulation weight, 0.5% alpha-tocopherol, 8.5% Pluronic P407, balance PCL). Results are shown in FIG. 11. Milling ivermectin with $SiO_2$ enhanced release of ivermectin from P407 formulations over P407 formulations using ivermectin milled without $SiO_2$, a desirable result given the very slow release of hydrophobic ivermectin from the formulations.

Example 18

Effect of Milling and Dispersant on Mechanical Strength of Arms

A four-point bending flexural test (ASTM D790) is used to evaluate the strength of the arms. Briefly, the arm is supported near each end of the arm. Two rods, which are disposed closer to the middle of the arms than the supports, apply force and cause the specimen to bend in flexion. The force and displacement are recorded and the maximum flexural force recorded.

Formulations of ivermectin agent-loaded arms were prepared as in Example 17, and were tested using this technique at Day 0, Day 2, and Day 7 of incubation in simulated gastric fluid (FASSGF). The results are shown in FIG. 12. P407 decreased the mechanical strength of the arms after incubation in simulated gastric fluid, as compared to formulations without P407. Milling the drug increased the mechanical strength of the arms over unmilled drugs for Day 0 and Day 2 of incubation.

Example 19

Rosuvastatin Formulation

Rosuvastatin calcium powder was weighed and blended with dry powder of hydrophilic excipient polymers in a glass vial. Polycaprolactone (PCL) beads were added and the vial was heated in an oven to 90° C. for 10-20 min or until PCL was completely melted. The vial was then transferred to a dry heating block at 90° C. where the ingredients were mixed thoroughly using a spatula. The mixture was then transferred to the desired mold, which returned to the 90° C. oven for 20-30 min for gravity molding. The mold was then removed from the oven and allowed to cool to room temperature. FIG. 19 shows that formulation of rosuvastatin in PCL does not alter the X-ray diffraction pattern of rosuvastatin. This indicates that blending the drug with the polymer does not alter the solid state of the drug.

Example 20

Liquid Chromatography/Mass Spectrometry Analysis for Rosuvastatin

Drug concentration was determined using a Waters Acquity UPLC with a Xevo QToF LC/MS. Samples were run on a Waters Acuity C18 column with a gradient of 5%-95% Acetonitrile with 0.1% formic acid:water with 0.1% formic acid in 3 min. Drug eluted at 1.75 minutes and showed a maximum UV absorbance at 241 nm. A standard curve for determination of rosuvastatin concentration was developed by integration of the UV absorbance trace at 241 nm. The standard curve was found to be linear for the range of samples tested (0.02 mg/mL to 0.5 mg/mL rosuvastatin). Forced degradation studies (see Stability methods) demonstrated that this UPLC method was able to distinguish intact rosuvastatin from rosuvastatin lactone and other degradants.

Example 21

In Vitro Release in Simulated Gastric Fluid

General Method:

Formulations of 25% rosuvastatin, 5-10% other excipients, and the balance PCL were prepared as described. Formulations were gravity molded into ~10 mm discs weighing roughly 200 mg each.

Fasted state simulated gastric fluid (FaSSGF) was prepared according to the vendor's instructions (Biorelevant.com, London, United Kingdom). First a NaCl/HCl solution was prepared by dissolving 2.0 g of NaCl in about 0.9 L of purified water. The pH was adjusted to 1.6 with HCl. The volume was made up to 1.0 L with purified water at room temperature. 0.060 g of FaSSIF, FeSSIF & FaSSGF powder was added to about 0.5 L HCl/NaCl solution, and the volume was made up to 1.0 L with HCl/NaCl solution at room temperature to make FaSSGF (also referred to herein as SGF).

Polymer-drug discs were submerged in 20 mL FaSSGF in glass vials with small stir bars. Vials were heated to 37° C. in a dry heating block and stirred at a rate of ~200 rpm. At each time point, release media was sampled for LCMS analysis and the entire volume of release media was replaced with fresh FaSSGF.

The results of the in vitro release experiments are shown in FIG. 15.

Example 22

Testing Release Variability with Respect to Different Solvents In Vitro

Formulations containing 25% Rosuvastatin, 10% Pluronic P407, and 65% PCL were prepared as described and molded into 200-mg discs. The discs were submerged in 10 mL FaSSGF, heated to 37° C. in a dry heating block and stirred at a rate of ~200 rpm for 3 h. After 3 h, 10 mL of either boiling water or ethanol were added to the vials. After one more hour, release media was sampled and analyzed by LCMS to determine rosuvastatin concentration and calculate total drug release in the 4-hour time frame as compared to a control formulation (which was incubated in 10 mL FaSSGF at 37° C. for 4 h). The results are shown in Table 4 below.

TABLE 4

| Condition | Peak integral | Concentration (mg/mL) | total volume (mL) | mg drug released after 4 h | ratio over control (mg released)/(mg released by control) |
|---|---|---|---|---|---|
| Control | 65842 | 0.489189153 | 10 | 4.9 | 1.0 |
| 10 mL boiling water added after 3 h | 39595 | 0.314314078 | 20 | 6.3 | 1.3 |
| 10 mL 200 proof ethanol added after 3 h | 68466 | 0.506671997 | 20 | 10.1 | 2.1 |
| Bubbles removed from formulation under hi vac | 27642 | 0.234675195 | 10 | 2.3 | 0.5 |
| Star arm shape (~200 mg) | 59236 | 0.445175561 | 10 | 4.5 | 0.9 |

Further tests of release of rosuvastatin in ethanol were conducted. Formulations were incubated in SGF for 24 hours before being transferred to ethanol solution or fresh SGF (at 37° C.) for 1 hour. The amount of drug release in 1 hour is shown in FIGS. 22, 24, and 25, and is further detailed in Example 25.

Example 23

Testing Drug Stability Under Different Solution and Heat Conditions In Vitro

Rosuvastatin calcium was subjected to various forced degradation conditions both in solution (in water or organic solvent) and in polycaprolactone (PCL) formulation, as summarized in Table 5 below.

SOLUTION CONDITIONS: For acid degradation studies, rosuvastatin was dissolved to 1 mg/mL in 0.1M HCl and heated for the specified time and temperature. For alkaline degradation, rosuvastatin was dissolved to 1 mg/mL in 0.1M NaOH and heated to 80° C. for 1 h. For oxidative degradation, rosuvastatin was dissolved to 1 mg/mL in 30% hydrogen peroxide and heated to 80° C. for 30 min. For stability over time, rosuvastatin was dissolved to 1 mg/mL in water at room temperature for 5 days. For thermal degradation studies in solution, rosuvastatin was dissolved to 1 mg/mL in dimethylsulfoxide and heated to the specified temperature for 2 h. In each case, samples of the solution were diluted in methanol and analyzed by LCMS to determine the ratio of intact drug to degraded drug.

POLYMER CONDITIONS: For thermal degradation studies in formulation, rosuvastatin was blended with PCL at a ratio of 25:75 drug:PCL and the blend was heated to the specified temperature for 2 h. The drug-polymer blend was then dissolved in dichloromethane and this solution was added to excess methanol to precipitate PCL. Samples of the methanol solution were then analyzed by LCMS to determine the ratio of intact drug to degraded drug.

Figure 20:
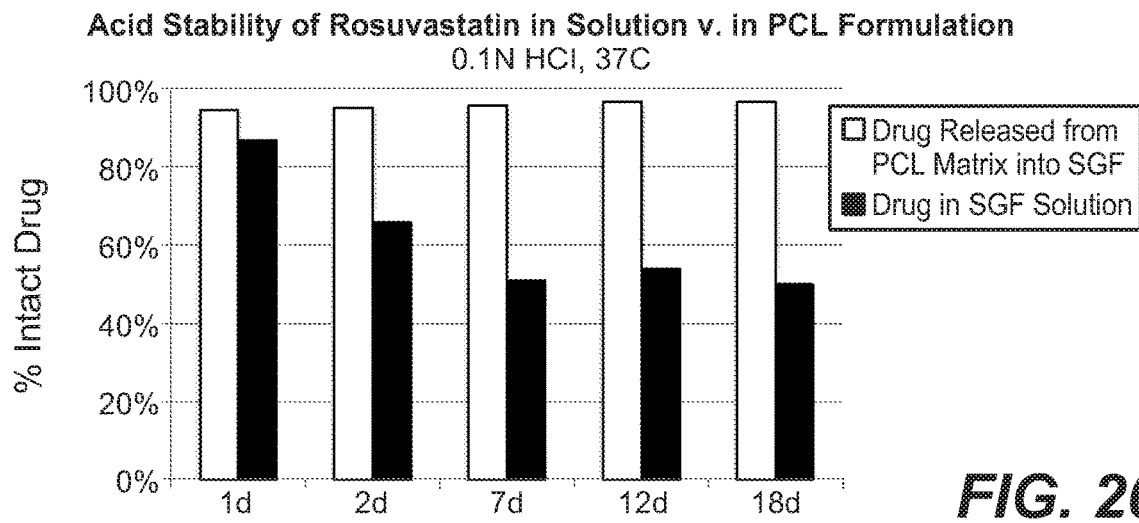
FIG. 20 shows acid stability of rosuvastatin in solution versus in PCL formulation.
Figure 21:
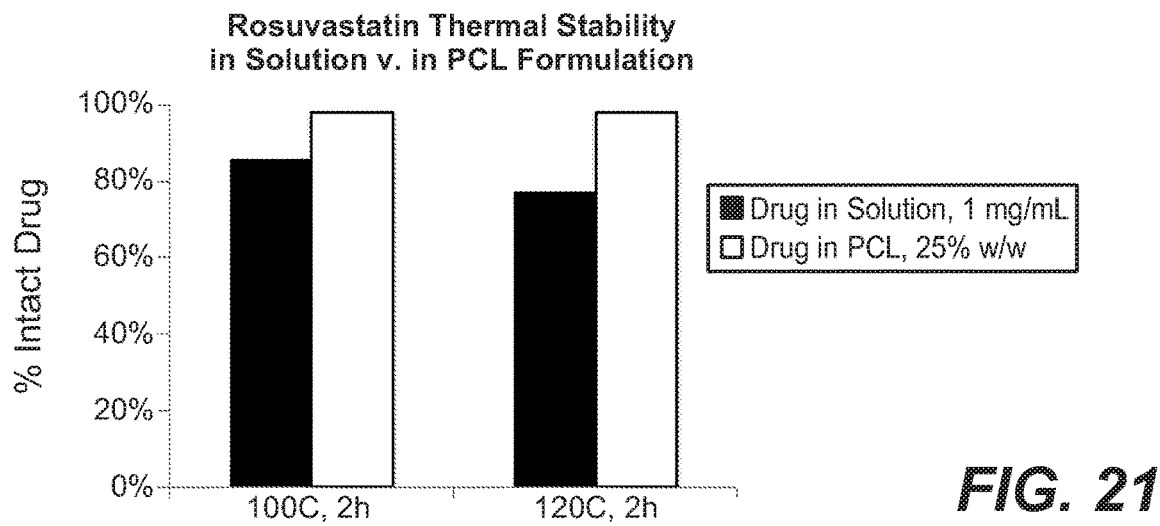
FIG. 21 shows thermal stability of rosuvastatin in solution versus in PCL formulation.

The results of the in vitro degradation experiments are shown in FIG. 20, FIG. 21, and in Table 5. FIG. 20 shows that formulation of rosuvastatin in PCL protects the drug from acid degradation. FIG. 21 shows that formulation of rosuvastatin in PCL protects the drug from degradation at elevated temperatures.

TABLE 5

| Condition | % Intact drug |
| --- | --- |
| Acid | |
| 0.1N HCl, 37 C., overnight | 87% |
| 0.1N HCl, 37 C., 2 d | 66% |
| 0.1N HCl, 50 C., 4 h | 93% |
| 0.1N HCl, 50 C., overnight | 58% |
| 0.1N HCl, 80 C., 1 h | ~100% |
| Base | |
| 0.1M NaOH, 80 C., 1 h | ~100% |
| Oxidation | |
| 30% H2O2, 80 C., 30 min | ~100% |
| Time | |
| 1 mg/mL drug in water, room temperature, 5 days | 62% |
| Heat | |
| 1 mg/mL drug in DMSO, 100 C., 1 h | 86% |
| 1 mg/mL drug in DMSO, 100 C., 2 h | 86% |
| 1 mg/mL drug in DMSO, 120 C., 1 h | >95% |
| 1 mg/mL drug in DMSO, 120 C., 2 h | 77% |

TABLE 5-continued

| Condition | % Intact drug |
| --- | --- |
| Polymer-blended | |
| 25% drug in polycaprolactone, 100 C., 2 h | >95% |
| 25% drug in polycaprolactone, 120 C., 2 h | >95% |

Example 24

Microscopy

Figure 18:
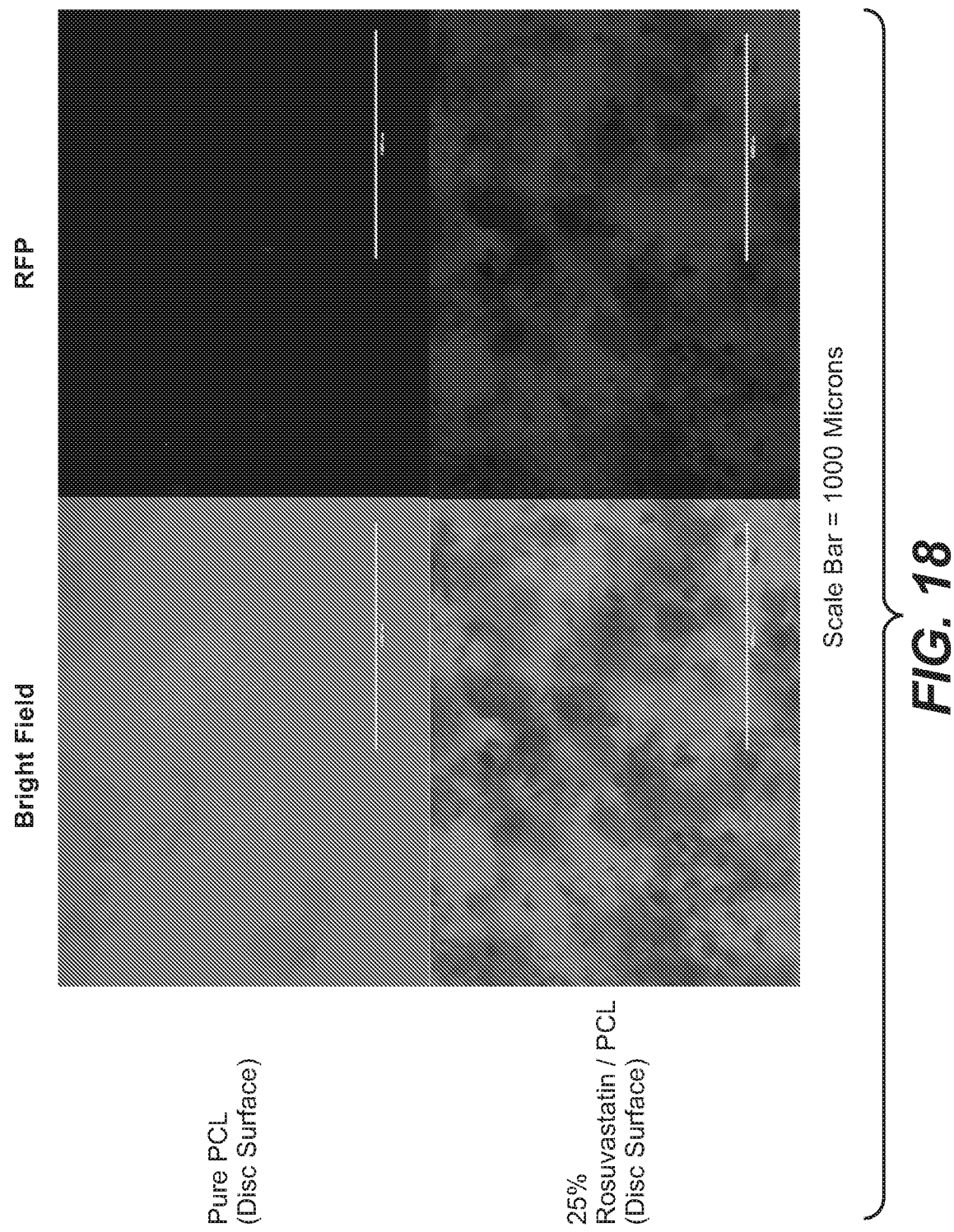
FIG. 18 shows evaluation of formulation mixing by microscopy.
Figure 19:
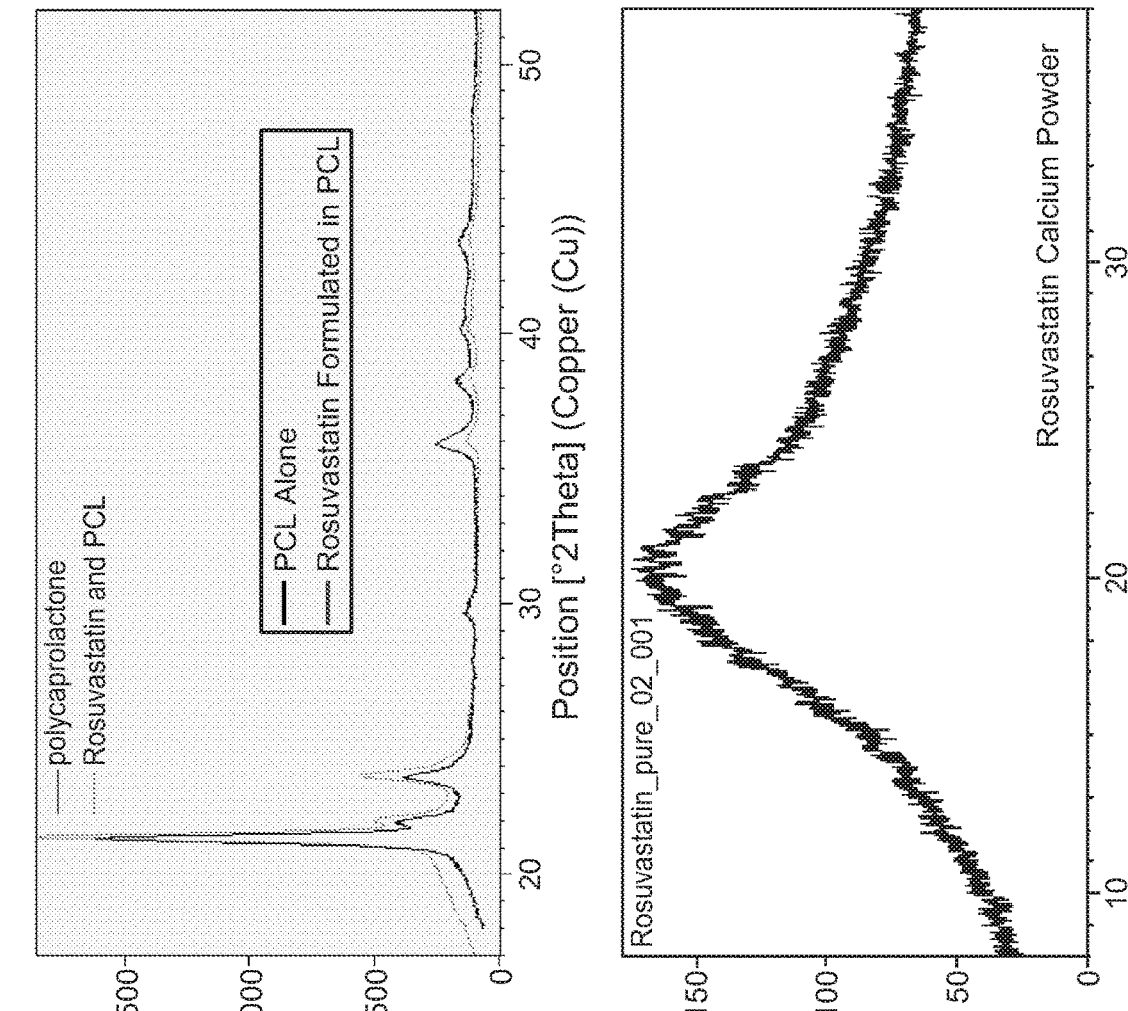
FIG. 19 shows X-ray diffraction patterns of rosuvastatin calcium powder, polycaprolactone (PCL), and rosuvastatin calcium formulated in PCL.

Samples were imaged using an EVOS fluorescence microscope. Rosuvastatin calcium powder, pure polycaprolactone (PCL), and drug-polymer formulations were imaged using both bright field and red fluorescent protein settings. FIG. 17A and FIG. 17B show images of rosuvastatin powder, while FIG. 18 shows images of PCL and drug-PCL formulations.

Example 25

Excipient Effect on Drug Elution Rate with Respect to Ethanol In Vitro

The effect of different excipients on the elution rate of rosuvastatin from carrier polymer-drug formulations was studied. The carrier polymer-drug formulations were in the shape of triangular prisms ("star arms") suitable for use in a system such as that depicted in FIG. 2 or FIG. 2A. The star arms were placed in simulated gastric fluid prepared as described in Example 21 or in 40% ethanol/60% SGF. The amount of drug released was assayed at 1 hour of immersion in SGF or 40% ethanol/SGF.

FIG. 24 shows the results of testing burst release of rosuvastatin. From left to right, the pairs of bars show: rosuvastatin (25%)+hydroxypropyl methylcellulose (5%), with polycaprolactone comprising the remainder of the material (bars labeled 5% HPMC); rosuvastatin (25%)+hydroxypropyl methylcellulose (10%), with polycaprolactone comprising the remainder of the material (bars labeled 10% HPMC); rosuvastatin (25%)+hydroxypropyl methylcellulose (5%)+0.5% $SiO_2$, with polycaprolactone comprising the remainder of the material (bars labeled 0.5% $SiO_2$, 5% HPMC); and rosuvastatin (25%)+hydroxypropyl methylcellulose (5%)+2% $SiO_2$, with polycaprolactone comprising the remainder of the material (bars labeled 2% $SiO_2$, 5% HPMC). The black (filled) bars show release after 1 hour immersion in SGF, while the white (unfilled) bars show release after 1 hour immersion in 40% ethanol/60% simulated gastric fluid.

When rosuvastatin was formulated in polycaprolactone (PCL) and 5% hydroxypropyl methylcellulose, there was only a 3.7-fold increase in the elution of rosuvastatin in 40% ethanol/60% simulated gastric fluid versus SGF. When rosuvastatin was formulated in polycaprolactone (PCL) and 10% hydroxypropyl methylcellulose, there was only a 3.5-fold increase in the elution of rosuvastatin in 40% ethanol/60% simulated gastric fluid versus SGF. When rosuvastatin was formulated in polycaprolactone (PCL), 0.5% $SiO_2$, and 5% hydroxypropyl methylcellulose, there was only a 3.6-fold increase in the elution of rosuvastatin in 40% ethanol/60% simulated gastric fluid versus SGF. When rosuvastatin was formulated in polycaprolactone (PCL), 0.5% $SiO_2$, and 5% hydroxypropyl methylcellulose, there was only a 4.6-fold increase in the elution of rosuvastatin in 40% ethanol/60% simulated gastric fluid versus SGF.

These formulations thus show a decrease in induced burst release after immersion in 40% ethanol/60% simulated gastric fluid when compared to other formulations studied.

FIG. 25 shows the results of testing burst release of rosuvastatin. From left to right, the pairs of bars show: rosuvastatin (25%)+P407 (5%), with polycaprolactone comprising the remainder of the material (bars labeled 5% P407); rosuvastatin (25%)+P407 (10%), with polycaprolactone comprising the remainder of the material (bars labeled 10% P407); and rosuvastatin (25%)+PVP (10%), with polycaprolactone comprising the remainder of the material (bars labeled 10% PVP) The black (filled) bars show release after 1 hour immersion in SGF, while the white (unfilled) bars show release after 1 hour immersion in 40% ethanol/60% simulated gastric fluid. These formulations showed a 5.5-fold, 4.9-fold, and 5.4-fold increase in the elution of rosuvastatin in 40% ethanol/60% simulated gastric fluid versus SGF, respectively.

Accordingly, HPMC and silica are particularly useful in controlling rosuvastatin burst release.

Example 26

Formulation Blending by Hot Melt Extrusion: Procedure

Drug loaded formulations were prepared by combining active pharmaceutical ingredient (API), polycaprolactone (PCL) structural polymer, and various excipients for controlling release and facilitating processing. API and excipient powders were blended and then combined with polymer pellets by hot melt extrusion (HME). In some cases, powdered excipients were granulated using a binder solution prior to HME. The granulation procedure is described in Example 33. Hot melt extrusion was performed on Thermo Fisher HAAKE MiniCTW extruder with counter rotating twin screws.

Formulations contain 10%-25% API, 0.5% silicon dioxide, 0.5% α-Tocopherol, 0.5-30% excipients and balance PCL as specified. API and powder excipients were weighed and blended using a spatula. PCL pellets were weighed separately and the powder and pellet phases were loaded into the extruder following principles of volumetric addition. The blend was batch mixed at 100° C. and a screw speed of 75 rpm for 10 minutes before extrusion at a rate of 20-30 rpm. Sections of extruded melt were placed into an aluminum compression mold and shaped into 20 mm long and 2 mm wide triangular rods. Up on cooling to ambient temperature, arms were trimmed to remove excess formulation and were stored in the freezer (~−20° C.). Composition and function of excipients used in the exemplified formulation are shown in Table 6.

TABLE 6

Composition and function of excipients in Aripiprazole formulation prepared by blending and hot melt extrusion

| | |
|---|---|
| 20% Aripiprazole | Active pharmaceutical ingredient |
| 10% Kolliphor P407 | Polymeric solubilizer |
| 10% Eudragit E PO | Release enhancer |
| 0.5% Silicon dioxide | Dispersant |
| 0.5% (±)-α-Tocopherol | Anti-oxidant |
| 59% Polycaprolactone (PCL) | Structural polymer |

Example 27

PCL/SGF Partition Coefficient

Partitioning of active pharmaceutical ingredient (API) between the structural polymer, polycaprolactone (PCL), and fasted state simulated gastric fluid (FaSSGF) is of interest for predicting API release rate from PCL-based formulations. To measure the PCL-SGF partition coefficient of an API, a concentrated stock solution of API was added to a mixture of 1 mL FaSSGF and 1 mL of 5:1 PCL diol (MW 530):ethyl acetate. The sample was vortexed and centrifuged at 10000 rpm for 5 minutes. The SGF phase was analyzed by HPLC to measure drug concentration. The PCL phase was diluted in methanol prior to quantification on HPLC. The PCL/SGF partition coefficient of different drugs with varied aqueous solubilities and lipophilicities are shown in Table 7.

TABLE 7

Comparison of PCL/SGF partition coefficient of different drugs

| Active Pharmaceutical Ingredient | PCL/SGF Partition Coefficient | LogP (PCL/SGF) | LogP (Octanol/water) |
|---|---|---|---|
| Aripiprazole | 49 | 1.67 | 5.59 |
| Risperidone | 0.03 | −1.49 | 3.27 |
| Doxycycline Hyclate | 1.88 | 0.27 | −1.9 |
| Donepezil | 1.65 | 0.22 | 3.08 |
| Memantine | 0.28 | −0.56 | 3.28 |
| Ivermectin | 398 | 2.60 | 4.1 |

Example 28

In-Vitro Release Study: Procedure

For in-vitro release approximately 50 mg of formulation arms (either extruded through a triangular die or compression molded) were cut and placed in 15 ml falcon tubes. To each tube, 10 ml fasted state simulated gastric fluid (FaSSGF) was added and placed in orbital shaker maintained at 37° C., 200 rpm. Study was performed for 7 days in triplicate and 1 ml sample aliquots were collected at approximately 0.25, 1, 2, 3, 4, 5 and 7 days. After each sampling, in order to maintain sink conditions remaining media was discarded and fresh 10 ml FaSSGF was added to falcon tubes. Tubes were replaced into the orbital shaker at 37° C., 200 rpm. Sample aliquots were analyzed by HPLC for API quantification at each time point.

Example 29

Figure 26:
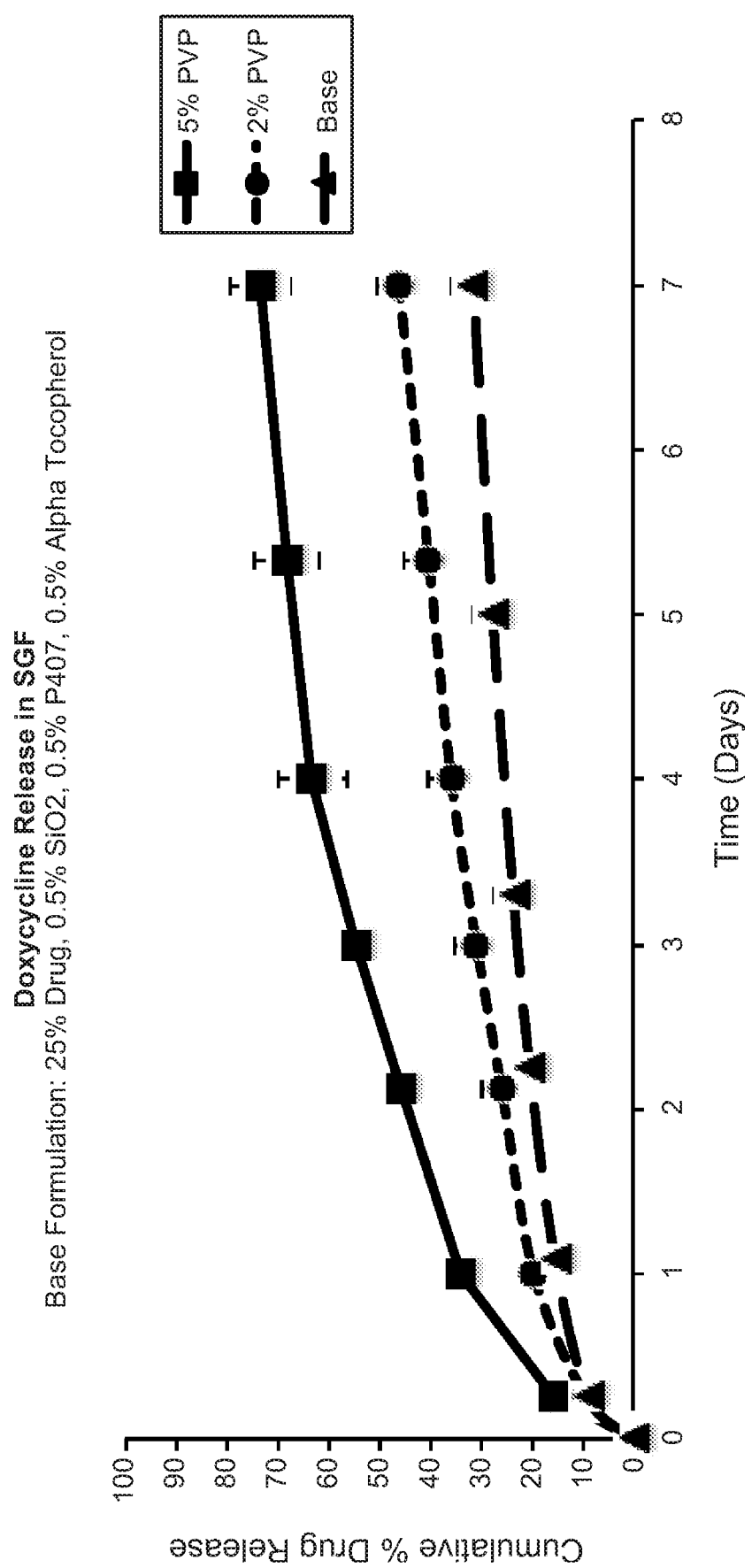
FIG. 26 shows in vitro release of doxycycline from drug formulations in FaSSGF (fasted state simulated gastric fluid). Doxycycline base formulation contains 25% doxycycline, 0.5% SiO2, 0.5% P407, and 0.5% alpha tocopherol. Release from doxycycline base formulation is compared to formulation containing additional 2% PVP and 5% PVP.

In Vitro Release of Doxycycline (Hydrophilic) Loaded Structures in FaSSGF in Response to Percent PVP in Formulation FIG. 26 shows the in vitro release of doxycycline from formulation arms in FaSSGF with varying amounts of PVP in formulation. Doxycycline was ball milled with 1% silica and sifted through a 75-micron sieve. Formulations were prepared as described in Example 26 and in vitro release assays were performed and analyzed by HPLC for API quantification at each time point as described in Example 28. Doxycycline formulations contain 25% API, 0.5% silica, 0.5% alpha tocopherol, 0.5% P407, the specified quantity of polyvinylpyrrolidone (PVP), and the balance 55 k PCL.

When doxycycline was formulated with the base formulation with no PVP (FIG. 26, base), there was a 30% complete release of drug after 7 days. Upon increasing the amount of PVP in formulation to 2%, the total release increased to 50%. When doxycycline was formulated with 5% PVP in addition to the base formulation, the total release of drug after 7 days was approximately 75%, linearity of release at 3 days was approximately 55%, and the burst release at 6 hours was 15%. These data show an increase in complete drug release in response to an increasing amount of PVP in the formulation.

Example 30

Figure 27:
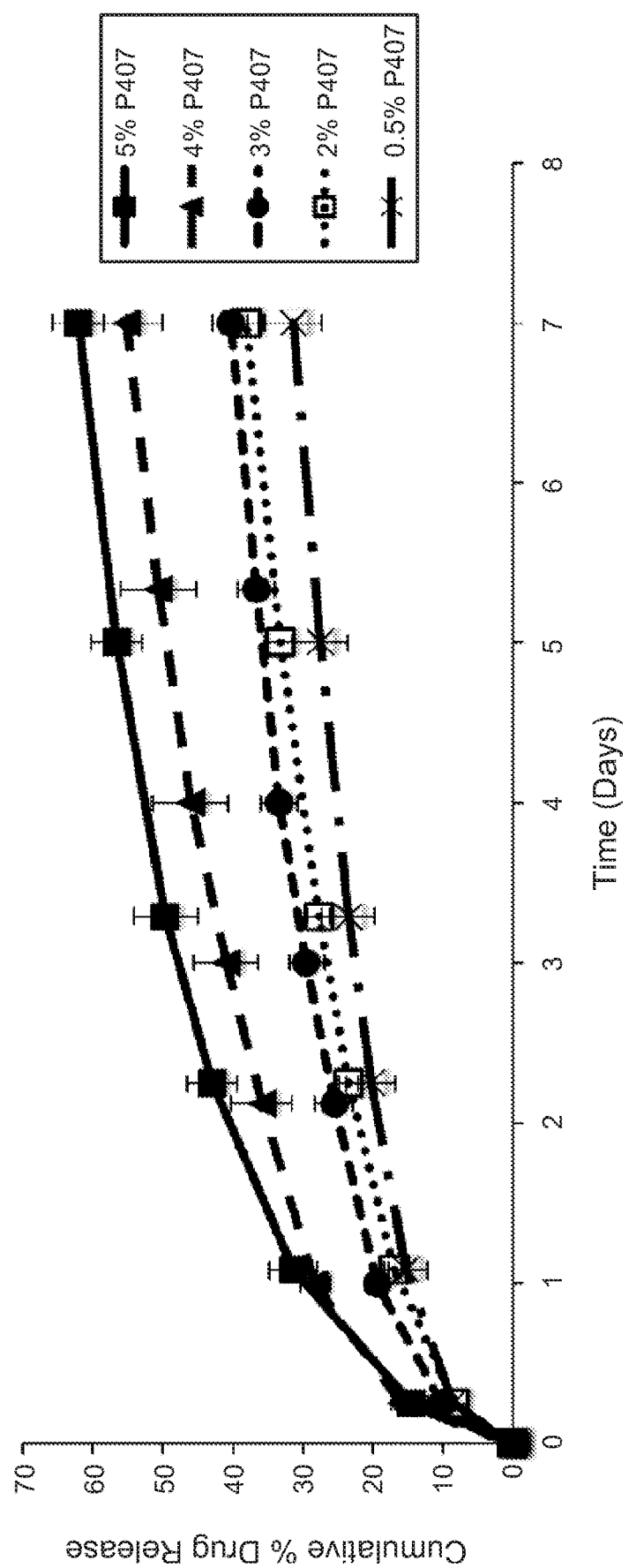
FIG. 27 shows in vitro release of doxycycline from drug formulations in FaSSGF. Doxycycline base formulation contains 25% doxycycline, 0.5% SiO2, and 0.5% alpha tocopherol. Doxycycline release is compared from formulations containing 0.5%, 2%, 3%, 4%, and 5% P407.

In Vitro Release of Doxycycline (Hydrophilic) Loaded Structures in FaSSGF in Response to Percent of P407 in Formulation FIG. 27 shows the in vitro release of doxycycline from formulation arms in FaSSGF with varying amounts of P407 in formulation. Doxycycline was ball milled with 1% silica and sifted through a 75-micron sieve. Formulations were prepared as described in Example 26 and in vitro release assays were performed and analyzed by HPLC for API quantification at each time point as described in Example 28. Doxycycline formulations contain 25% API, 0.5% silica, 0.5% alpha tocopherol, the specified quantity of P407, and the balance 55 k PCL. When doxycycline was formulated with 0.5% P407, there was about 10% burst release at 6 hours, about 22% drug release within 3 hours, and about 34% total release after 7 hours (FIG. 27). When doxycycline was formulated with 2% P407, the total release after 7 hours increased to about 40%. Upon increasing the amount of P407 further, there was an increase in total release of drug such that formulations containing 3%, 4%, and 5% of P407 showed total release after 7 hours of about 43%, 57%, and 65%, respectively. When the doxycycline is formulated with 5% P407 in addition to the base formulation, the total release of drug after 7 days was approximately 65%, linear release at 3 days was about 48%, and burst release at 6 hours was 15%.

Example 31

In Vitro Release of Donepezil Loaded Structures in FaSSGF

Figure 28:
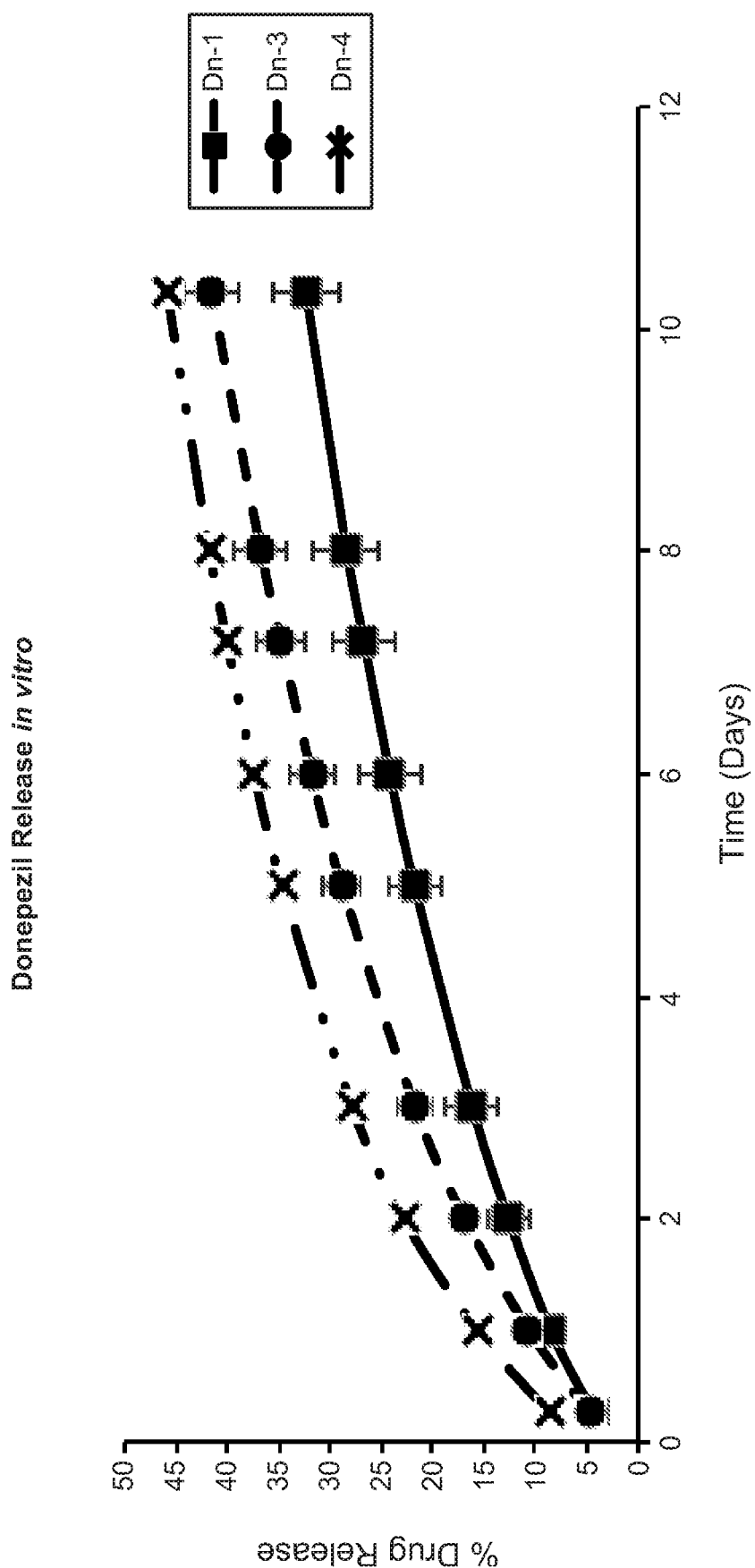
FIG. 28 shows in vitro release assay for donepezil formulations Dn-1, Dn-2 and Dn-3 in FaSSGF.

FIG. 28 shows the in vitro release of donepezil from formulation arms in FaSSGF. Unmilled donepezil was used to prepare formulations as described in Example 26. In vitro release assays were performed and analyzed by HPLC for API quantification at each time point as described in Example 28. The donepezil formulations contain 20% donepezil, 0.5% alpha tocopherol, the specified excipients listed in Table 8, and the balance 80 k PCL.

When donepezil was formulated with 0.5% Silica, 0.5% alpha tocopherol, 25% Eudragit RS, and 5% P407, there was about 35% complete release of drug at 7 days, about 16% linear release at 3 days, and 5% burst release at 6 hours (FIG. 28, Dn-1). When donepezil was formulated with 2% Silica, 0.5% alpha tocopherol, 10% Eudragit RS, and 5% P407, there was an increase of complete release to about 45% at 7 days, 21% at 3 days, and the burst release remained at about 5% (FIG. 28, Dn-3). When donepezil was formulated with 0.5% Silica, 0.5% alpha tocopherol, 9% Eudragit RS, and no P407, there was a further increase to 48% complete release of drug at 7 days, 27% release at 3 days, and the burst release remained low at about 8% after 6 hours (FIG. 28, Dn-4).

TABLE 8

Donepezil Formulations. All formulations contain 20% donepezil, 0.5% alpha tocopherol, other excipients specified below, and the balance 80k PCL.

| Name | Composition |
|---|---|
| Dn-1 | 0.5% Silica, 25% Eudragit RS, 5% P407 |
| Dn-3 | 2% Silica, 10% Eudragit RS, 5% P407 |
| Dn-4 | 0.5% Silica, 9% Eudragit RS |

Example 32

Content Uniformity Analysis by API Extraction

To measure API content in PCL based formulations, drug was extracted from formulation by dissolution and precipitation. Drug loaded formulation (50 mg) was dissolved in dichloromethane (2 ml) and stirred at ambient temperature to obtain a clear solution. Methanol was added slowly to a final volume of 10 ml. Samples were transferred to 15 ml centrifuge tubes and centrifuged at 800 rpm for approximately 5 minutes to separate precipitated polymer from supernatant. The supernatant solution was diluted with methanol and drug was quantified by HPLC. For Aripiprazole, API recovery averaged 94.73% (Table 9).

TABLE 9

Content uniformity of Aripiprazole formulations. Formulation consisted of 20% Aripiprazole, 10% Kolliphor P407, 10% Eudragit E, 0.5% SiO2, 0.5% α-Tocopherol and balance 80K PCL.

| Sample | % Recovery |
|---|---|
| 1 | 103.20 |
| 2 | 95.71 |
| 3 | 94.25 |
| 4 | 97.00 |
| 5 | 93.82 |
| 6 | 92.86 |
| Average | 94.73 |
| SD | 1.63 |

Example 33

Granulation

Granulation was performed to assist in mixing of drug with excipients, to enhance the flow properties of the blend and improve batch mixing in the extruder. Granulation was performed by using 5% Kolliphor P407 in water as the binder solution. This solution was added drop-wise to the powder blend containing drug and excipients. The wet mass was passed through size 18 mesh hand screen and granules were dried in hot air oven maintained at 40° C. for approximately 15 minutes. Resulting granules were visually observed for flow and wetness and were stored under a desiccant at ambient temperature.

Example 34

Heat Welding

Drug-loaded formulations (20% Memantine, 25% Eudragit RS, 5% P407, 0.5% Silica, 0.5% alpha tocopherol)

were prepared by extrusion and compression molding as in Example 26 and thermally welded to triangular rods of 80 k PCL. Welding was performed using a custom fixture that enables control of weld temperature and alignment. Weld temperature was varied from 93-170° C. and welded parts were stored at room temperature or at 8° C. for 24 hours (n=6 samples per condition). Weld strength was characterized using a 4-point bending assay with a displacement of 600 microns. Maximum flexural force was recorded for each sample, as well as the number of welds that failed during the bending assay. Results are shown in Table 10.

TABLE 10

Heat welding of Memantine formulations.

| Heat Weld Temp | Time/Temp After Weld Before Bending | % Welds broken | Average Bending Force (N) |
|---|---|---|---|
| 93° C. | 24 hr/RT | 0% | 66.65-95.48 |
| 140° C. | 24 hr/RT | 67% | 96.68 ± 6.25 |
| 160° C. |  | 50% | 98.00 ± 2.17 |
| 140° C. | 24 hr/8° C. | 17% | 102.72 ± 3.97 |
| 160° C. |  | 0% | 100.39 ± 2.41 |
| 170° C. |  | 17% | 98.95 ± 3.29 |

Example 35

Solid State Characterization of Drug Formulations for Monitoring of Storage Stability Solid state stability of formulations during storage can be assessed by characterization techniques such as Fourier transform infrared spectroscopy (FTIR), Raman spectroscopy, X-ray diffraction, and differential scanning calorimetry. Spectra collected over time can be used to detect changes in composition or structure that could affect performance.

Example 36

Figure 29:
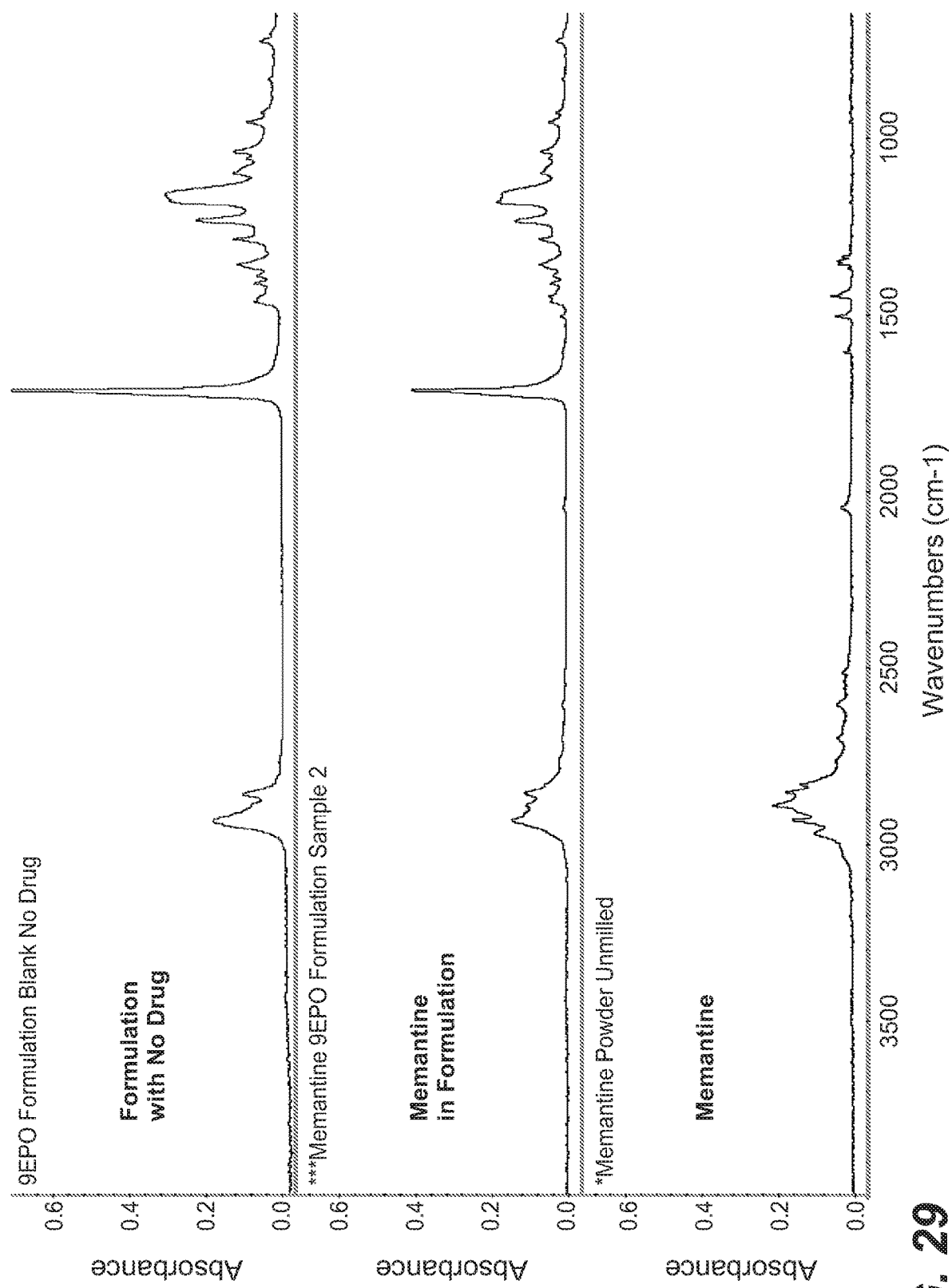
FIG. 29 shows Fourier transform infrared spectroscopy for formulation containing no drug (top), formulation containing memantine (middle), and drug with no formulation (bottom).

Solid State Characterization of Memantine by Fourier Transform Infrared Spectroscopy Memantine was ball milled with 1% silica and sifted through a 75-micron sieve. A memantine formulation containing 20% memantine, 9% Eudragit E, 0.5% silica, and 0.5% alpha tocopherol and 70% PCL was prepared as described in Example 26. FITR was conducted on a Thermo Fisher Continuum Fourier Transform Infrared Microscope in ATR mode (attenuated total reflectance). Drug in formulation (FIG. 29, middle) was compared with formulation with no drug (9% Eudragit E, 0.5% silica, and 0.5% alpha tocopherol and the balance PCL) (FIG. 29, top) and memantine alone (FIG. 29, bottom). Memantine lacks a strong FTIR signature to distinguish the drug from other formulation components using this method. FTIR provides limited information about formulation homogeneity. The same formulation was tested using X-ray diffraction (Example 36) and Raman spectroscopy (Example 37).

Example 37

Solid State Characterization of Memantine by X-Ray Diffraction

Figure 30:
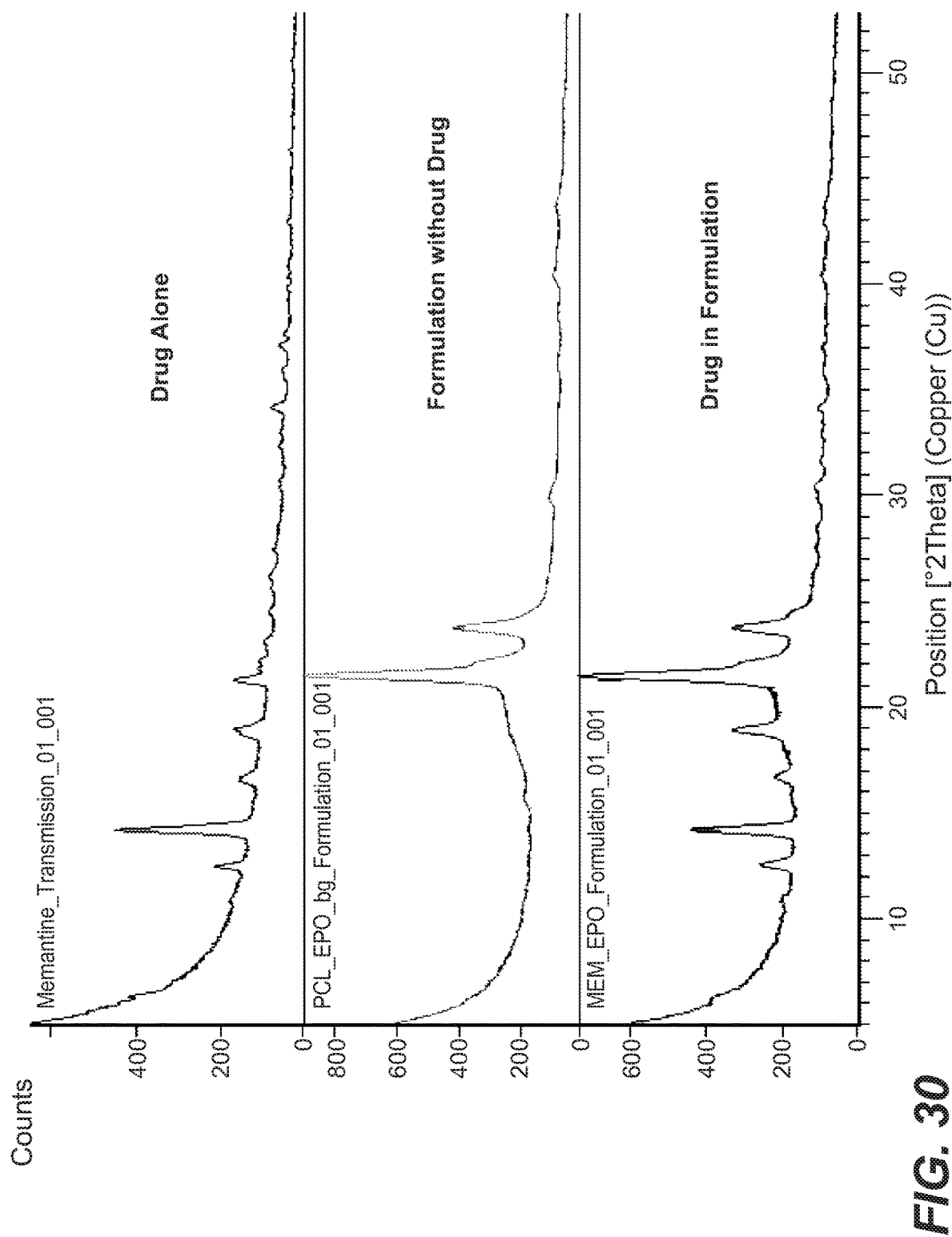
FIG. 30 shows X-ray diffraction patterns of memantine (top), formulation containing no drug (middle), and that formulation containing memantine (bottom).

The same formulations of memantine described in Examples 36 was analyzed by X-ray diffraction using a Bruker D8 General Area Detector Diffraction System in transmission mode. FIG. 30 shows X-ray diffraction patterns of drug alone (top), formulation without drug (middle), and drug in formulation (bottom). Unique peaks can be observed for memantine, indicating that X-ray diffraction can also be used for quality control and monitoring during manufacture and storage. Curve-fitting software can enable integration of memantine peaks for approximate quantitation of drug crystallinity. X-ray diffraction confirms the crystallinity of memantine is maintained in formulation.

Example 38

Solid State Characterization of Memantine by Raman Spectroscopy

Figure 31:
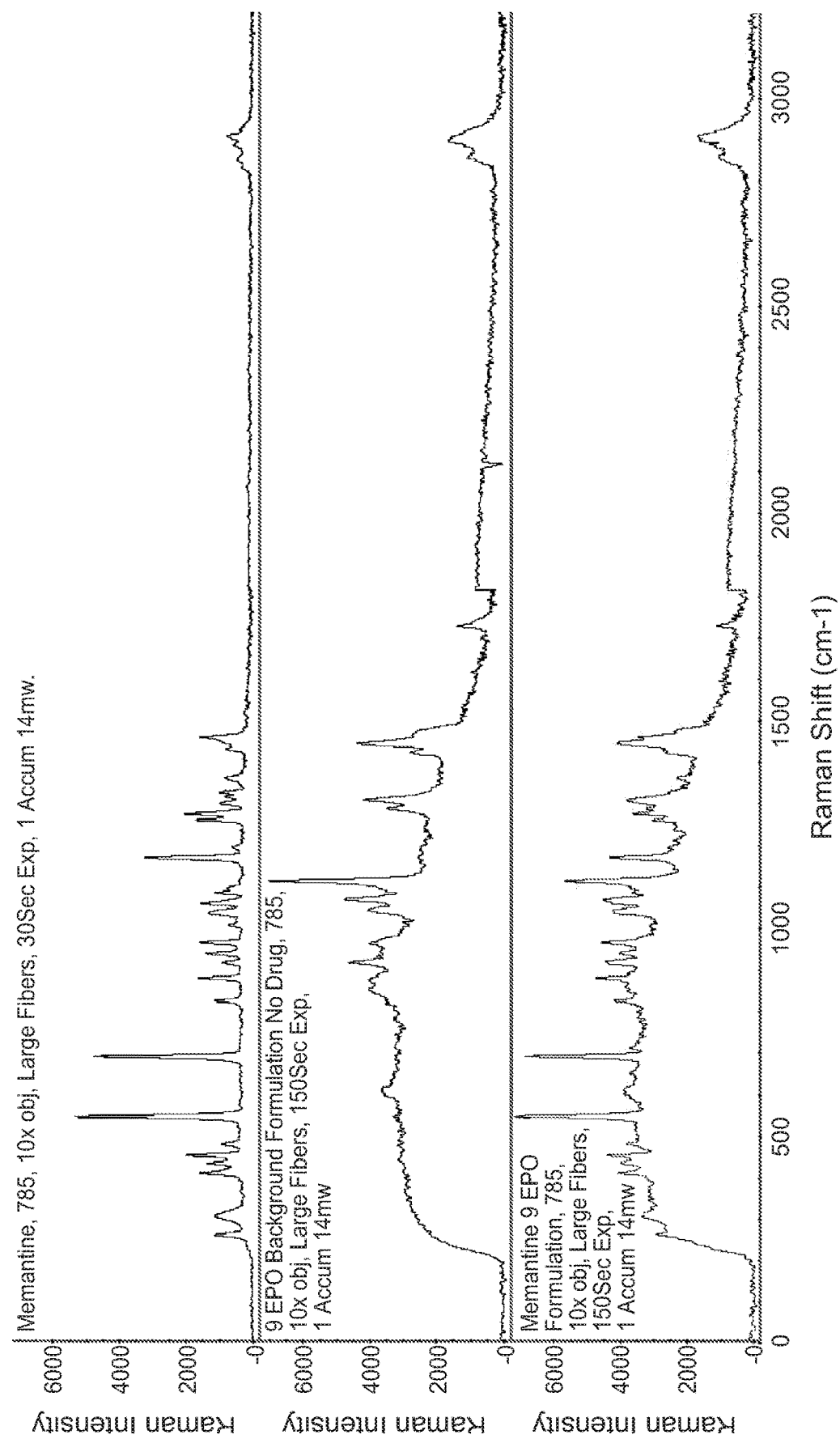
FIG. 31 shows Raman spectra of memantine (top spectrum), a formulation containing no drug (middle spectrum), and that formulation containing memantine (bottom spectrum).

The same formulations of memantine described in Examples 36 were analyzed by Raman spectroscopy using a Kaiser Optical Hololab 5000R Raman Microscope using a 785 nm excitation. FIG. 31 shows Raman spectra of memantine (top), formulation containing no drug (middle), and that formulation containing memantine (bottom). Characteristic peaks for memantine occur between 500 and 700 $cm^{-1}$, and are visible in spectra for memantine (top) and memantine formulation (bottom), confirming the presence of crystalline memantine. The spectrum for formulation without drug (middle) provides a fingerprint of the formulation that can be monitored over time to detect changes resulting from long term storage. Raman spectroscopy can thus distinguish memantine from other formulation components and can be used for monitoring of formulations during manufacture and storage.

Example 39

In Vivo Comparison of Memantine Provided by Gastric Residence Systems Versus Memantine Extended Release Formulation in Capsules In vivo testing of gastric residence systems was performed in a dog (hound) model to compare the pharmacokinetics of daily Namenda XR with the gastric residence systems of the invention. Namenda XR is an extended release form of memantine supplied in capsules. The studies were performed at Tufts University Cummings School of Veterinary Medicine (North Grafton, Mass., USA).

Lyndra-Memantine formulation contains 20% memantine, 0.5% silicon dioxide (Cab-O-Sil), 0.5% alpha tocopherol, 25% Eudragit RS 5% P407, and the balance 80 k PCL (Table 13, Formulation M18). The stellate gastric residence systems were designed with a single time-dependent linker and contained memantine. Each stellate system had six arms projecting from a central polycaprolactone-polyurethane elastomer; the elastomer was 5 mm in diameter. The arms were heat-welded to the elastomer center with a time dependent linker consisting of an extruded blend of Aquaprene/polycaprolactone at a 30/70 ratio. Memantine particles were milled and sieved to <75 um, and memantine was incorporated into the drug-polymer arms at 20% drug load, using Formulation M18.

The systems were placed in 00EL HPMC capsules (Capsugel) for administration. Two encapsulated systems (stars) were administered to the back of the throat in four hound dogs, followed by food chasing. This provides potential release of about 44 mg/day over 7 days. X-ray visualization was acquired within 1 hr of dose administration to ensure full deployment of the stellate dose form, and then on days 0, 1-7, 9, and 11 (or until the systems exited the body) via left lateral abdominal radiograph.

Four hound dogs (~20 kg) were fasted for 12 hr prior to administration, then Lyndra-memantine dosage forms were administered orally in HPMC capsules. Total drug load per system was about 322 mg. The dogs were then fed a standard daily dog diet.

For the dogs receiving stellate gastric residence systems, blood samples were collected at 0, 2, 4 and 6 hours on Day 0, and then daily for the following 8 days. Blood was collected in red top collection tubes (3 mL collected per time point after wasting 1 mL), centrifuged, and the serum pipetted into Eppendorf tubes and frozen at −20° C. Blood was then shipped to Agilux Laboratories for bioanalysis.

For comparison, another group of dogs received commercial extended release memantine capsules, Namenda XR. Six hound dogs (~20 kg) were dosed daily with a standard dose (28 mg Nameda XR capsules), administered to the back of the throat for 5 days. Blood samples were collected at 0, 2, 4 and 6 hours on Day 1, and at 0 (prior to dose administration) and 4 hr on Days 2 through 4. Blood was processed to serum and shipped to Agilux Laboratories (Worcester, Mass.) for bioanalysis.

Experimental animals are used in compliance with applicable laws and institutional guidelines. Dogs were monitored over the period of time from several days prior to introduction of the system until several days after passage of the system. X-rays are taken periodically to determine the position and condition of the gastric residence system. All of the stellate gastric residence systems deployed correctly. In the comparison group, Namenda XR was dosed without incident and well tolerated.

Figure 32:
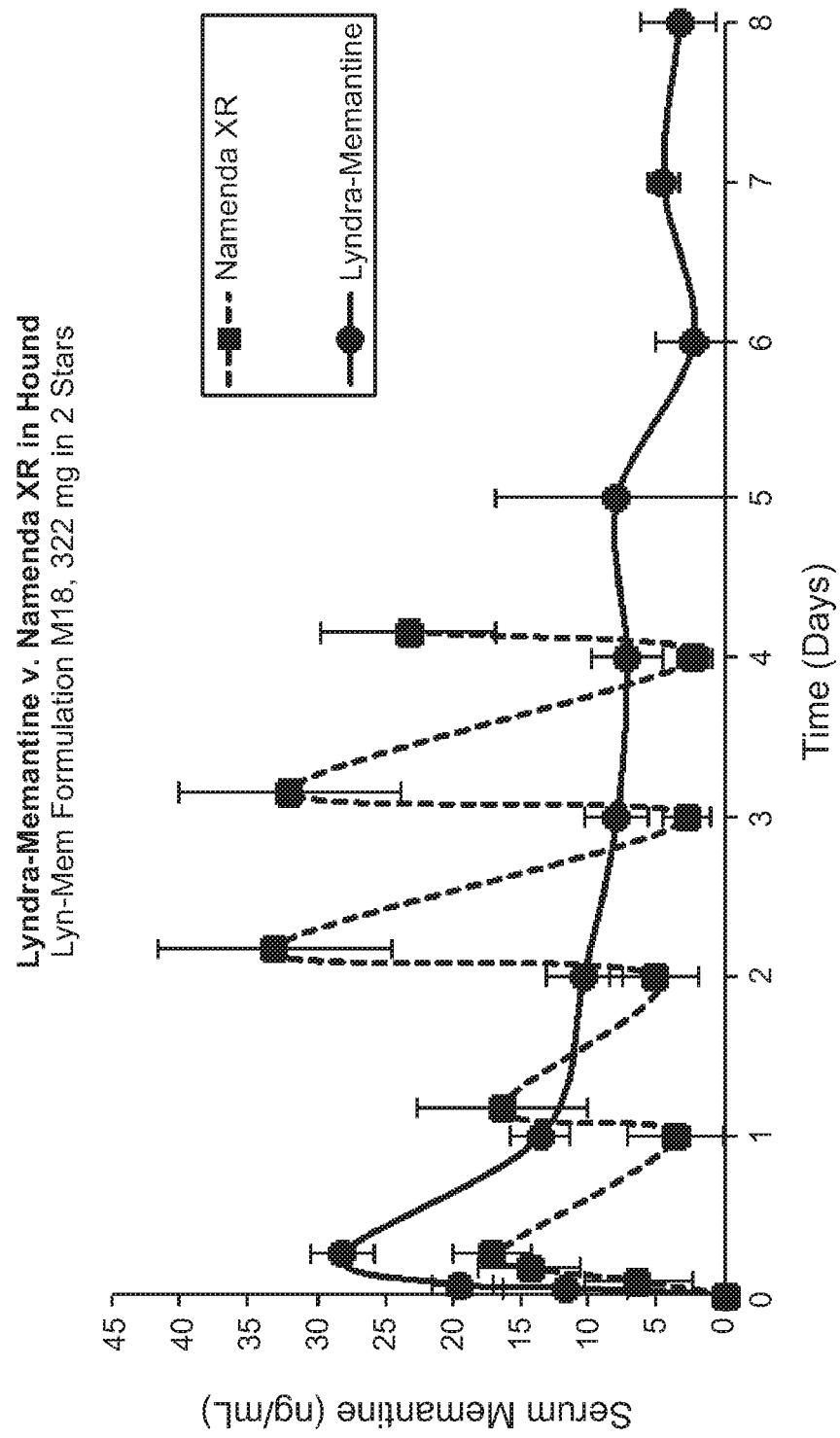
FIG. 32 shows in vivo pharmacokinetics of Lyndra-Memantine formulation M18 and Namenda XR memantine capsules in dogs.

The pharmacokinetics of the in vivo memantine concentration after administration of the stellate gastric residence system (Lyndra-Memantine) or the Namenda XR capsules are depicted in FIG. 32. The results show that oral administration of the gastric residence systems in dogs, via swallowing, is readily achievable and the systems deploy correctly. The gastric residence systems are retained in the stomach for up to 8 days. Notably, the serum levels of memantine from the gastric residence systems are more consistent than those from Namenda XR daily dosing. There were no adverse events in this safety study in a hound model in either the Namenda XR or gastric residence test animals.

Example 40

In Vivo Pharmacokinetics of Lyndra-Ivermectin in Swine Model

Figure 33:
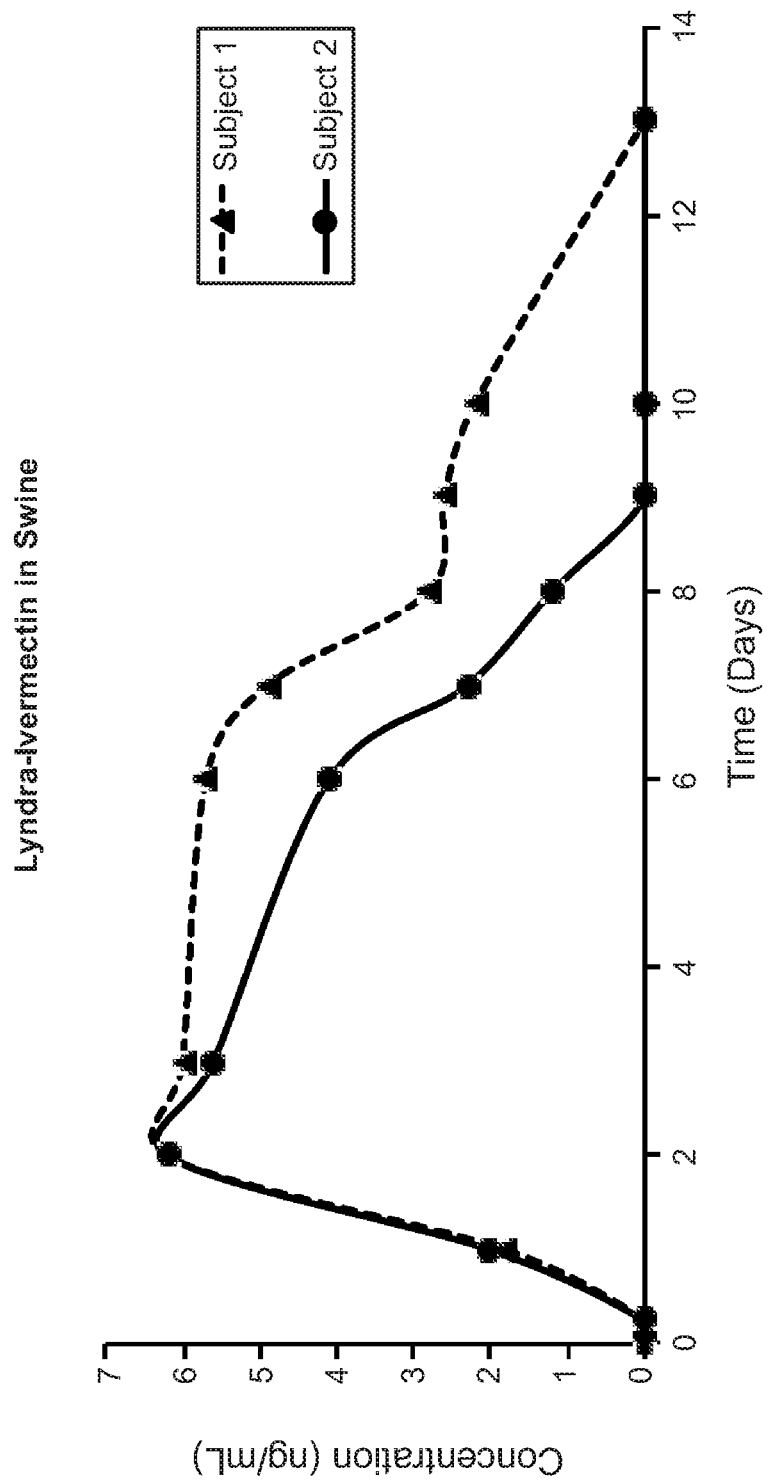
FIG. 33 shows in vivo pharmacokinetics of Lyndra-Memantine in swine.

Ivermectin formulations containing 15% Ivermectin, 0.5% silica, 0.5% alpha tocopherol, 2% P407, 10% Eudragit EPO, and the balance 80 k PCL were prepared by hand mixing and gravity molding as described in Example 26. One dosage of 135 mg API was given to each of two Yorkshire swine (35-50 kg) (FIG. 33, Subject 1 and Subject 2). Animals were monitored over a period of time from several days prior to introduction of the system until several days after passage of the system. X-rays are taken periodically to determine the position and condition of the gastric residence system. Dosage forms remained in stomach for 3-5 days. Blood samples are drawn at day 0, 1, 2, 3, 6, 7, 8, 10, and 13 to determine plasma levels delivered by the gastric residence system. Serum drug levels are shown in FIG. 33. Dosage forms remained in the stomach for 8-12 days.

Gastric residence systems were administered to two Yorkshire swine (35-50 kg) under sedation and through an endoscopic overtube into the gastric cavity. Serial radiographs were obtained in multiple positions (anteroposterior, left lateral, right lateral) of the chest, abdomen, and pelvis.

15 Radiographs were taken after delivery for up to 15 minutes to confirm deployment from the outer capsule and/or restraining system. Radiographs were then obtained daily for the next 4 days and three times weekly after the first 5 days.

Example 41

In Vitro Release of Aripiprazole Loaded Structures in FaSSGF

FIG. 34 through FIG. 45 show the in vitro release of aripiprazole from formulation arms in FaSSGF. Aripiprazole was ball milled with 1% silica and sifted through a 75-micron sieve.

Formulations were prepared as described in Example 26 and are described in Table 3. In vitro release assays were performed and analyzed by HPLC for API quantification at each time point as described in Example 28. Aripiprazole formulations contain 20% Aripiprazole, 0.5% silica, 0.5% alpha tocopherol, other excipients specified in Table 11, and the balance 80 k PCL.

Figure 34:
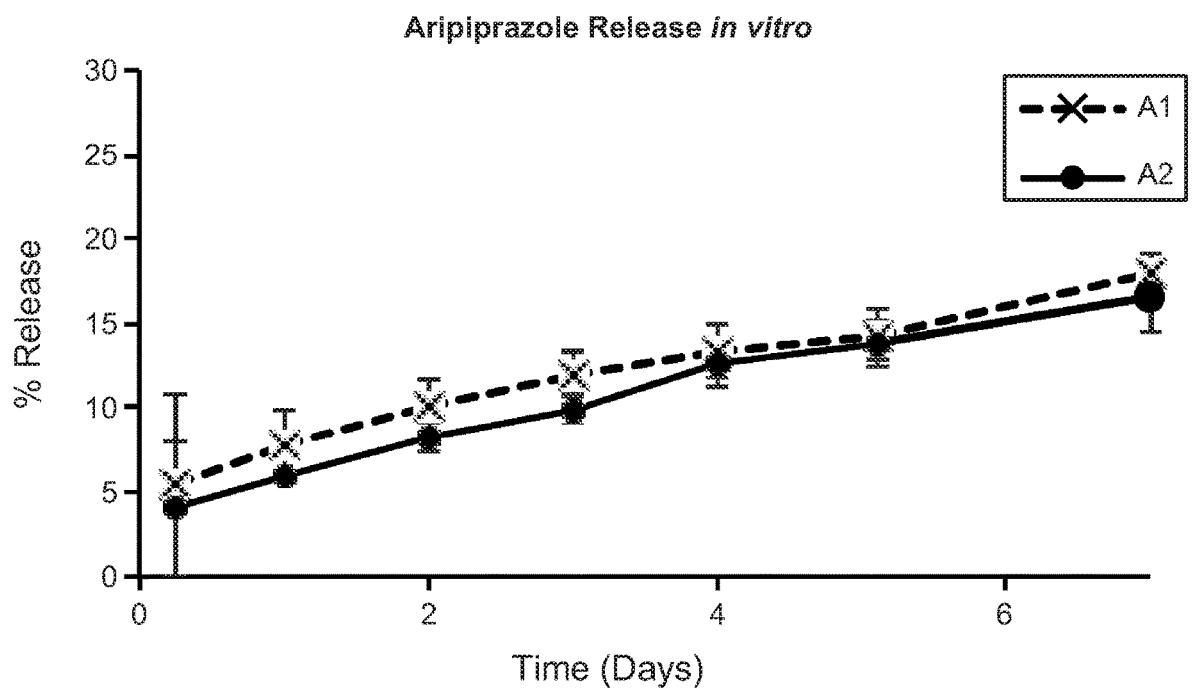
FIG. 34 shows in vitro release assay for aripiprazole formulations A1 and A2 in FaSSGF.

FIG. 34 shows in vitro release data for aripiprazole formulations A1 and A2. When aripiprazole is in formulation with 10% P407 and 10% Eudragit E (EPO), the total burst after 7 days was about 18% (FIG. 34, A1). There is a similar total burst of about 16% when aripiprazole is in formulation with 25% EPO and 5% P407 (FIG. 34, A2). Both formulations had a release of about 10% at 3 days and a burst of about 5% at 6 hours.

Figure 35:
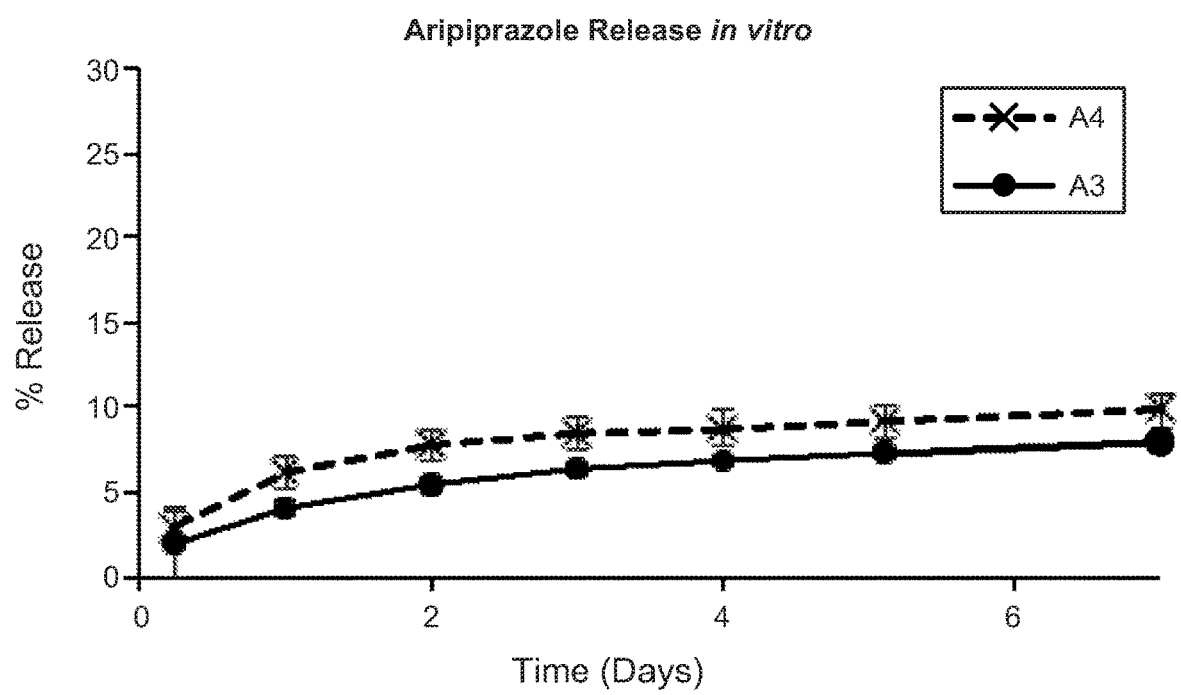
FIG. 35 shows in vitro release assay for aripiprazole formulations A3 and A4 in FaSSGF.

FIG. 35 shows in vitro release data for formulations A3 and A4. Both A3 and A4 contain 2% P407 and 28% Eudragit RS or 28% Eudragit RL, respectively. These formulations yielded a low total release of drug of about 8-9% after 7 days.

Figure 36:
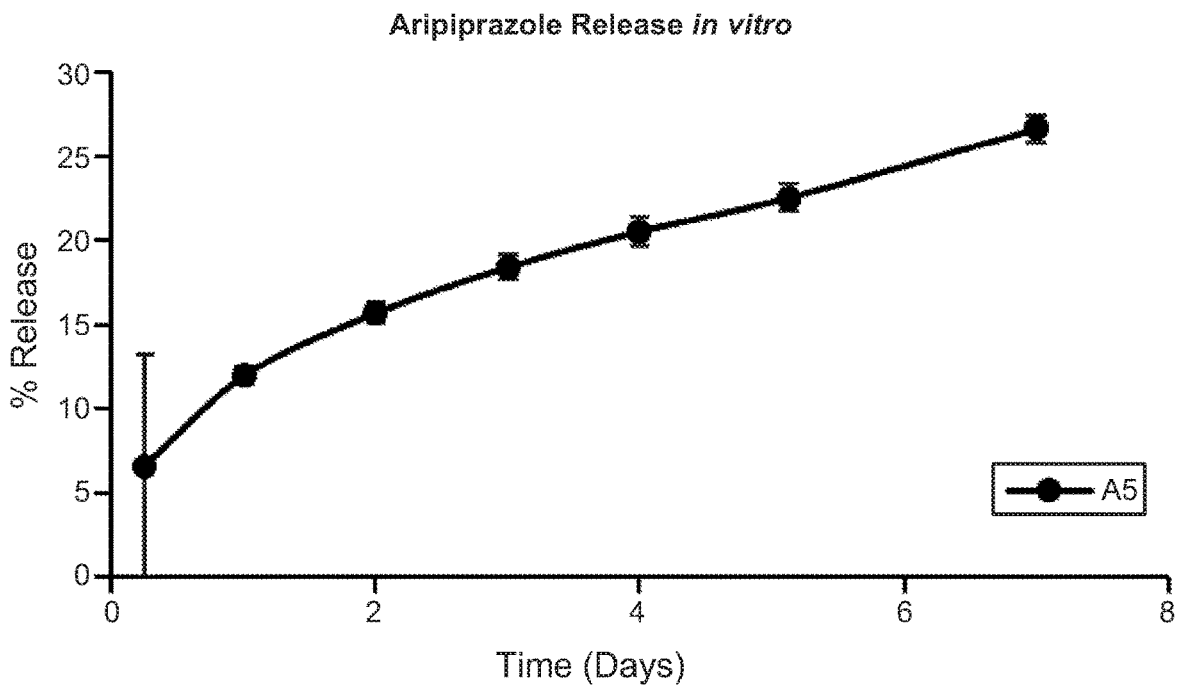
FIG. 36 shows in vitro release assay for aripiprazole formulation A5 in FaSSGF.

FIG. 36 shows in vitro release data for formulations A5, which contains the base formulation with the addition of 5% SDS (sodium dodecyl sulfate). This formulation results in total drug release of about 30%, linear release at 3 days of about 18%, and burst release of about 7%.

Figure 37:
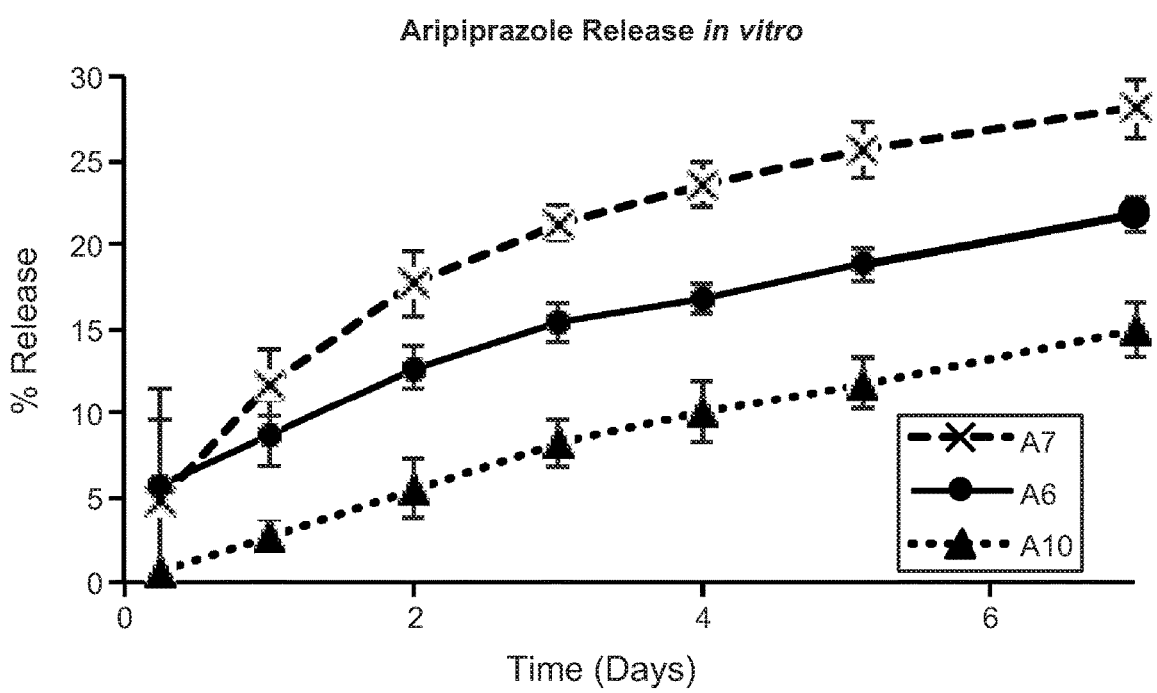
FIG. 37 shows in vitro release assay for aripiprazole formulations A6, A7 and A10 in FaSSGF.

FIG. 37 shows in vitro release data for formulations A6, A7, and A10. Formulation A6 contains the base formulation with the addition of 30% Aquaprene and results in about 22% total release of drug, 15% release after 3 days, and 5% burst release after 6 hours. Formulation A10 contains the base formulation with the addition of 20% NaCl, which results in a reduction of total release to about 15%, a linear release of about 7%, and a burst release of about 1%. Formulation A7 contains the base formulation with the addition of 30% croscarmellose (a cellulose derivative which is a beta-(1,4)-D-glucopyranose polymer). This formulation results in an improved complete release of about 30%, a linear release of 22%, and a burst release of 5%.

Figure 38:
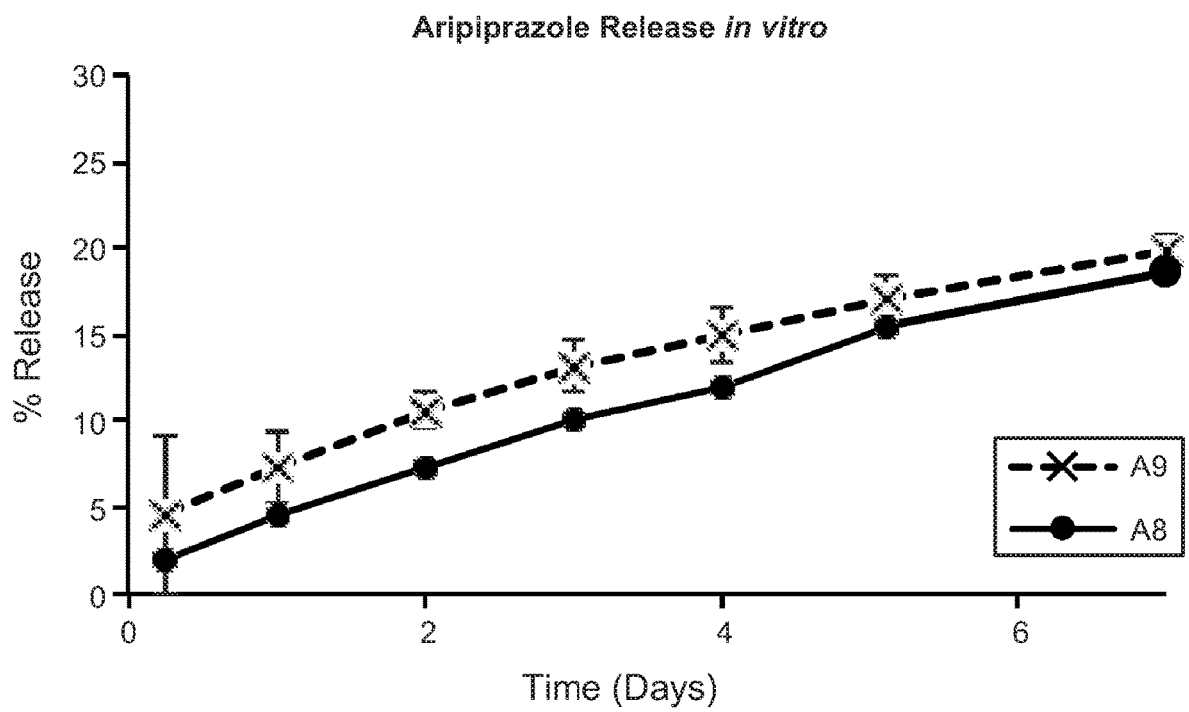
FIG. 38 shows in vitro release assay for aripiprazole formulations A8 and A9 in FaSSGF.

FIG. 38 shows in vitro release data for formulations A8 and A9, which contain the base formulation with the addition of 10% P407 and 10% Eudragit E and also contain 10% or 5% citric acid, respectively. They yield similar results, with total release of drug of about 19% and linear release of about 10-12% after 3 days.

Figure 39:
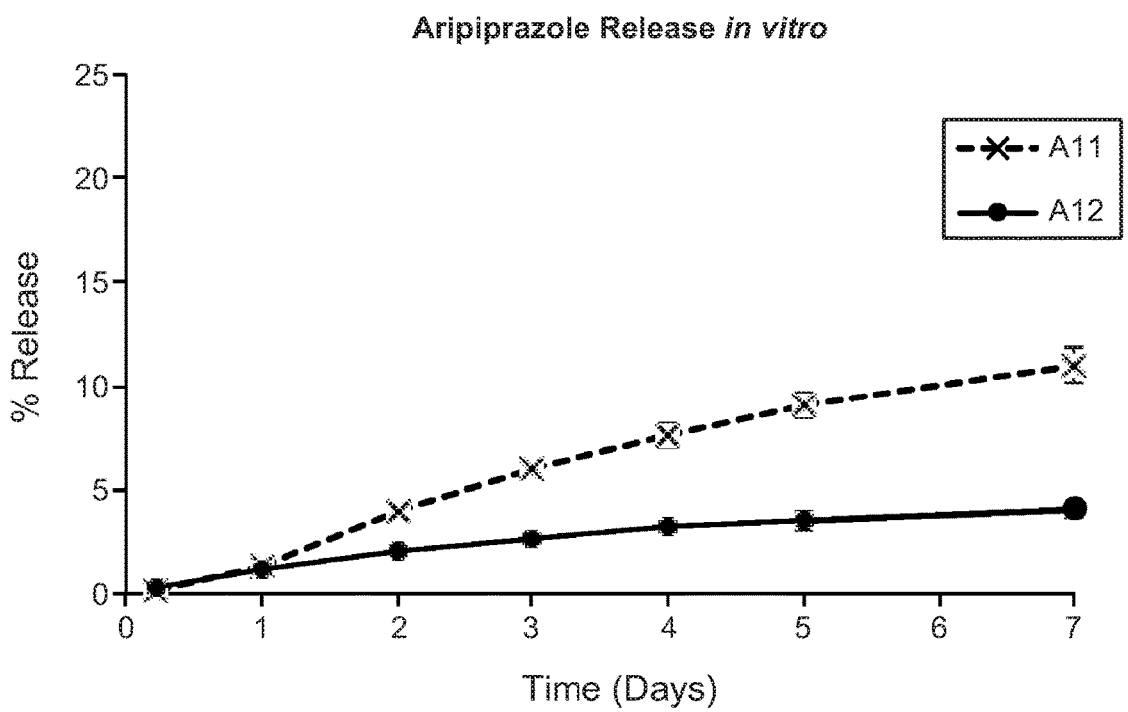
FIG. 39 shows in vitro release assay for aripiprazole formulations A11 and A12 in FaSSGF.

FIG. 39 shows in vitro release data for formulations A11 and A12, which contain the base formulation with the addition of 10% SDS and either 20% cross-linked sodium carboxymethyl cellulose (crosCMC) or 5% citric acid, respectively.

Figure 40:
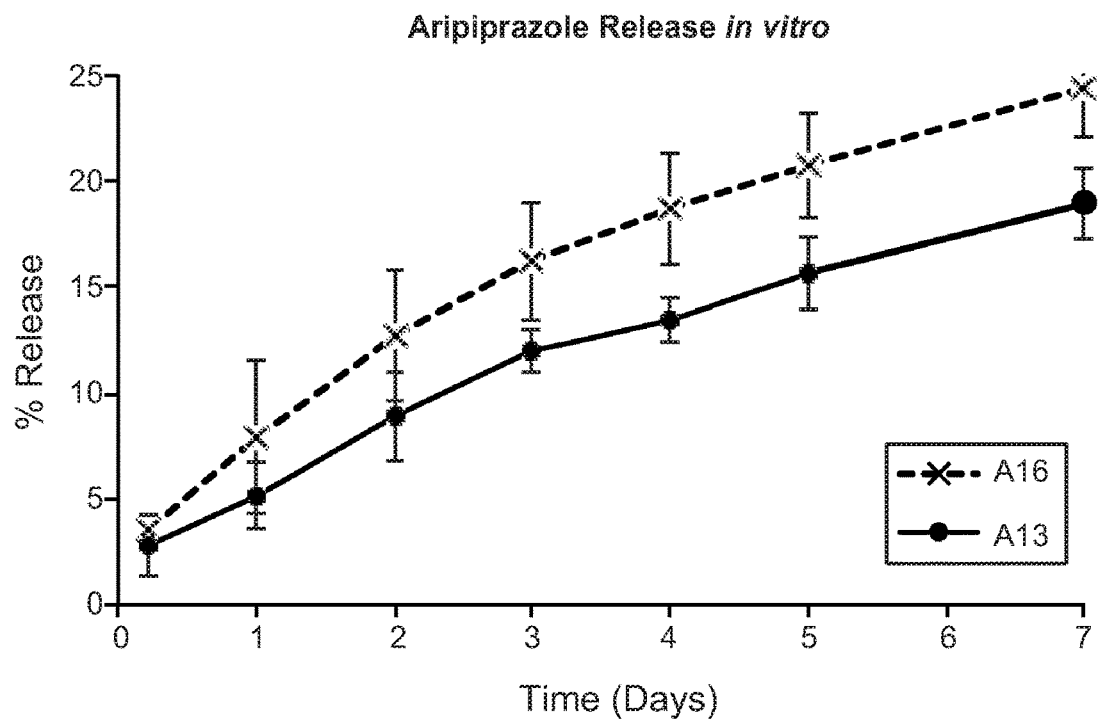
FIG. 40 shows in vitro release assay for aripiprazole formulations A13 and A16 in FaSSGF.

FIG. 40 shows in vitro release data for formulations A13 and A16. Formulation A13 contains the base formulation with the addition of 20% CrosCMC and 10% Soluplus and A16 contains the base formulation with the addition of 20% CrosCMC. Formulation A13 results in a total release of about 19%, linear release of about 13%, and burst release of about 3%. Formulation A16 showed a total release of about 25%, linear release of about 16%, and a burst release of about 3%.

Figure 41:
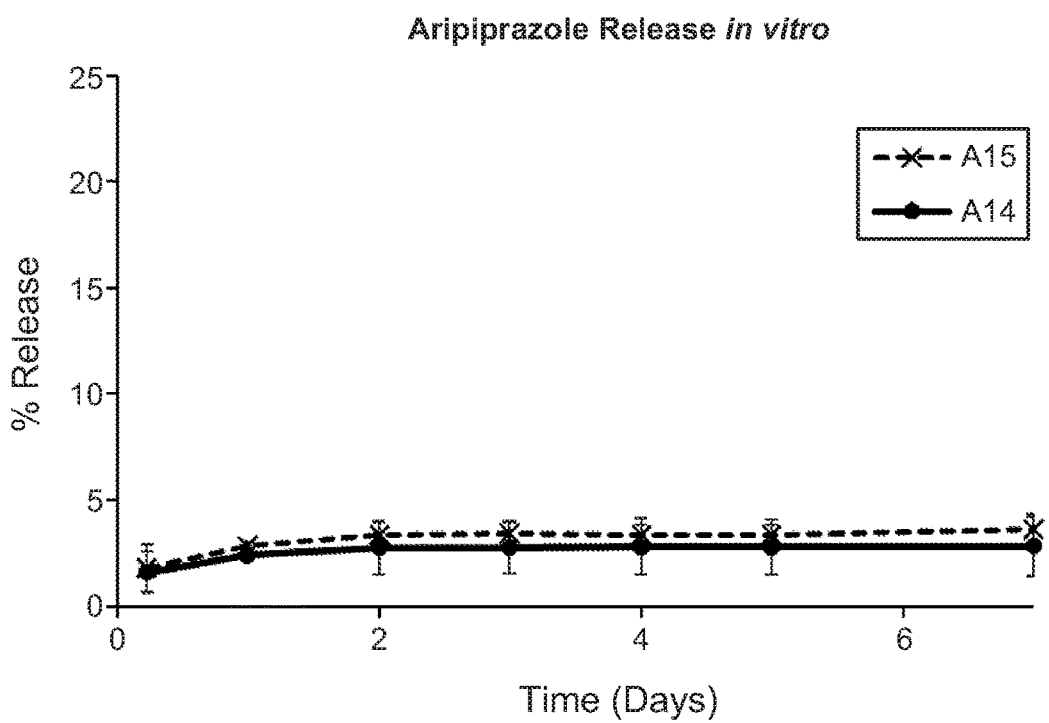
FIG. 41 shows in vitro release assay for aripiprazole formulations A14 and A1 in FaSSGF 5.

FIG. 41 shows in vitro release data for formulations A14 and A15. These formulations contain the base formulation with the addition of 10% SDS in addition to either 20% lyophilized NaCl or 20% granulated NaCl, respectively. These formulations resulted in a similar total drug release of about 3% after 7 days.

Figure 42:
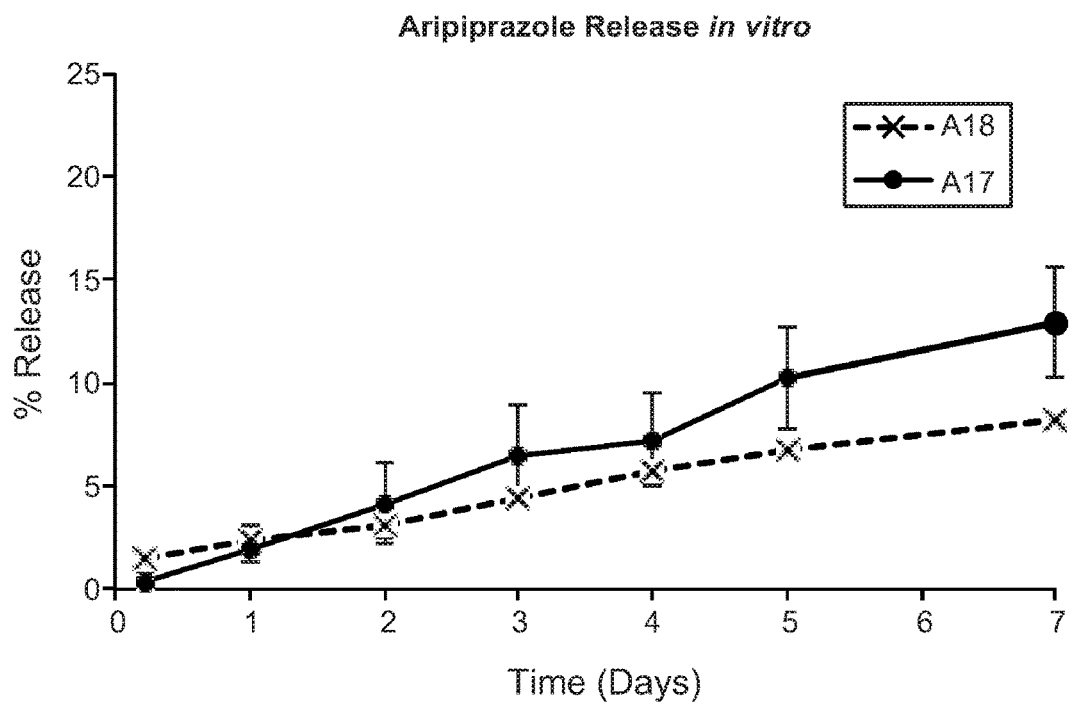
FIG. 42 shows in vitro release assay for aripiprazole formulations A17 and A18 in FaSSGF.

FIG. 42 shows in vitro release data for formulations A17 and A18. A17 contains the base formulation with the addition of 20% NaCl (granules) and 10% CrosCMC. A18 contains the base formulation with the addition of 10% NaCl (granules), 10% CrosCMC, and 10% SDS. A17 had a total release of about 13%, linear release of about 6%, and a burst release of about 1%. A18 showed a total release of about 9%, linear release of about 4%, and a burst release of about 2%.

Figure 43:
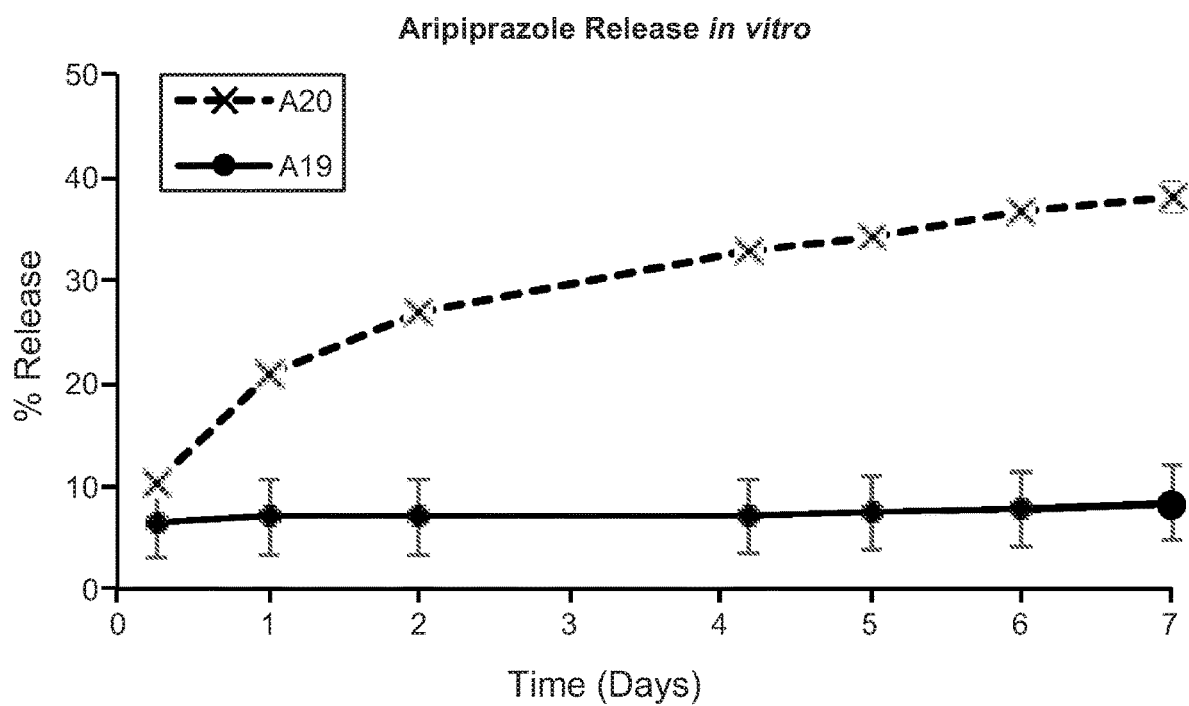
FIG. 43 shows in vitro release assay for aripiprazole formulations A19 and A20 in FaSSGF.

FIG. 43 shows in vitro release data for formulations A19 and A20, which contain the base formulation in addition to 30% SDS or 30% Soluplus, respectively. Formulation A19 resulted in a very low total release of about 7%, with a linear and burst release of about 7%. However, formulation A20, which contained 30% Soluplus, resulted in a total release of about 40%, linear release of about 30%, and burst release of about 10%.

Figure 44:
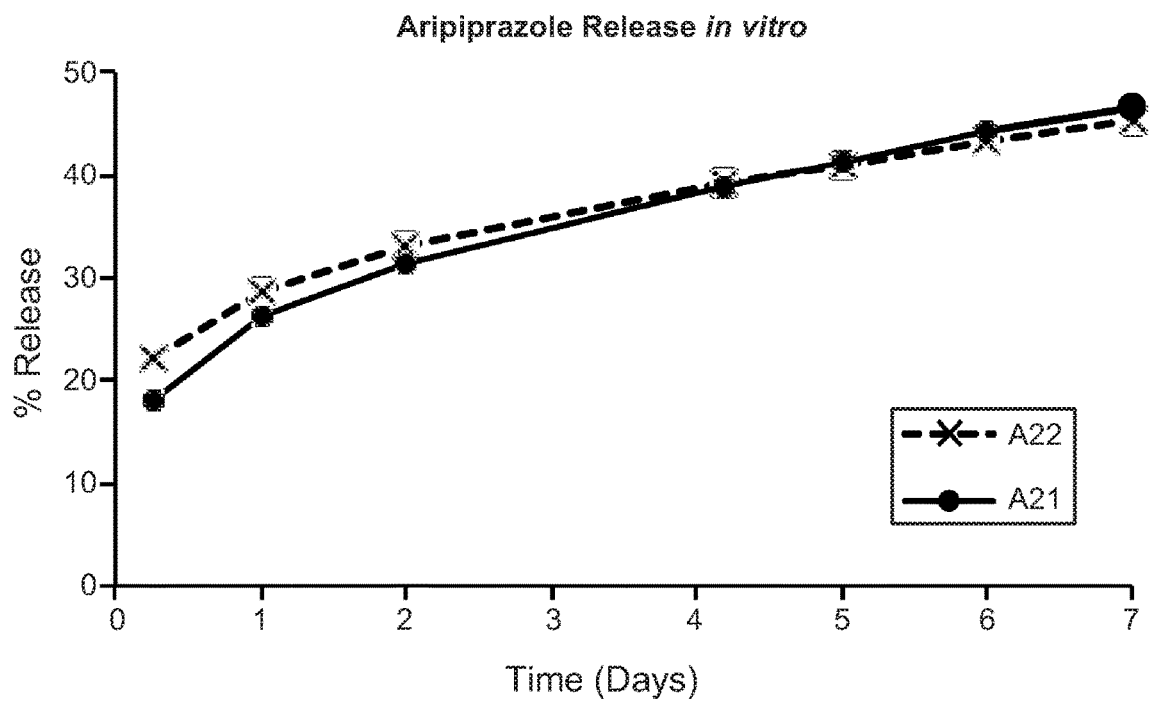
FIG. 44 shows in vitro release assay for aripiprazole formulations A 21 and A22 in FaSSGF.

FIG. 44 shows in vitro release data for formulations A21 and A22, which contain the base formulation in addition to 30% sodium starch glycolate (SSG) or 30% P407, respectively. Formulation A21 showed the highest levels of drug release, with about 47% total release, about 36% linear release, and about 19% burst release. Formulation A22 showed similar results, with about 46% total release, about 36% linear release, and about 23% burst release.

Figure 45:
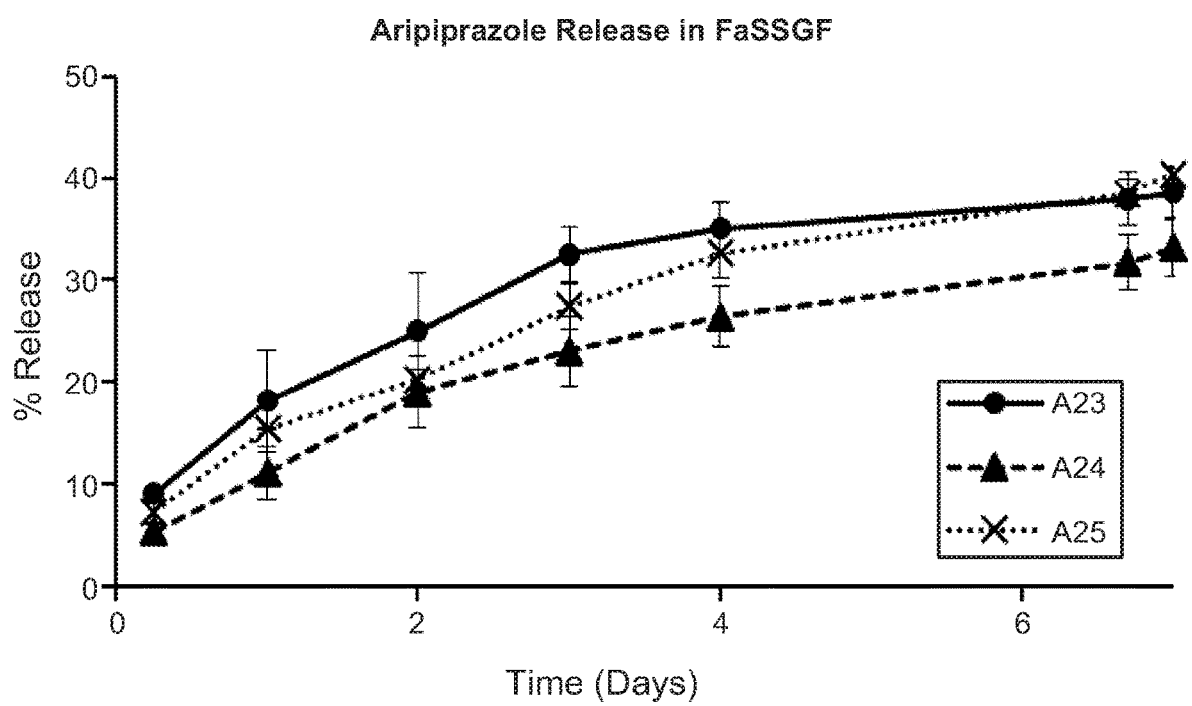
FIG. 45 shows in vitro release assay for aripiprazole formulations A23, A24 and A25 in FaSSGF.

FIG. 45 shows in vitro release data for formulations A23, A24, and A25. A 23 and A25 contain the base formulation in addition to Cremophor EL (polyoxyl 35 hydrogenated castor oil) at a quantity of 20% and 9%, respectively. A24 contains 20% Capmul MCM+ Captex 355+ Cremophore EL in a blend of 4.5%, 1.5%, and 14%, respectively. Capmul MCM is glyceryl monocaprylate, Captex 355 is Glycerol Tricaprylate/Caprate, and Cremphor EL is polyoxyl 35 hydrogenated castor oil. A23 and A25 resulted in total drug release of about 40%, linear release of about 32%, and burst release of about 8%. A24 resulted in a slightly lower total release of about 32%, linear release of about 22%, and burst release of about 5%.

TABLE 11

Aripiprazole formulations. All formulations contain 20% Aripiprazole, 0.5% silica, 0.5% alpha tocopherol, other excipients specified below, and the balance 80k PCL.

| Name | Composition |
| --- | --- |
| A1 | 10% Eudragit EPO, 10% P407 |
| A2 | 25% Eudragit EPO, 5% P407 |
| A3 | 28% RS, 2% P407 |
| A4 | 28% RL, 2% P407 |

TABLE 11-continued

Aripiprazole formulations. All formulations contain 20% Aripiprazole, 0.5% silica, 0.5% alpha tocopherol, other excipients specified below, and the balance 80k PCL.

| Name | Composition |
| --- | --- |
| A5 | 5% SDS |
| A6 | 30% Aquaprene |
| A7 | 30% CrosCMC |
| A8 | 10% P407, 10% Eudragit EPO, 10% Citric acid |
| A9 | 10% P407, 10% Eudragit EPO, 5% Citric acid |
| A10 | 20% NaCl (granules) |
| A11 | 10% SDS, 20% CrosCMC |
| A12 | 10% SDS, 05% CITRIC ACID |
| A13 | 10% SOLUPLUS, 20% CrosCMC |
| A14 | 10% SDS, 20% NaCl (Lyophilized) |
| A15 | 10% SDS, 20% NaCl (granules) |
| A16 | 5% SOLUPLUS |
| A17 | 20% NaCl (granules), 10% CrosCMC |
| A18 | 10% NaCl (granules), 10% SDS, 10% CrosCMC |
| A19 | 30% SDS |
| A20 | 30% SOLUPLUS |
| A21 | 30% SSG |
| A22 | 30% P407 |
| A23 | 20% Cremophore EL |
| A24 | 20% Capmul MCM + Captex 355 + Cremophore EL |
| A25 | 9% Cremophore EL |

Example 42

In Vitro Release of Risperidone Loaded Structures in FaSSGF

FIG. 46 through FIG. 52 show the in vitro release of risperidone from formulation arms in FaSSGF. Formulations were prepared as described in Example 15 and Example 26 and are described in Table 12. In vitro release assays were performed and analyzed by HPLC for API quantification at each time point as described in Example 28. Risperidone formulations contain 10% Risperidone, 0.5% silica, 0.5% alpha tocopherol, other excipients specified in Table 12, and the balance 80 k PCL.

TABLE 12

Risperidone formulations. All formulations contain 10% Risperidone, 0.5% silica, 0.5% alpha tocopherol, other excipients specified below, and the balance 80k PCL.

| Formulation | Additional Excipients |
| --- | --- |
| R1 | 89% 80K PCL |
| R3 | 89% Strataprene 3534 |
| R6 | 9% Aquaprene |
| R7 | 18% Aquaprene |
| R8 | 89% Polydioxanone |
| R9 | 44.5% Strataprene, 44.5% Eudragit RS |
| R13 | 42% Eudragit RS, 5% P407 |
| R14 | 5% Taurocholate/Lecithin |
| R15 | 44.5% Eudragit RS 5% P407 |
| R16 | 28% Aquaprene |
| R18 | 28% Eudragit RL |
| R19 | 9.33% Aquaprene, 9.33% Eudragit RS, 9.33% Eudragit RL |
| R20 | 14% Eudragit RS, 14% Aquaprene |
| R21 | 14% Eudragit RS, 14% Eudragit RL |
| R22 | 28% Eudragit RS |

Figure 46:
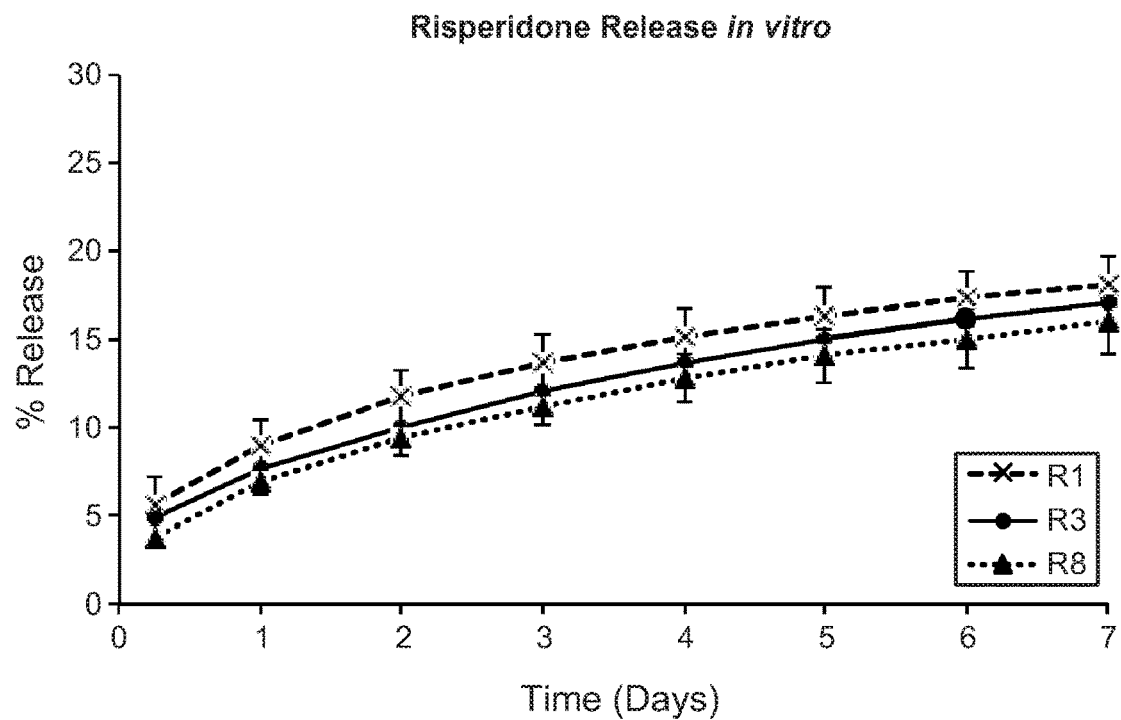
FIG. 46 shows in vitro release assay for risperidone formulations R1, R3 and R8 in FaSSGF.

FIG. 46 shows in vitro release data for formulations R1, R3, and R8. The R1 formulation contains only the base formulation, whereas R3 contains an additional 98% Strataprene 3534 (Strataprene 3534, Poly-Med, Inc.: 35% caprolactone, 34% lactide, 17% glycolide, and 14% trimethylene carbonate). R8 contains an additional 89% polydioxanone.

The base formulation R1 showed about 19% total release, about 13% linear release, and about 5% burst release. Formulations R3 and R8 did not result in an improved drug release. R3 showed about 18% total release, 12% linear release, and 5% burst release. R8 showed similar results, with about 17% total release, about 11% linear release, and about 4% burst release.

Figure 47:
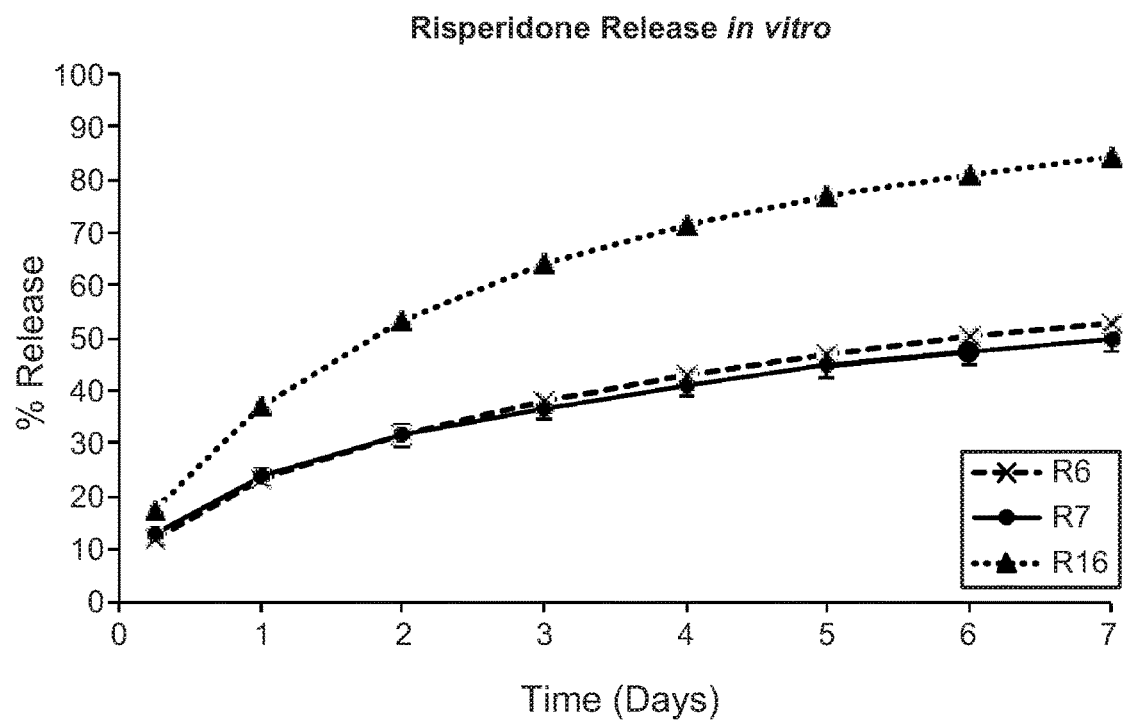
FIG. 47 shows in vitro release assay for risperidone formulations R6, R7 and R16 in FaSSGF.

FIG. 47 shows in vitro release data for formulations R6, R7, and R16. Formulation R6 contains the base formulation in addition to 9% Aquaprene (Aquaprene 8020, Poly-Med, Inc.: 80% dioxanone, 20% polyethylene glycol) and formulation R7 contains the base formulation in addition to 18% Aquaprene. Formulations R6 and R7 have similar results, showing total release of about 55%, linear release of about 37%, and burst release of about 13%. Formulation R16 contains the base formulation in addition to 28% Aquaprene.

Figure 48:
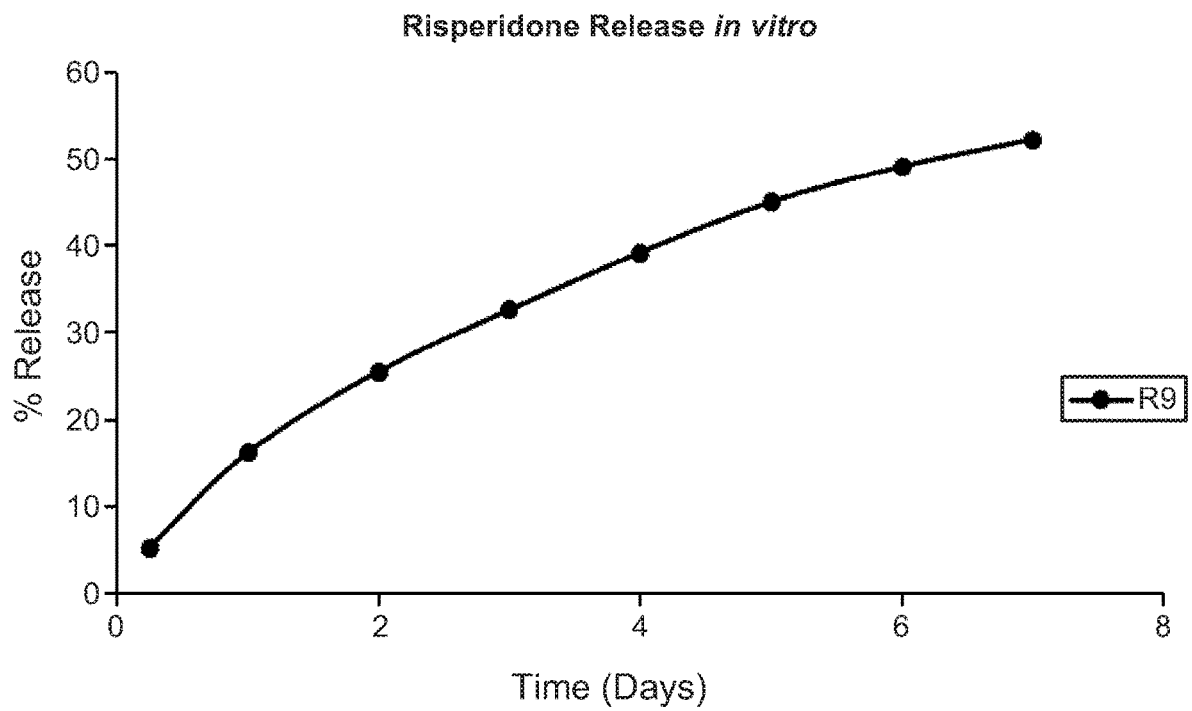
FIG. 48 shows in vitro release assay for risperidone formulations R9 in FaSSGF.

FIG. 48 shows in vitro release data for formulations R9, which contains the base formulation with the addition of 44.5% Strataprene and 44.5% Eudragit RS. This formulation resulted in a total release of about 55%, linear release of about 33%, and burst release of about 5%.

Figure 49:
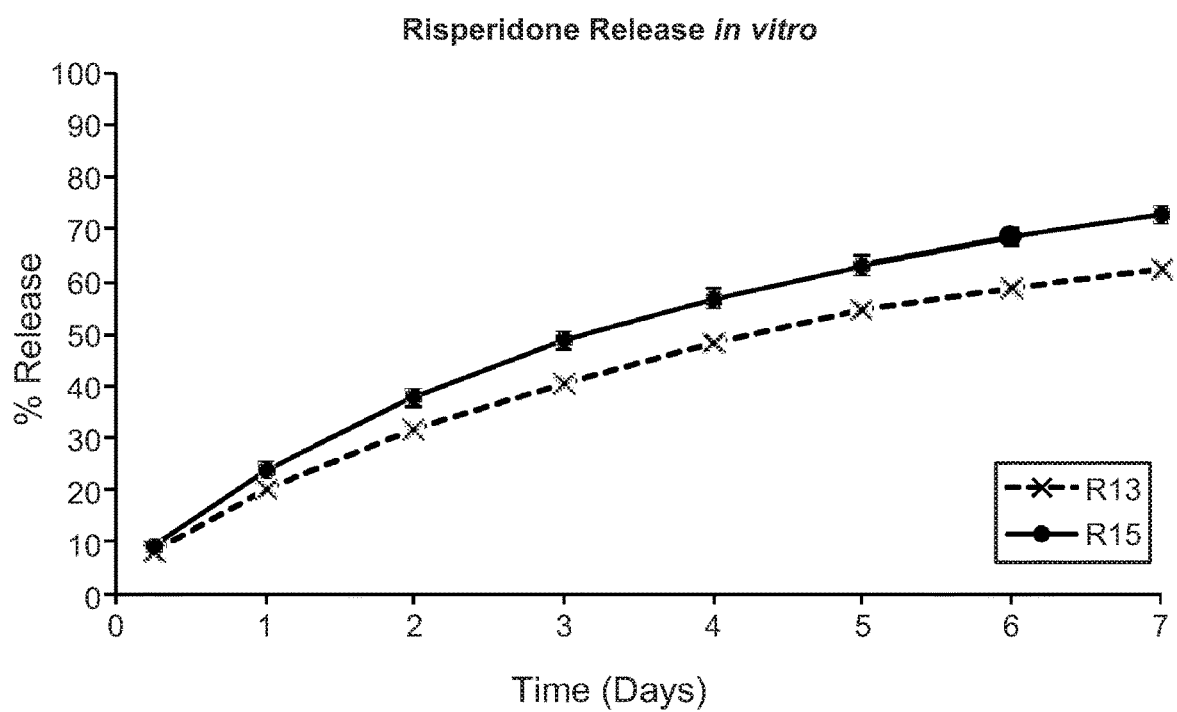
FIG. 49 shows in vitro release assay for risperidone formulations R13 and R15 in FaSSGF.

FIG. 49 shows in vitro release data for formulations R13 and R15, which contain the base formulation in addition to 5% P407 and 42% or 44.5% Eudragit RS, respectively. Formulation R13 yielded a total drug release of 62%, linear release of 40%, and burst release of 9%. Upon increasing the amount of Eudragit RS, formulation R15 showed an increase in drug release to 75% total release, 50% linear release, and 9% burst release.

Figure 50:
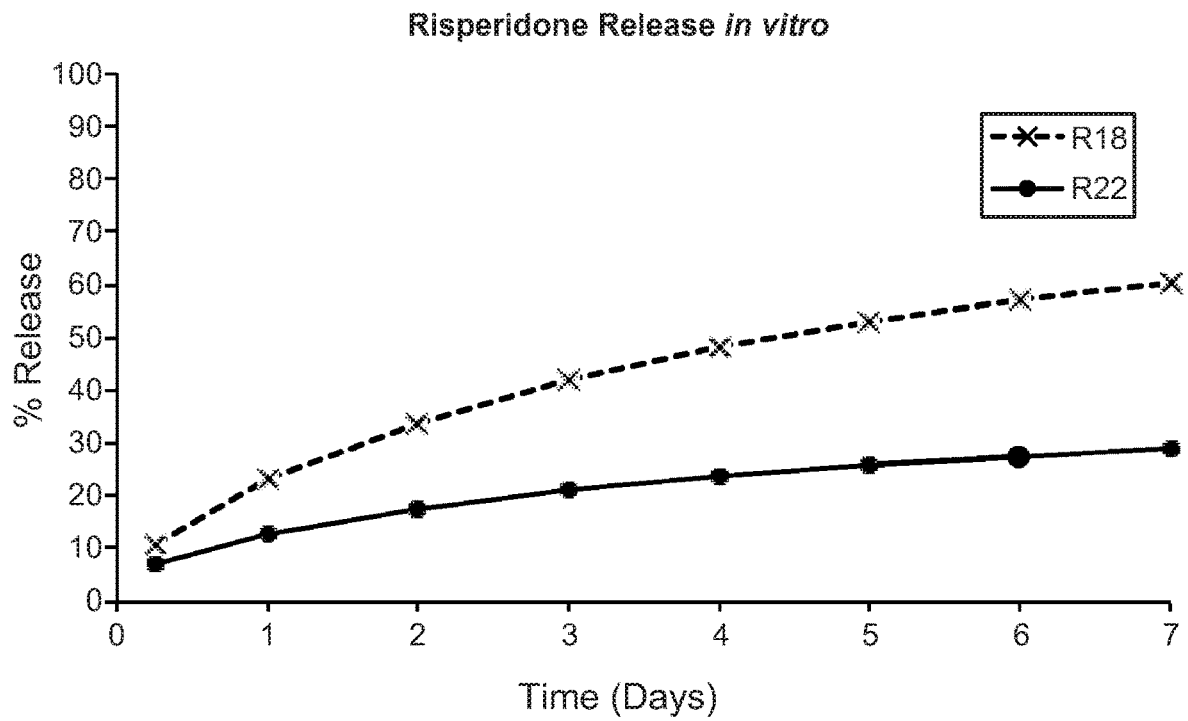
FIG. 50 shows in vitro release assay for risperidone formulations R18 and R22 in FaSSGF.

FIG. 50 shows the in vitro release data for formulations R18 and R22, in which base formulations are supplemented with 28% Eudragit RL or 28% Eudragit RS, respectively. Formulation R22 results in 33% total release, 20% linear release, and 9% burst release. Formulation R18 results in an increased total release of 64%, linear release of 45%, and 10% burst release.

Figure 51:
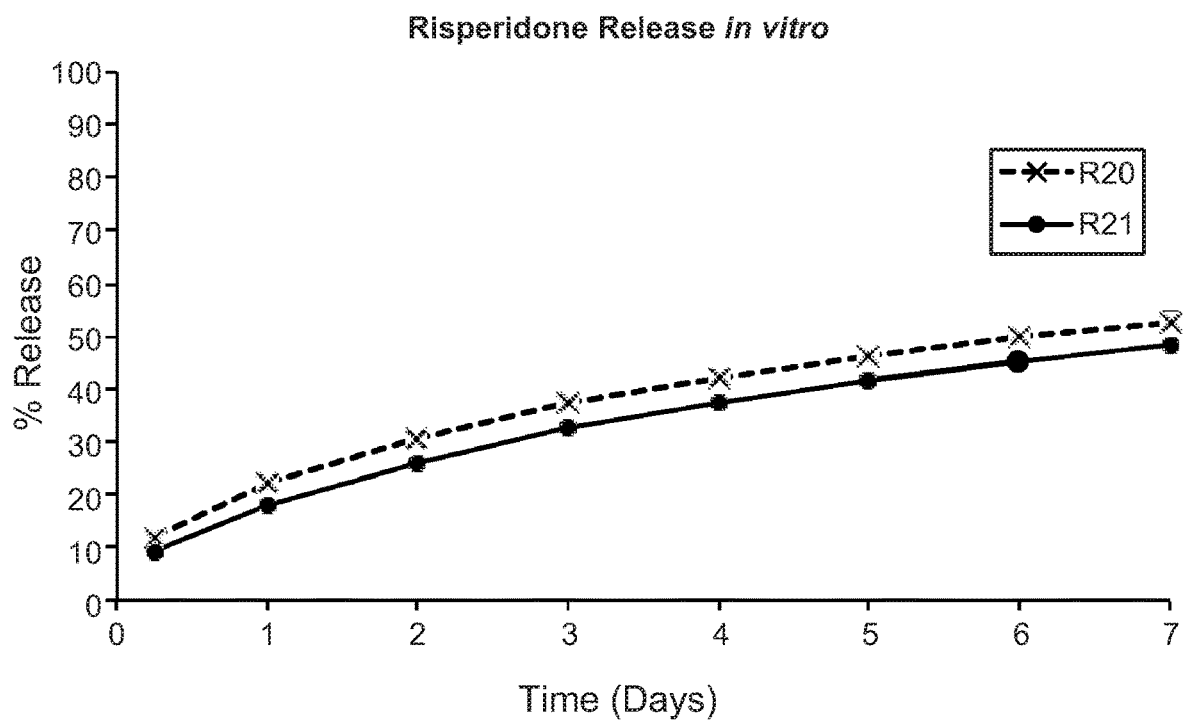
FIG. 51 shows in vitro release assay for risperidone formulations R20 and R21 in FaSSGF.

FIG. 51 shows in vitro release data for formulations R20 and R21, which contained the base formulation and 14% Eudragit RS with the addition of 14% Aquaprene or 14% Eudragit RL, respectively. Both formulations had similar results, with total release of about 51%, linear release of about 33%, and burst release of about 10%.

Figure 52:
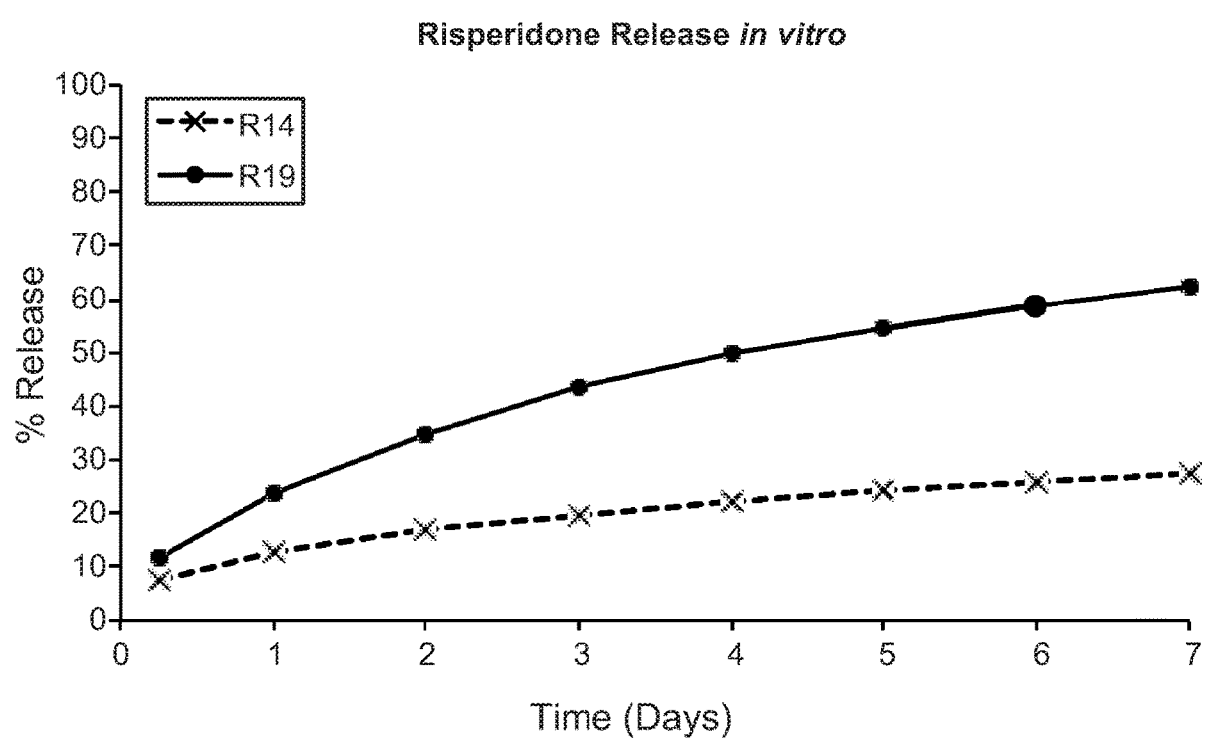
FIG. 52 shows in vitro release assay for risperidone formulations R14 and R19 in FaSSGF.

FIG. 52 shows in vitro release data for formulations for R14 and R19. R14 contains the base formulation with 5% Taurocholate/Lecithin. R19 contains the base formulation with 9.33% of Eudragit RS, 9.33% Eudragit RL, and 9.33% Aquaprene. R14 resulted in total release of about 28%, linear release of about 19%, and burst release of about 9%. R19 resulted in a higher total burst of about 67%, linear release of about 44%, and burst release of about 11%.

Example 43

In Vitro Release of Memantine Loaded Structures in FaSSGF

Various formulations of carrier polymers and excipients blended with memantine were tested. Memantine was ball milled with 1% silica and sifted through a 75-micron sieve and formulations were prepared as described in Example 26. The formulations contained the following ingredients: 20% memantine, 0.5% silicon dioxide (Cab-O-Sil), 0.5% alpha tocopherol, and the additional excipients listed in Table 13; the balance of the formulation was made up with polycaprolactone (MW 80,000). In vitro release assays were performed and analyzed by HPLC for API quantification at each time point as described in Example 28.

TABLE 13

Memantine formulations. All formulations contain 20% memantine, 0.5% silicon dioxide (Cab-O-Sil), 0.5% alpha tocopherol, the additional excipients listed below, and the balance 80k PCL.

| Formulation | Additional Excipients |
| --- | --- |
| M1 | 9% Eudragit E |
| M2 | 9% P407 |
| M3 | 4.5% Eudragit E, 4.5% P407 |
| M4 | 9% Poly Vinyl Acetate |
| M5 | 9% PVP |
| M6 | 9% Eudragit E |
| M7 | 5% Kolliphor RH40 |
| M17 | 7% Eudragit E, 2% P407 |
| M18 | 25% Eudragit RS 5% P407 |
| M19 | 5% Taurocholate/Lecithin |
| M20 | 9% Taurocholate/Lecithin |
| M21 | 25% Eudragit RL, 5% P407 |
| M22 | 30% polydioxanone |
| M23 | 9% Eudragit E |
| M24 | 20% Eudragit RS, 2% P407 |
| M25 | 19.85% Eudragit RS, 0% P407 |
| M26 | 17.5% Eudragit RS, 5% P407 |
| M27 | 10% Eudragit RS and 5% P407 |
| M29 | 25% Eudragit RS, 0% P407 |
| M30 | 21.25% Eudragit RS, 2.5% P407 |
| M31 | 25% Eudragit RS, 5% P407 |

Figure 53:
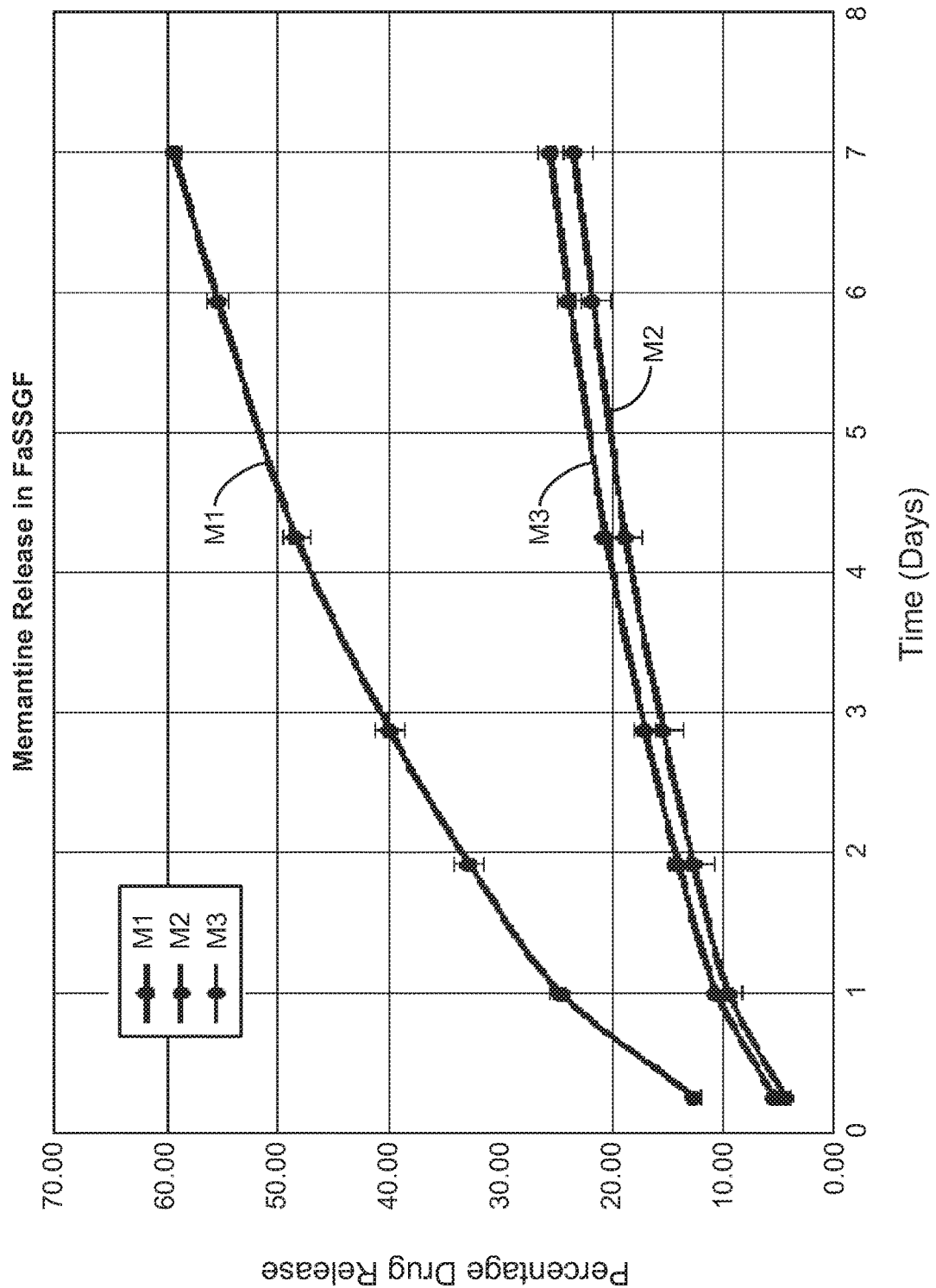
FIG. 53 shows in vitro release assay for memantine formulations M1, M2 and M3 in FaSSGF.

FIG. 53 shows in vitro release data for memantine formulations M1, M2 and M3, which contain varying amounts of Eudragit E and P407. Formulation M3 contains the base formulation with the addition of 9% P407 and results in a total release of about 24%, a linear release of about 16%, and a burst release of about 5%. Formulation M1 contains the base formulation with the addition of 9% Eudragit E and results in a much higher total release of about 60%, a linear release of about 40%, and maintains a low burst release of about 12%. When the formulation contains 4.5% Eudragit E and 4.5% P407, there is a lower total release of about 26%, linear release of about 18%, and burst release of about 5%.

Figure 54:
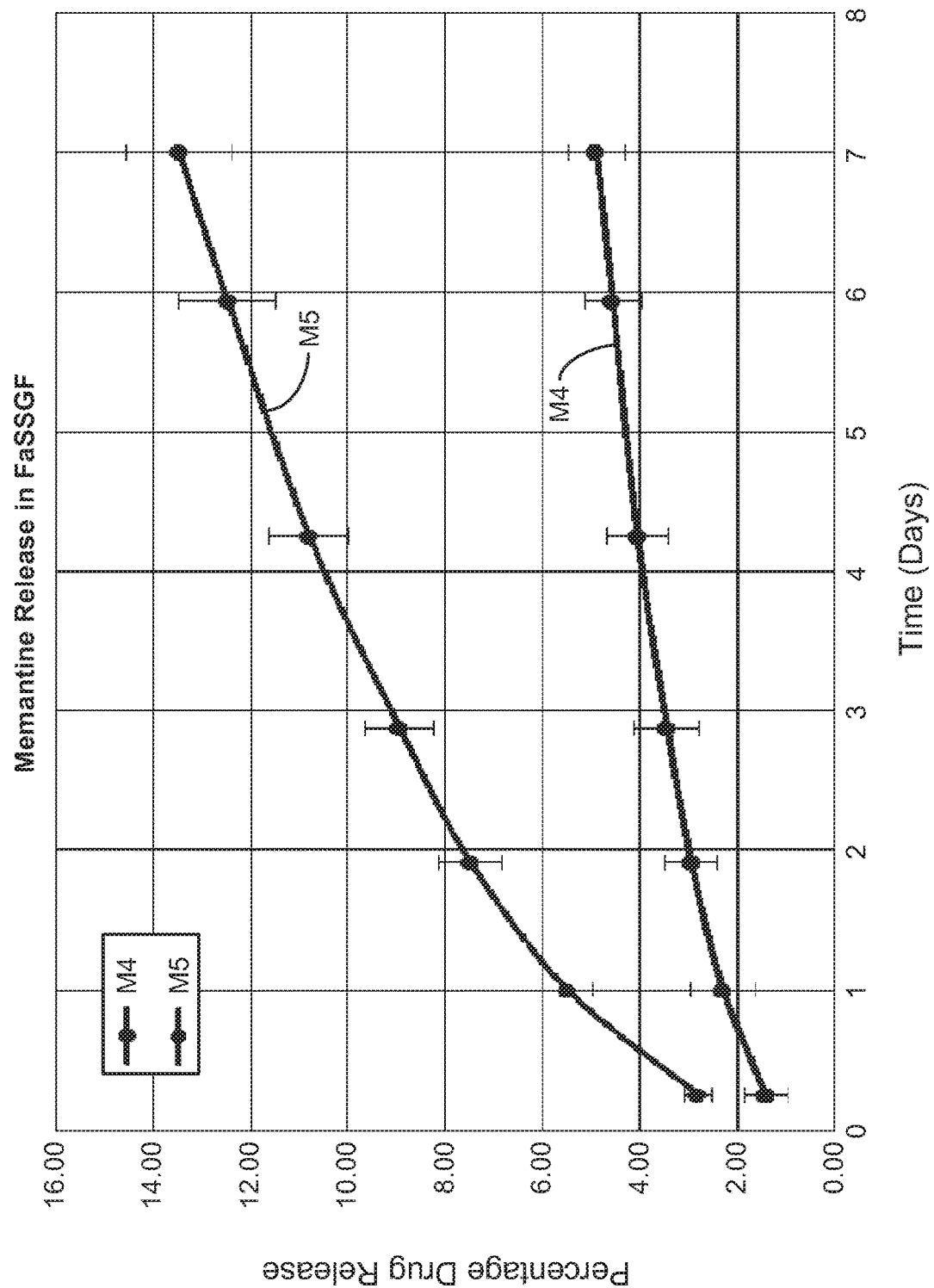
FIG. 54 shows in vitro release assay for memantine formulations M4 and M5 in FaSSGF.

FIG. 54 shows in vitro release data for formulations M4 and M5, which contain the base formulation with the addition of 9% polyvinyl acetate (PVA) or 9% polyvinylpyrrolidone (PVP), respectively. The addition of PVA resulted in only about 5% total release and the addition of PVP resulted in a slightly higher total release of about 13%.

Figure 55:
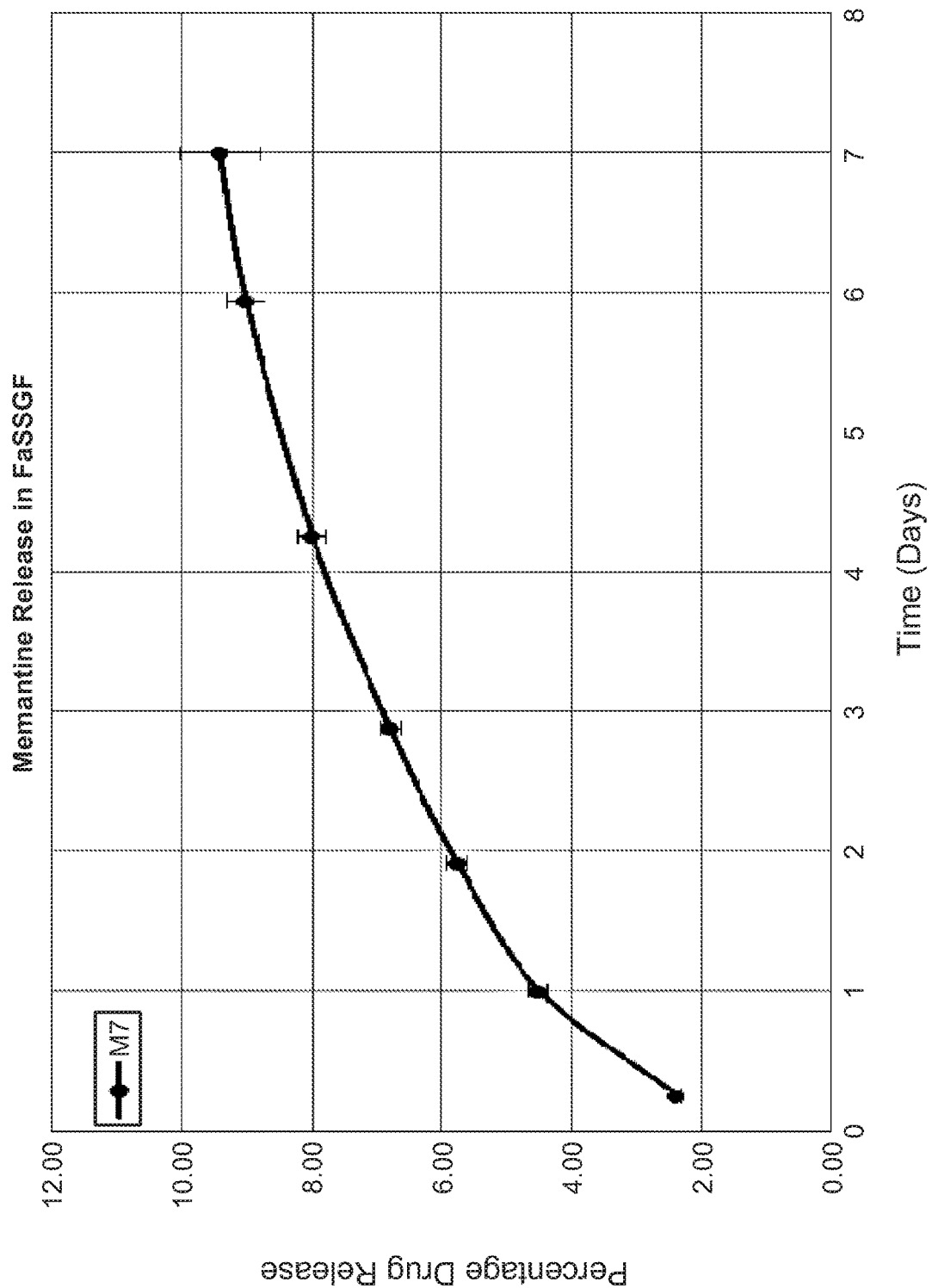
FIG. 55 shows in vitro release assay for memantine formulation M7 in FaSSGF.

FIG. 55 shows in vitro release data for formulation M7, which contains the base formulation with the addition of 5% Kolliphor RH40. This formulation has a low total drug release of about 9%, linear release of about 7%, and a burst release of about 2%.

Figure 56:
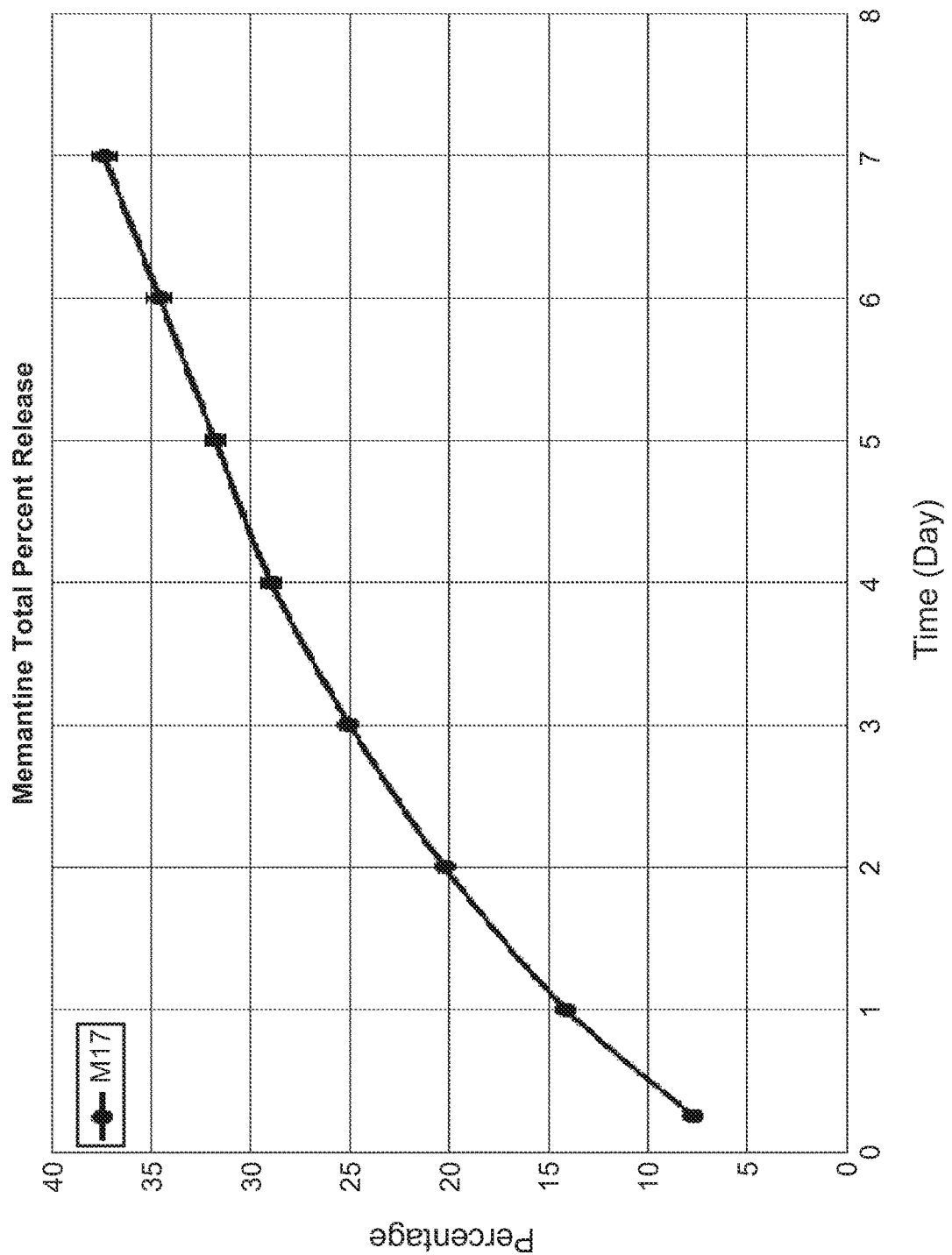
FIG. 56 shows in vitro release assay for memantine formulation M17 in FaSSGF.

FIG. 56 shows in vitro release data for formulation M17, which contains the base formulation with the addition of 2% P407 and 7% Eudragit E. This results in a total release of about 37%, linear release of about 25%, and burst release of about 7%.

Figure 57:
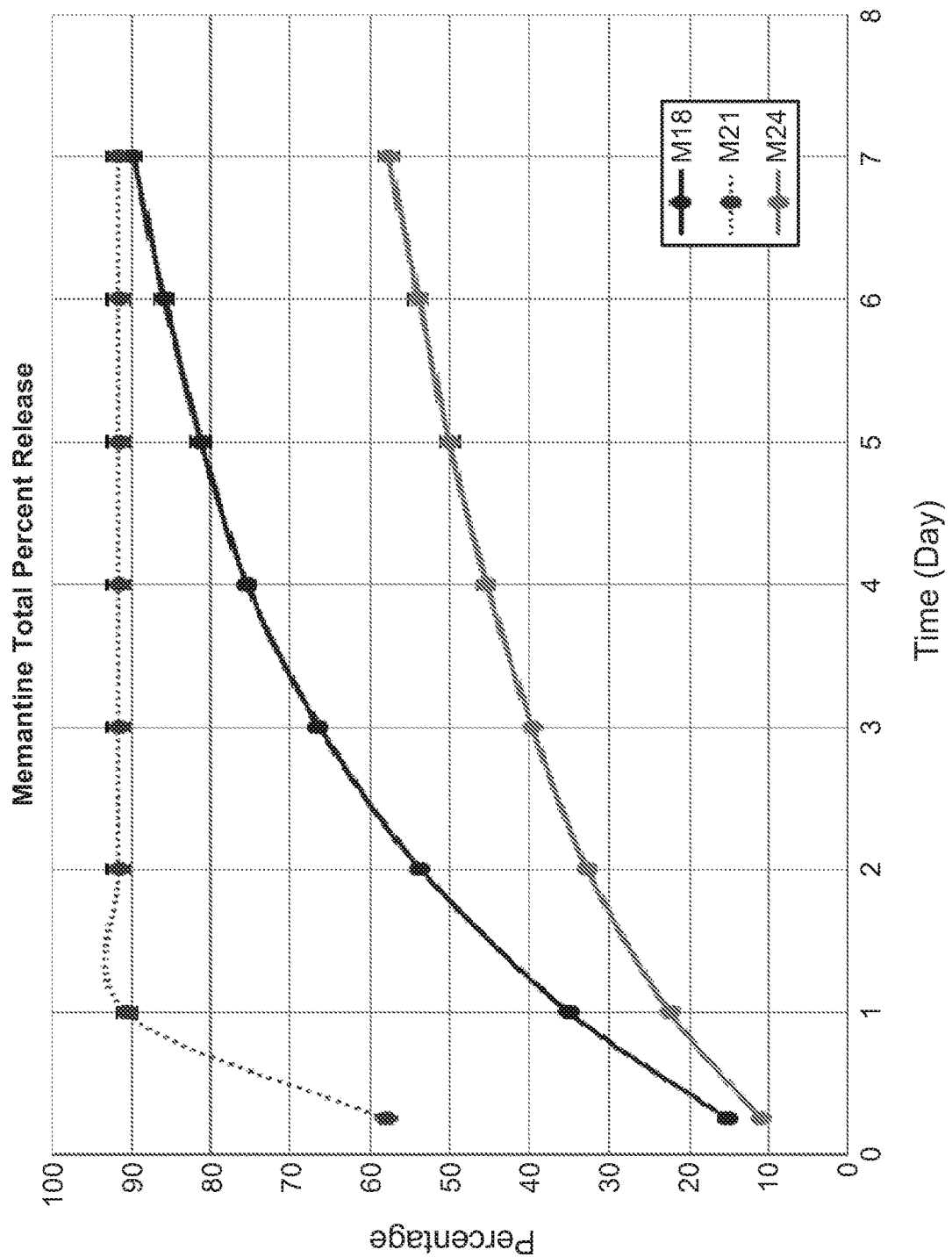
FIG. 57 shows in vitro release assay for memantine formulations M18, M21 and M24 in FaSSGF.

FIG. 57 shows in vitro release data for formulations M18, M21, and M24, which contain the base formulation and varying amounts of P407 and Eudragit RS. M21 contains 5% P407 and no additional Eudragit RS and results in a very high total release of about 92%. However, this formulation also showed a high linear release of about 92% and a burst of about 58%. Formulation M24, containing both 2% P407 and 20% Eudragit RS, resulted in a more favorable total release of about 58%, linear release of about 40%, and a burst release of about 12%. Formulation M18, containing 5% P407 and 25% Eudragit RS, resulted in a high total release of about 90%, a linear release of about 68%, and a low burst release of about 15%.

Figure 58:
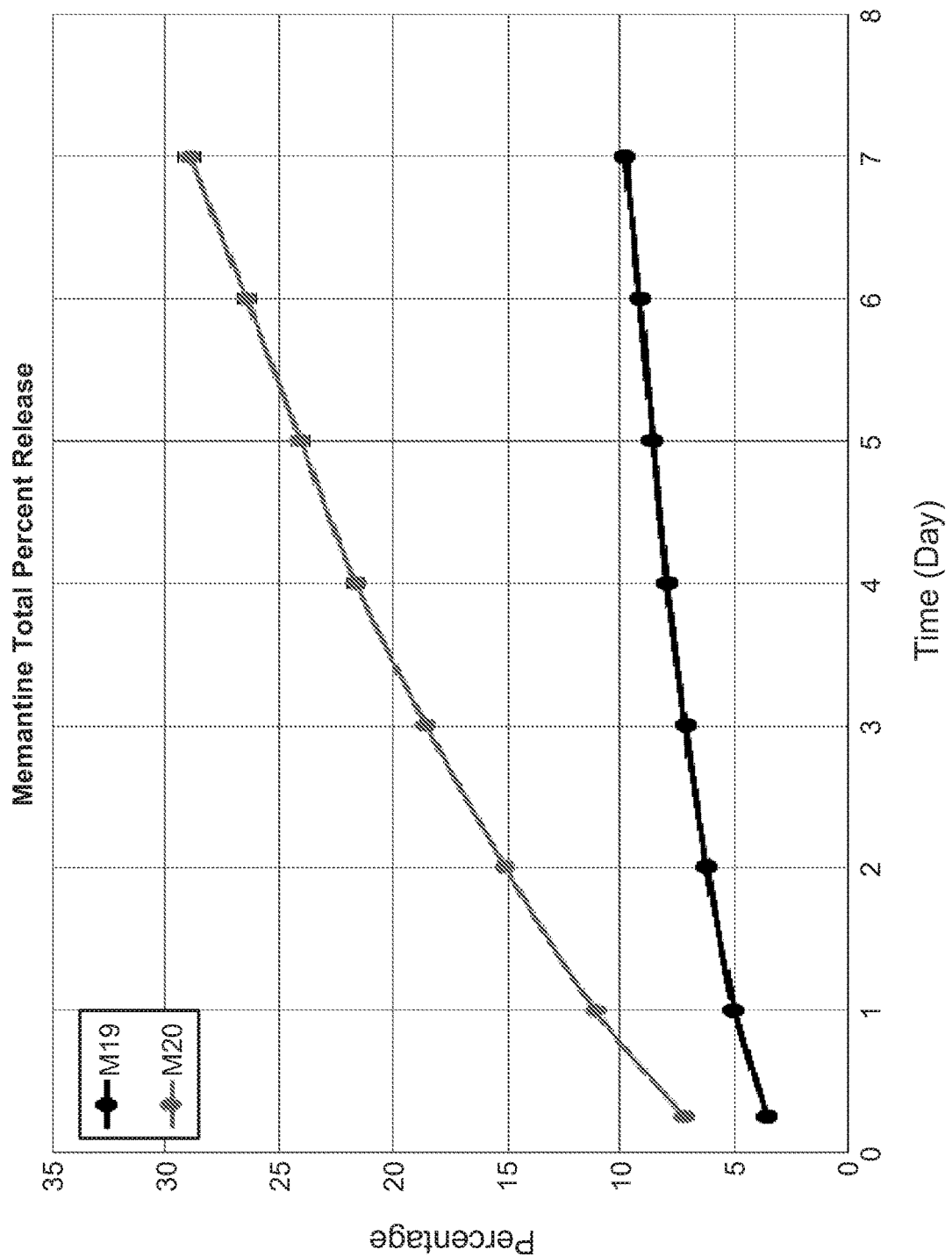
FIG. 58 shows in vitro release assay for memantine formulations M19 and M20 in FaSSGF.

FIG. 58 shows in vitro release data for formulations M19 and M20, which contain the base formulation with the addition of 5% or 9% Taurocholate/Lecithin, respectively. This yielded a total drug release of about 10% for M19. M20 resulted in a total release of about 29%, with a linear release of about 18% and a burst release of about 7%.

Figure 59:
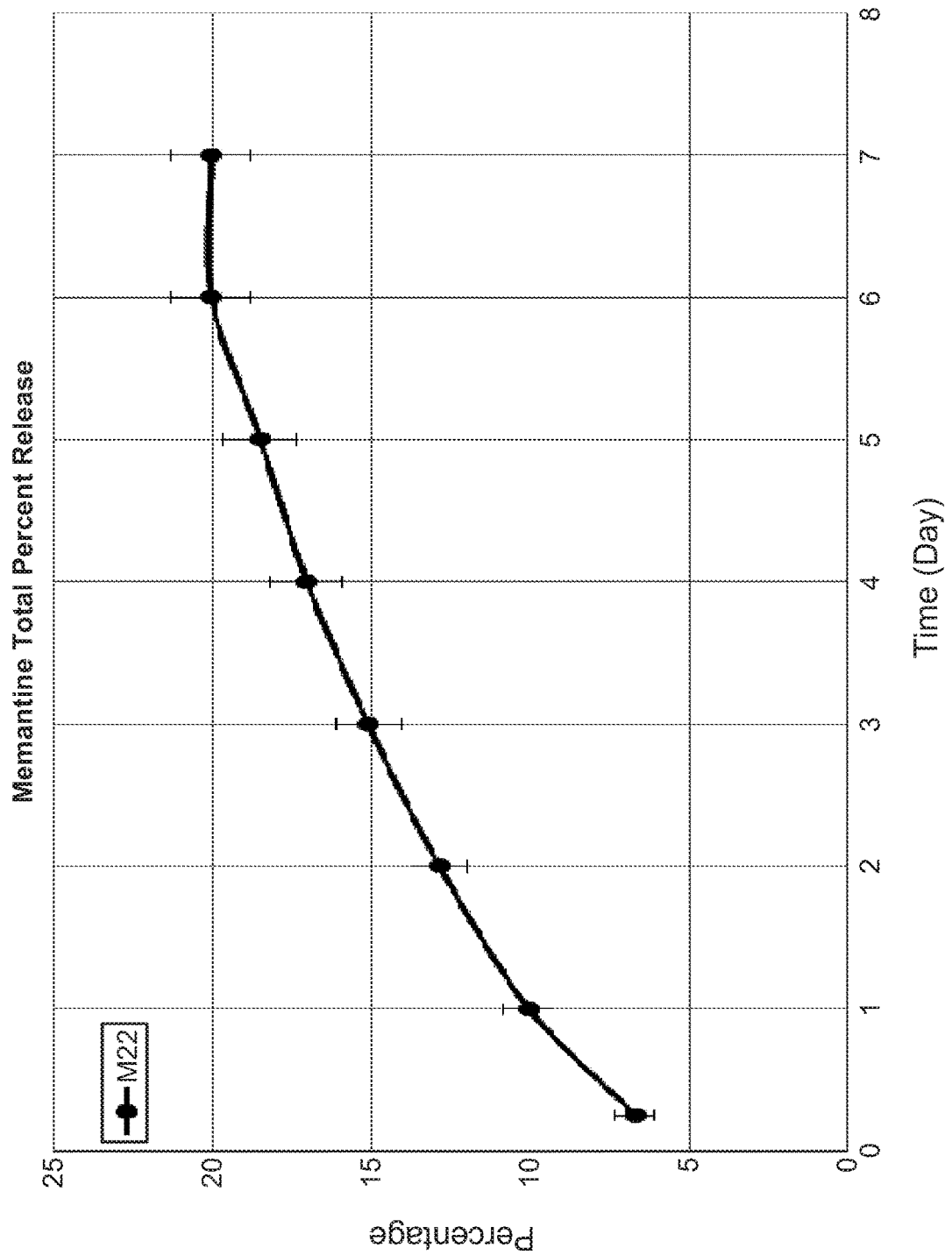
FIG. 59 shows in vitro release assay for memantine formulations M22 in FaSSGF.

FIG. 59 shows in vitro release data for formulation M22, which contains the base formulation with the addition of 30% polydioxanone. This formulation had a total drug release of about 20%, linear release of about 15%, and a burst release of about 7%.

Figure 60:
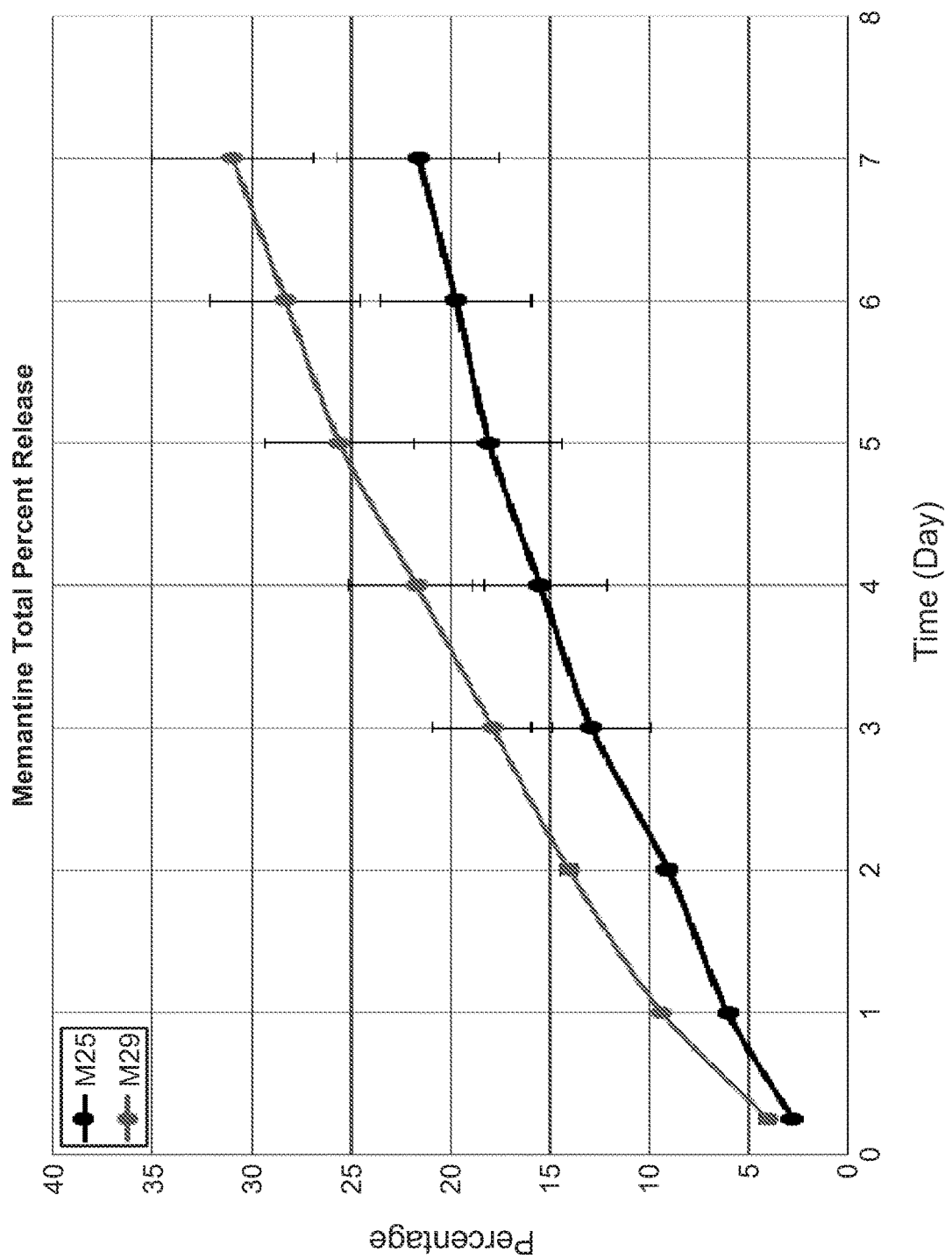
FIG. 60 shows in vitro release assay for memantine formulations M25 and M29 in FaSSGF.

FIG. 60 shows in vitro release data for formulations M25 and M29, which contain the base formulation with the addition of 19.85% and 25% Eudragit RS, respectively. M25 resulted in a total release of about 22%, linear release of about 12%, and a burst release of about 3%. M29 resulted in a higher total drug release of about 31%, linear release of about 18%, and a burst release of about 4%.

Figure 61:
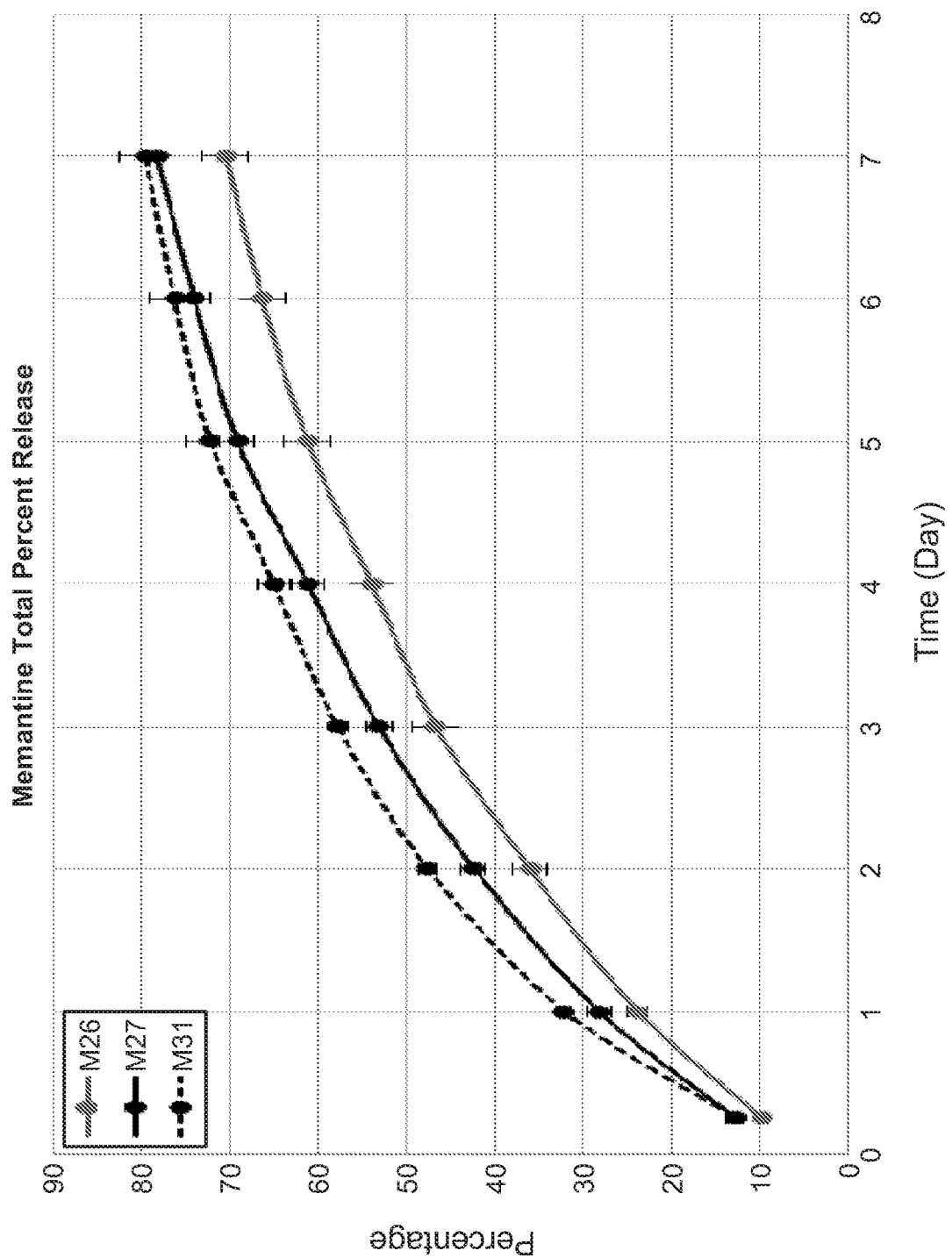
FIG. 61 shows in vitro release assay for memantine formulations M26, M27 and M31 in FaSSGF.

FIG. 61 shows in vitro release data for formulations M26, M27, and M31, which contain the base formulation, 5% P407, and varying amounts of Eudragit RS. The M31 formulation is identical to M18 but the drug-loaded formulation was prepared in a separate milling batch, resulting in slight differences in particle size and particle size distribution. M26 contains 17.5% Eudragit RS and resulted in a 70% total release, 47% linear release, and 10% burst release. M27 contains 10% Eudragit RS and resulted in 79% total release, 54% linear release, and 12% burst release. M31 contains 25% Eudragit RS and resulted in 79% total release, 58% linear release, and 12% burst release.

Figure 62:
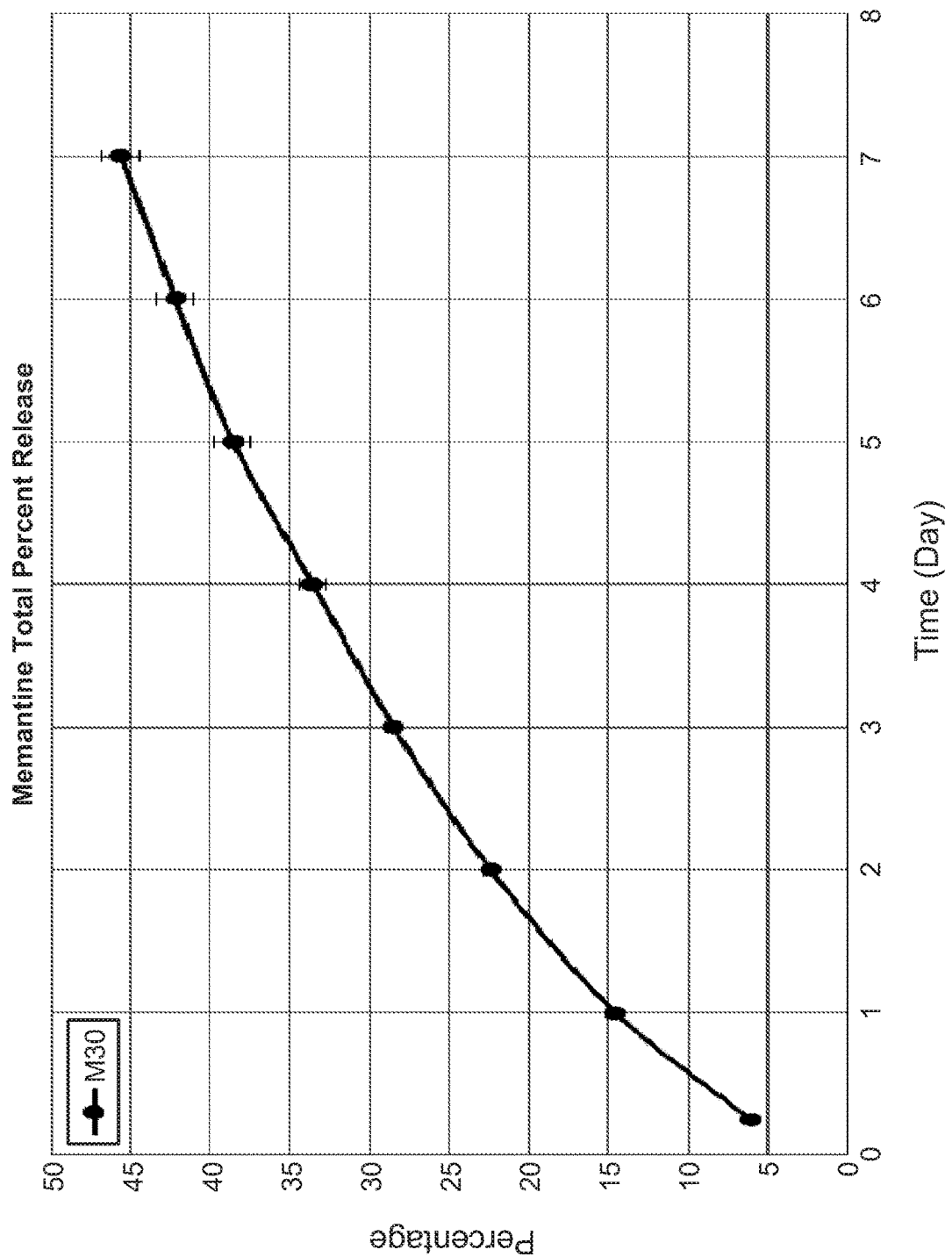
FIG. 62 shows in vitro release assay for memantine formulations M30 in FaSSGF.

FIG. 62 shows in vitro release data for formulation M30, which contains the base formulation with the addition of 2.5% P407 and 21.25% Eudragit RS. This formulation results in total drug release of about 45%, linear release of about 29%, and burst release of about 6%.

Example 44

Memantine Release in Fed Vs. Fasted State

Figure 63:
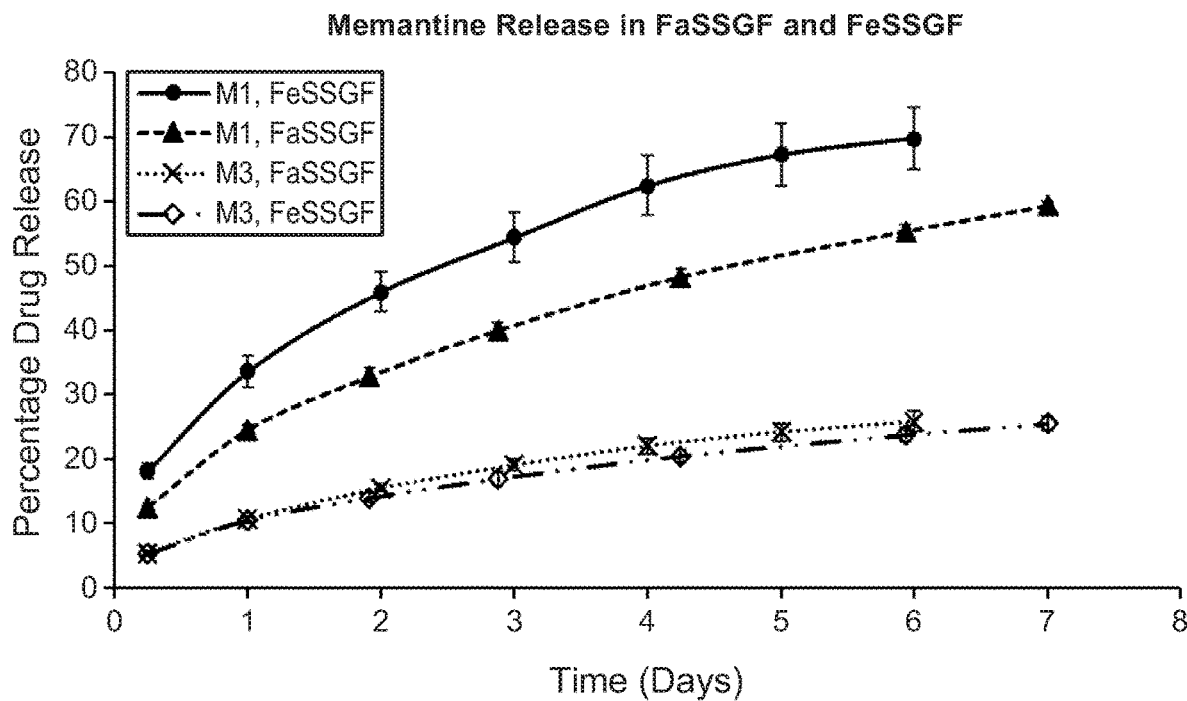
FIG. 63 shows in vitro release assay for memantine formulations M1 and M3 in FaSSGF and FeSSGF.

Memantine formulations were evaluated for the effect of media pH and composition on in vitro release profiles. FIG. 63 shows a comparison of the drug release from formulation M1 and M3 in fasted state simulated gastric fluid (FaSSGF) and fed state simulated gastric fluid (FeSSGF). Samples of formulations were incubated in fasted state simulated gastric fluid (FaSSGF, pH 1.6) and fed state simulated gastric fluid (FeSSGF, pH 5.0) media. Formulations were subjected to a seven-day release study at 37° C., 200 rpm. In FaSSGF, total drug release from M1 was about 60%, linear release was about 40%, and burst release was about 12%. The same formulation showed a higher drug release in FeSSGF, with a total release of about 70% (sample was tested on Day 6 rather than Day 7), linear release of about 55%, and a burst release of about 19%. Formulation M3 showed similar release in FaSSGF and FESSGF, with a total release of about 20%.

Figure 64:
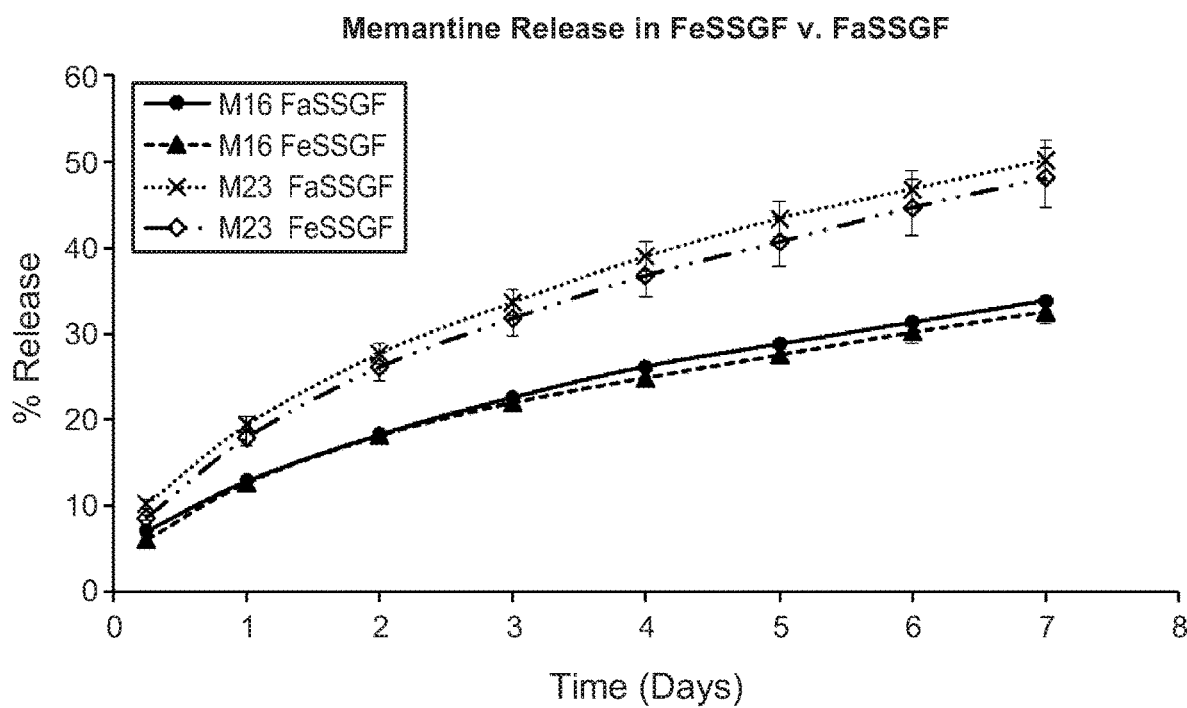
FIG. 64 shows in vitro release assay for memantine formulations M16 and M23 in FaSSGF and FeSSGF.

FIG. 64 shows comparison of in vitro drug release from formulation M16 and M23 in fasted state simulated gastric fluid (FaSSGF) and fed state simulated gastric fluid (FeSSGF). Both M16 and M23 are different milling batches with the same composition as formulation M1 (20% memantine, 9% Eudragit E, 0.5% silica, 0.5% alpha tocopherol, balance 80 k PCL. Formulation M16 resulted in a total release of about 30% in both fasted and fed states. Formulation M23 shows similar results in both fasted and fed states, with a total release of about 50%, linear release of about 33%, and a burst release of about 10%.

Example 45

Risperidone Release in Fed v. Fasted State

Figure 65:
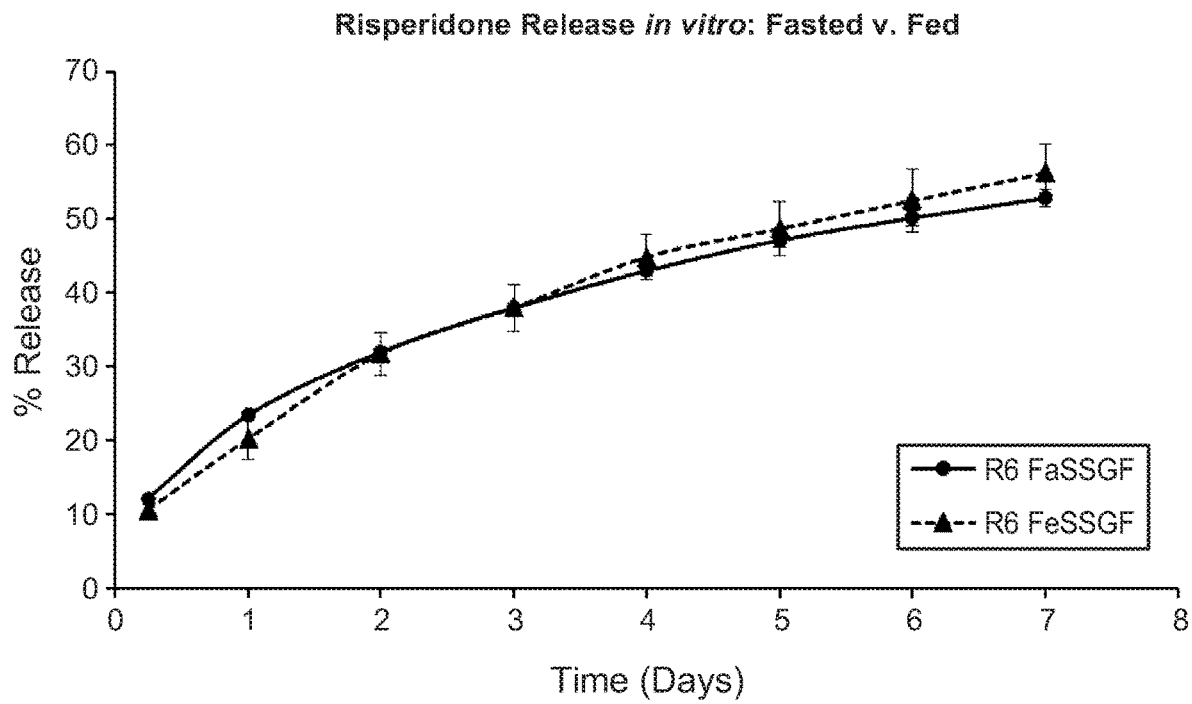
FIG. 65 shows in vitro release assay for risperidone formulation R6 in FaSSGF and FeSSGF.
Figure 66:
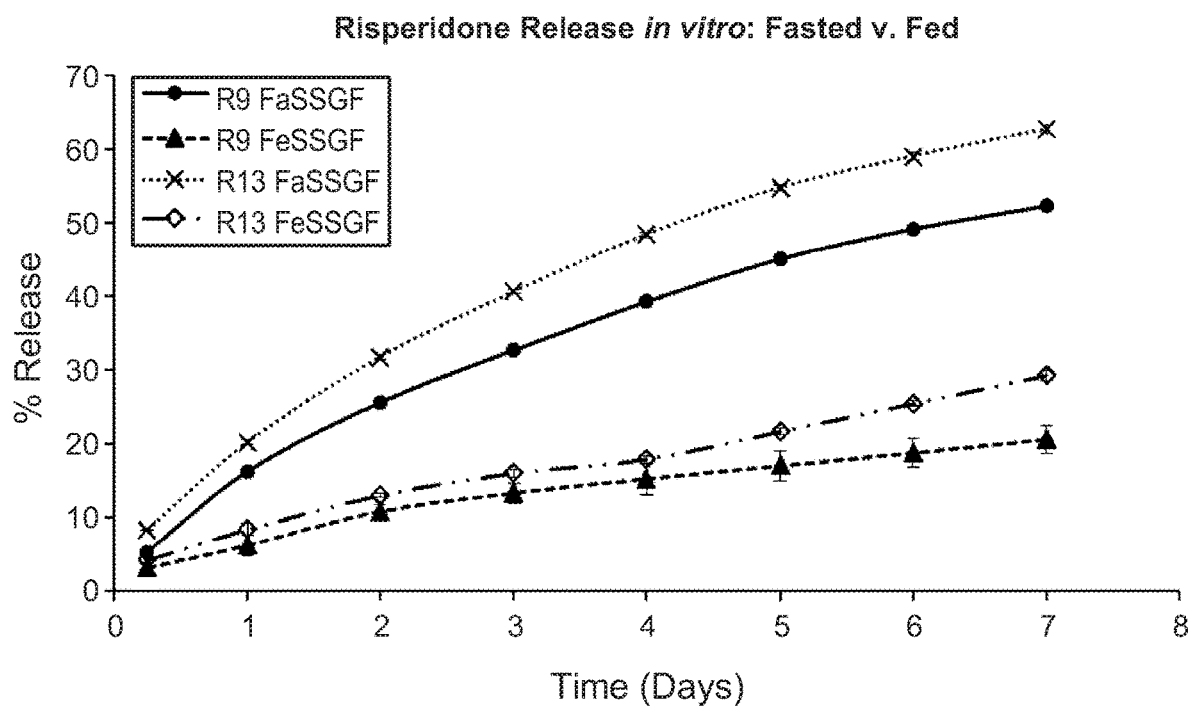
FIG. 66 shows in vitro release assay for risperidone formulations R9 and R13 in FaSSGF and FeSSGF.

Risperadone formulations were evaluated for the effect of media pH and composition on in vitro release profiles. Samples of formulations were incubated in fasted state simulated gastric fluid (FaSSGF, pH 1.6) and fed state simulated gastric fluid (FeSSGF, pH 5.0) media. Formulations were subjected to a seven-day release study at 37° C., 200 rpm. The pH of the release media can have a significant effect on the release of drugs that have pH-dependent solubility profiles, such as risperidone. In most formulations, risperidone is released more quickly in FaSSGF (pH 1.6) than in FeSSGF (pH 5). However, the difference in release rate can be minimized in certain formulations. For example, risperidone in a formulation consisting of 10% drug, 0.5% silicon dioxide, 0.5% α-tocopherol and 9% Aquaprene (Formulation R6) showed similar release in FaSSGF and FeSSGF (FIG. 65) However, formulations containing 44.5% Strataprene and 44.5% Eudragit RS (Formulation R9) or 42% Eudragit RS and 5% Kolliphor P407 (Formulation R13) resulted in significant reduction in release in fed state compared to that of fasted state (FIG. 66).

Example 46

Excipient Compatibility

To compare the excipient compatibility of API during HME, various formulations were analyzed for drug stability. All formulations were processed at 100° C. for 10 min on a twin screw extruder. After processing, drug was extracted from formulation by dissolution and precipitation as described in Example 32. API impurities were quantified by HPLC.

Total API impurities for several aripiprazole formulations are reported in Table 14. Stability of aripiprazole is adequate in the presence of all excipients studied.

TABLE 14

Aripiprazole degradation during processing.

| Formulation | Composition* | % Impurity |
|---|---|---|
| A1 | 10% Kolliphor P407, 10% Eudragit E PO | 0.12 at 1.10 RRT |
| A2 | 25% Eudragit E PO, 5% Kolliphor P407 | 0.16 at 1.10 RRT |
| A3 | 28% Eudragit RS, 2% Kolliphor P407 | NA |
| A4 | 28% Eudragit RL, 2% Kolliphor P407 | NA |
| A5 | 5% SDS | NA |
| A6 | 30% Aquaprene | <0.05 at 0.64 RRT |
| A7 | 30% Croscarmellose | NA |
| A8 | 10% Kolliphor P407, 10% Eudragit E PO, 10% Citric acid | NA |
| A9 | 10% Kolliphor P407, 10% Eudragit E PO, 5% Citric acid | NA |
| A10 | 20% NaCl | NA |

*All formulations contained 20% Aripiprazole, 0.5% silicon dioxide, 0.5% α-tocopherol, excipients mentioned above and balance 80K PCL.

Example 47

API Stability Versus Processing Temperature

API stability to a range of processing temperatures was assessed. Drug-loaded formulations were extruded at temperatures ranging from 90° C. to 180° C. with 10 minutes of batch mixing at 75 rpm. Extruded samples were analyzed for degradation by visual observation and by drug extraction followed by HPLC.

Table 15 below shows that Aripiprazole was stable up to 120° C. without any visual discoloration and degradants were less than 0.05%. Therefore, 100° C. was chosen as the processing temperature because drug is stable at that temperature and it will be suitable to melt the base polymer, PCL.

TABLE 15

Temperature Dependent Thermal Processing Stability Study of Aripiprazole

| Temperature ° C. | Visual Observation | % Impurity at RRT | | | | | | | Total |
|---|---|---|---|---|---|---|---|---|---|
| | | 0.22 | 0.42 | 0.64 | 0.71 | 0.81 | 0.86 | 0.93 | |
| 90 | White colored extrudate | — | — | <0.05 | — | — | — | — | <0.05 |
| 100 | White colored extrudate | — | — | <0.05 | — | — | — | — | <0.05 |
| 120 | White colored extrudate | — | — | <0.05 | — | — | — | — | <0.05 |
| 140 | Slight pink colored extrudate | — | — | <0.05 | — | — | 0.14 | — | 0.14 |
| 160 | Brown colored extrudate | 0.08 | 0.08 | 0.05 | — | — | — | — | 0.21 |
| 180 | Brown colored extrudate | 0.28 | 0.12 | 0.07 | <0.05 | 0.05 | — | 0.08 | 0.60 |

Formulation was composed of 20% Aripiprazole, 10% Kolliphor P407, 10% Eudragit EPO, 0.5% silicon dioxide, 0.5% α-Tocopherol and balance 80 K PCL.

Example 48

Formulation Extrudability: Die Expansion

In order to extrude drug-polymer formulations into the desired triangular geometry, dies are designed to compensate for the tendency of extrudates to swell upon exiting the die. Characterization of die swell of extruded formulations aids in the design of triangular dies. Die swell is characterized by extrusion of a filament through a circular die and comparison of the diameter of the extrudate to the diameter of the die orifice. As die swell is known to vary with temperature, die swell was characterized for a temperature range of 90-180° C. Results of die swell vs. temperature for an aripiprazole formulation (20% aripiprazole, 10% Kolliphor P407, 10% Eudragit EPO, 0.5% silicon dioxide, 0.5% α-Tocopherol and balance 80 K PCL) are shown in Table 16. Results of die swell vs. temperature for a doxycycline formulation (25% Doxycycline Hyclate, 10% Kolliphor P407, 0.5% silicon dioxide, 0.5% α-Tocopherol and balance 80 K PCL) are shown in Table. 17.

Figure 67:
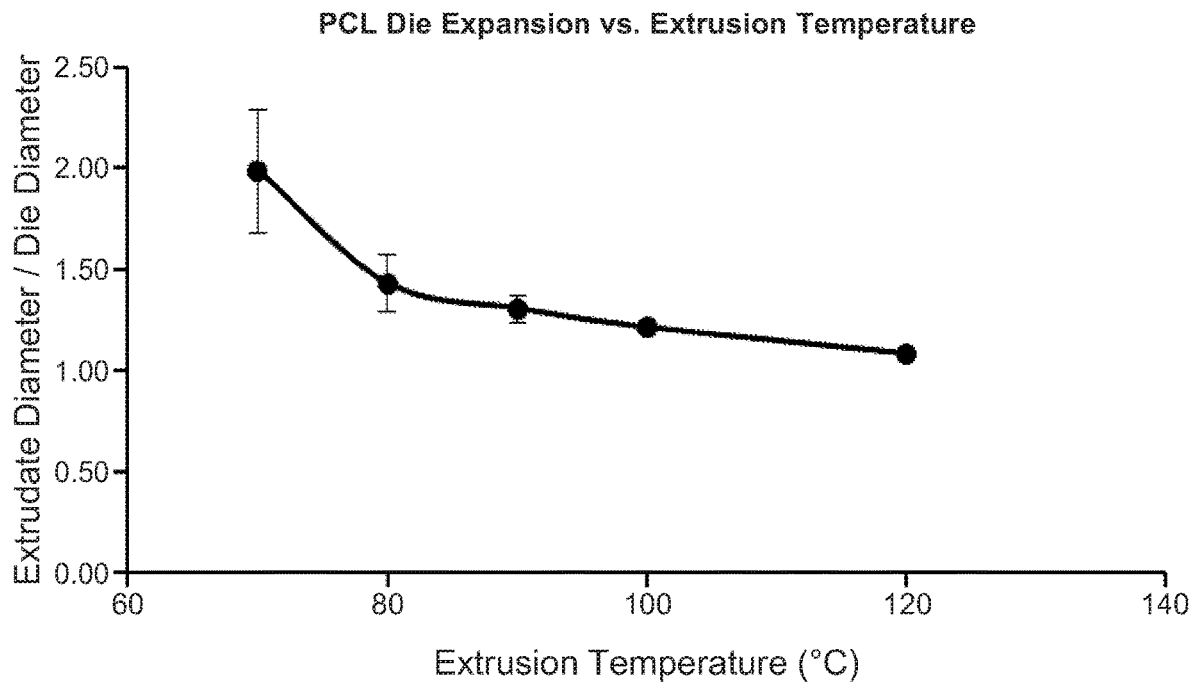
FIG. 67 shows PCL die extrusion.

FIG. 67 shows die expansion versus temperature for PCL. At temperatures below 90° C., die expansion becomes significant, making it difficult to extrude PCL into a stable triangular geometry. Based on this result, drug-loaded formulations based on PCL were processed at temperatures of at least 90° C.

TABLE 16

Die swell vs. Temperature for Aripiprazole

| Temperature ° C. | Die swell (%) | |
|---|---|---|
| | average | s.d. |
| 90 | 28% | 4% |
| 100 | 17% | 1% |
| 120 | 22% | 5% |
| 140 | 26% | 5% |

TABLE 16-continued

Die swell vs. Temperature for Aripiprazole

| Temperature ° C. | Die swell (%) | |
|---|---|---|
| | average | s.d. |
| 160 | 13% | 5% |
| 180 | 21% | 7% |

Formulation was composed of 20% Aripiprazole, 10% Kolliphor P407, 10% Eudragit EPO, 0.5% silicon dioxide, 0.5% α-Tocopherol and balance 80 K PCL.

TABLE 17

Die Swell vs. Temperature for Doxycycline Hyclate

| Temperature ° C. | Average ± SD |
|---|---|
| 90 | 48 ± 1% |
| 100 | 32 ± 2% |
| 120 | 14 ± 1% |
| 140 | 27 ± 1% |
| 160 | 18 ± 1% |

Formulation was composed of 25% Doxycycline Hyclate, 10% Kolliphor P407, 0.5% silicon dioxide, 0.5% α-Tocopherol and balance 80 K PCL

Example 49

Stability Criteria: Time Dependence

Based on the thermal processing stability study discussed in Example 47, 100° C. was chosen for time dependent thermal processing in order to evaluate the stability of drug during hot melt extrusion with respect to time. Formulation containing drug was extruded at 100° C. for time ranging from 5 minutes to 30 minutes with batch mixing at 75 rpm. Extruded samples were analyzed by visual observation and presence of degradants by API extraction and HPLC.

Visually, all the samples had no sign of discoloration and were white in color upon cooling to ambient temperature. Table 18 shows that for an aripiprazole formulation (20% aripiprazole, 10% Kolliphor P407, 10% Eudragit EPO, 0.5% silicon dioxide, 0.5% α-Tocopherol and balance 80 K PCL) all the samples were stable at 100° C. with no significant degradation at all the timepoints.

TABLE 18

Time Dependent Thermal Processing Stability Study of Aripiprazole at 100° C.

| Time (min) | Visual Observation | Impurity % 0.86 RRT |
|---|---|---|
| 5 | White colored extrudate | 0.08 |
| 10 | White colored extrudate | 0.08 |
| 15 | White colored extrudate | 0.08 |
| 20 | White colored extrudate | 0.08 |
| 30 | White colored extrudate | 0.08 |

Formulation was composed of 20% Aripiprazole, 10% Kolliphor P407, 10% Eudragit EPO, 0.5% silicon dioxide, 0.5% α-Tocopherol and balance 80 K PCL.

Example 50 pH Dependence of API Solubility

It is of interest to estimate pH dependent solubility of drugs under development to predict the effect of pH variation on release. Solubility estimates were conducted at varying pH ranging from acidic to basic. Equilibrium solubility was measured by preparing saturated solutions of drug at pH 1.06, 3.00, 4.65, 6.50, and 8.00 at ambient temperature, allowing equilibration overnight at ambient temperature, and measuring drug concentration in solution by HPLC.

Table 19 shows enhancement of aripiprazole solubility with reduction in the pH. Risperidone showed enhancement in solubility with increase in pH up to 4.65, followed by reduction in solubility at the higher pH, thereby confirming that both drugs exhibit pH-dependent solubility.

TABLE 19

Solubility of Aripiprazole and Risperidone at varying pH

| pH | Aripiprazole Solubility (mg/ml) | Risperidone solubility (mg/ml) |
|---|---|---|
| 1.06 | 0.5 | 9.94 |
| 3 | 0.12 | 22.8 |
| 4.65 | 0.11 | 40.78 |
| 6.5 | 0 | 1.39 |
| 8 | 0 | 0.19 |

Example 51

Solubility Enhancement Techniques

Aripiprazole has a poor aqueous solubility (approximately 0.456 μg/ml), which resulted in poor in vitro release of the drug from typical formulations. To improve release, solubility enhancement of aripiprazole was explored using surfactants, pore formers, and granulation techniques.

First, various surfactants were screened for their ability to improve aripiprazole solubility in FaSSGF and water. Equilibrium solubility of aripiprazole in the presence of surfactants was estimated in water and FaSSGF by the procedure described in Example 50. Table 20 shows that several surfactants increased solubility of aripiprazole. Kolliphor EL enhanced aripiprazole solubility by 4.5 fold in aqueous solution of and 120 folds in FaSSGF.

Those that provided the greatest increase in API solubility (Soluplus, SDS, and Kolliphor EL) were selected for evaluation in formulations. To maximize the contact between drug and solubility enhancers, API and other excipients were granulated before blending by hot melt extrusion (HME). Granulation was performed as discussed in Example 33, including API, solubilizer, and other powdered excipients (Formulations A18, A20, A21, and A22). Granules were combined with PCL pellets by HME at 100° C. and compression molded as detailed in Example 26. The extruded samples were subjected to in vitro release study for seven days. Results are shown in FIG. 34 through FIG. 45. Addition of solubilizers to formulations significantly increased release rates (Formulations A20, A22-A25) and release was further improved by incorporation of pore forming agents such as superdisintigrants (Formulations A21, A18).

TABLE 20

Solubility enhancement of Aripiprazole

| Solubilizer | Solvent | Folds increase | Solubility (mg/mg of agent) |
|---|---|---|---|
| CAPROL 3GO | Water | 0 | 0 |
| CAPTEX 355 | | 0 | 0 |
| CAPMUL MCM | | 0.14 | 0.0003 |
| Kolliphor P407 | | 0.3 | 0.0007 |
| PVP | | 0.54 | 0.0012 |
| Kolliphor RH-40 | | 1.27 | 0.0029 |
| SOLUPLUS | | 3.46 | 0.0079 |
| Kolliphor EL | | 4.5 | 0.0103 |
| SDS | | 12.51 | 0.0285 |
| CAPROL 3GO | FaSSGF | 24.32 | 0.0555 |
| CAPMUL MCM | | 34.01 | 0.0775 |
| CAPTEX 355 | | 48.81 | 0.1113 |
| Kolliphor EL | | 120.11 | 0.2739 |

Example 52

API Stability in Formulation, Before and after Incubation in SGF

Stability of API remaining in formulation after 7 day incubation in FaSSGF was analyzed. Release assays were performed as in Example 28. After the release assay, samples of formulation were recovered for extraction and analysis as per the procedure discussed in Example 32. Aripiprazole formulations analyzed pre- and post-incubation show that no significant degradation of drug occurs during the 7-day incubation in FaSSGF (Table 21).

TABLE 21

Aripiprazole stability in formulation, before and after 7 day incubation in FaSSGF

| | | Total impurities (%) | |
|---|---|---|---|
| Name | Formulation components | Post processing | Post 7-day incubation in SGF |
| A23 | 20% Cremophore EL | <0.05% | <0.05% |
| A24 | 20% Capmul MCM + Captex 355 + Cremophore EL | <0.05% | <0.05% |
| A25 | 9% Cremophore EL | <0.05% | <0.05% |

All formulations: 20% drug, 0.5% silica, 0.5% alpha tocopherol, excipients above, balance 80 k PCL Example 53

Extrudability: Formulation Melt Viscosity

Formulation melt viscosity and extrudability is dependent upon formulation composition. Melt viscosity can be modulated by addition of plasticizers to the formulation. During batch mixing and extrusion on the Hake MiniCTW microcompounder (screw speed=75 rpm), torque is monitored as a measure of melt viscosity. Equilibrium torque measurements are for various formulations are shown in Table 22. In general, addition of plasticizers to formulations significantly reduces processing torque. Formulations without added plasticizer typically exhibited torques ranging from 0.8-1.0 Nm at a mixing speed of 75 rpm, while formulation A22, containing 30% Kolliphor P407, had a torque of 0.13 Nm, reflecting a low melt viscosity.

TABLE 22

Processing torque for aripiprazole formulations

| Formulation | Composition | Average Processing Torque (Nm) |
|---|---|---|
| A5 | 5% SDS | 0.83 |
| A6 | 30% Aquaprene | 1.02 |
| A7 | 30% croscarmellose | 0.94 |
| A10 | 20% NaCl | 0.87 |
| A21 | 30% SSG | 0.43 |
| A22 | 30% Kolliphor P407 | 0.12 |

Example 54

Flexural Strength of Drug Loaded Formulation Arms

A four-point bending flexural test (ASTM D790) is used to evaluate the strength of the arms as described in Example 18. Briefly, the arm is supported near each end of the arm. Two rods, which are disposed closer to the middle of the arms than the supports, apply force and cause the specimen to bend in flexion. The force and displacement are recorded and the maximum flexural force recorded. Formulations of 20% ivermectin agent-loaded arms 20% doxycycline agent-loaded arms were prepared and were tested using this technique at Day 0, Day 2, and Day 7 of incubation in simulated gastric fluid (FASSGF). The results are shown in Table 23.

TABLE 23

Flexural strength of drug loaded formulation arms.

| Formulation | Day 0 | Day 2 | Day 7 |
|---|---|---|---|
| 20% Ivermectin; 80% PCL | 9.2 +/− 1.1 N | 8.1 +/− 0.9 N | 8.2 +/− 1.0 N |
| 20% Doxycycline; 80% PCL | 52 +/− 4.3 N | 49 +/− 5.8 N | 45 +/− 5.1 N |

Example 55

Ivermectin Release In Vitro with Respect to pH Variability

Figure 68:
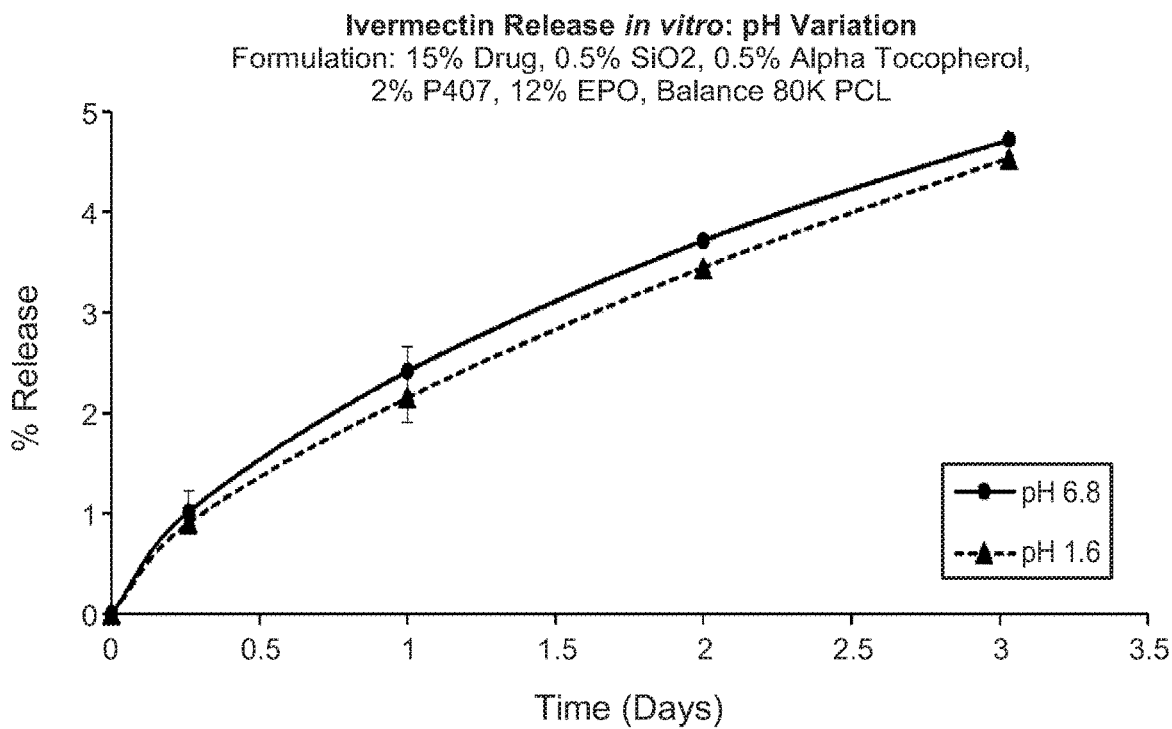
FIG. 68 shows in vitro release assay for ivermectin formulation at pH 1.6 and 6.8.

An ivermectin formulation was evaluated for the effect of media pH and composition on in vitro release profiles. Ivermectin was ball milled with and without 1% silica and sifted through a 180-micron sieve. Drug-polymer blends were prepared as described in Example 12 in a formulation containing 15% API, 0.5% SiO2, 0.5% alpha tocopherol, 2% P407, and 12% Eudragit E, with the balance 80 k PCL. FIG. 68 shows a comparison of the drug release at pH 6.8 and pH 1.6. This formulation results in approximately 4.75% release of ivermectin after 3 days in pH 6.8, and only a slight lower release at pH 1.6.

The disclosures of all publications, patents, patent applications and published patent applications referred to herein by an identifying citation are hereby incorporated herein by reference in their entirety. Web sites references using "World-Wide-Web" at the beginning of the Uniform Resource Locator (URL) can be accessed by replacing "World-Wide-Web" with "www."

Although the foregoing invention has been described in some detail by way of illustration and example for purposes of clarity of understanding, it is apparent to those skilled in the art that certain changes and modifications will be practiced. Therefore, the description and examples should not be construed as limiting the scope of the invention.

What is claimed is:

1. A gastric residence system for administration to a patient, comprising:
    a plurality of carrier polymer-agent components comprising:
        a carrier polymer, wherein the carrier polymer comprises:
            vinylpyrrolidone-vinyl acetate copolymer (VA64), wherein the carrier-polymer-agent components comprise about 5% to about 10% of vinylpyrrolidone-vinyl acetate copolymer (VA64); and
            polycaprolactone, wherein the carrier polymer-agent components comprise about 50.5% to about 89% polycaprolactone;
        a therapeutic agent or a pharmaceutically-acceptable salt thereof blended into the carrier polymer;
        a dispersant comprising silica (SiO2), wherein the carrier-polymer-agent components comprise about 0.1% to about 1% of silica (SiO2);
        an excipient, wherein the excipient comprises:
            a release enhancer comprising poloxamer P407, wherein the carrier-polymer-agent components comprise about 1% to about 5% of poloxamer P407; and
        a stabilizer, wherein the carrier-polymer-agent components comprise about 0.1% to about 2% of stabilizer;

wherein the carrier polymer-agent components are linked together by one or more coupling polymer components, wherein at least one of the one or more coupling polymer components is an elastomer;

wherein the gastric residence system is configured to have a compacted form in a container, suitable for administration orally or through a feeding tube; and an uncompacted form when released from the container;

wherein the gastric residence system is retained in the stomach for a residence period of between at least about 24 hours and about one month; and wherein:

the system releases a therapeutically effective amount of the therapeutic agent over an effective release period; and the system releases less than about 20% of the therapeutic agent or pharmaceutically-acceptable salt thereof within about a six-hour period;

wherein the therapeutic agent or a pharmaceutically-acceptable salt thereof is selected from the group consisting of doxycycline, donepezil, ivermectin, risperidone, cetirizine, and rosuvastatin, or a pharmaceutically-acceptable salt thereof.

2. The gastric residence system of claim 1, wherein the system releases about 30% to about 70% of the therapeutic agent or pharmaceutically-acceptable salt thereof within a time of about 40% to 60% of the effective release period.

3. The gastric residence system of claim 1, wherein the system releases greater than about 70% of the therapeutic agent or pharmaceutically-acceptable salt thereof within a time of about 90% of the effective release period.

4. The gastric residence system of claim 1, wherein the release of the therapeutic agent or pharmaceutically-acceptable salt thereof is measured in simulated gastric fluid.

5. The gastric residence system of claim 1, wherein the release of the therapeutic agent or pharmaceutically-acceptable salt thereof increases by no more than about 40% in 40% ethanol/60% simulated gastric fluid versus the release over the same period of time in simulated gastric fluid.

6. The gastric residence system of claim 1, wherein:

the therapeutic agent or a pharmaceutically-acceptable salt thereof comprises about 10% to about 35% of the carrier polymer-agent components.

7. The gastric residence system of claim 1, wherein the release enhancer further comprises one or more compounds selected from the group consisting of an acrylate polymer, an acrylate co-polymer, a polydioxanone-polyethylene glycol polymer, and polyvinylpyrrolidone.

8. The gastric residence system of claim 1, wherein the dispersant further comprises one or more compounds selected from the group consisting of a porous inorganic material, a polar inorganic material, a non-toxic metal oxide, an amphiphilic organic molecule, a polysaccharide, cellulose, a cellulose derivative, a fatty acid, a detergent, hydrophilic-fumed silica, hydrophobic colloidal silica, magnesium aluminum silicate, a stearate salt, calcium stearate, magnesium stearate, microcrystalline cellulose, carboxymethylcellulose, hypromellose, a phospholipid, a polyoxyethylene stearate, zinc acetate, alginic acid, lecithin, sodium lauryl sulfate, and aluminum oxide.

9. The gastric residence system of claim 1, wherein the excipient further comprises a solubilizer.

10. The gastric residence system of claim 9, wherein the solubilizer is selected from the group consisting of a polyalkylene oxide, a polyethoxylated castor oil, and a detergent.

11. The gastric residence system of claim 1, wherein the stabilizer comprises about 0.1% to about 1% of the carrier polymer-agent components.

12. The gastric residence system of claim 11, wherein the stabilizer comprises one or more compounds selected from the group consisting of an anti-oxidant, tocopherol, alpha-tocopherol, ascorbic acid, an ascorbate salt, a carotene, butylated hydroxyanisole, butylated hydroxytoluene, fumaric acid, an anti-microbial, a buffering substance, calcium carbonate, calcium lactate, calcium phosphate, sodium phosphate, and sodium bicarbonate.

13. The gastric residence system of claim 1, wherein the polycaprolactone has an average $M_n$ of about 60,000 to about 100,000.

14. The gastric residence system of claim 1, wherein the therapeutic agent or pharmaceutically acceptable salt thereof has a solubility in water of less than 1 mg/ml.

15. The gastric residence system of claim 9, wherein the solubilizer is a copolymer of polyvinyl caprolactam, polyvinyl acetate, and polyethylene glycol.

16. A gastric residence system for administration to a patient, comprising:

at least one carrier polymer-agent component comprising:

a carrier polymer, wherein the carrier polymer comprises:

vinylpyrrolidone-vinyl acetate copolymer (VA64), wherein the at least one carrier-polymer-agent component comprises about 5% to about 10% of vinylpyrrolidone-vinyl acetate copolymer (VA64); and polycaprolactone, wherein the carrier polymer-agent components comprise about 50.5% to about 89% polycaprolactone;

a therapeutic agent or a pharmaceutically-acceptable salt thereof blended into the carrier polymer;

a dispersant comprising silica (SiO2), wherein the at least one carrier-polymer-agent component comprises about 0.1% to about 1% of silica (SiO2);

an excipient, wherein the excipient comprises:

a release enhancer comprising poloxamer P407, wherein the at least one carrier-polymer-agent component comprises about 1% to about 15% of poloxamer P407; and a stabilizer, wherein the at least one carrier-polymer-agent component comprises about 0.1% to about 1% of stabilizer;

wherein the at least one carrier polymer-agent component is linked to the gastric residence system by one or more coupling polymer components, wherein at least one of the one or more coupling polymer components is an elastomer;

wherein the gastric residence system is configured to have a compacted form in a container, suitable for administration orally or through a feeding tube; and an uncompacted form when released from the container;

wherein the gastric residence system is retained in the stomach for a residence period of between at least about 24 hours and about one month; and wherein:

the system releases a therapeutically effective amount of the therapeutic agent over an effective release period; and the system releases less than about 20% of the therapeutic agent or pharmaceutically-acceptable salt thereof within about a six-hour period;

wherein the therapeutic agent or a pharmaceutically-acceptable salt thereof is selected from the group consisting of doxycycline, donepezil, ivermectin, risperidone, cetirizine, and rosuvastatin, or a pharmaceutically-acceptable salt thereof.

17. The gastric residence system of claim 9, wherein the solubilizer is a block copolymer of polyethylene glycol (PEG) and polypropylene glycol (PPG).

18. The gastric residence system of claim 1, wherein the therapeutic agent or a pharmaceutically-acceptable salt thereof is risperidone.

19. The gastric residence system of claim 1, wherein:
the carrier polymer-agent components comprises about 35% of the therapeutic agent or a pharmaceutically-acceptable salt thereof,
the carrier-polymer-agent components comprises about 0.5% of silica ($SiO_2$),
the carrier-polymer-agent components comprises about 3% of poloxamer P407,
the carrier-polymer-agent components comprises about 0.5% of stabilizer;
the carrier-polymer-agent components comprises about 5% of vinylpyrrolidone-vinyl acetate copolymer (VA64);
the remaining balance of the carrier-polymer-agent components comprises polycaprolactone.

20. The gastric residence system of claim 1, wherein the stabilizer comprises tocopherol and/or alpha-tocopherol.

21. The gastric residence system of claim 16, wherein the stabilizer comprises tocopherol and/or alpha-tocopherol.

22. The gastric residence system of claim 19, wherein the stabilizer comprises tocopherol and/or alpha-tocopherol.

* * * * *